United States Patent
Giampietro et al.

(10) Patent No.: US 10,701,940 B2
(45) Date of Patent: *Jul. 7, 2020

(54) MOLECULES HAVING CERTAIN PESTICIDAL UTILITIES, AND INTERMEDIATES, COMPOSITIONS, AND PROCESSES RELATED THERETO

(71) Applicant: Dow AgroSciences LLC, Indianapolis, IN (US)

(72) Inventors: Natalie C. Giampietro, Carmel, IN (US); David A. Demeter, Fishers, IN (US); Lindsey G. (Fischer) Horty, Indianapolis, IN (US); Gary D. Crouse, Noblesville, IN (US); Thomas C. Sparks, Greenfield, IN (US)

(73) Assignee: DOW AGROSCIENCES LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/805,710

(22) Filed: Nov. 7, 2017

(65) Prior Publication Data

US 2018/0125072 A1    May 10, 2018

Related U.S. Application Data

(60) Provisional application No. 62/477,577, filed on Mar. 28, 2017, provisional application No. 62/464,427, filed on Feb. 28, 2017, provisional application No. 62/419,622, filed on Nov. 9, 2016.

(51) Int. Cl.
*A01N 47/36* (2006.01)
*A01N 47/46* (2006.01)
*A01N 47/48* (2006.01)
*C07D 417/12* (2006.01)

(52) U.S. Cl.
CPC ............ *A01N 47/36* (2013.01); *A01N 47/46* (2013.01); *A01N 47/48* (2013.01); *C07D 417/12* (2013.01)

(58) Field of Classification Search
None
See application file for complete search history.

(56) References Cited

U.S. PATENT DOCUMENTS

| | | | | |
|---|---|---|---|---|
| 9,029,560 B2* | 5/2015 | Fischer | .................. | A01N 47/42 548/146 |
| 9,249,133 B2* | 2/2016 | Fischer | .................. | A01N 47/42 |
| 9,278,964 B2* | 3/2016 | Fischer | .................. | A01N 47/42 |
| 9,783,532 B2* | 10/2017 | Giampietro | ............ | A01N 47/42 |
| 9,834,547 B2* | 12/2017 | Fischer | .................. | A01N 47/42 |
| 2018/0111924 A1* | 4/2018 | Webster | ................. | A01N 55/08 |

OTHER PUBLICATIONS

MItsos, C. Isosteres in Medicinal Chemistry, Baran Group meeting notes https://www.scripps.edu/baran/images/grpmtgpdf/Mitsos_Feb_06.pdf, no pagination (Year: 2006).*
Patani, G.; LaVoie, E. J. "Bioisosterism: A Rational Approach in Drug Design" Chemical Reviews, 1996, 96, 3147-3176 (Year: 1996).*

* cited by examiner

*Primary Examiner* — Erin E Hirt

(57) ABSTRACT

This disclosure relates to the field of molecules having pesticidal utility against pests in phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the following formula ("Formula One" and "Formula Two").

Formula One

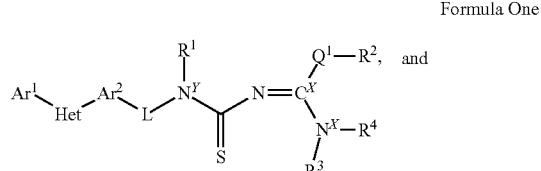

Formula Two

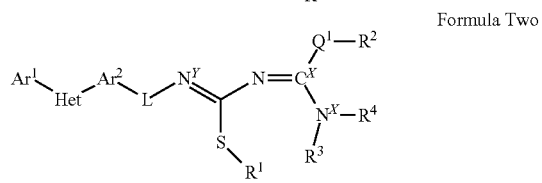

8 Claims, No Drawings

MOLECULES HAVING CERTAIN PESTICIDAL UTILITIES, AND INTERMEDIATES, COMPOSITIONS, AND PROCESSES RELATED THERETO

CROSS REFERENCES TO RELATED APPLICATIONS

This application claims priorities under 35 U.S.C. § 119 of U.S. provisional patent application Ser. Nos. 62/419,622 filed Nov. 9, 2016, 62/464,427 filed Feb. 28, 2017, and 62/477,577 filed Mar. 28, 2017, which applications are hereby incorporated by reference in their entireties.

FIELD OF THE DISCLOSURE

This disclosure relates to the field of molecules having pesticidal utility against pests in Phyla Nematoda, Arthropoda, and Mollusca, processes to produce such molecules and intermediates used in such processes, compositions containing such molecules, and processes of using such molecules against such pests. These molecules may be used, for example, as nematicides, acaricides, insecticides, miticides, and molluscicides.

BACKGROUND OF THE DISCLOSURE

"Many of the most dangerous human diseases are transmitted by insect vectors" (Rivero, A. et al., Insect Control of Vector-Borne Diseases: When is Insect Resistance a Problem? Public Library of Science Pathogens, 6(8) (2010)). Historically, vector-borne diseases, such as, malaria, dengue, yellow fever, plague, and louse-borne typhus, among others, were responsible for more human disease and death from the 1600's through the early 1900's than all other causes combined (Gubler D., Resurgent Vector-Borne Diseases as a Global Health Problem, Emerging Infectious Diseases, Vol. 4, No. 3, July-September (1998)). Currently, vector-borne diseases are responsible for about 17% of the global parasitic and infectious diseases. It has been estimated that about 250 million people around the world have malaria and about 800,000 deaths occur each year—85% of those deaths are children under the age of five. A further 250,000 to 500,000 cases of dengue hemorrhagic fever occur each year (Matthews, G., Integrated Vector Management: controlling vectors of malaria and other insect vector borne diseases (2011)). Vector control plays a critical role in the prevention and control of infectious diseases. However, insecticide resistance, including resistance to multiple insecticides, has arisen in all insect species that are major vectors of human diseases (Rivero, A. et al.).

Each year insects, plant pathogens, and weeds destroy more than 40% of all potential food production. This loss occurs despite the application of pesticides and the use of a wide array of non-chemical controls, such as crop rotations and biological controls. If just some of this food could be saved, it could be used to feed the more than three billion people in the world who are malnourished (Pimental, D., Pest Control in World Agriculture, Agricultural Sciences—Vol. 11 (2009)).

Plant parasitic nematodes are among the most widespread pests, and are frequently one of the most insidious and costly. It has been estimated that losses attributable to nematodes are from about 9% in developed countries to about 15% in undeveloped countries. However, in the United States of America, a survey of 35 States on various crops indicated nematode-derived losses of up to 25% (Nicol, J. et al., Current Nematode Threats to World Agriculture, Genomic and Molecular Genetics of Plant—Nematode Interactions (Eds. Jones, J. et al.), Chapter 2, (2011)).

It is noted that gastropods (slugs and snails) are pests of less economic importance than insects or nematodes, but in certain areas, gastropods may reduce yields substantially, severely affecting the quality of harvested products, as well as transmitting human, animal, and plant diseases. While only a few dozen species of gastropods are serious regional pests, a handful of species are important pests on a worldwide scale. In particular, gastropods affect a wide variety of agricultural and horticultural crops, such as arable, pastoral, and fiber crops; vegetables; bush and tree fruits; herbs; and ornamentals (Speiser, B., Molluscicides, Encyclopedia of Pest Management (2002)).

Termites cause damage to all kinds of private and public structures, as well as to agricultural and forestry resources. In 2003, it was estimated that termites cause over US$20 billion in damage world-wide each year (Su, N.Y., Overview of the global distribution and control of the Formosan subterranean termite, *Sociobiology* 2003, 41, 177-192).

Therefore, for many reasons, including the above reasons, a need exists for new pesticides.

Definitions

The examples given in the definitions are generally non-exhaustive and must not be construed as limiting the molecules disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, tetrahydrofuranyl, and tetrahydropyranyl. Examples of partially unsaturated heterocyclyls include, but are not limited to, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

DETAILED DESCRIPTION OF THE DISCLOSURE

This document discloses molecules having the following formula ("Formula One" and/or "Formula Two")

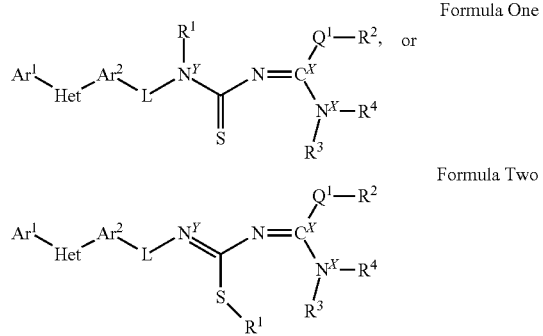

wherein:
(A) $Ar^1$ is selected from
(1) furanyl, phenyl, pyridazinyl, pyridyl, pyrimidinyl, or thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, or substituted thienyl, has one or more substituents independently selected from H, F, Cl, Br, I, CN, $NO_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $OSO_2$—$(C_1-C_8)$alkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-$O$—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy, wherein each alkyl, cycloalkyl, alkoxy, alkenyl, alkynyl, phenyl, and phenoxy substituent may be optionally substituted with one or more substituents independently selected from the group consisting of H, F, Cl, Br, I, CN, $NO_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_1-C_8)$haloalkyl, $C(O)O$—$(C_1-C_8)$haloalkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-$O$—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy;

(B) Het is a 5- or 6-membered, saturated or unsaturated, heterocyclic ring, containing one or more heteroatoms independently selected from nitrogen, sulfur, or oxygen, and where $Ar^1$ and $Ar^2$ are not ortho to each other (but may be meta or para, such as, for a five-membered ring they are 1,3 and for a 6-membered ring they are either 1,3 or 1,4) and where said heterocyclic ring may also be substituted with one or more substituents independently selected from the group consisting of H, F, Cl, Br, I, CN, $NO_2$, oxo, $(C_1-C_8)$alkyl, $(C_3-C_8)$cycloalkyl, $(C_1-C_8)$alkoxy, $(C_2-C_8)$alkenyl, $(C_2-C_8)$alkynyl, $S(O)_n$—$(C_1-C_8)$alkyl, $OSO_2$—$(C_1-C_8)$alkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-$O$—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy, wherein each alkyl, cycloalkyl, alkoxy, alkenyl, alkynyl, phenyl, and phenoxy substituent may be optionally substituted with one or more substituents independently selected from the group consisting of H, F, Cl, Br, I, CN, $NO_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_1-C_8)$haloalkyl, $C(O)O$—$(C_1-C_8)$haloalkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-$O$—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy;

(C) $Ar^2$ is selected from
(1) furanyl, phenyl, pyridazinyl, pyridyl, pyrimidinyl, or thienyl, or
(2) substituted furanyl, substituted phenyl, substituted pyridazinyl, substituted pyridyl, substituted pyrimidinyl, or substituted thienyl,
   wherein said substituted furanyl, substituted phenyl, substituted pyridazinyl, substituted pyridyl, substituted pyrimidinyl, or substituted thienyl, has one or more substituents independently selected from H, F, Cl, Br, I, CN, $NO_2$, $NR^xR^y$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $OSO_2$—$(C_1-C_8)$alkyl, C(O)—$NR^xR^y$, $(C_1-C_8)$alkyl-$NR^xR^y$, C(O)—$(C_1-C_8)$alkyl, C(O)O—$(C_1-C_8)$alkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and phenoxy,
   wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, $NO_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, C(O)—$NR^xR^y$, $(C_1-C_8)$alkyl-$NR^xR^y$, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and phenoxy;
(D) L is linker selected from
(1) a saturated or unsaturated, substituted or unsubstituted, linear $(C_1-C_4)$hydrocarbyl linker, and
(2) a saturated or unsaturated, substituted or unsubstituted, cyclic $(C_3-C_8)$hydrocarbyl group linker,
   wherein each of said linkers connects $Ar^2$ to $N^y$ and
   wherein said substituted linear $(C_1-C_4)$hydrocarbyl linker and substituted cyclic $(C_3-C_8)$hydrocarbyl linker has one or more substituents independently selected from $R^8$, $R^9$, $R^{10}$, $R^{11}$, and $R^{12}$, wherein each $R^8$, $R^9$, $R^{10}$, $R^{11}$, and $R^{12}$, is selected from F, Cl, Br, I, CN, oxo, $(C_1-C_6)$alkyl, $(C_2-C_6)$alkenyl, $(C_2-C_6)$haloalkenyl, $(C_2-C_6)$alkynyl, $(C_1-C_6)$haloalkyl, $(C_3-C_6)$cycloalkyl, $(C_3-C_6)$cycloalkenyl, $(C_3-C_6)$halocycloalkyl, $(C_1-C_6)$alkoxy, $(C_1-C_6)$haloalkoxy, or phenyl;
(E) $R^1$ is selected from the group consisting of H, $(C_1-C_8)$alkyl, $(C_3-C_8)$cycloalkyl, $(C_2-C_8)$alkenyl, $(C_2-C_8)$alkynyl, $S(O)_n$—$(C_1-C_8)$alkyl, C(O)—$NR^xR^y$, $(C_1-C_8)$alkyl-$NR^xR^y$, C(O)O—$(C_1-C_8)$alkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-OC(O)—$(C_1-C_8)$alkyl, $(C_1-C_8)$alkyl-S(O)$_n$—$(C_1-C_8)$alkyl, $(C_1-C_8)$alkyl-OC(O)O—$(C_1-C_8)$alkyl, $(C_1-C_8)$alkyl-C(O)O—$(C_1-C_8)$alkyl, C(O)alkyl, $(C_1-C_8)$alkyl-C(O)—$(C_1-C_8)$alkyl, $(C_1-C_8)$alkylphenyl, $(C_1-C_8)$alkyl-O-phenyl,
   wherein each alkyl, cycloalkyl, alkenyl, and alkynyl may be optionally substituted with one or more substituents independently selected from the group consisting of H, F, Cl, Br, I, CN, $NO_2$, oxo, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, C(O)—$NR^xR^y$, $(C_1-C_8)$alkyl-$NR^xR^y$, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and phenoxy;
(F) $Q^1$ is selected from the group consisting of O and S;
(G) $R^2$ is selected from the group consisting of (J), H, $(C_1-C_8)$alkyl, $(C_3-C_8)$cycloalkyl, $(C_2-C_8)$alkenyl, $(C_2-C_8)$alkynyl, C(O)—$(C_1-C_8)$alkyl, $(C_1-C_8)$alkyl-O—$(C_1-C_8)$alkyl, $(C_1-C_8)$alkyl-S(O)$_n$—$(C_1-C_8)$alkyl, $(C_1-C_8)$alkylphenyl, $(C_1-C_8)$alkyl-O-phenyl, C(O)-(Het-1), (Het-1), $(C_1-C_8)$alkyl-(Het-1), $(C_1-C_8)$alkyl-OC(O)—$(C_1-C_8)$alkyl, $(C_1-C_8)$alkyl-OC(O)O—$(C_1-C_8)$alkyl, $(C_1-C_8)$alkyl-OC(O)—$NR^xR^y$, $(C_1-C_8)$alkyl-C(O)—N($R^x$)$(C_1-C_8)$alkyl-(Het-1), $(C_1-C_8)$alkyl-C(O)-(Het-1), $(C_1-C_8)$alkyl-C(O)—N($R^x$)$(C_1-C_8)$alkyl(N$R^xR^y$)—C(O)OH, $(C_1-C_8)$alkyl-C(O)—N($R^x$)$(C_1-C_8)$alkyl-N$R^xR^y$, $(C_1-C_8)$alkyl-C(O)—N($R^x$)$(C_1-C_8)$alkyl-N($R^x$)—C(O)O—$(C_1-C_8)$alkyl, $(C_1-C_8)$alkyl-C(O)—N($R^x$)$(C_1-C_8)$alkyl(N($R^x$)—C(O)O—$(C_1-C_8)$alkyl)-C(O)OH, $(C_1-C_8)$alkyl-C(O)-(Het-1)-C(O)O—$(C_1-C_8)$alkyl, $(C_1-C_8)$alkyl-OC(O)O—$(C_1-C_8)$alkyl, $(C_1-C_8)$alkyl-OC(O)—$(C_1-C_8)$alkyl, $(C_1-C_8)$alkyl-OC(O)—$(C_3-C_8)$cycloalkyl, $(C_1-C_8)$alkyl-OC(O)-(Het-1), $(C_1-C_8)$alkyl-OC(O)—$(C_1-C_8)$alkyl-N($R^x$)—C(O)O—$(C_1-C_8)$alkyl, $(C_1-C_8)$alkyl-N$R^xR^y$, $(C_1-C_8)$alkyl-S(O)$_n$-(Het-1), and $(C_1-C_8)$alkyl-O-(Het-1),
   wherein each alkyl, cycloalkyl, alkenyl, alkynyl, phenyl, and (Het-1) may be optionally substituted with one or more substituents independently selected from the group consisting of H, F, Cl, Br, I, CN, $NO_2$, $NR^xR^y$, $(C_1-C_8)$alkyl, $(C_1-C_8)$haloalkyl, $(C_3-C_8)$cycloalkyl, $(C_1-C_8)$alkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, C(O)H, C(O)OH, C(O)—$NR^xR^y$, $(C_1-C_8)$alkyl-$NR^xR^y$, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl), phenyl, phenoxy, Si(($(C_1-C_8)$alkyl)$_3$, $S(O)_n$—$NR^xR^y$, and (Het-1);
(H) $R^3$ is selected from the group consisting of $(C_3-C_8)$cycloalkyl, phenyl, $(C_1-C_8)$alkylphenyl, $(C_1-C_8)$alkyl-O-phenyl, $(C_2-C_8)$alkenyl-O-phenyl, (Het-1), $(C_1-C_8)$alkyl-(Het-1), and $(C_1-C_8)$alkyl-O-(Het-1),
   wherein each alkyl, cycloalkyl, alkenyl, phenyl, and (Het-1) may be optionally substituted with one or more substituents independently selected from the group consisting of H, F, Cl, Br, I, CN, $NO_2$, $NR^xR^y$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, C(O)H, C(O)—$NR^xR^y$, $(C_1-C_8)$alkyl-$NR^xR^y$, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_1-C_8)$cycloalkyl, C(O)—$(C_2-C_8)$alkenyl, C(O)O—$(C_2-C_8)$alkenyl, O—$(C_1-C_8)$alkyl, S—$(C_1-C_8)$alkyl, $(C_1-C_8)$alkyl-O—$(C_1-C_8)$alkyl, C(O)—$(C_1-C_8)$alkyl-C(O)O—$(C_1-C_8)$alkyl, phenyl, phenoxy, and (Het-1),
(I) $R^4$ is selected from the group consisting of (J), H, $(C_1-C_8)$alkyl, $(C_3-C_8)$cycloalkyl, $(C_2-C_8)$alkenyl, $(C_2-C_8)$alkynyl, C(O)—$(C_1-C_8)$alkyl, $(C_1-C_8)$alkyl-O—$(C_1-C_8)$alkyl, $(C_1-C_8)$alkyl-S(O)$_n$—$(C_1-C_8)$alkyl, $(C_1-C_8)$alkylphenyl, $(C_1-C_8)$alkyl-O-phenyl, C(O)-(Het-1), (Het-1), $(C_1-C_8)$alkyl-(Het-1), $(C_1-C_8)$alkyl-OC(O)—$(C_1-C_8)$alkyl, $(C_1-C_8)$alkyl-OC(O)O—$(C_1-C_8)$alkyl, $(C_1-C_8)$alkyl-OC(O)—NR$^x$R$^y$, $(C_1-C_8)$alkyl-C(O)—N(R$^x$)$(C_1-C_8)$alkyl-(Het-1), $(C_1-C_8)$alkyl-C(O)-(Het-1), $(C_1-C_8)$alkyl-C(O)—N(R$^x$)$(C_1-C_8)$alkyl(NR$^x$R$^y$)—C(O)OH, $(C_1-C_8)$alkyl-C(O)—N(R$^x$)$(C_1-C_8)$alkyl-NR$^x$R$^y$, $(C_1-C_8)$alkyl-C(O)—N(R$^x$)$(C_1-C_8)$alkyl-N(R$^x$)—C(O)O—$(C_1-C_8)$alkyl, $(C_1-C_8)$alkyl-C(O)—N(R$^x$)$(C_1-C_8)$alkyl(N(R$^x$)—C(O)O—$(C_1-C_8)$alkyl)-C(O)OH, $(C_1-C_8)$alkyl-C(O)-(Het-1)-C(O)O—$(C_1-C_8)$alkyl, $(C_1-C_8)$alkyl-OC(O)O—$(C_1-C_8)$alkyl, $(C_1-C_8)$alkyl-OC(O)—$(C_1-C_8)$alkyl, $(C_1-C_8)$alkyl-OC(O)—$(C_3-C_8)$cycloalkyl, $(C_1-C_8)$alkyl-OC(O)-(Het-1), $(C_1-C_8)$alkyl-OC(O)—$(C_1-C_8)$alkyl-N(R$^x$)—C(O)O—$(C_1-C_8)$alkyl, $(C_1-C_8)$alkyl-NR$^x$R$^y$, $(C_1-C_8)$alkyl-S(O)$_n$-(Het-1), and $(C_1-C_8)$alkyl-O-(Het-1), wherein each alkyl, cycloalkyl, alkenyl, alkynyl, phenyl, and (Het-1) may be optionally substituted with one or more substituents independently selected from the group consisting of H, F, Cl, Br, I, CN, NO$_2$, NR$^x$R$^y$, $(C_1-C_8)$alkyl, $(C_1-C_8)$haloalkyl, $(C_3-C_8)$cycloalkyl, $(C_1-C_8)$alkoxy, $(C_2-C_8)$alkenyl, $(C_2-C_8)$alkynyl, S(O)$_n$—$(C_1-C_8)$alkyl, S(O)$_n$—$(C_1-C_8)$haloalkyl, OSO$_2$—$(C_1-C_8)$alkyl, OSO$_2$—$(C_1-C_8)$haloalkyl, C(O)H, C(O)OH, C(O)—NR$^x$R$^y$, $(C_1-C)$alkyl-NR$^x$R$^y$, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, phenoxy, Si$((C_1-C_8)$alkyl$)_3$, S(O)$_n$—NR$^x$R$^y$, and (Het-1);

(J) R$^2$ and R$^4$ together with C$^X$(Q$^1$)(N$^X$), may form a 4- to 7-membered saturated or unsaturated, heterocyclic ring, which may further contain one or more heteroatoms selected from the group consisting of nitrogen, sulfur, and oxygen, wherein each heterocyclic ring may be optionally substituted with one or more substituents independently selected from the group consisting of R$^5$, R$^6$, and R$^7$, wherein R$^5$, R$^6$, and R$^7$ are each independently selected from the group consisting of H, F, Cl, Br, I, CN, OH, SH, NO$_2$, NR$^x$R$^y$, oxo, thioxo, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, S(C$_1$—C alkyl), S(C$_1$—C haloalkyl), S(O)$_n$—$(C_1-C_8)$alkyl, S(O)$_n$—$(C_1-C_8)$haloalkyl, OSO$_2$—$(C_1-C_8)$alkyl, OSO$_2$—$(C_1-C_8)$haloalkyl, C(O)H, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and (Het-1);

(K) R$^x$ and R$^y$ are each independently selected from the group consisting of H, $(C_1-C_8)$alkyl, $(C_3-C_8)$cycloalkyl, $(C_1-C_8)$alkoxy, $(C_2-C_8)$alkenyl, $(C_2-C_8)$alkynyl, S(O)$_n$—$(C_1-C_8)$alkyl, OSO$_2$—$(C_1-C_8)$alkyl, C(O)H, C(O)—$(C_1-C_8)$alkyl, C(O)O—$(C_1-C_8)$alkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and $(C_1-C_8)$alkylphenyl, wherein each alkyl, cycloalkyl, alkoxy, alkenyl, phenyl, and alkylphenyl may be optionally substituted with one or more substituents independently selected from the group consisting of H, F, Cl, Br, I, CN, NO$_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, S(O)$_n$—$(C_1-C_8)$alkyl, S(O)$_n$—$(C_1-C_8)$haloalkyl, OSO$_2$—$(C_1-C_8)$alkyl, OSO$_2$—$(C_1-C_8)$haloalkyl, C(O)H, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and (Het-1);

(L) (Het-1) is a 5- or 6-membered, saturated or unsaturated, heterocyclic ring, containing one or more heteroatoms independently selected from nitrogen, sulfur or oxygen, wherein said heterocyclic ring may be optionally substituted with one or more substituents independently selected from the group consisting of H, F, Cl, Br, I, CN, NO$_2$, oxo, $(C_1-C_8)$alkyl, $(C_3-C_8)$cycloalkyl, $(C_1-C_8)$alkoxy, $(C_2-C_8)$alkenyl, $(C_2-C_8)$alkynyl, S(O)$_n$—$(C_1-C_8)$alkyl, OSO$_2$—$(C_1-C_8)$alkyl, C(O)—NR$^x$R$^y$, $(C_1-C_8)$alkyl-NR$^x$R$^y$, C(O)—$(C_1-C_8)$alkyl, C(O)O—$(C_1-C_8)$alkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and phenoxy, wherein each alkyl, cycloalkyl, alkoxy, alkenyl, alkynyl, phenyl, and phenoxy substituent may be optionally substituted with one or more substituents independently selected from the group consisting of H, F, Cl, Br, I, CN, NO$_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, S(O)$_n$—$(C_1-C_8)$alkyl, S(O)$_n$—$(C_1-C_8)$haloalkyl, OSO$_2$—$(C_1-C_8)$alkyl, OSO$_2$—$(C_1-C_8)$haloalkyl, C(O)—NR$^x$R$^y$, $(C_1-C_8)$alkyl-NR$^x$R$^y$, C(O)—$(C_1-C_8)$alkyl, C(O)O—$(C_1-C_8)$alkyl, C(O)—$(C_1-C_8)$haloalkyl, C(O)O—$(C_1-C_8)$haloalkyl, C(O)—$(C_3-C_8)$cycloalkyl, C(O)O—$(C_3-C_8)$cycloalkyl, C(O)—$(C_2-C_8)$alkenyl, C(O)O—$(C_2-C_8)$alkenyl, $(C_1-C_8)$alkyl-O—$(C_1-C_8)$alkyl, $(C_1-C_8)$alkyl-S(O)$_n$—$(C_1-C_8)$alkyl, C(O)—$(C_1-C_8)$alkyl-C(O)O—$(C_1-C_8)$alkyl, phenyl, and phenoxy;

(M) n is each individually 0, 1, or 2; and

N-oxides, agriculturally acceptable acid addition salts, salt derivatives, solvates, ester derivatives, crystal polymorphs, isotopes, resolved stereoisomers, and/or tautomers.

To avoid doubt, the designations of N$^X$ and N$^Y$ refer to ordinary nitrogen atoms at the specific locations as shown in Formula One and Formula Two. Similarly the designation of C$^X$ refers to an ordinary carbon atom at the specific location as shown in Formula One and Formula Two.

In one embodiment Ar$^1$ is a substituted phenyl. This embodiment may be used in combination with the other embodiments of Het, Ar$^2$, R$^1$, R$^2$, R$^3$, R$^4$, Q$^1$, R$^2$ and R$^4$ hydrocarbyl links, and/or L.

In another embodiment Ar$^1$ is a substituted phenyl that has one or more substituents selected from $C_1-C_6$ haloalkyl and $C_1-C_6$ haloalkoxy. This embodiment may be used in combination with the other embodiments of Het, Ar$^2$, R$^1$, R$^2$, R$^3$, R$^4$, Q$^1$, R$^2$ and R$^4$ hydrocarbyl links, and/or L.

In another embodiment Ar$^1$ is a substituted phenyl that has one or more substituents selected from CF$_3$, OCF$_3$, and OC$_2$F$_5$. This embodiment may be used in combination with the other embodiments of Het, Ar$^2$, R$^1$, R$^2$, R$^3$, R$^4$, Q$^1$, R$^2$ and R$^4$ hydrocarbyl links, and/or L.

In another embodiment Het is selected from benzofuranyl, benzoisothiazolyl, benzoisoxazolyl, benzoxazolyl, benzothienyl, benzothiazolyl, cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, triazolyl, piperazinyl, piperidinyl, morpholinyl, pyrrolidinyl, tetrahydrofuranyl, tetrahydropyranyl, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

In another embodiment Het is triazolyl. This embodiment may be used in combination with the other embodiments of $Ar^1$, $Ar^2$, $R^1$, $R^2$, $R^3$, $R^4$, $Q^1$, $R^2$ and $R^4$ hydrocarbyl links, and/or L.

In another embodiment Het is 1,2,4-triazolyl. This embodiment may be used in combination with the other embodiments of $Ar^1$, $Ar^2$, $R^1$, $R^2$, $R^3$, $R^4$, $Q^1$, $R^2$ and $R^4$ hydrocarbyl links, and/or L.

In another embodiment Het is oxadiazolyl. This embodiment may be used in combination with the other embodiments of $Ar^1$, $Ar^2$, $R^1$, $R^2$, $R^3$, $R^4$, $Q^1$, $R^2$ and $R^4$ hydrocarbyl links, and/or L.

In another embodiment Het is 1,3,4-oxadiazolyl. This embodiment may be used in combination with the other embodiments of $Ar^1$, $Ar^2$, $R^1$, $R^2$, $R^3$, $R^4$, $Q^1$, $R^2$ and $R^4$ hydrocarbyl links, and/or L.

In another embodiment Het is pyrazolyl. This embodiment may be used in combination with the other embodiments of $Ar^1$, $Ar^2$, $R^1$, $R^2$, $R^3$, $R^4$, $Q^1$, $R^2$ and $R^4$ hydrocarbyl links, and/or L.

In another embodiment $Ar^2$ is phenyl. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $Ar^2$ is a substituted phenyl. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $Ar^2$ is a substituted phenyl that has one or more substituents selected from $C_1$-$C_6$ alkyl. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $Ar^2$ is a substituted phenyl that has one or more substituents wherein said substituent is $CH_3$. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $R^1$ is H. This embodiment may be used in combination with the other embodiments of $Ar^1$, Het, $Ar^2$, $R^2$, $R^3$, $R^4$, $Q^1$, $R^2$ and $R^4$ hydrocarbyl links, and/or L.

In another embodiment $R^2$ is (J), H, ($C_1$-$C_6$)alkyl, ($C_1$-$C_6$)alkyl-O—C(O)—($C_1$-$C_6$)alkyl, ($C_1$-$C_6$)alkyl-O—C(O)—N($R^x R^y$), or ($C_1$-$C_6$ alkyl)-S-(Het-1). This embodiment may be used in combination with the other embodiments of $Ar^1$, Het, $Ar^2$, $R^1$, $R^3$, $R^4$, $Q^1$, $R^2$ and $R^4$ hydrocarbyl links, and/or L.

In another embodiment $R^2$ is (J), H, $CH_3$, ($C_1$-$C_6$)alkyl, $CH_2OC(O)CH(CH_3)_2$, $CH_2OC(O)N(H)(C(O)OCH_2Ph)$, or $CH_2S$ (3,4,5-trimethoxy-2-tetrahydropyran). This embodiment may be used in combination with the other embodiments of $Ar^1$, Het, $Ar^2$, $R^1$, $R^3$, $R^4$, $Q^1$, $R^2$ and $R^4$ hydrocarbyl links, and/or L.

In another embodiment $R^3$ is substituted phenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is substituted phenyl wherein said substituted phenyl has one or more substituents selected from F, Cl, ($C_1$-$C_6$)alkyl, ($C_3$-$C_6$)cycloalkyl, ($C_1$-$C_6$)alkoxy, and phenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is substituted phenyl wherein said substituted phenyl has one or more substituents selected from F, $CH_3$, 2-$CH(CH_3)_2$, $CH(CH_3)(C_2H_5)$, $OCH_3$, and phenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is substituted phenyl wherein said substituted phenyl has more than one substituent and at least one pair of said substituents are not ortho to each other. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is ($C_1$-$C_6$)alkylphenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is (Het-1). This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^4$ is H. This embodiment may be used in combination with the other embodiments of $Ar^1$, Het, $Ar^2$, $R^1$, $R^2$, $R^3$, $Q^1$, $R^2$ and $R^4$ hydrocarbyl links, and/or L.

In another embodiment $Q^1$ is O. This embodiment may be used in combination with the other embodiments of $Ar^1$, Het, $Ar^2$, $R^1$, $R^2$, $R^3$, $R^4$, $R^2$ and $R^4$ hydrocarbyl links, and/or L.

In another embodiment $R^2$ and $R^4$ is a hydrocarbyl link wherein said hydrocarbyl link is substituted with oxo or ($C_1$-$C_6$)alkyl. This embodiment may be used in combination with the other embodiments of $Ar^1$, Het, $Ar^2$, $R^1$, $R^2$, $R^3$, $R^4$, $Q^1$, and/or L.

In another embodiment $R^2$ and $R^4$ is a hydrocarbyl link wherein said hydrocarbyl link is $CH_2C(O)$, $C(C(OH)(CH_3)_2)C(O)$, $C(cyclopropyl)C(O)$, $C(CH_3)_2C(O)$, $CFHC(O)$, $CBrHC(O)$, $CH(CH_3)C(O)$, $CH_2CH_2$, $CH_2C(OH)(CH_3)$, $CH_2CH_2CH_2$, $CH_2CH_2C(O)$, $CH_2CH(CH_3)CH_2$, $N(CH_3)C(O)$, $N(CH_2CH_3)C(O)$, $CH=C(CH_3)$, or $CH_2CH(CH_3)$. This embodiment may be used in combination with the other embodiments of $Ar^1$, Het, $Ar^2$, $R^1$, $R^2$, $R^3$, $R^4$, $Q^1$, and/or L.

In another embodiment L is $CH_2$, $CH_2CH_2$, $CH_2CH(CH_3)$, $CH_2C(CH_3)_2$, $CH_2CH(CH_2CH_3)$, $CH=CH$, $CH(CH_3)CH_2$, $C(CH_3)_2CH_2$, $CHBrCH_2$, $CH_2C(cyclopropyl)$, $CH(CH_2CH_3)CH_2$, $C(CH_3)=CH$, $CH_2CH_2CH_2$, $CH(CH_3)CH(CH_3)$, $CH_2CH_2CH_2CH_2$, $C\equiv CCH_2CH_2$, cyclopropyl, or cyclohexyl. This embodiment may be used in combination with the other embodiments of $Ar^1$, Het, $Ar^2$, $R^1$, $R^2$, $R^3$, $R^4$, $Q^1$, and/or $R^2$ and $R^4$ hydrocarbyl links.

Many of the molecules of Formula One and Formula Two may be depicted in two or more tautomeric forms such as when $R^1$, $R^2$, or $R^4$, is H. Any and all alternative tautomers are included within the scope of this Formula One and this Formula Two, and no inference should be made as to whether the molecule exists as the tautomeric form in which it is drawn.

Preparation of Triaryl-Intermediates

Molecules of Formula One and Formula Two can be prepared by making a triaryl intermediate, $Ar^1$-Het-$Ar^2$, and then linking it to an appropriate intermediate to form a desired compound. A wide variety of triaryl intermediates can be used to prepare molecules of Formula One and Formula Two, provided that such triaryl intermediates contain a suitable functional group on $Ar^2$ to which the rest of the desired functional group can be attached. Suitable functional groups include an amino, isocyanate, carboxyl, or a halogen (preferably bromo or iodo). These triaryl intermediates can be prepared by methods previously described in the chemical literature, including Crouse, et al., WO2009102736 (the entire disclosure of which is hereby incorporated by reference).

The triaryl aldehydes used as precursors in preparation of the molecules of Formula One and Formula Two can be prepared according to procedures described in Crouse, et al., US 2012/0202688 A1. Some of the procedures described above require use of halo-aryl intermediates, $Ar^1$-Het-Ph-Br, which are novel intermediates. These may be prepared as described in Scheme 1 below. 3-(4-Bromophenyl)-1,2,4-triazole (1-2) is prepared in two steps from 4-bromobenzamide (1-1) under conditions described previously (step a, Crouse, et al., WO2009102736). This triazole can then be coupled to an aryl halide 1-3 (R=($C_1$-$C_6$)haloalkoxy) such as 4-trifluoromethoxyphenyl bromobenzene, in the presence of cesium carbonate or potassium phosphate, in a polar aprotic solvent such as dimethylformamide. This reaction is catalyzed by a copper salt such as copper(I) iodide and a chelator such as 8-hydroxyquinoline, both present in about 0.05 to about 0.25 equivalents, at a temperature ranging between about 80° C. and about 140° C., to form the 1-aryl-3-(4-bromophenyl)triazole 1-4 (step b)

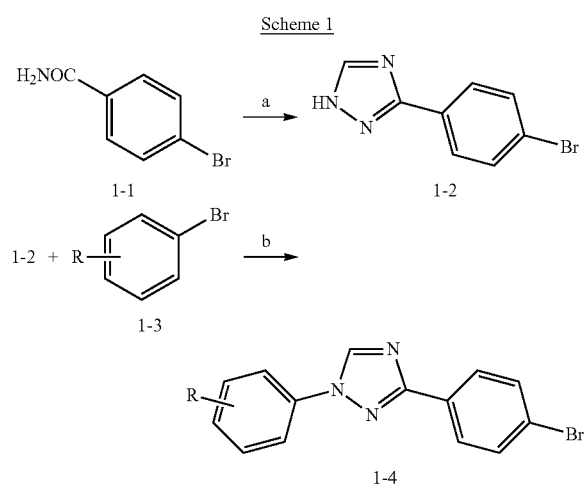

Preparation of One-Atom Linked Intermediates

Molecules of Formula One and Formula Two wherein L is a one-carbon linker, can be prepared from acid or amine intermediates described in Scheme 2 and Scheme 3, respectively. Acid precursors 2-5 ($Ar^1$-Het-$Ar^2$-L-$CO_2H$), unsubstituted or mono- or di-substituted with $R^8$; can be prepared as shown in the Scheme 2. Boronic esters 2-2 (step a) can be prepared using Miyaura conditions from halophenyl esters 2-1. Coupling of the boronate esters with a bromo-heterocycle 2-3 (step b) can be accomplished using a palladium catalyst and phosphine ligand, in the presence of a base, such as sodium bicarbonate, potassium phosphate, or cesium fluoride, in a suitable solvent system, such as dioxane/water, at temperatures from about 50° C. to about 120° C. to form triaryl ester intermediates 2-4. Among palladium catalysts, tetrakis(triphenylphosphine)palladium(0) is preferred, although other well-known palladium catalysts may be used. Saponification of the ester may be achieved by using a strong base such as sodium hydroxide or lithium hydroxide in methanol or ethanol with or without tetrahydrofuran/water to furnish the desired carboxylic acid 2-5 (step c).

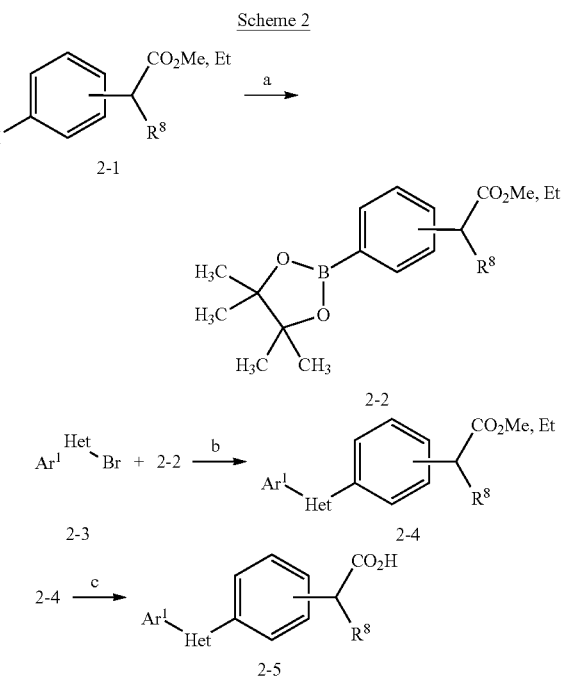

Amine precursors 3-5 ($Ar^1$-Het-$Ar^2$-L-$NH_2$), unsubstituted or mono- or di-substituted with $R^8$, can be prepared as shown in Scheme 3. Halobenzyl amines 3-1 may be protected using benzyl chloroformate in the presence of a base such as triethylamine in an aprotic solvent such as dichloromethane at about −10° C. to about 10° C. to provide N-carboxybenzyl (Cbz)-protected benzyl amines 3-2 (step a).

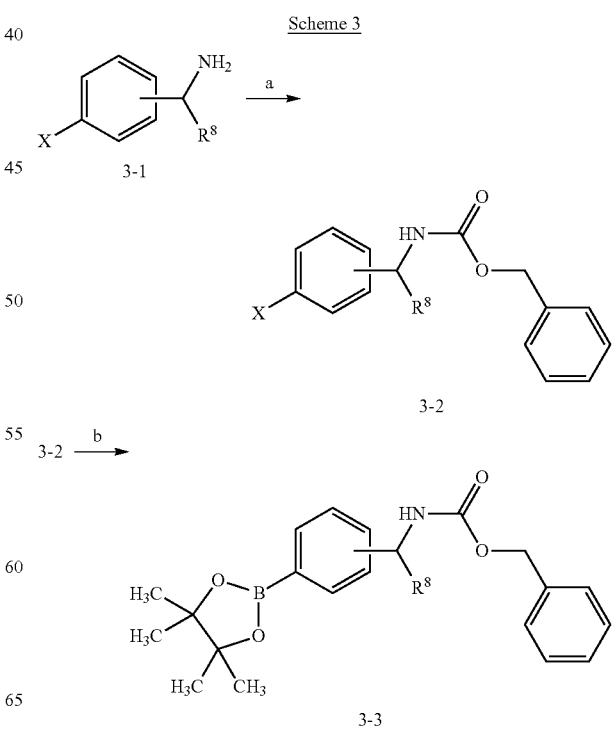

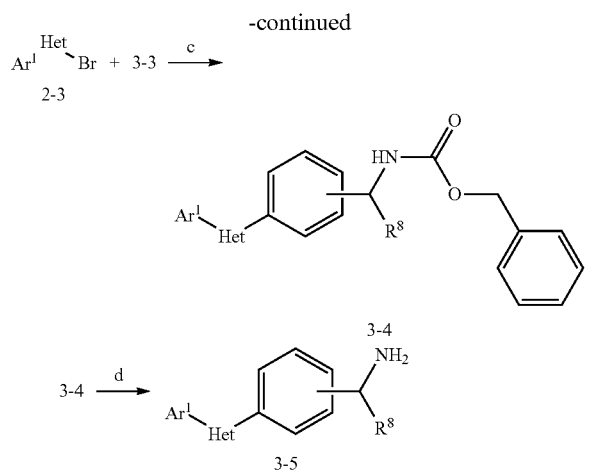

Alternatively, other N-protecting groups such as tert-butoxycarbonyl (BOC) or 9-fluorenylmethyloxycarbonyl (Fmoc) may be employed in step a using similar conditions described above for Cbz. The Cbz-protected boronic ester 3-3 can be prepared using Miyaura conditions (step b). Coupling of the boronate esters with a bromo-heterocycle 2-3 can be accomplished using a palladium catalyst and phosphine ligand, in the presence of a base, such as sodium bicarbonate, potassium phosphate, or cesium fluoride, in a suitable solvent system, such as dioxane/water, at temperatures from about 50° C. to about 120° C. to form N-protected aminoalkylphenyl intermediates 3-4 (step c). Removal of the Cbz group can be accomplished under acidic conditions with a strong acid such as hydrogen bromide, followed by neutralization with a base such as sodium bicarbonate or sodium hydroxide, to furnish the free amine precursors 3-5 ($Ar^1$-Het-$Ar^2$-L-$NH_2$, step d). Similar methods could be applied to compounds wherein L is greater than 1-carbon.

Preparation of Ethyl Linked Intermediates

Preparation of compounds wherein L is a two-atom group is described in Schemes 4 to Schemes 6. Condensation of the aldehyde 4-1 ($R^9$=H) (described in US 2012/0202688 A1) with reagents such as ethyl diethylphosphonoacetate or a Wittig reagent such as ethyl 2-(triphenylphosphoranylidene) propanoate) or α-substituted acetates such as ethyl 2-fluoroacetate or ethyl 2-cyanoacetate in the presence of a suitable base such as sodium hydride or n-butyl lithium in aprotic solvents such as tetrahydrofuran or diethyl ether at temperatures from about −78° C. to about 20° C. can be used to prepare acrylic esters 4-2 (step a) unsubstituted or monosubstituted with $R^9$ and/or $R^{10}$. Saponification of the resultant ester may be achieved by using a strong base such as sodium hydroxide in methanol or ethanol with or without tetrahydrofuran/water to furnish the vinyl carboxylic acid 4-3 (step b). In some cases the partial condensation of aldehyde 4-1 ($R^9$=H) may result in the isolation of the alcohol intermediate 4-4 (step c) especially when $R^{10}$ is electron-withdrawing. Substitution of this alcohol with nucleophilic reagents such as Deoxo-Fluor® (step d) followed by saponification as described above (step e) can generate highly substituted ethyl carboxylic acids 4-5 additionally substituted with $R^{11}$, wherein $R^{11}$ is defined as $R^8$ above. When the saturated linkage is preferred, the acrylic ester 4-2 can be converted to the corresponding cyclopropane 4-6 unsubstituted or mono- or di-substituted with $R^{12}$; with sulfur ylides such as those formed in situ from trimethylsulfonium iodide in the presence of an inorganic base such as sodium hydride in a polar aprotic solvent such as dimethyl sulfoxide or tetrahydrofuran (step f). Likewise the acrylic ester 4-2 can be reduced to the parent alkane 4-8 using hydrogen gas and a palladium catalyst (step h). Both the cyclopropane and the alkane esters can be saponified under basic conditions described above to generate the free carboxylic acids 4-7 (step g) and 4-9 (step i), respectively.

In a similar manner, condensation of the ketone 4-1 ($R^9$=Alkyl) (described in WO 2011017504 A1) with either ethyl diethylphosphonoacetate or a Wittig reagent such as ethyl 2-(triphenylphosphoranylidene)propanoate or α-substituted alkyl esters such as ethyl 2-fluoroacetate or ethyl 2-cyanoacetate under similar conditions described above may afford the α-alkyl acrylic esters 4-2 or alcohols 4-4. Subsequent treatment of 4-2 or 4-4 as described above for $R^9$=H may lead to either the corresponding unsaturated (4-3) or saturated (4-5, 4-7, 4-9) carboxylic acids.

Scheme 4

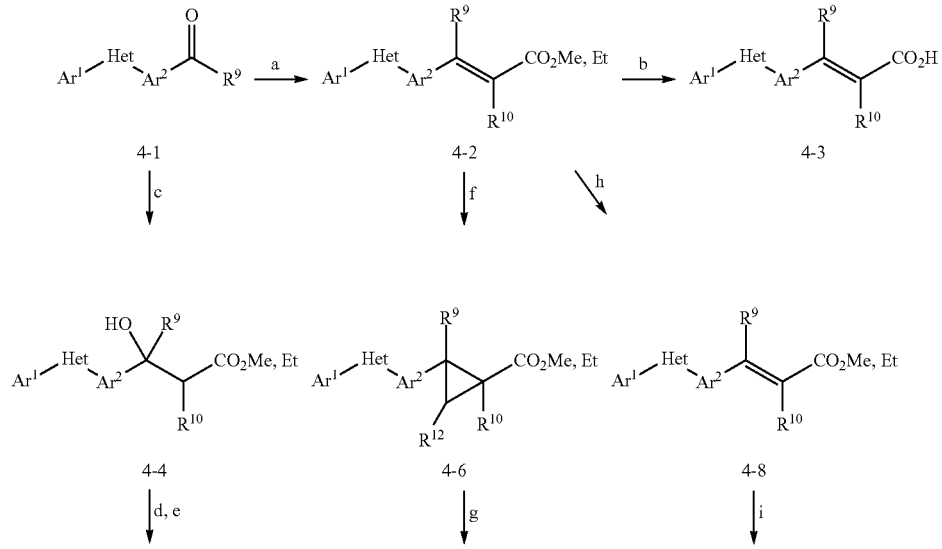

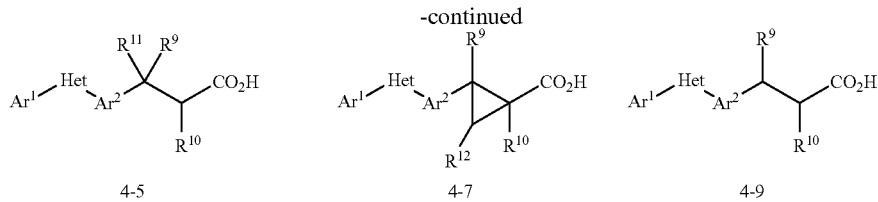

Alternatively, compounds wherein L is a two-carbon linker may also be prepared as shown in Scheme 5. Using conditions first described by Molander et al. *Org. Lett.* 2007, 9, pp 203-206, coupling of a bromide 5-1 (Ar$^1$-Het-Ar$^2$—Br, step a), with potassium (2-((tert-butoxycarbonyl)amino) ethyl)trifluoroborate in the presence of a palladium catalyst such as palladium(II) acetate, and a base such as cesium carbonate, at temperatures from about 80° C. to about 120° C., results in the formation of the corresponding 2-(tert-butoxycarbonyl)amino)ethyl derivative 5-2. Further treatment of this material with from about 1 to about 5 equivalents of an acid such as trifluoroacetic acid (TFA) or hydrogen chloride, in an aprotic solvent such as dichloromethane or dioxane at temperatures from about 0° C. to about 50° C., results in the cleavage of the tert-butoxycarbonyl group and formation of the salt of the amine 5-3 (Ar$^1$-Het-Ar$^2$-L-NH$_3$,A$^-$, wherein A$^-$ is CF$_3$CO$_2^-$ or Cl$^-$, step b).

Scheme 5

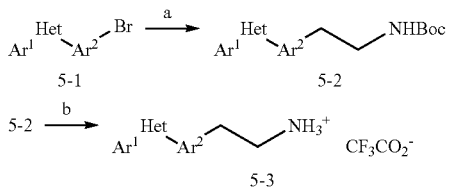

Aminoalkyl precursors 6-5 (Ar$^1$-Het-Ar$^2$-L-NH$_2$), wherein L is two-carbon atoms, mono- or di-substituted with R$^9$, wherein R$^9$ is defined as above; and unsubstituted or mono-substituted with R$^{10}$, wherein R$^{10}$ is defined as above, can be prepared as shown in Scheme 6. Unsubstituted halophenyl carbinols 6-1 (R$^9$ and R$^{10}$ are H), wherein X can be selected from Cl, Br, or I, are available commercially. Carbinols 6-1 that are mono- or di-substituted at R$^9$ can be prepared from the corresponding halophenyl acetate 6-1 (step a) in similar fashion to that described by Shin et al. *Bioorg. Med. Chem. Lett.* 2008, 18, pp 4424-4427 followed by reduction with a metal hydride such as lithium aluminum hydride in an ethereal solvent such as tetrahydrofuran or diethyl ether at temperatures at or below about 0° C. Both 6-I and 6-II may be further mono-substituted (step b or step c) with R$^{10}$ via reduction to the corresponding aldehyde with a metal hydride such as diisobutylaluminum hydride and further treatment with a Grignard reagent in a similar fashion to that described by Brimble et al. *Org. Lett.* 2012, 14, pp 5820-5823. Carbinols 6-1 can be treated with phthalimide under Mitsunobu conditions to generate N-phthalimido intermediates 6-2 (step d). The halide can be converted into a boronic ester under Miyaura conditions to form boronate esters 6-3 (step e). Coupling of the boronate esters with a bromo-heterocycle 2-3 can be accomplished using a palladium catalyst, such tetrakis(triphenylphosphine)palladium(0), in the presence of a base, such as sodium bicarbonate, in a suitable solvent system, such as dioxane/water, at temperatures from about 50° C. to about 120° C. to provide N-phthalimido intermediates 6-4 (step f). Deprotection using hydrazine and methanol or other suitable solvent can furnish the amine 6-5 (step g).

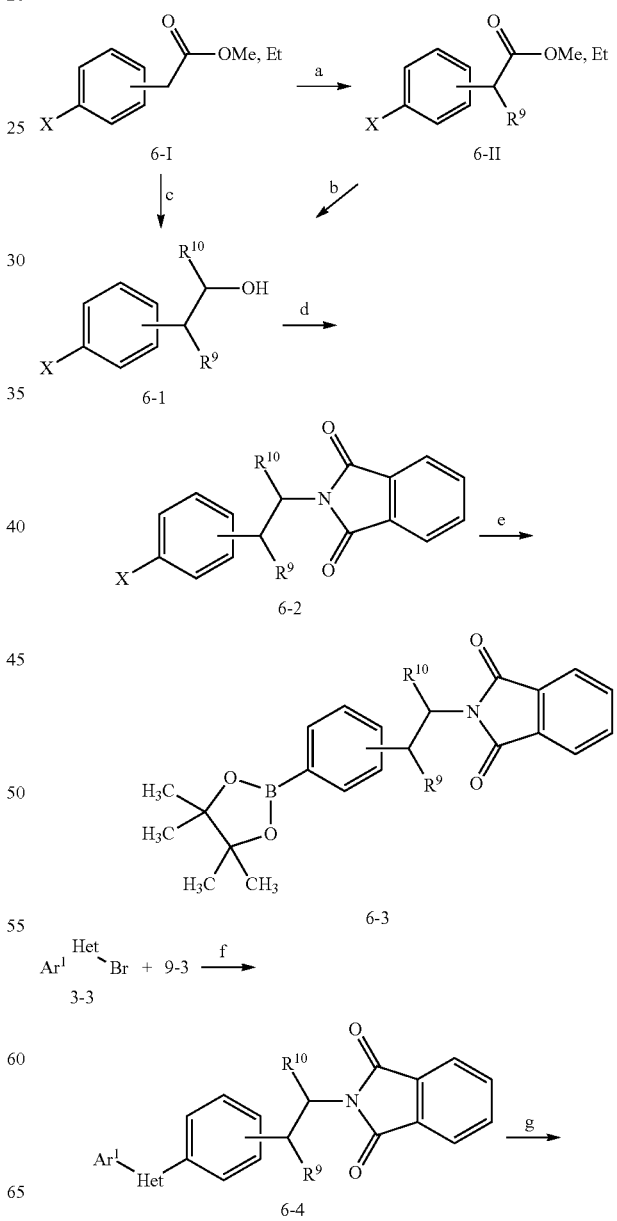

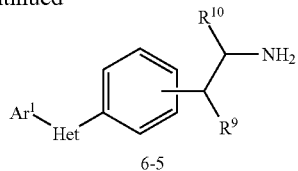

Alternatively, compounds wherein L is a two-atom linker may also be prepared as shown in Scheme 6a. Olefination of aldehyde 4-1 (R⁹=H, step a) may be achieved with methylenetriphenylphosphorane which can be prepared from methyl triphenylphosphonium iodide in the presence of a base such as sodium hydride or 1,8-diazabicycloundec-7-ene in an aprotic solvent such as tetrahydrofuran or dichloromethane at temperatures of about −78° C. to about 40° C. Hydroboration of 6-2a with a reagent such as 9-borabicyclo (3.3.1)nonane (9-BBN) in an aprotic solvent such as tetrahydrofuran followed by oxidation with an oxidant such as hydrogen peroxide can generate ethyl alcohol 6-3a (step b). Carbinols 6-3a can be treated with phthalimide under Mitsunobu conditions to generate N-phthalimido intermediates 6-5a, wherein $R^{10}$=H (step c). Deprotection using hydrazine and methanol or other suitable solvent can furnish the amine 6-6a (step f). Additionally, 6-3a may be further mono-substituted with $R^{10}$, wherein $R^{10}$ is defined as above (step d), via oxidation to the corresponding aldehyde under Swern conditions followed by addition of a Grignard reagent such as described above (Scheme 6). Carbinols 6-4a can be further treated with phthalimide under Mitsunobu conditions to generate N-phthalimido intermediates 6-5a (step e). Deprotection using hydrazine and methanol or other suitable solvent can furnish the amine 6-6a (step f).

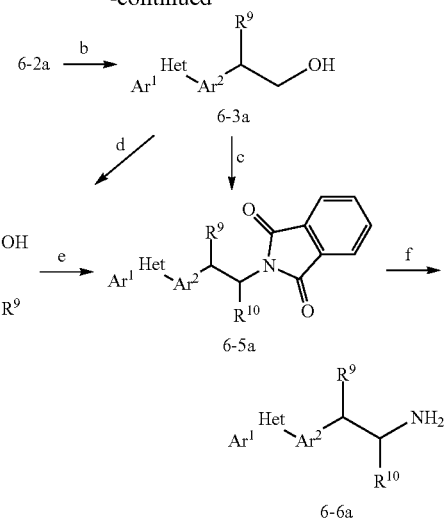

Scheme 6b outlines an alternative route for constructing analogs wherein the linker L is a two-atom linker. Copper-catalyzed arylation of 2,4-pentane-2,4-dione with 5-1 (*J. Am. Chem. Soc.* 2010, 132, 8273) may provide the substituted acetone intermediate 6-1b (step a). Reductive amination (step b), using any of a variety of conditions familiar to those skilled in the art, may generate amine 6-2b. When a linker contains a chiral center, such as with intermediate 6-2b, these intermediates may be separated into their pure isomeric forms either by means of a chiral column, or by fractional crystallization of the salt prepared from a chiral acid such as (+)- and (−)-tartaric acid.

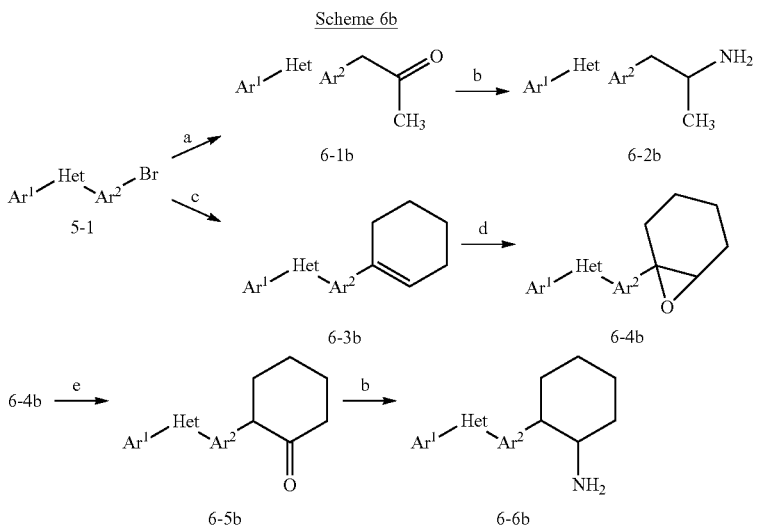

Construction of analogs wherein the ethyl linking group is part of a 6-membered ring may also be accomplished starting from bromide 5-1. Coupling of 5-1 with 2-cyclohex-1-enyl-4,4,5,5-tetramethyl-1,3,2-dioxaborolane (Scheme 6b, step c) under standard Suzuki coupling conditions can lead to alkene 6-3b. Epoxidation with standard reagents, such as meta-chloroperoxybenzoic acid (step d), followed by acid-catalyzed rearrangement using indium trichloride (*J. Org. Chem.* 1998, 63, 8212), may generate ketone 6-5b.

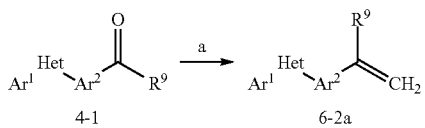

Reductive amination and conversion into the target molecules can be accomplished using conditions described above.

Preparation of Propyl Linked Intermediates

Preparation of compounds wherein L is a three-atom group is described in Schemes 7 and 8. Aminoalkyl precursors 7-5 ($Ar^1$-Het-$Ar^2$-L-$NH_2$), wherein L is three-carbon atoms, mono- or di-substituted with $R^9$, wherein $R^9$ is defined as above; and unsubstituted or mono-substituted with $R^{10}$, wherein $R^{10}$ is defined as above; can be prepared as shown in Scheme 7. Halophenyl carbinols 7-1, wherein X is Br and $R^9$ and $R^{10}$ are H, are available commercially. Carbinols 7-1 that are mono- or di-substituted at $R^9$ can be prepared from the corresponding halophenyl acetate 7-I (step a) in similar fashion to that described by Shin et al. *Bioorg. Med. Chem. Lett.* 2008, 18, pp 4424-4427, followed by reduction with a metal hydride such as lithium aluminum hydride in an ethereal solvent such as tetrahydrofuran at temperatures at or below about 0° C. Both 7-I and 7-II may be further mono-substituted (step b or step c) with $R^{10}$ via reduction to the corresponding aldehyde with a metal hydride such as diisobutylaluminum hydride and treatment with a Grignard reagent such as methylmagnesium bromide in a similar fashion to that described by Brimble et al. *Org. Lett.* 2012, 14, pp 5820-5823. Carbinols 7-1 can be treated with phthalimide under Mitsunobu conditions to generate N-phthalimido intermediates 7-2 (step d).

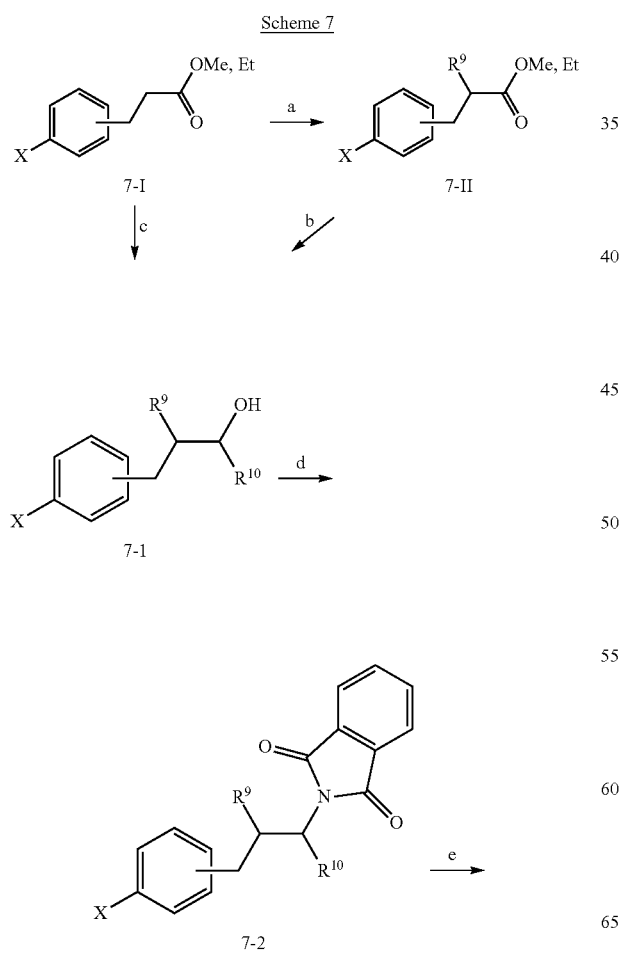

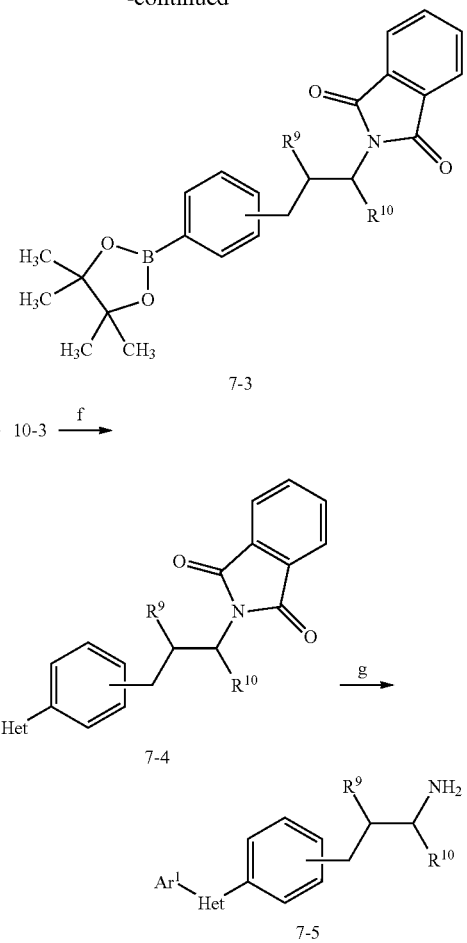

The halide can be converted under Miyaura conditions to form boronate esters 7-3 (step e). Coupling of the boronate esters with a bromo-heterocycle 2-3 can be accomplished using a palladium catalyst, for example tetrakis(triphenyl phosphine)palladium(0), in the presence of a base, for example sodium bicarbonate, in a suitable solvent system, for example dioxane/water, at temperatures from about 50° C. to about 120° C. to provide N-phthalimido intermediates 7-4 (step f). Deprotection using hydrazine and methanol or other suitable solvent can furnish the amine 7-5 (step g).

Alternatively, compounds wherein L is a three-atom linker may also be prepared as shown in Scheme 8. Bromide 5-1 ($Ar^1$-Het-$Ar^2$—Br) can be coupled with an appropriate alkynyl alcohol 8-1 unsubstituted or mono-substituted with $R^{10}$, wherein $R^{10}$ is defined as above, in the presence of a palladium catalyst such as bistriphenylphosphinepalladium (II) dichloride, copper(I) iodide, and a base such as triethylamine, at temperatures from about 50° C. to about 120° C., to generate the corresponding alkynyl alcohol derivatives 8-2 (step a). The resultant carbinols 8-2 can be treated with phthalimide under Mitsunobu conditions to generate N-phthalimido intermediates 8-3 (step b) which can be converted to amines 8-7 (step e) using hydrazine and methanol or other suitable solvent. Carbinols 8-2 can be reduced using a transition metal catalyst, such as palladium under an atmosphere of hydrogen to provide alkenyl or fully saturated alkyl carbinols 8-4 unsubstituted at $R^{10}$. Additionally, carbinols 8-2 can be treated with a metal hydride such as lithium aluminum hydride to provide the (E)-alkenyl carbinol 8-4. Likewise, carbinol 8-2 may be protected with a group such as tert-butyl diphenylsilyl (TBDPS) and treated with a hydrometallation reagent such as Schwartz's reagent followed by quenching with an electrophile such as elemental iodine or N-bromosuccinimide (NBS). Alternatively, the carbinol 8-2 may be treated with a transmetallation reagent such as pinacol diboron for further use in transition metal-catalyzed reactions, such as Suzuki Negishi couplings, to prepare carbinols 8-4 mono- or di-substituted with $R^9$, wherein $R^9$ is defined as above (step c). Following deprotection, the resultant carbinols 8-4 can be treated with phthalimide under Mitsunobu conditions to generate N-phthalimido intermediates 8-5 (step d) which can be converted.

a palladium catalyst such as bistriphenylphosphine palladium(II) dichloride, copper(I) iodide, and a base such as triethylamine, at temperatures from about 50° C. to about 120° C., to generate the corresponding alkynyl alcohol derivatives 9-2. The resultant carbinols 9-2 can be treated with phthalimide under Mitsunobu conditions (step b) to generate N-phthalimido intermediates 9-3 which can be converted to an amine 9-7 (step e) using hydrazine and methanol or other suitable solvents. Carbinols 9-2 can be reduced using a transition metal catalyst, such as palladium, under an atmosphere of hydrogen to provide alkenyl or fully saturated alkyl carbinols 9-4 (step c) unsubstituted at $R^{13}$. Additionally, carbinols 9-2 can be treated with a metal hydride such as lithium aluminum hydride to provide the (E)-alkenyl carbinols 9-4 (step c). Likewise, carbinol 9-2 may be protected with a group such as tert-butyl diphenylsilyl (TBDPS) and treated with a hydrometallation reagent Scheme 8

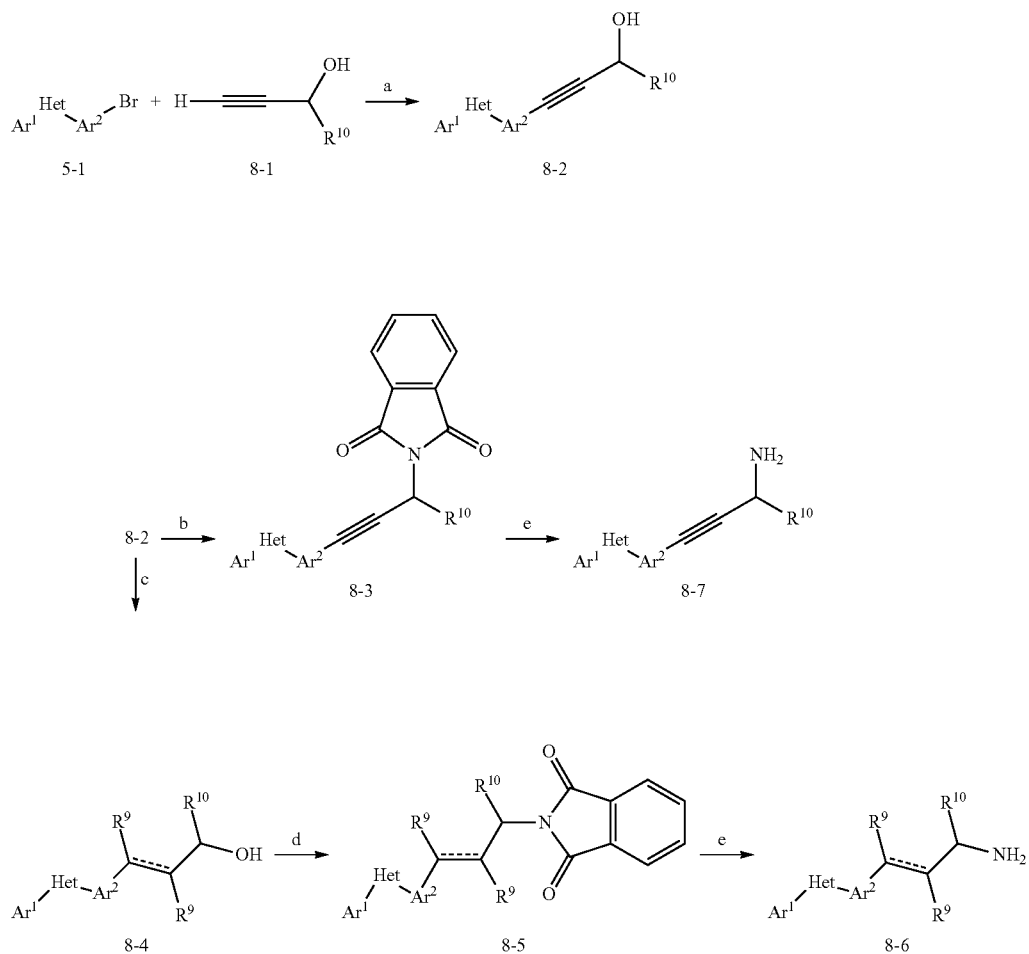

Preparation of Butyl Linked Intermediates

Compounds wherein L is a four-atom linker may be prepared as shown in Scheme 9. Bromide 5-1 ($Ar^1$-Het-$Ar^2$—Br) can be coupled with an appropriate alkynyl alcohol 9-1 (step a) unsubstituted or mono-substituted with $R^{10}$, wherein $R^{10}$ is defined as above; mono- or di-substituted with $R^9$, wherein $R^9$ is defined as above; in the presence of such as Schwartz's reagent followed by quenching with an electrophile such as elemental iodine or NBS. Alternatively the carbinol 9-2 may be treated with a transmetallation reagent such as pinacol diboron for further use in transition metal-catalyzed reactions, such as Suzuki or Negishi couplings, to prepare carbinols 9-4 mono- or di-substituted with $R^{13}$, wherein $R^{13}$ is defined as $R^8$ above (step c).

Scheme 9

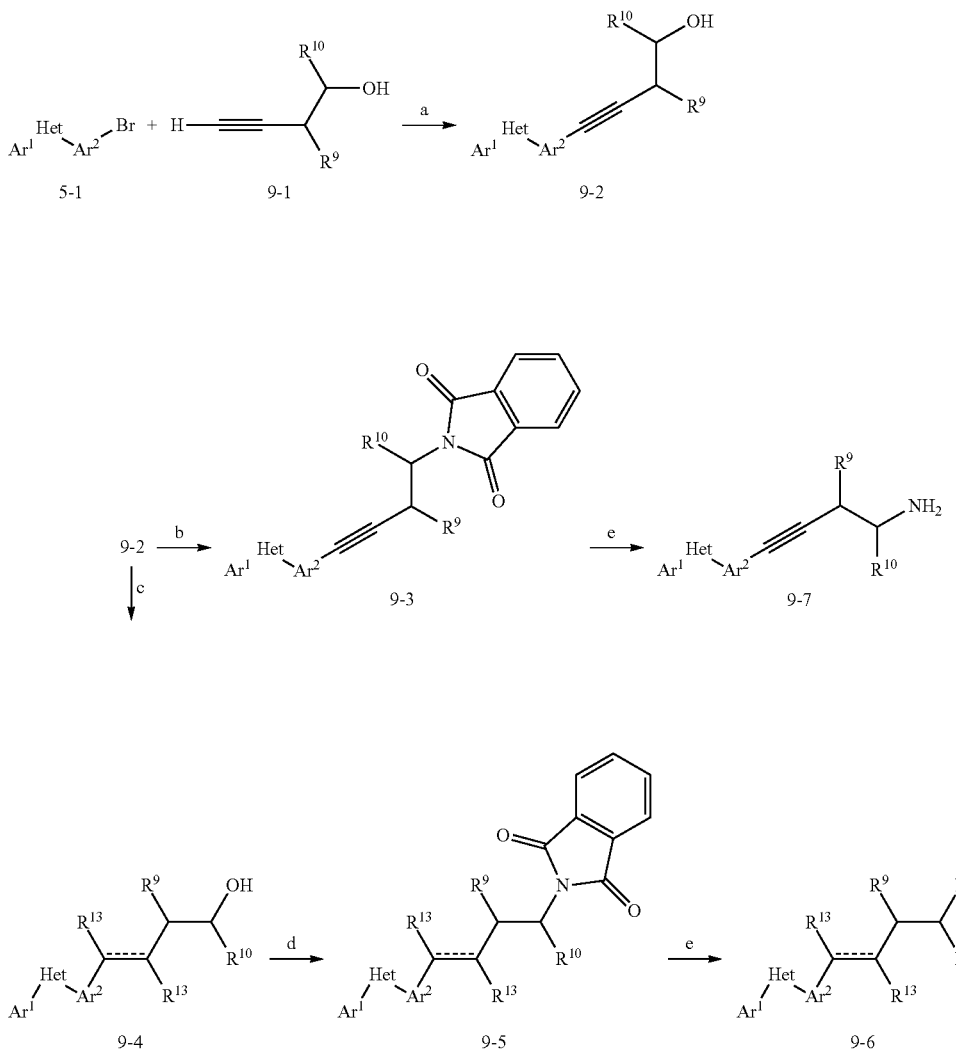

Following deprotection, the resultant carbinols 9-4 can be treated with phthalimide under Mitsunobu conditions (step d) to generate N-phthalimido intermediates 9-5 which can be converted to an amine 9-6 (step e) using hydrazine and methanol or other suitable solvent.

Preparation of N-Aryl Thiazolidinone Thioureas

The N-aryl thiazolidinone thioureas (e.g. 10-4) can be prepared by reacting the thiazolidinone imines (e.g. 10-3) with the triaryl isothiocyanates (e.g. 10-2). As shown in Scheme 10, the triaryl isothiocyanate can be prepared from the fluoroamine intermediate (e.g. 10-1). The fluoroamine intermediate can be prepared from the corresponding aldehyde (from U.S. Pat. No. 8,178,658 B2) in three steps using methodology familiar to one skilled in the art involving cyanohydrin formation, fluorination and reduction.

Scheme 10

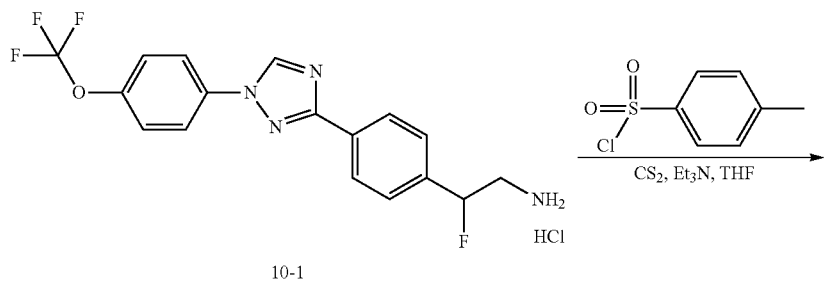

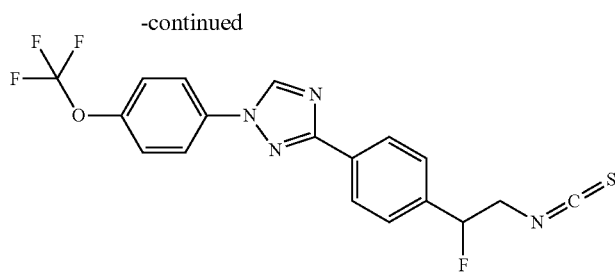

10-2

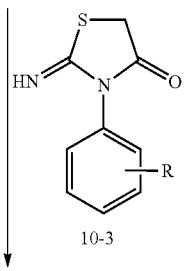

10-3

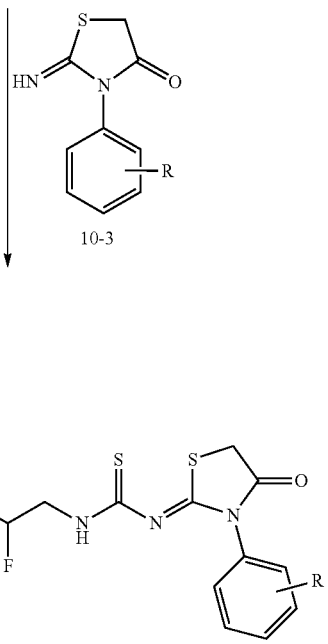

10-4

The triaryl ethylisothiocyanate compound 11-3 can be prepared from the triarylethyl amine salt compound 11-2 using carbon disulfide in the presence of triethylamine and tosyl chloride in THF. As shown in Scheme 11, the amine salt 11-1 originates from the triaryl bromide compound after a Suzuki coupling with BOC-protected ethylamine potassium fluoroborate and deprotection with TFA in dichloromethane.

Scheme 11

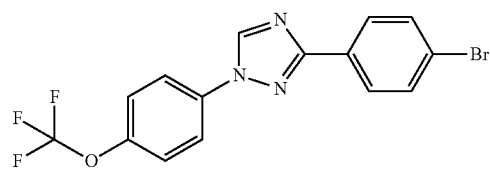

11-1

1. KBF₄CH₂CH₂NHBoc, Pd(OAc)₂, Cs₂CO₃, dicyclohexyl(2',6'-diisopropoxy-[1,1'-biphenyl]-2-yl)phosphine, Toluene/H₂O, 90° C.
2. TFA, DCM -continued

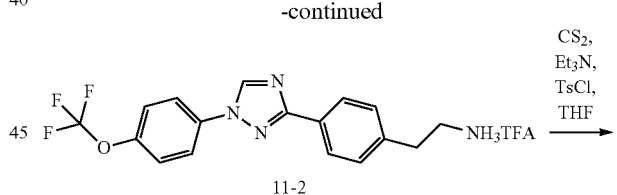

11-2

CS₂, Et₃N, TsCl, THF

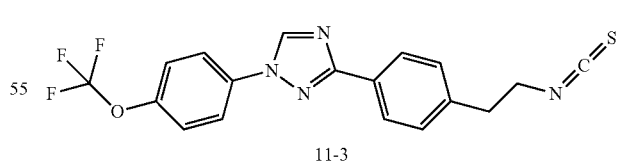

11-3

Preparation of N-Aryl Thioxothiazolidine Thioureas

The N-aryl thioxothiazolidine thioureas (e.g. 12-2) can be prepared by reacting the N-arylthiazolidinone ureas (e.g. 12-1; prepared as in US Patent Application Publication 20140274688 A1) with Lawesson's reagent in a non-polar solvent such as toluene at a temperature from 90 to 120° C. for 3 to 6 hours as in Scheme 12.

Scheme 12

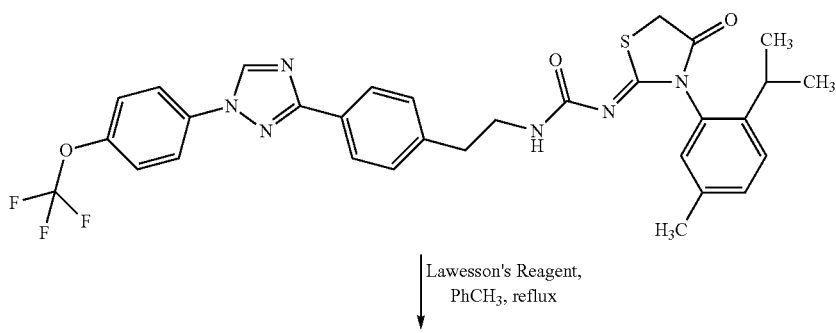

Lawesson's Reagent,
PhCH₃, reflux

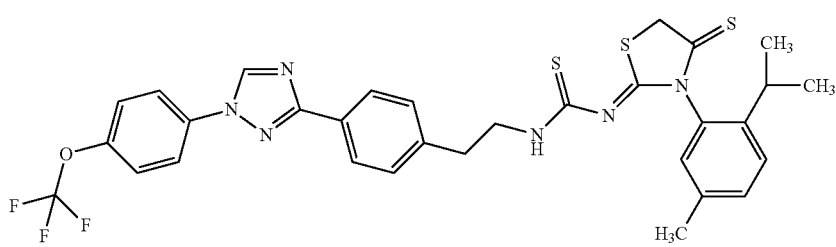

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within Symyx Draw, ChemDraw or ACD Name Pro. If such programs are unable to name a molecule, the molecule is named using conventional naming rules. $^1$H NMR spectral data are in ppm (δ) and were recorded at 300, 400 or 600 MHz, and $^{13}$C NMR spectral data are in ppm (δ) and were recorded at 75, 100 or 150 MHz, unless otherwise stated.

Example 1: Preparation of 3-(4-bromophenyl)-1-(4-(trifluoromethoxy)phenyl)-1H-1,2,4-triazole

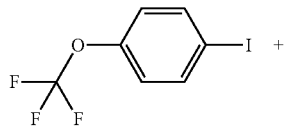 +

-continued

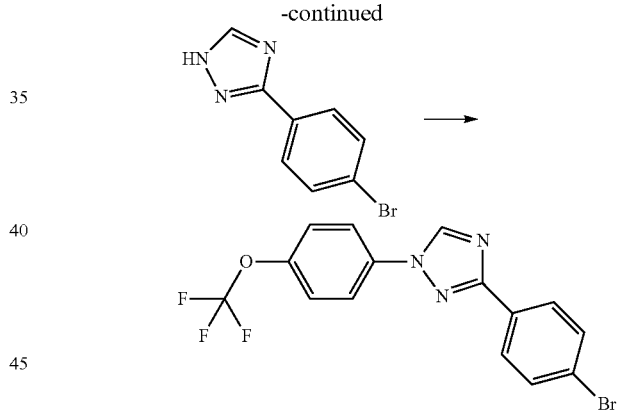

To 3-(4-Bromophenyl)-1H-1,2,4-triazole (14.52 grams (g), 64.8 millimoles (mmol)), copper(I) iodide (CuI; 3.55 g, 18.6 mmol), and cesium carbonate (39.0 g, 120 mmol) in a round-bottomed flask were added dimethyl sulfoxide (DMSO; 100 milliliters (mL)) and 1-iodo-4-(trifluoromethoxy)benzene (16.63 g, 57.7 mmol). The reaction mixture was degassed for 5 minutes (min) and then heated overnight at 100° C. The reaction mixture was cooled to room temperature, diluted with ethyl acetate (EtOAc), and filtered through Celite®. The Celite® cake was washed with EtOAc. Saturated (satd) ammonium chloride (NH₄Cl) solution was added to the filtrate and the mixture was stirred for 1 hour (h). The layers were separated and the aqueous layer was extracted with EtOAc (3×). The combined organic layers were dried over anhydrous magnesium sulfate (MgSO₄) and concentrated onto Celite®. Purification by flash chromatography (0-40% EtOAc/hexanes) provided the title compound (12.8 g, 55%) as a white solid: $^1$H NMR (400 MHz, CDCl₃) δ 8.55 (s, 1H), 8.08-8.03 (m, 2H), 7.80-7.75 (m, 2H), 7.63-7.57 (m, 2H), 7.41-7.35 (m, 2H). ESIMS m/z 384, 386 ([M]⁺).

Example 2: Preparation of tert-butyl (4-(1-(4-(trifluoromethoxy)phenyl)-1H-1,2,4-triazol-3-yl)phenethyl)carbamate

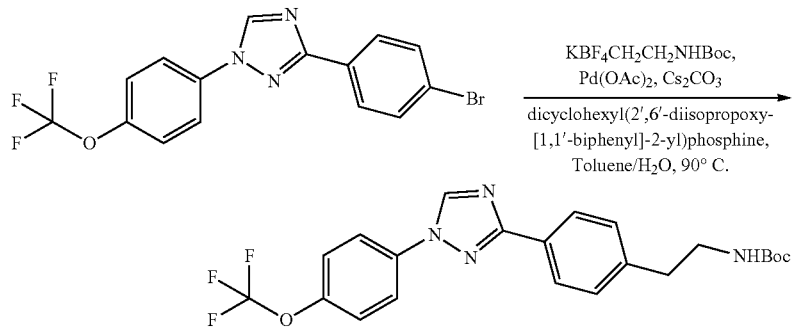

A mixture of 3-(4-bromophenyl)-1-(4-(trifluoromethoxy)phenyl)-1H-1,2,4-triazole (5.15 g, 13.4 mmol), potassium (2-((tert-butoxycarbonyl)amino)ethyl)trifluoroborate (3.37 g, 13.4 mmol), dicyclohexyl(2',6'-diisopropoxy-[1,1'-biphenyl]-2-yl)phosphine (634 milligrams (mg), 1.36 mmol), palladium(II) acetate (249 mg, 1.1 mmol), and cesium carbonate (13.52 g, 41.5 mmol) in toluene/water (4:1; 125 mL) was heated at 95° C. over the weekend. The reaction mixture was cooled to room temperature and filtered through Celite® rinsing with EtOAc. The layers were separated and the aqueous layers were extracted with EtOAc. The combined organic layers were dried over anhydrous MgSO$_4$, filtered, and concentrated. Purification by flash column chromatography (0-50% EtOAc/hexanes) provided the desired compound as an off-white solid (5.23 g, 83%): mp 149-153° C.; $^1$H NMR (400 MHz, CDCl$_3$) δ 8.55 (s, 1H), 8.13 (d, J=8.3 Hz, 2H), 7.83-7.76 (m, 2H), 7.41-7.36 (m, 2H), 7.31 (d, J=8.2 Hz, 2H), 4.56 (s, 1H), 3.42 (d, J=6.3 Hz, 2H), 2.86 (t, J=6.9 Hz, 2H), 1.44 (s, 9H); ESIMS m/z 449 ([M+H]+).

Example 3: Preparation of 2-(4-(1-(4-(trifluoromethoxy)phenyl)-1H-1,2,4-triazol-3-yl)phenyl)ethan-1-aminium 2,2,2-trifluoroacetate

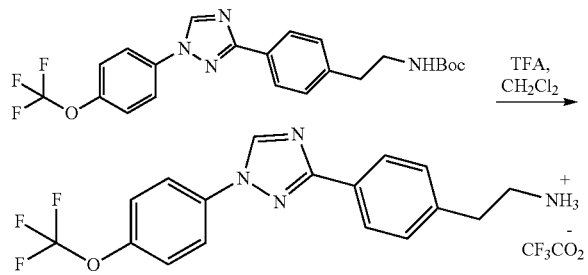

To tert-butyl 4-(1-(4-(trifluoromethoxy)phenyl)-1H-1,2,4-triazol-3-yl)phenethylcarbamate (0.48 g, 1.07 mmol) in dichloromethane (5.4 mL) was added trifluoroacetic acid (TFA; 0.25 mL, 3.2 mmol) and the mixture was stirred at room temperature overnight. Liquid chromatography-mass spectrometry (LC-MS) analysis showed a 2:1 mixture of starting material-product, so additional TFA (0.25 mL, 3.2 mmol) was added. The mixture was stirred overnight at room temperature. The reaction mixture was concentrated and dried in the vacuum oven to provide the desired compound as a yellow solid (803 mg, 100%): $^1$H NMR (400 MHz, DMSO-d$_6$) δ 9.41 (s, 1H), 8.17-7.99 (m, 4H), 7.88 (s, 3H), 7.66-7.60 (m, 2H), 7.43 (dd, J=8.5, 2.3 Hz, 2H), 3.11 (dt, J=8.7, 5.9 Hz, 2H), 2.94 (dd, J=9.3, 6.4 Hz, 2H); $^{19}$F NMR (376 MHz, DMSO-d$_6$) δ −57.00, −74.71, −74.85; $^{13}$C NMR (101 MHz, DMSO-d$_6$) δ 161.90, 147.12, 143.81, 138.89, 135.65, 129.22, 128.78, 126.36, 122.57, 121.10, 32.87, 24.91; ESIMS m/z 349 ([M+H]$^+$).

Example 4: Preparation of 3-(4-(2-isothiocyanatoethyl)phenyl)-1-(4-(trifluoromethoxy)phenyl)-1H-1,2,4-triazole

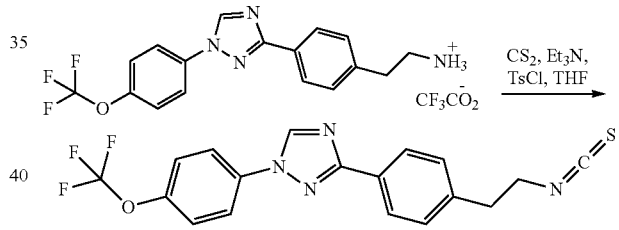

2-(4-(1-(4-(Trifluoromethoxy)phenyl)-1H-1,2,4-triazol-3-yl)phenyl)ethan-1-aminium 2,2,2-trifluoroacetate (325 mg, 0.70 mmol) was dissolved in tetrahydrofuran (THF; 12 mL) under nitrogen (N$_2$) at room temperature and triethylamine (0.32 mL, 2.296 mmol) was added. Carbon disulfide (43 microliters (μL), 0.713 mmol) was added in portions via syringe over 26 min. The reaction mixture was stirred at room temperature overnight. The reaction mixture was cooled to 0° C. and tosyl chloride (156 mg, 0.82 mmol) was added. The reaction mixture was warmed to room temperature over 1 h in which a thick precipitate formed. The reaction mixture was quenched with 1 Normal (N) hydrochloric acid (HCl). The reaction mixture was extracted with ether (3×), and the organic layers were washed with water (3×) and freshly prepared saturated sodium bicarbonate (NaHCO$_3$) solution, dried over anhydrous MgSO$_4$, and concentrated to obtain a yellow oil. Purification by flash chromatography (0-40% EtOAc/hexanes) provided the desired compound as a white solid (228 mg, 71%): $^1$H NMR (400 MHz, CDCl$_3$) δ 8.58 (s, 1H), 8.19-8.14 (m, 2H), 7.81 (dd, J=8.9, 1.5 Hz, 2H), 7.39 (d, J=8.9 Hz, 2H), 7.34 (d, J=8.2 Hz, 2H), 3.78 (td, J=6.9, 1.5 Hz, 2H), 3.06 (t, J=6.9 Hz, 2H); ESIMS m/z 391 ([M+H]$^+$).

Example 5: Preparation of (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)thiourea

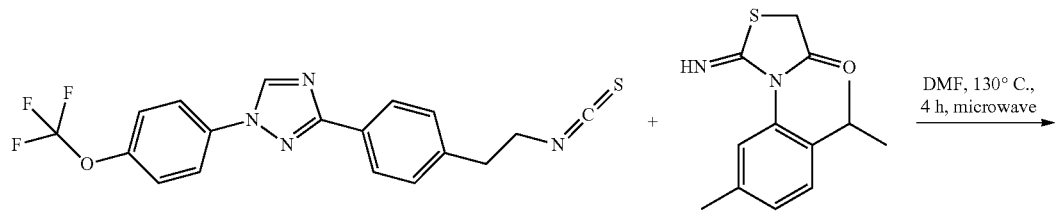

A solution of 3-(4-(2-isothiocyanatoethyl)phenyl)-1-(4-(trifluoromethoxy)phenyl)-1H-1,2,4-triazole (55 mg, 0.14 mmol) and 2-imino-3-(2-isopropyl-5-methylphenyl)thiazolidin-4-one (50 mg, 0.20 mmol) in N,N-dimethylformamide (DMF; 0.47 mL) was heated at 130° C. for 4 h. LC-MS analysis showed conversion to the desired product. The reaction mixture was diluted with water and extracted with dichloromethane. The organic layers were filtered through a phase separator, concentrated, and loaded onto a Celite® cartridge. Purification by flash chromatography (0-40, 40-60, 60-100% EtOAc/B, where B=1:1 dichloromethane/hexanes) provided impure product. Further purification by reverse-phase flash chromatography (0-100% acetonitrile/H$_2$O) provided the desired compound as a yellow oily solid (44 mg, 47%): $^1$H NMR (400 MHz, CDCl$_3$) δ 8.55 (d, J=3.6 Hz, 1H), 8.13-7.98 (m, 2H), 7.80 (dd, J=9.0, 3.4 Hz, 2H), 7.43-7.35 (m, 2H), 7.32-7.19 (m, 4H), 6.92 (dt, J=5.7, 2.8 Hz, 1H), 6.86-6.76 (m, 1H), 3.95-3.85 (m, 3H), 3.75 (dq, J=13.6, 6.9 Hz, 1H), 3.04-2.87 (m, 2H), 2.72-2.47 (m, 1H), 2.32 (d, J=3.4 Hz, 3H), 1.22-1.05 (m, 6H); $^{19}$F NMR (376 MHz, CDCl$_3$) δ −58.02; ESIMS m/z 639 ([M+H]$^+$).

Preparation of (Z)-1-(3-(2-Isopropylphenyl)-4-oxothiazolidin-2-ylidene)-3-(4-(1-(4-(trifluoromethoxy)phenyl)-1H-1,2,4-triazol-3-yl)phenethyl)thiourea was also Carried Out in Accordance to the Procedure in Example 5

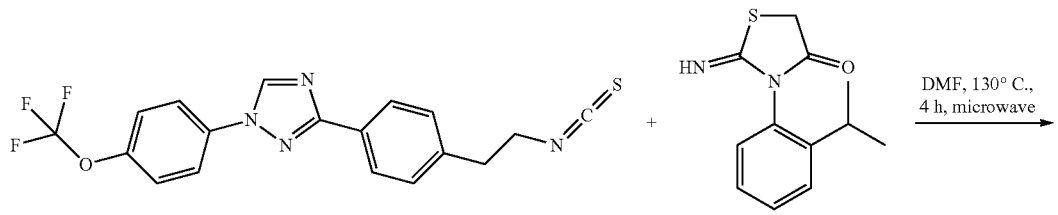

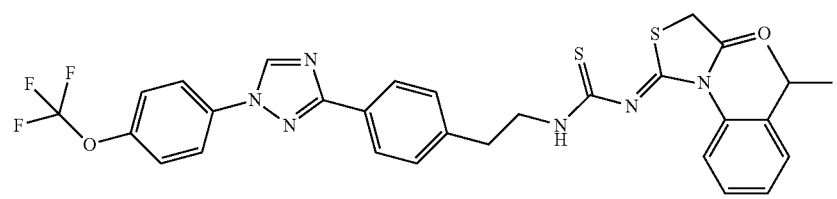

The title compound was isolated as a yellow oil (76 mg, 79%): $^1$H NMR (400 MHz, CDCl$_3$) δ 8.56 (d, J=2.2 Hz, 1H), 8.11-8.03 (m, 2H), 7.81 (dd, J=9.2, 2.6 Hz, 2H), 7.53-7.31 (m, 4H), 7.30-7.27 (m, 1H), 7.25 (s, 1H), 7.05-6.86 (m, 2H), 3.97-3.70 (m, 4H), 3.06-2.90 (m, 2H), 2.73-2.59 (m, 1H), 1.30-1.05 (m, 6H); $^{19}$F NMR (376 MHz, CDCl$_3$) δ −58.03; ESIMS m/z 625 ([M+H]$^+$).

Example 6: Preparation of 3-(4-(1-fluoro-2-isothiocyanatoethyl)phenyl)-1-(4-(trifluoromethoxy)phenyl)-1H-1,2,4-triazole

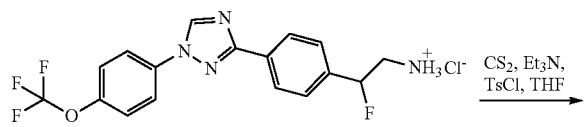

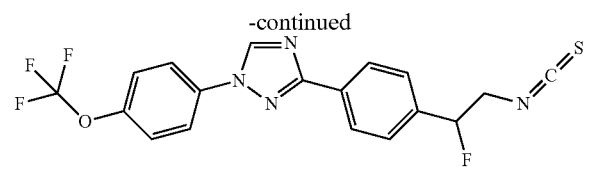

2-Fluoro-2-(4-(1-(4-(trifluoromethoxy)phenyl)-1H-1,2,4-triazol-3-yl)phenyl)ethan-1-aminium hydrochloride (500 mg, 1.24 mmol) was dissolved in THF (3.10 mL) under N$_2$ at room temperature, and triethylamine (0.190 mL, 1.366 mmol) was added. Carbon disulfide (0.075 mL, 1.24 mmol) was added in portions via syringe, and the reaction mixture was allowed to stir at room temperature for 3 h. The reaction flask was placed in an ice bath and cooled to 0° C. Tosyl chloride (0.97 g, 5.09 mmol) was added in one portion, and the reaction mixture was stirred and allowed to warm to room temperature overnight. The reaction mixture was quenched with 1 N HCl and was extracted with ether (3×). The combined organic extracts were washed with water and saturated NaHCO$_3$ solution, dried over anhydrous MgSO$_4$ and concentrated in vacuo to afford (200 mg, 38%) which was used without further purification: $^1$H NMR (400 MHz, CDCl$_3$) δ 8.58 (s, 1H), 8.33-8.19 (m, 2H), 7.86-7.75 (m, 2H), 7.53-7.44 (m, 2H), 7.40 (dq, J=8.9, 1.0 Hz, 2H), 5.70 (ddd, J=46.8, 6.7, 3.9 Hz, 1H), 4.08-3.75 (m, 2H); $^{19}$F NMR (376 MHz, CDCl$_3$) δ −58.02, −182.46; HRMS-ESI (m/z) [M+H]$^+$ calcd for C$_{18}$H$_{13}$F$_4$N$_4$OS, 409.0668; found, 409.0703.

Example 7: Preparation of (Z)-1-(2-fluoro-2-(4-(1-(4-(trifluoromethoxy)phenyl)-1H-1,2,4-triazol-3-yl)phenyl)ethyl)-3-(3-(2-isopropyl-5-methylphenyl)-4-oxothiazolidin-2-ylidene)thiourea

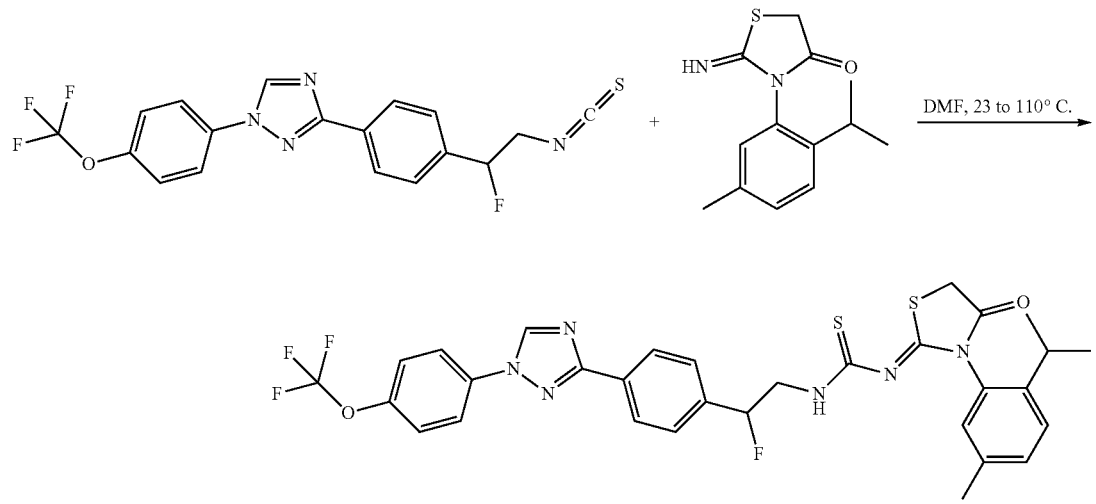 [SMILES: FC(CN=C=S)c1ccc(-c2ncn(-c3ccc(OC(F)(F)F)cc3)n2)cc1 ; Cc1ccc(C(C)C)c(N2C(=N)SCC2=O)c1 ; Cc1ccc(C(C)C)c(N2C(=O)CS/C2=N\C(=S)NCC(F)c2ccc(-c3ncn(-c4ccc(OC(F)(F)F)cc4)n3)cc2)c1]

A mixture of 3-(4-(1-fluoro-2-isothiocyanatoethyl)phenyl)-1-(4-(trifluoromethoxy)phenyl)-1H-1,2,4-triazole (85 mg, 0.208 mmol) and 2-imino-3-(2-isopropyl-5-methylphenyl)thiazolidin-4-one (51.7 mg, 0.208 mmol) in DMF (0.47 mL) was stirred at room temperature for 2 h and at 110° C. using a Vigreux column until consumption of the starting material was noted. The reaction mixture was then cooled to room temperature and loaded onto a Celite® cartridge. Purification via flash chromatography yielded the title compound as a yellow foam (62 mg, 43%): $^1$H NMR (400 MHz, CDCl$_3$) δ 8.57 (s, 1H), 8.21 (dd, J=8.1, 2.4 Hz, 2H), 7.82-7.75 (m, 2H), 7.51-7.44 (m, 2H), 7.40 (dd, J=8.7, 6.6 Hz, 3H), 6.91-6.83 (m, 1H), 5.85 (td, J=9.4, 2.7 Hz, 1H), 4.46-4.17 (m, 1H), 3.97-3.83 (m, 3H), 3.80-3.56 (m, 1H), 2.66 (dq, J=13.2, 6.6 Hz, 2H), 2.36 (d, J=5.7 Hz, 3H), 1.21-1.13 (m, 6H); $^{19}$F NMR (376 MHz, CDCl$_3$) δ −58.02, −184.83; $^{13}$C NMR (126 MHz, CDCl$_3$) δ 189.81, 172.39, 169.87, 162.90, 148.47, 143.09, 141.62, 138.41, 136.86, 135.49, 132.67, 131.13, 128.46, 126.84, 125.68, 122.43, 121.26, 33.64, 28.37, 23.68, 20.83; HRMS-ESI (m/z) ([M+H]$^+$) calcd for C$_{31}$H$_{29}$F$_4$N$_6$O$_2$S$_2$, 657.1651; found, 657.1719.

Using the procedures disclosed herein the following list of molecules are provided as examples (Table 1).

TABLE 1
P1
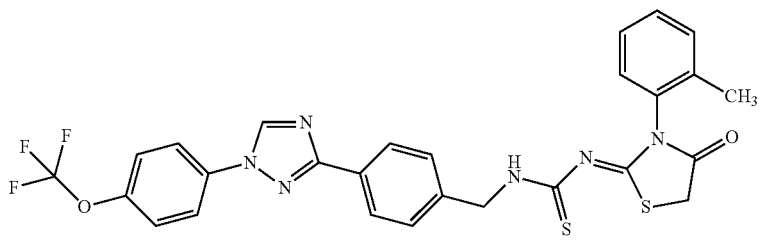 [SMILES: Cc1ccccc1N1C(=O)CS/C1=N\C(=S)NCc1ccc(-c2ncn(-c3ccc(OC(F)(F)F)cc3)n2)cc1]
P2
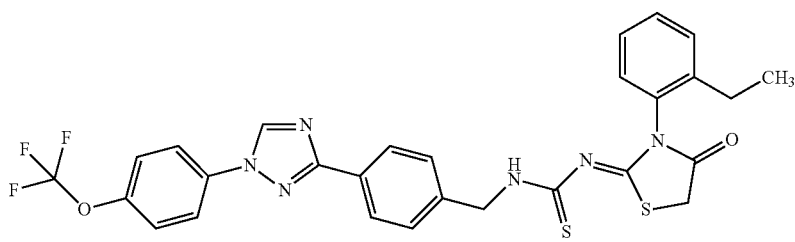 [SMILES: CCc1ccccc1N1C(=O)CS/C1=N\C(=S)NCc1ccc(-c2ncn(-c3ccc(OC(F)(F)F)cc3)n2)cc1]
P3
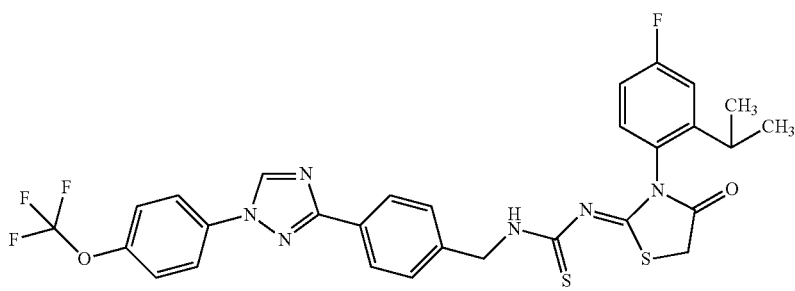 [SMILES: CC(C)c1cc(F)ccc1N1C(=O)CS/C1=N\C(=S)NCc1ccc(-c2ncn(-c3ccc(OC(F)(F)F)cc3)n2)cc1]
P4
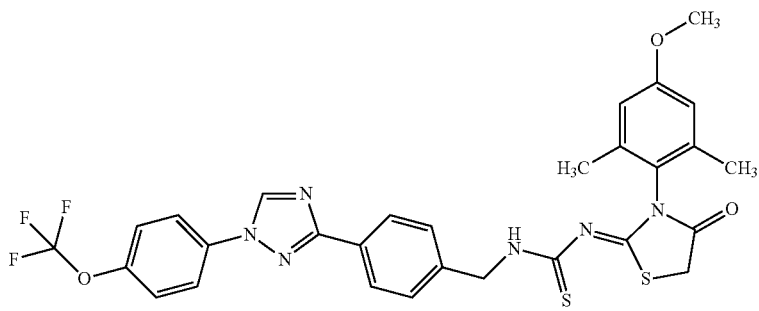 [SMILES: COc1cc(C)c(N2C(=O)CS/C2=N\C(=S)NCc2ccc(-c3ncn(-c4ccc(OC(F)(F)F)cc4)n3)cc2)c(C)c1]
P5
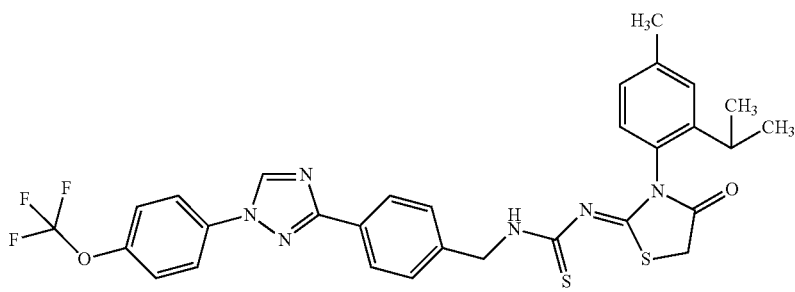 [SMILES: Cc1ccc(N2C(=O)CS/C2=N\C(=S)NCc2ccc(-c3ncn(-c4ccc(OC(F)(F)F)cc4)n3)cc2)c(C(C)C)c1]

TABLE 1-continued
P6 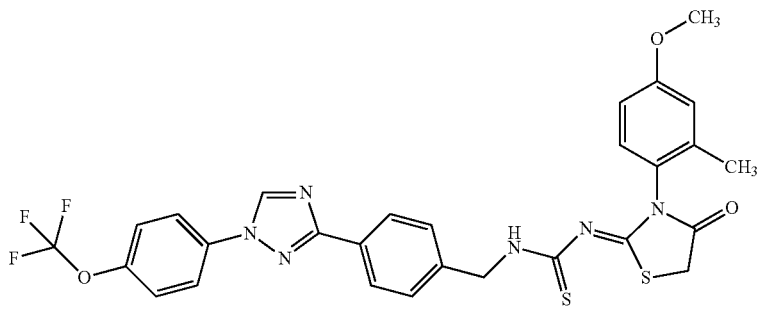 [SMILES: COc1ccc(N2C(=O)CS/C2=N\C(=S)NCc2ccc(-c3ncn(-c4ccc(OC(F)(F)F)cc4)n3)cc2)c(C)c1]
P7 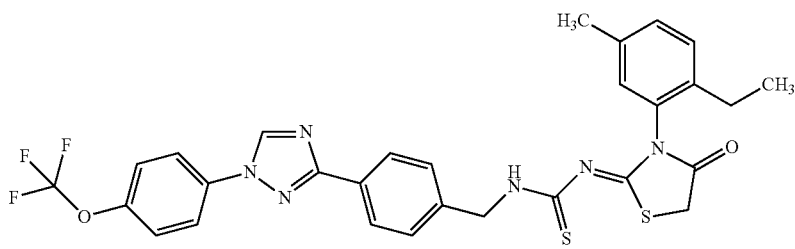 [SMILES: CCc1ccc(C)cc1N1C(=O)CS/C1=N\C(=S)NCc1ccc(-c2ncn(-c3ccc(OC(F)(F)F)cc3)n2)cc1]
P8 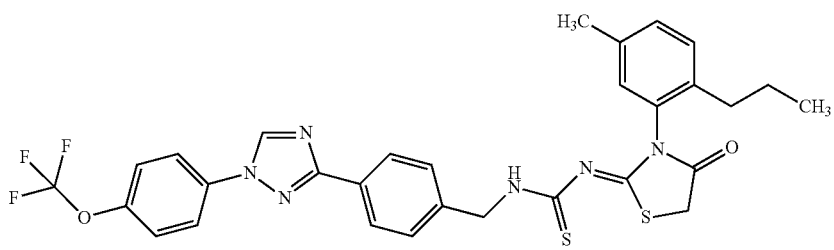 [SMILES: CCCc1ccc(C)cc1N1C(=O)CS/C1=N\C(=S)NCc1ccc(-c2ncn(-c3ccc(OC(F)(F)F)cc3)n2)cc1]
P9 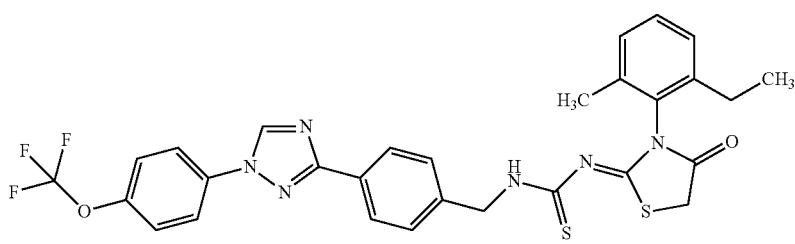 [SMILES: CCc1cccc(C)c1N1C(=O)CS/C1=N\C(=S)NCc1ccc(-c2ncn(-c3ccc(OC(F)(F)F)cc3)n2)cc1]
P10 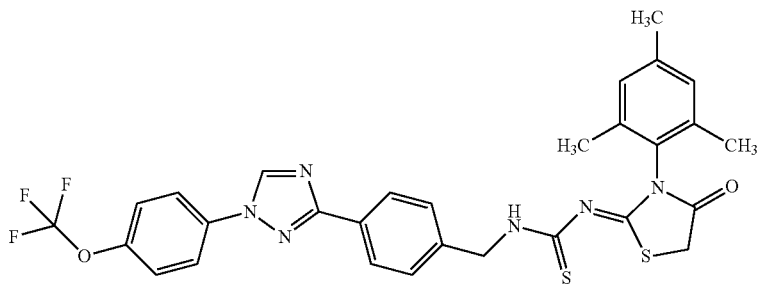 [SMILES: Cc1cc(C)c(N2C(=O)CS/C2=N\C(=S)NCc2ccc(-c3ncn(-c4ccc(OC(F)(F)F)cc4)n3)cc2)c(C)c1]
P11 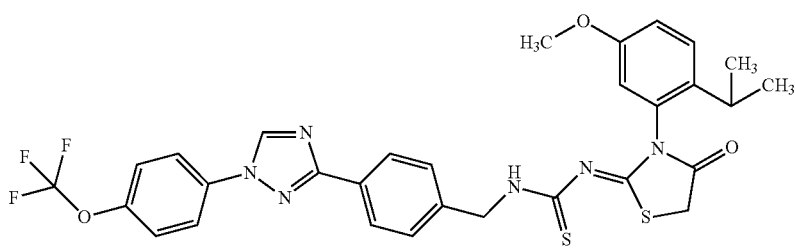 [SMILES: COc1ccc(C(C)C)c(N2C(=O)CS/C2=N\C(=S)NCc2ccc(-c3ncn(-c4ccc(OC(F)(F)F)cc4)n3)cc2)c1]

TABLE 1-continued
P12
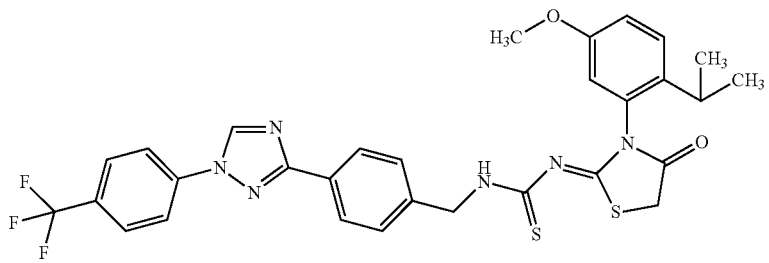 [SMILES: COc1ccc(C(C)C)c(N2C(=O)CS/C2=N\C(=S)NCc2ccc(-c3ncn(-c4ccc(C(F)(F)F)cc4)n3)cc2)c1]
P13
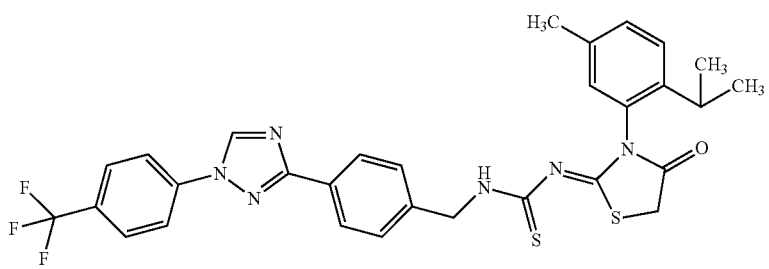 [SMILES: Cc1ccc(C(C)C)c(N2C(=O)CS/C2=N\C(=S)NCc2ccc(-c3ncn(-c4ccc(C(F)(F)F)cc4)n3)cc2)c1]
P14
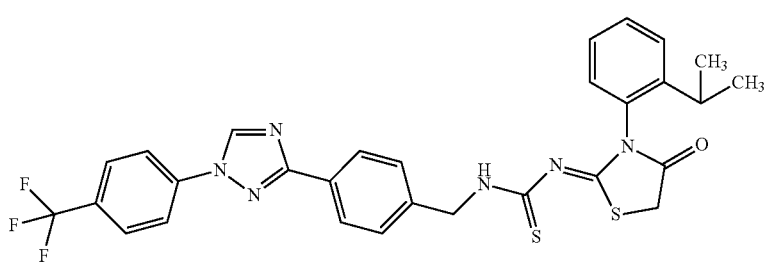 [SMILES: CC(C)c1ccccc1N1C(=O)CS/C1=N\C(=S)NCc1ccc(-c2ncn(-c3ccc(C(F)(F)F)cc3)n2)cc1]
P15
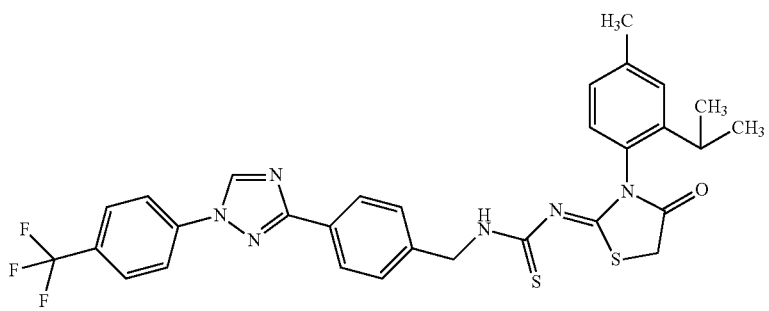 [SMILES: Cc1ccc(N2C(=O)CS/C2=N\C(=S)NCc2ccc(-c3ncn(-c4ccc(C(F)(F)F)cc4)n3)cc2)c(C(C)C)c1]
P16
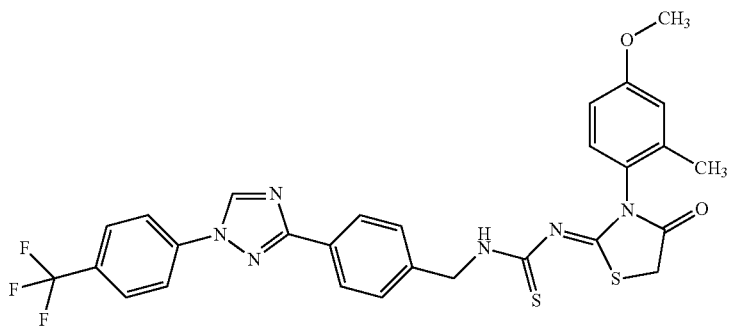 [SMILES: COc1ccc(N2C(=O)CS/C2=N\C(=S)NCc2ccc(-c3ncn(-c4ccc(C(F)(F)F)cc4)n3)cc2)c(C)c1]

TABLE 1-continued
P17 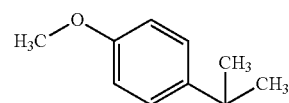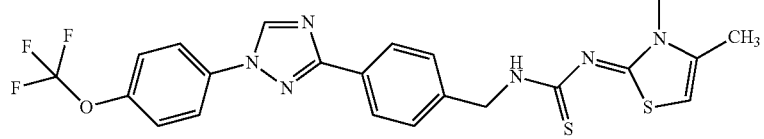
P18 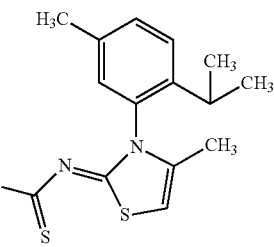
P19 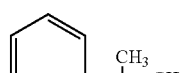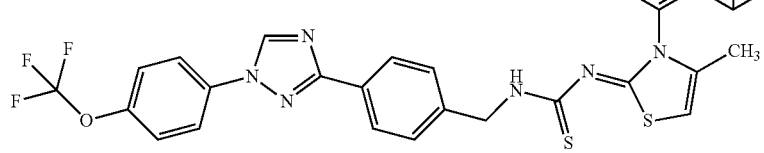
P20 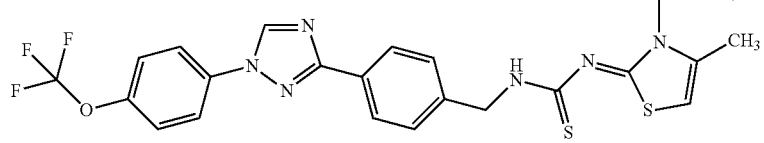
P21 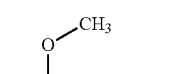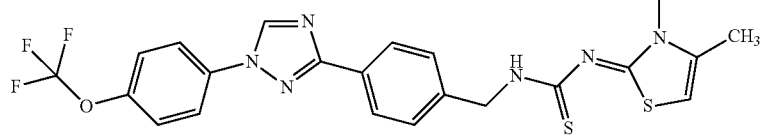
P22 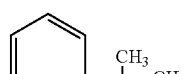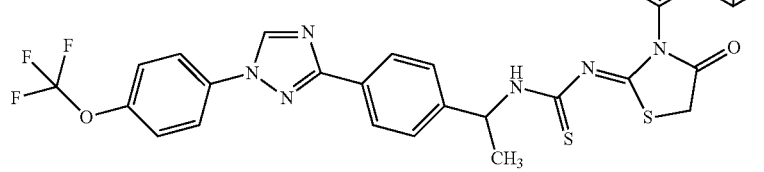

TABLE 1-continued
P23 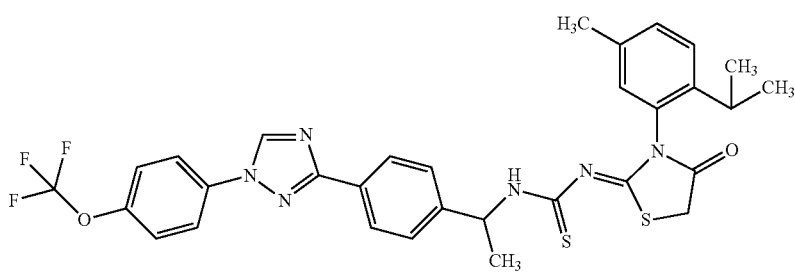 [SMILES: Cc1ccc(C(C)C)c(N2C(=O)CS/C2=N\C(=S)NC(C)c2ccc(-c3ncn(-c4ccc(OC(F)(F)F)cc4)n3)cc2)c1]
P24 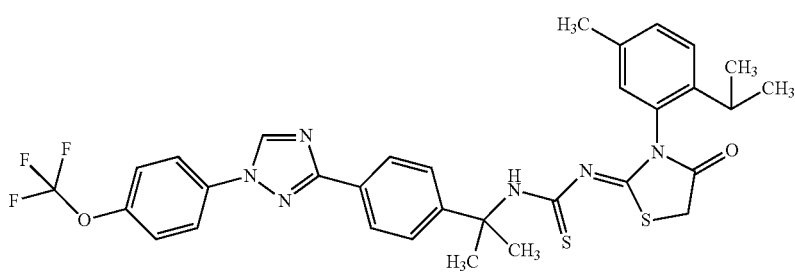 [SMILES: Cc1ccc(C(C)C)c(N2C(=O)CS/C2=N\C(=S)NC(C)(C)c2ccc(-c3ncn(-c4ccc(OC(F)(F)F)cc4)n3)cc2)c1]
P25 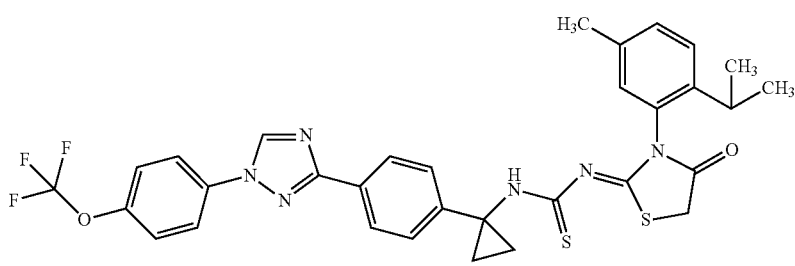 [SMILES: Cc1ccc(C(C)C)c(N2C(=O)CS/C2=N\C(=S)NC2(c3ccc(-c4ncn(-c5ccc(OC(F)(F)F)cc5)n4)cc3)CC2)c1]
P26 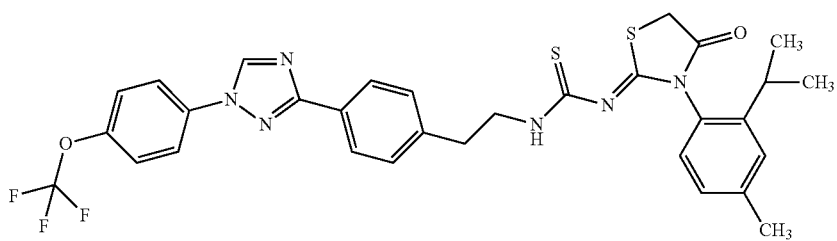 [SMILES: Cc1ccc(N2C(=O)CS/C2=N\C(=S)NCCc2ccc(-c3ncn(-c4ccc(OC(F)(F)F)cc4)n3)cc2)c(C(C)C)c1]
P27 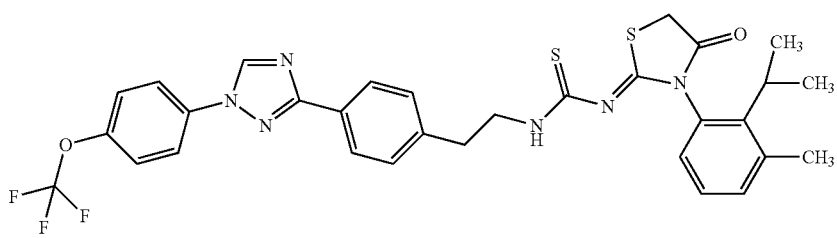 [SMILES: Cc1cccc(N2C(=O)CS/C2=N\C(=S)NCCc2ccc(-c3ncn(-c4ccc(OC(F)(F)F)cc4)n3)cc2)c1C(C)C]
P28 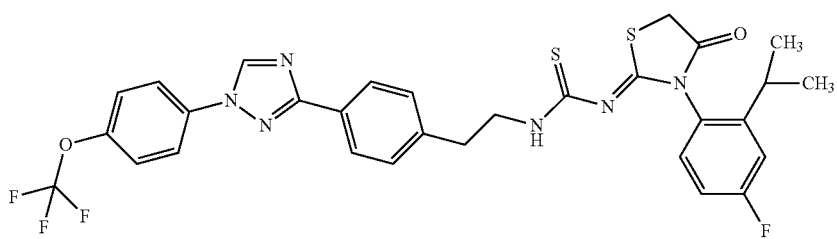 [SMILES: CC(C)c1cc(F)ccc1N1C(=O)CS/C1=N\C(=S)NCCc1ccc(-c2ncn(-c3ccc(OC(F)(F)F)cc3)n2)cc1]

TABLE 1-continued
P29 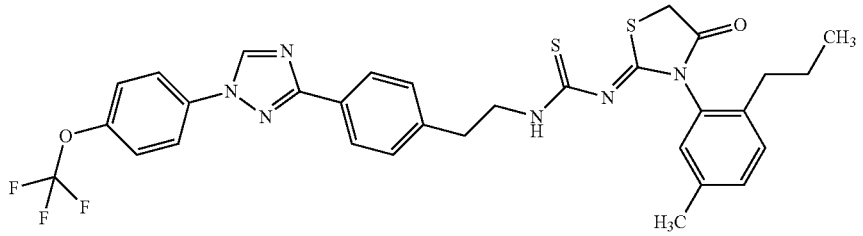 [SMILES: CCCc1ccc(C)cc1N1C(=O)CS/C1=N\C(=S)NCCc1ccc(-c2ncn(-c3ccc(OC(F)(F)F)cc3)n2)cc1]
P30 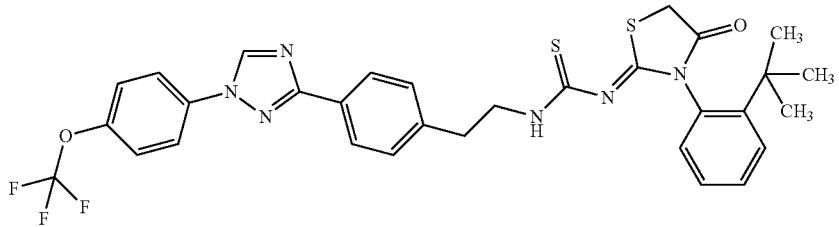 [SMILES: CC(C)(C)c1ccccc1N1C(=O)CS/C1=N\C(=S)NCCc1ccc(-c2ncn(-c3ccc(OC(F)(F)F)cc3)n2)cc1]
P31 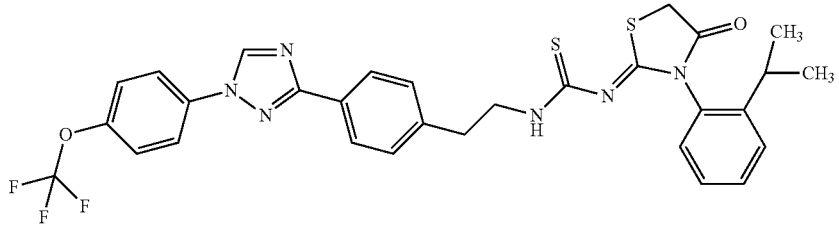 [SMILES: CC(C)c1ccccc1N1C(=O)CS/C1=N\C(=S)NCCc1ccc(-c2ncn(-c3ccc(OC(F)(F)F)cc3)n2)cc1]
P32 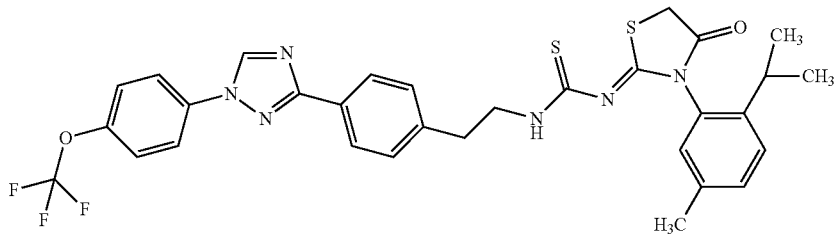 [SMILES: Cc1ccc(C(C)C)c(N2C(=O)CS/C2=N\C(=S)NCCc2ccc(-c3ncn(-c4ccc(OC(F)(F)F)cc4)n3)cc2)c1]
P33 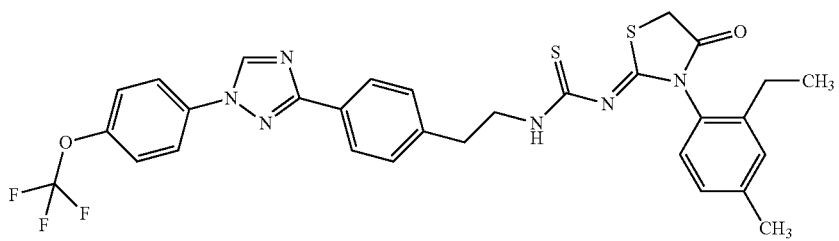
P34 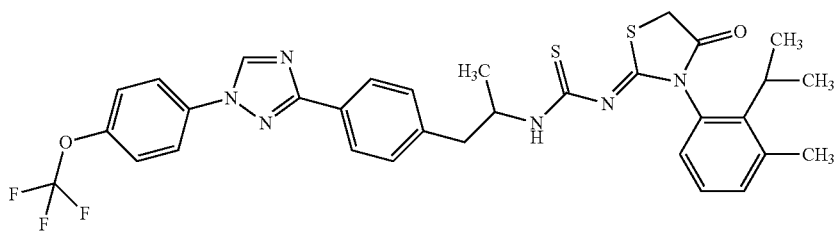 [SMILES: Cc1cccc(N2C(=O)CS/C2=N\C(=S)NC(C)Cc2ccc(-c3ncn(-c4ccc(OC(F)(F)F)cc4)n3)cc2)c1C(C)C]

TABLE 1-continued
P35 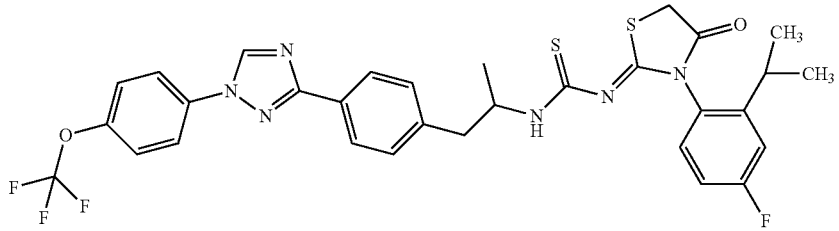 [SMILES: CC(Cc1ccc(-c2ncn(-c3ccc(OC(F)(F)F)cc3)n2)cc1)NC(=S)/N=C1\SCC(=O)N1c1ccc(F)cc1C(C)C]
P36 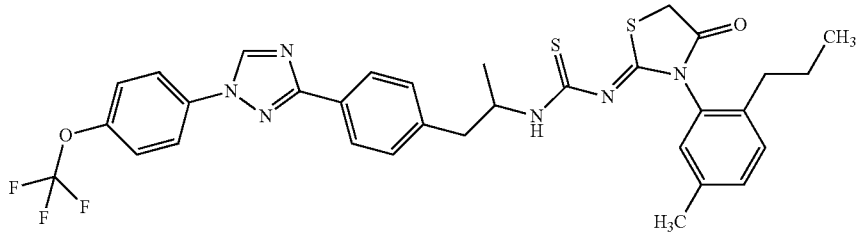 [SMILES: CCCc1ccc(C)cc1N1C(=O)CS/C1=N\C(=S)NC(C)Cc1ccc(-c2ncn(-c3ccc(OC(F)(F)F)cc3)n2)cc1]
P37 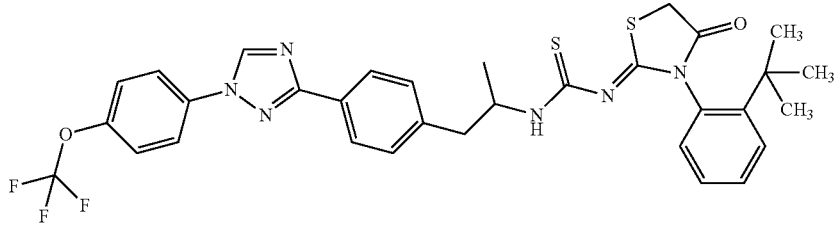 [SMILES: CC(Cc1ccc(-c2ncn(-c3ccc(OC(F)(F)F)cc3)n2)cc1)NC(=S)/N=C1\SCC(=O)N1c1ccccc1C(C)(C)C]
P38 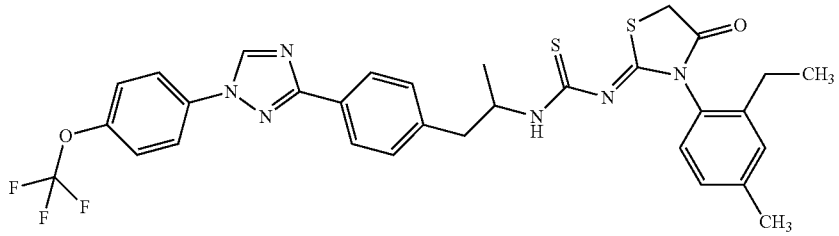 [SMILES: CCc1cc(C)ccc1N1C(=O)CS/C1=N\C(=S)NC(C)Cc1ccc(-c2ncn(-c3ccc(OC(F)(F)F)cc3)n2)cc1]
P39 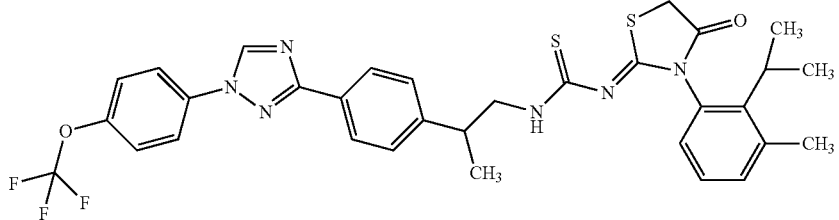 [SMILES: Cc1cccc(N2C(=O)CS/C2=N\C(=S)NCC(C)c2ccc(-c3ncn(-c4ccc(OC(F)(F)F)cc4)n3)cc2)c1C(C)C]
P40 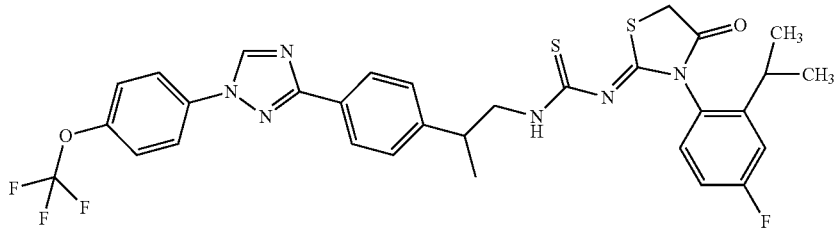 [SMILES: CC(C)c1cc(F)ccc1N1C(=O)CS/C1=N\C(=S)NCC(C)c1ccc(-c2ncn(-c3ccc(OC(F)(F)F)cc3)n2)cc1]

TABLE 1-continued
P41 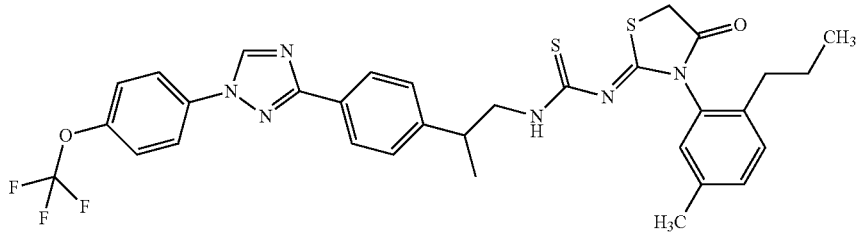
P42 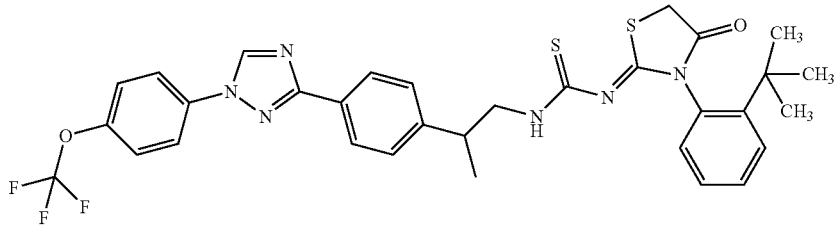 [SMILES: CC(CNC(=S)/N=C1\SCC(=O)N1c1ccccc1C(C)(C)C)c1ccc(-c2ncn(-c3ccc(OC(F)(F)F)cc3)n2)cc1]
P43 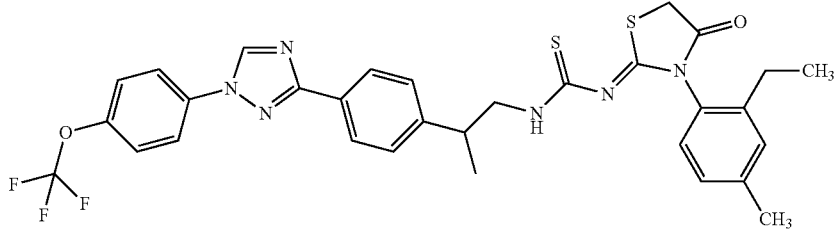
P44 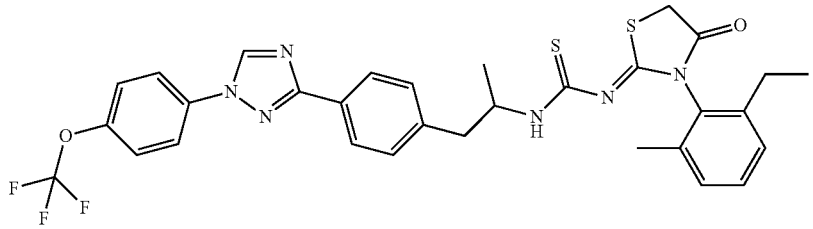 [SMILES: CCc1cccc(C)c1N1C(=O)CS/C1=N\C(=S)NC(C)Cc1ccc(-c2ncn(-c3ccc(OC(F)(F)F)cc3)n2)cc1]
P45 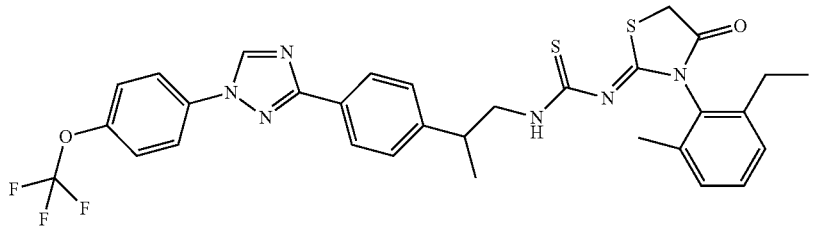 [SMILES: CCc1cccc(C)c1N1C(=O)CS/C1=N\C(=S)NCC(C)c1ccc(-c2ncn(-c3ccc(OC(F)(F)F)cc3)n2)cc1]
P46 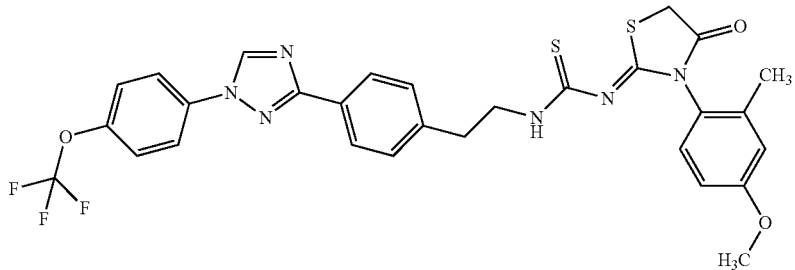 [SMILES: COc1ccc(N2C(=O)CS/C2=N\C(=S)NCCc2ccc(-c3ncn(-c4ccc(OC(F)(F)F)cc4)n3)cc2)c(C)c1]

TABLE 1-continued
P47 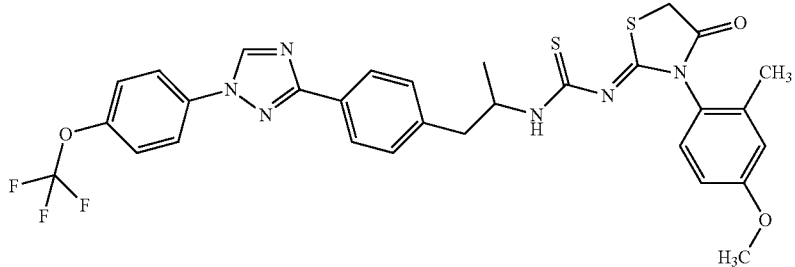 [SMILES: COc1ccc(N2C(=O)CS/C2=N\C(=S)NC(C)Cc2ccc(-c3ncn(-c4ccc(OC(F)(F)F)cc4)n3)cc2)c(C)c1]
P48 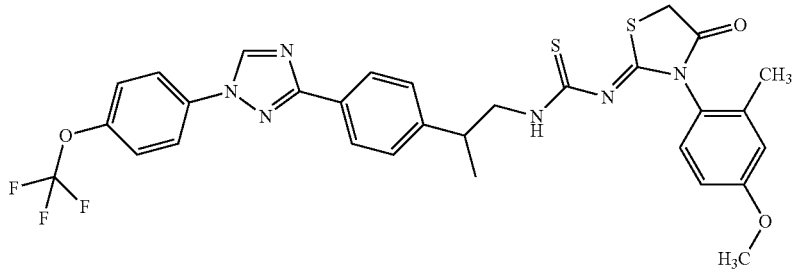 [SMILES: COc1ccc(N2C(=O)CS/C2=N\C(=S)NCC(C)c2ccc(-c3ncn(-c4ccc(OC(F)(F)F)cc4)n3)cc2)c(C)c1]
P49 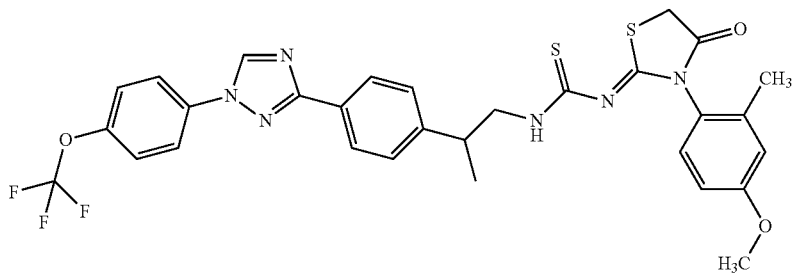 [SMILES: COc1ccc(N2C(=O)CS/C2=N\C(=S)NCC(C)c2ccc(-c3ncn(-c4ccc(OC(F)(F)F)cc4)n3)cc2)c(C)c1]
P50 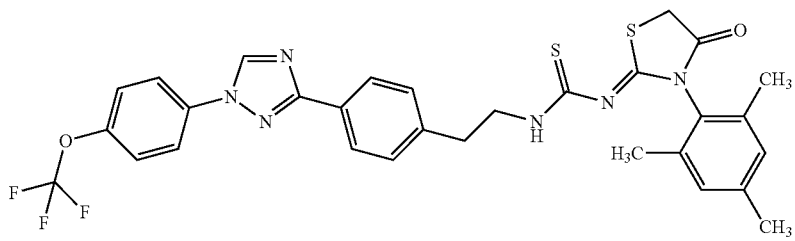 [SMILES: Cc1cc(C)c(N2C(=O)CS/C2=N\C(=S)NCCc2ccc(-c3ncn(-c4ccc(OC(F)(F)F)cc4)n3)cc2)c(C)c1]
P51 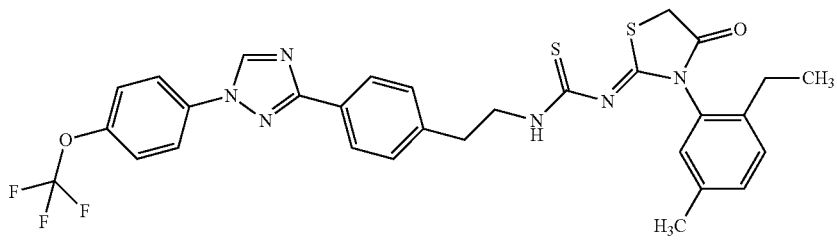 [SMILES: CCc1ccc(C)cc1N1C(=O)CS/C1=N\C(=S)NCCc1ccc(-c2ncn(-c3ccc(OC(F)(F)F)cc3)n2)cc1]
P52 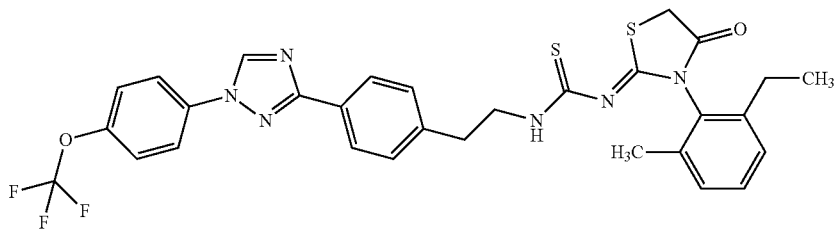 [SMILES: CCc1cccc(C)c1N1C(=O)CS/C1=N\C(=S)NCCc1ccc(-c2ncn(-c3ccc(OC(F)(F)F)cc3)n2)cc1]

TABLE 1-continued
P53 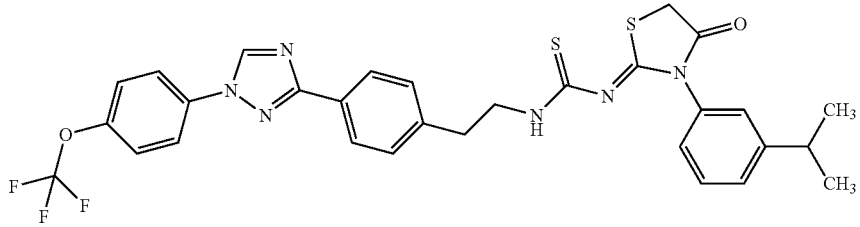 [SMILES: CC(C)c1cccc(N2C(=O)CS/C2=N\C(=S)NCCc2ccc(-c3ncn(-c4ccc(OC(F)(F)F)cc4)n3)cc2)c1]
P54 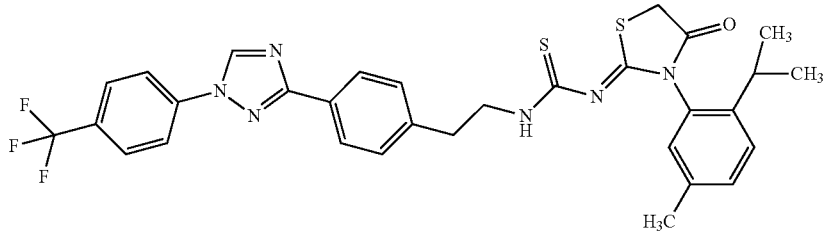 [SMILES: Cc1ccc(C(C)C)c(N2C(=O)CS/C2=N\C(=S)NCCc2ccc(-c3ncn(-c4ccc(C(F)(F)F)cc4)n3)cc2)c1]
P55 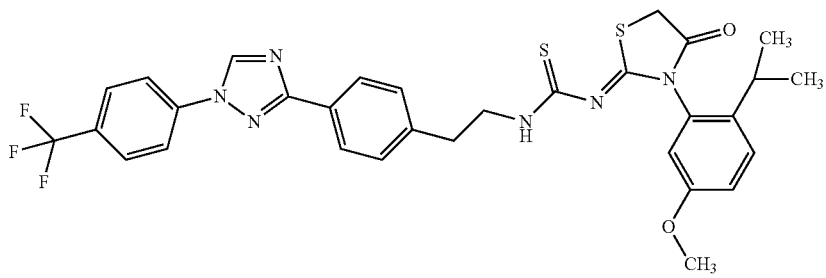 [SMILES: COc1ccc(C(C)C)c(N2C(=O)CS/C2=N\C(=S)NCCc2ccc(-c3ncn(-c4ccc(C(F)(F)F)cc4)n3)cc2)c1]
P56 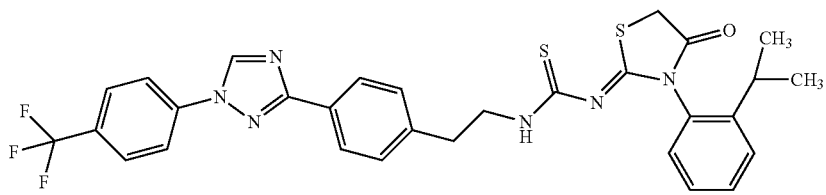 [SMILES: CC(C)c1ccccc1N1C(=O)CS/C1=N\C(=S)NCCc1ccc(-c2ncn(-c3ccc(C(F)(F)F)cc3)n2)cc1]
P57 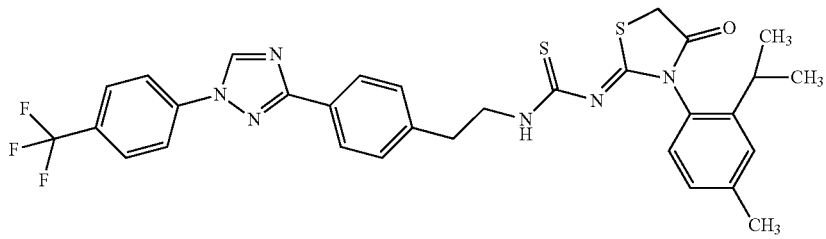 [SMILES: Cc1ccc(N2C(=O)CS/C2=N\C(=S)NCCc2ccc(-c3ncn(-c4ccc(C(F)(F)F)cc4)n3)cc2)c(C(C)C)c1]
P58 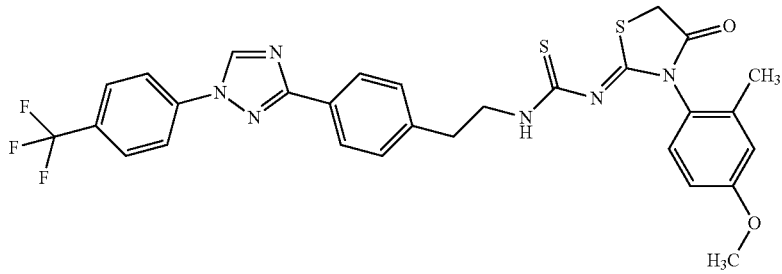 [SMILES: COc1ccc(N2C(=O)CS/C2=N\C(=S)NCCc2ccc(-c3ncn(-c4ccc(C(F)(F)F)cc4)n3)cc2)c(C)c1]

TABLE 1-continued
P59 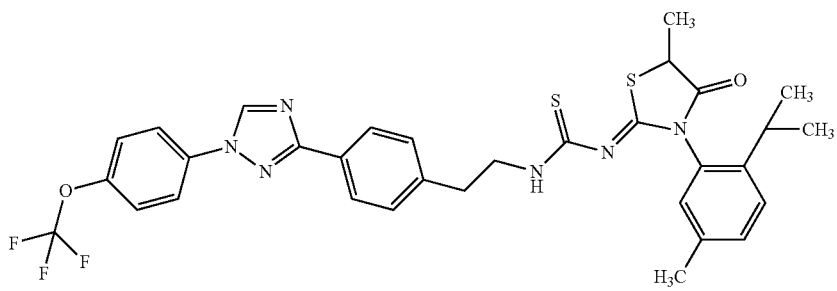 [SMILES: Cc1ccc(C(C)C)c(N2C(=O)C(C)S/C2=N\C(=S)NCCc2ccc(-c3ncn(-c4ccc(OC(F)(F)F)cc4)n3)cc2)c1]
P60 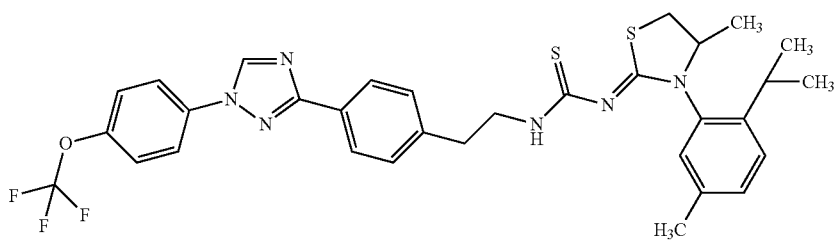 [SMILES: Cc1ccc(C(C)C)c(N2/C(=N/C(=S)NCCc3ccc(-c4ncn(-c5ccc(OC(F)(F)F)cc5)n4)cc3)SCC2C)c1]
P61 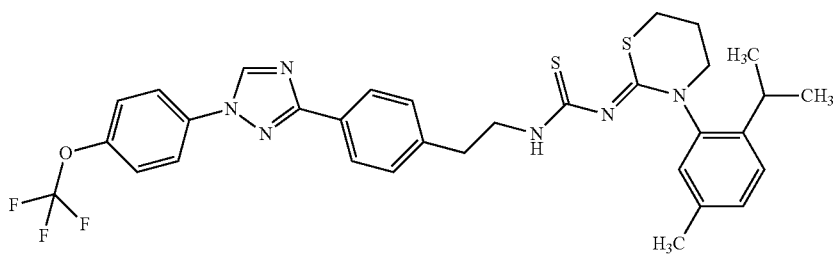 [SMILES: Cc1ccc(C(C)C)c(N2CCCS/C2=N\C(=S)NCCc2ccc(-c3ncn(-c4ccc(OC(F)(F)F)cc4)n3)cc2)c1]
P62 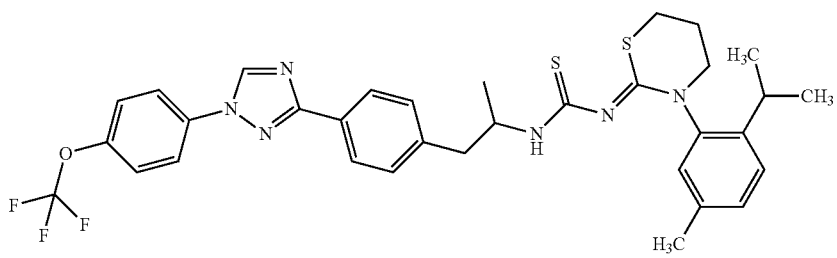
P63 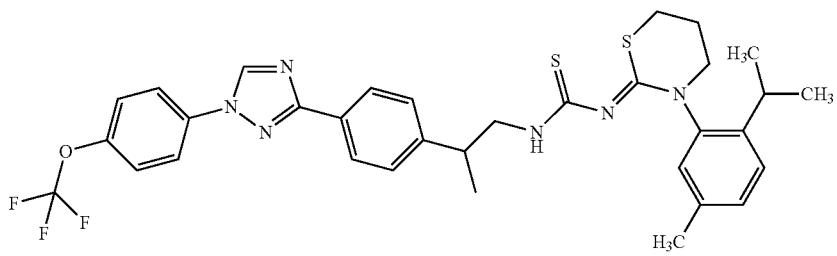 [SMILES: Cc1ccc(C(C)C)c(N2CCCS/C2=N\C(=S)NCC(C)c2ccc(-c3ncn(-c4ccc(OC(F)(F)F)cc4)n3)cc2)c1]
P64 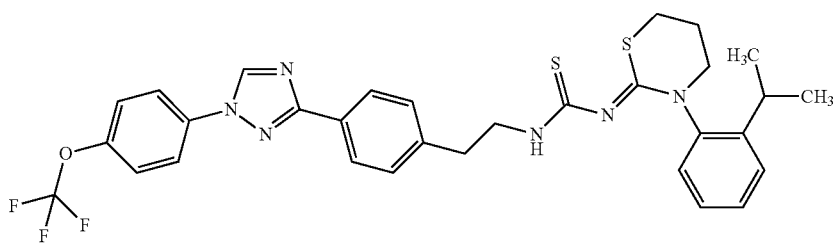 [SMILES: CC(C)c1ccccc1N1CCCS/C1=N\C(=S)NCCc1ccc(-c2ncn(-c3ccc(OC(F)(F)F)cc3)n2)cc1]

TABLE 1-continued
P65
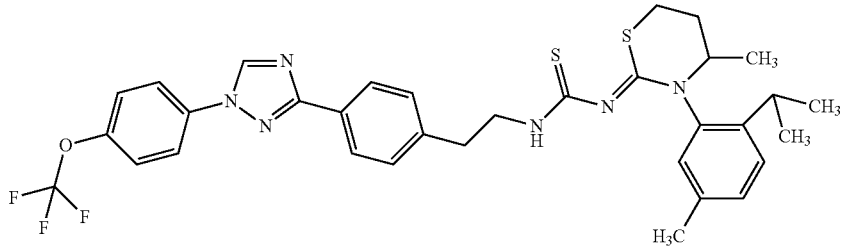 [SMILES: Cc1ccc(C(C)C)c(N2/C(=N/C(=S)NCCc3ccc(-c4ncn(-c5ccc(OC(F)(F)F)cc5)n4)cc3)SCCC2C)c1]
P66
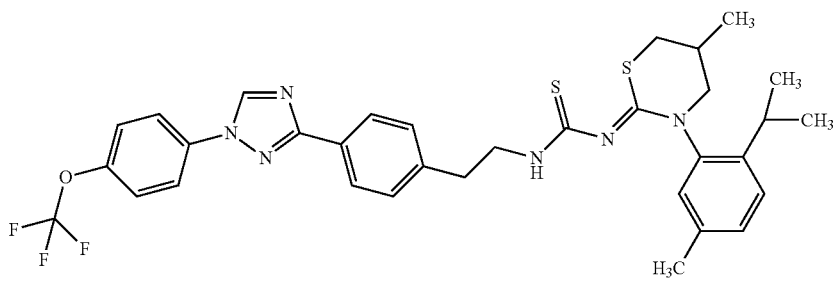 [SMILES: Cc1ccc(C(C)C)c(N2CC(C)CS/C2=N\C(=S)NCCc2ccc(-c3ncn(-c4ccc(OC(F)(F)F)cc4)n3)cc2)c1]
P67
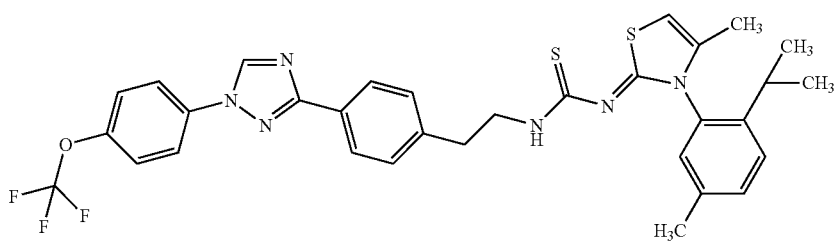
P68
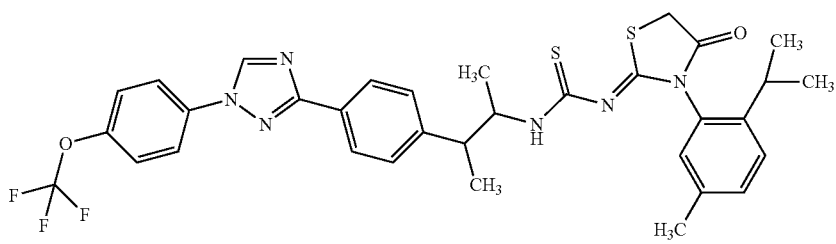 [SMILES: Cc1ccc(C(C)C)c(N2C(=O)CS/C2=N\C(=S)NC(C)C(C)c2ccc(-c3ncn(-c4ccc(OC(F)(F)F)cc4)n3)cc2)c1]
P69
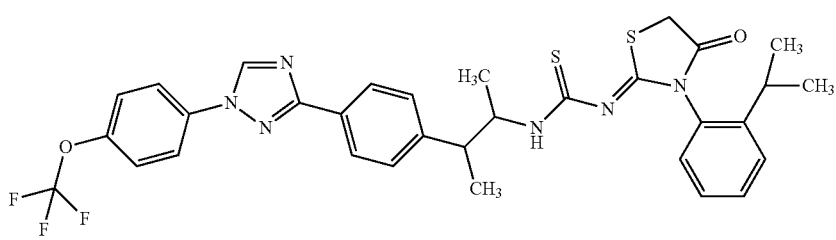 [SMILES: CC(C)c1ccccc1N1C(=O)CS/C1=N\C(=S)NC(C)C(C)c1ccc(-c2ncn(-c3ccc(OC(F)(F)F)cc3)n2)cc1]
P70
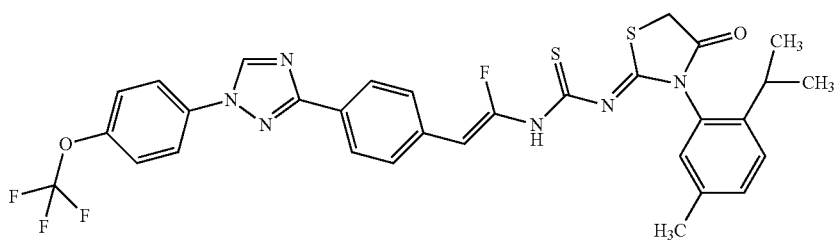 [SMILES: Cc1ccc(C(C)C)c(N2C(=O)CS/C2=N\C(=S)N/C(F)=C/c2ccc(-c3ncn(-c4ccc(OC(F)(F)F)cc4)n3)cc2)c1]

TABLE 1-continued
P71 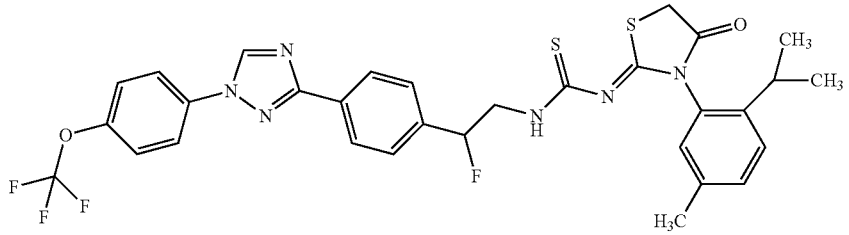 [SMILES: Cc1ccc(C(C)C)c(N2C(=O)CS/C2=N\C(=S)NCC(F)c2ccc(-c3ncn(-c4ccc(OC(F)(F)F)cc4)n3)cc2)c1]
P72 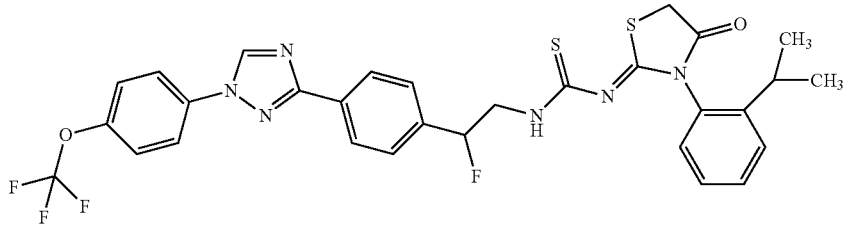 [SMILES: CC(C)c1ccccc1N1C(=O)CS/C1=N\C(=S)NCC(F)c1ccc(-c2ncn(-c3ccc(OC(F)(F)F)cc3)n2)cc1]
P73 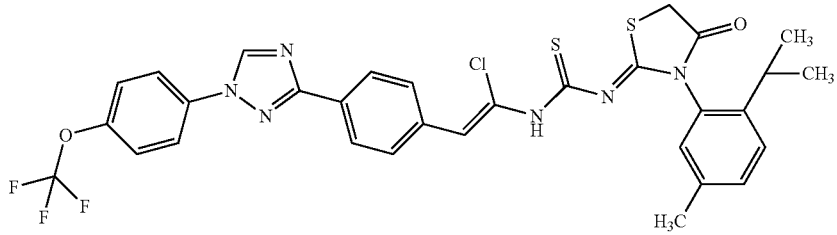
P74 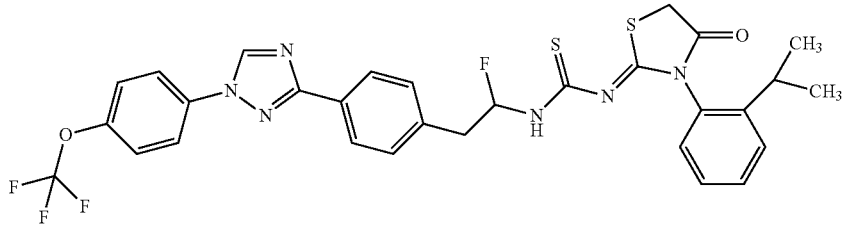 [SMILES: CC(C)c1ccccc1N1C(=O)CS/C1=N\C(=S)NC(F)Cc1ccc(-c2ncn(-c3ccc(OC(F)(F)F)cc3)n2)cc1]
P75 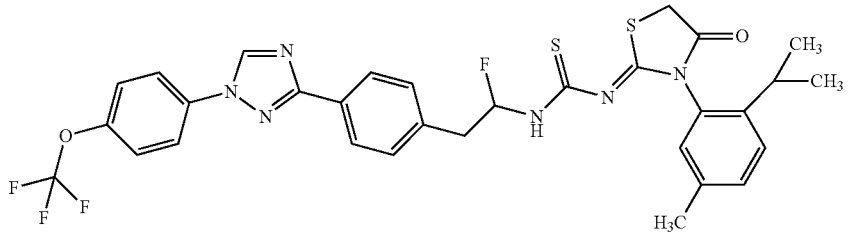 [SMILES: Cc1ccc(C(C)C)c(N2C(=O)CS/C2=N\C(=S)NC(F)Cc2ccc(-c3ncn(-c4ccc(OC(F)(F)F)cc4)n3)cc2)c1]
P76 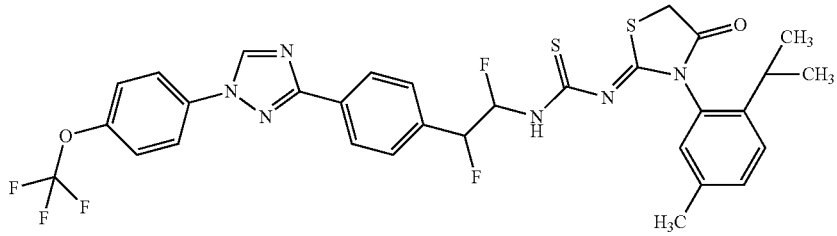

TABLE 1-continued
P77 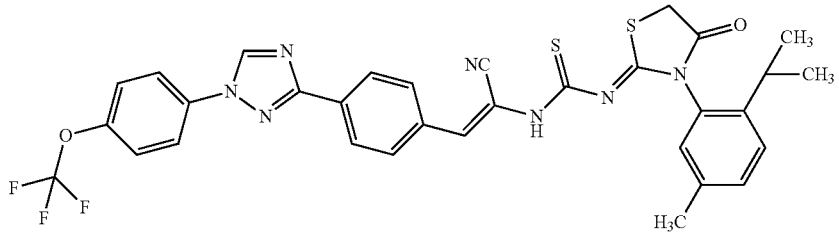 [SMILES: Cc1ccc(C(C)C)c(N2C(=O)CS/C2=N\C(=S)N/C(C#N)=C/c2ccc(-c3ncn(-c4ccc(OC(F)(F)F)cc4)n3)cc2)c1]
P78 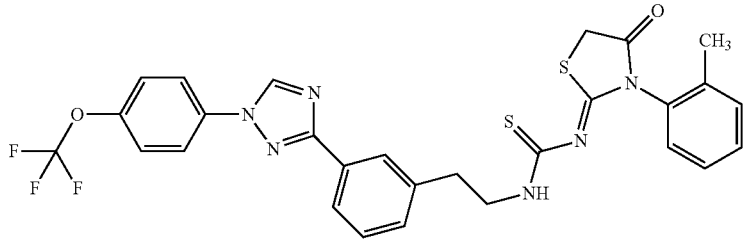
P79 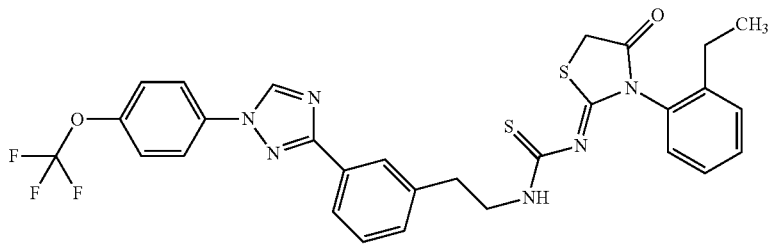 [SMILES: CCc1ccccc1N1C(=O)CS/C1=N\C(=S)NCCc1cccc(-c2ncn(-c3ccc(OC(F)(F)F)cc3)n2)c1]
P80 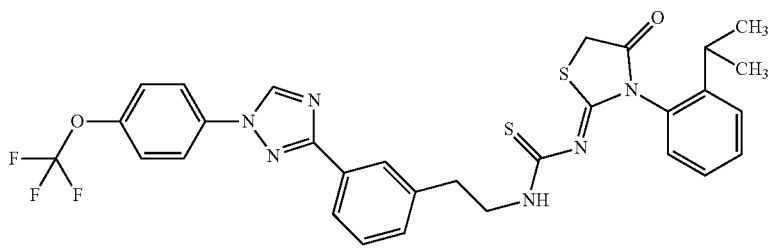 [SMILES: CC(C)c1ccccc1N1C(=O)CS/C1=N\C(=S)NCCc1cccc(-c2ncn(-c3ccc(OC(F)(F)F)cc3)n2)c1]
P81 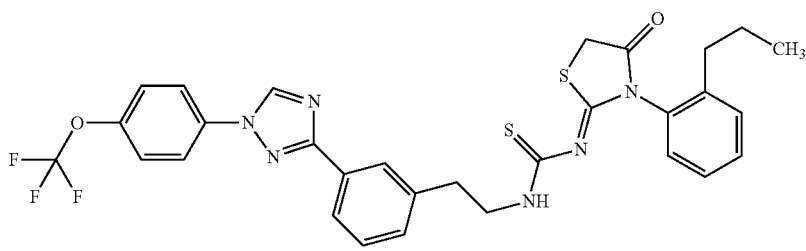 [SMILES: CCCc1ccccc1N1C(=O)CS/C1=N\C(=S)NCCc1cccc(-c2ncn(-c3ccc(OC(F)(F)F)cc3)n2)c1]
P82 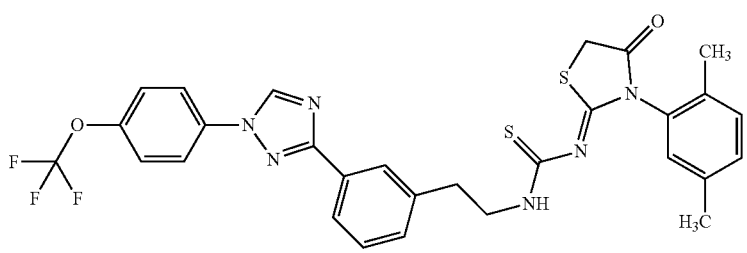 [SMILES: Cc1ccc(C)c(N2C(=O)CS/C2=N\C(=S)NCCc2cccc(-c3ncn(-c4ccc(OC(F)(F)F)cc4)n3)c2)c1]

TABLE 1-continued
P83
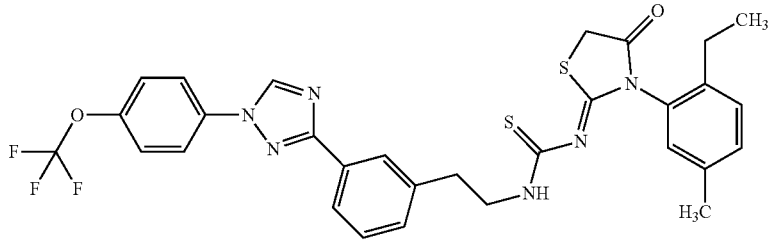 [SMILES: CCc1ccc(C)cc1N1C(=O)CS/C1=N\C(=S)NCCc1cccc(-c2ncn(-c3ccc(OC(F)(F)F)cc3)n2)c1]
P84
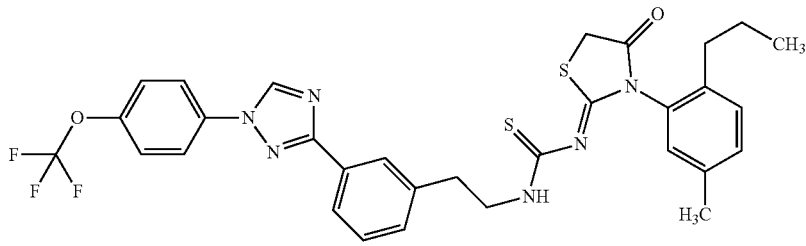 [SMILES: CCCc1ccc(C)cc1N1C(=O)CS/C1=N\C(=S)NCCc1cccc(-c2ncn(-c3ccc(OC(F)(F)F)cc3)n2)c1]
P85
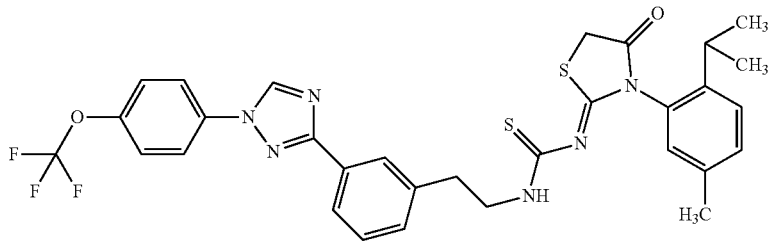 [SMILES: Cc1ccc(C(C)C)c(N2C(=O)CS/C2=N\C(=S)NCCc2cccc(-c3ncn(-c4ccc(OC(F)(F)F)cc4)n3)c2)c1]
P86
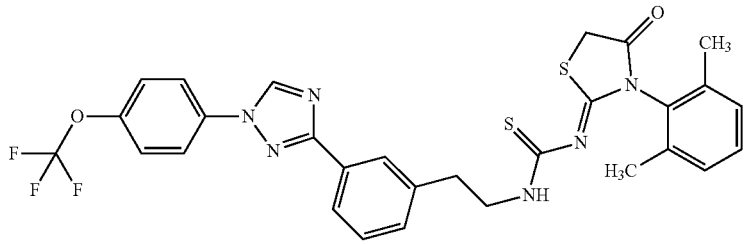 [SMILES: Cc1cccc(C)c1N1C(=O)CS/C1=N\C(=S)NCCc1cccc(-c2ncn(-c3ccc(OC(F)(F)F)cc3)n2)c1]
P87
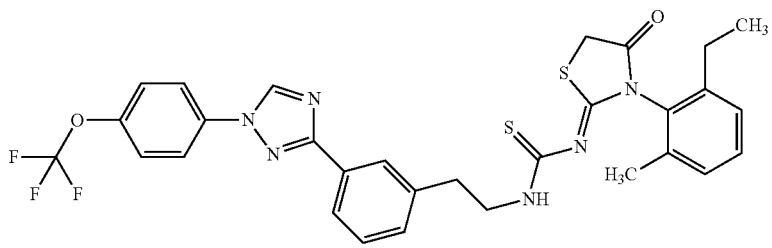 [SMILES: CCc1cccc(C)c1N1C(=O)CS/C1=N\C(=S)NCCc1cccc(-c2ncn(-c3ccc(OC(F)(F)F)cc3)n2)c1]
P88
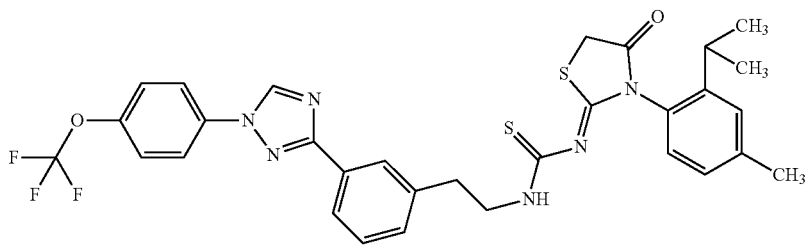 [SMILES: Cc1ccc(N2C(=O)CS/C2=N\C(=S)NCCc2cccc(-c3ncn(-c4ccc(OC(F)(F)F)cc4)n3)c2)c(C(C)C)c1]

TABLE 1-continued
P89
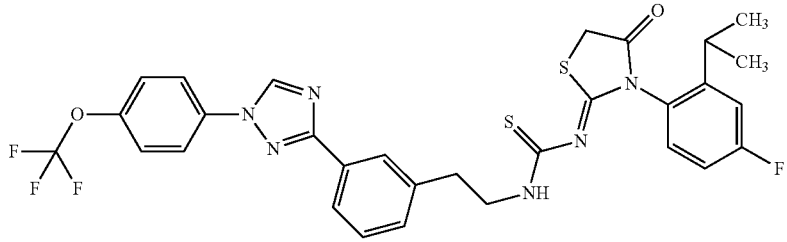 [SMILES: CC(C)c1cc(F)ccc1N1C(=O)CS/C1=N\C(=S)NCCc1cccc(-c2ncn(-c3ccc(OC(F)(F)F)cc3)n2)c1]
P90
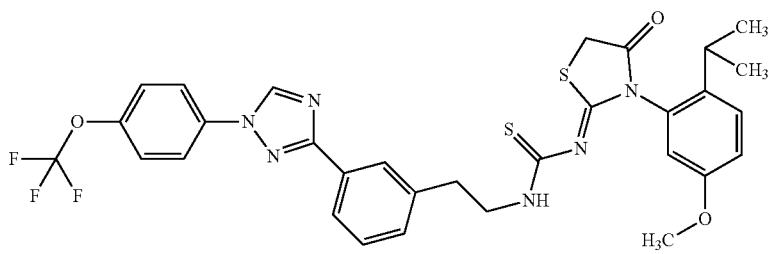 [SMILES: COc1ccc(C(C)C)c(N2C(=O)CS/C2=N\C(=S)NCCc2cccc(-c3ncn(-c4ccc(OC(F)(F)F)cc4)n3)c2)c1]
P91
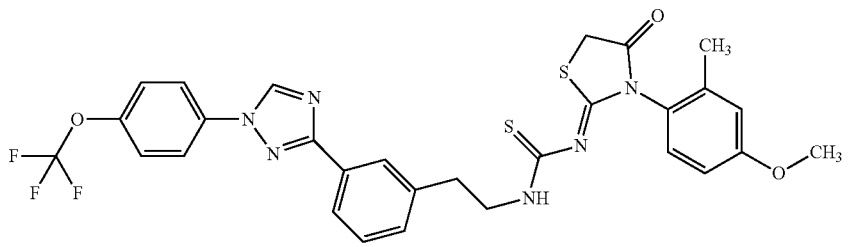 [SMILES: COc1ccc(N2C(=O)CS/C2=N\C(=S)NCCc2cccc(-c3ncn(-c4ccc(OC(F)(F)F)cc4)n3)c2)c(C)c1]
P92
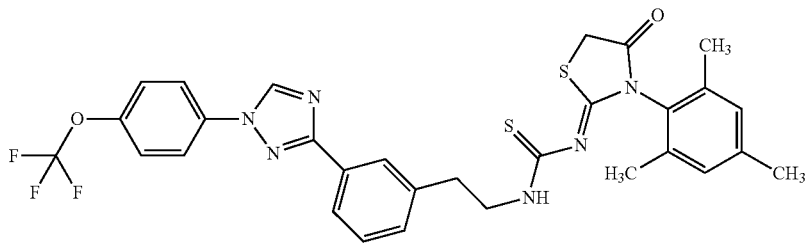 [SMILES: Cc1cc(C)c(N2C(=O)CS/C2=N\C(=S)NCCc2cccc(-c3ncn(-c4ccc(OC(F)(F)F)cc4)n3)c2)c(C)c1]
P93
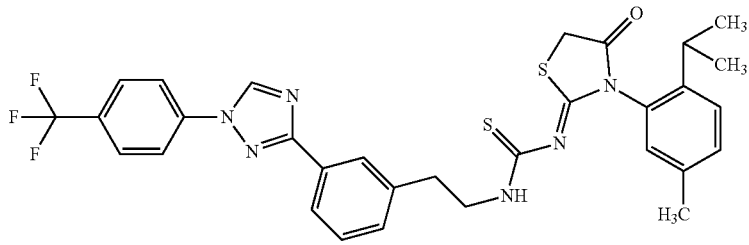 [SMILES: Cc1ccc(C(C)C)c(N2C(=O)CS/C2=N\C(=S)NCCc2cccc(-c3ncn(-c4ccc(C(F)(F)F)cc4)n3)c2)c1]
P94
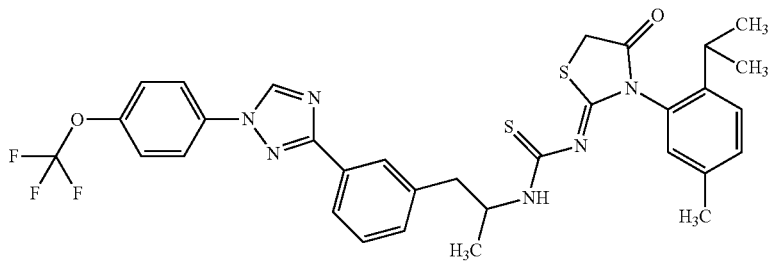 [SMILES: Cc1ccc(C(C)C)c(N2C(=O)CS/C2=N\C(=S)NC(C)Cc2cccc(-c3ncn(-c4ccc(OC(F)(F)F)cc4)n3)c2)c1]

TABLE 1-continued
P95 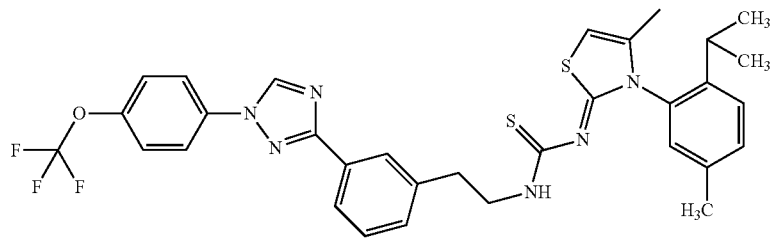 [SMILES: Cc1ccc(C(C)C)c(-n2c(C)cs/c2=N\C(=S)NCCc2cccc(-c3ncn(-c4ccc(OC(F)(F)F)cc4)n3)c2)c1]
P96 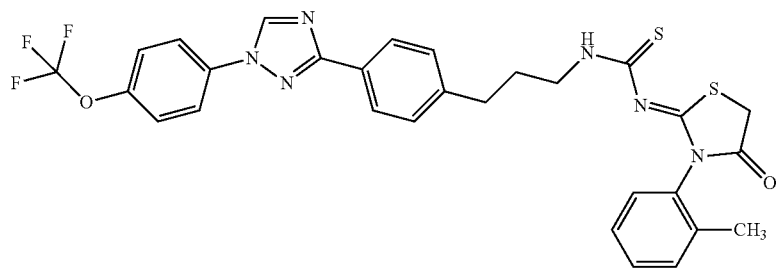 [SMILES: Cc1ccccc1N1C(=O)CS/C1=N\C(=S)NCCCc1ccc(-c2ncn(-c3ccc(OC(F)(F)F)cc3)n2)cc1]
P97 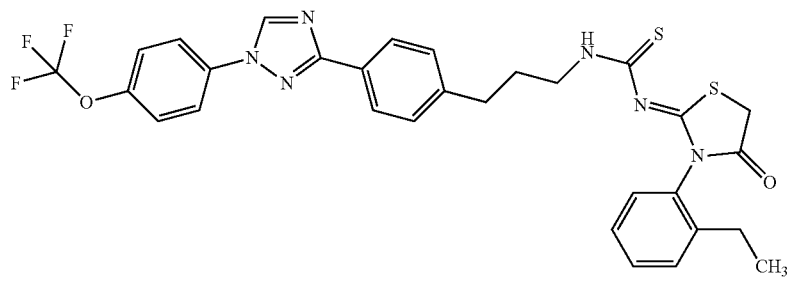 [SMILES: CCc1ccccc1N1C(=O)CS/C1=N\C(=S)NCCCc1ccc(-c2ncn(-c3ccc(OC(F)(F)F)cc3)n2)cc1]
P98 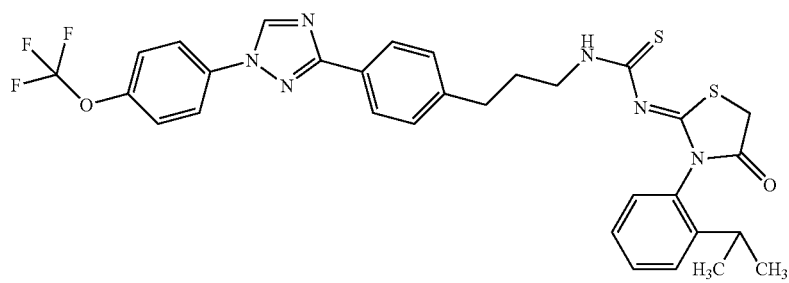 [SMILES: CC(C)c1ccccc1N1C(=O)CS/C1=N\C(=S)NCCCc1ccc(-c2ncn(-c3ccc(OC(F)(F)F)cc3)n2)cc1]
P99 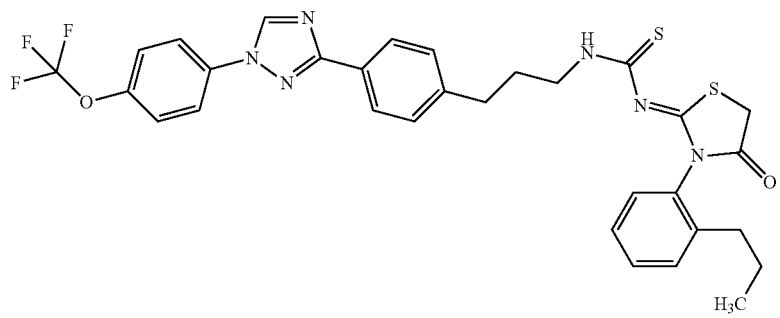 [SMILES: CCCc1ccccc1N1C(=O)CS/C1=N\C(=S)NCCCc1ccc(-c2ncn(-c3ccc(OC(F)(F)F)cc3)n2)cc1]

TABLE 1-continued
P100 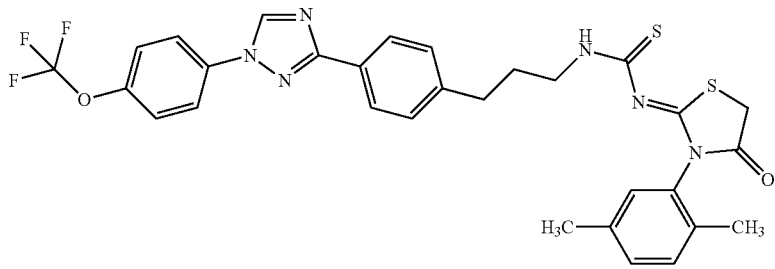 [SMILES: Cc1ccc(C)c(N2C(=O)CS/C2=N\C(=S)NCCCc2ccc(-c3ncn(-c4ccc(OC(F)(F)F)cc4)n3)cc2)c1]
P101 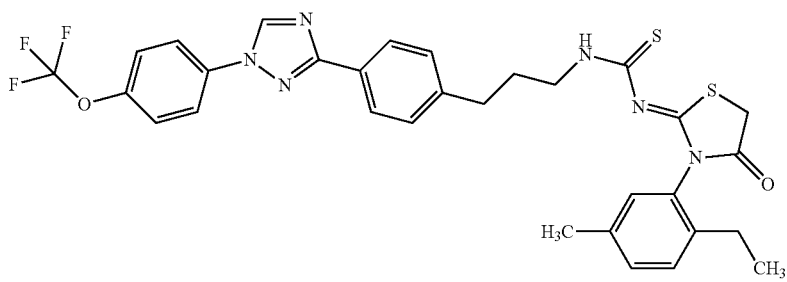 [SMILES: CCc1ccc(C)cc1N1C(=O)CS/C1=N\C(=S)NCCCc1ccc(-c2ncn(-c3ccc(OC(F)(F)F)cc3)n2)cc1]
P102 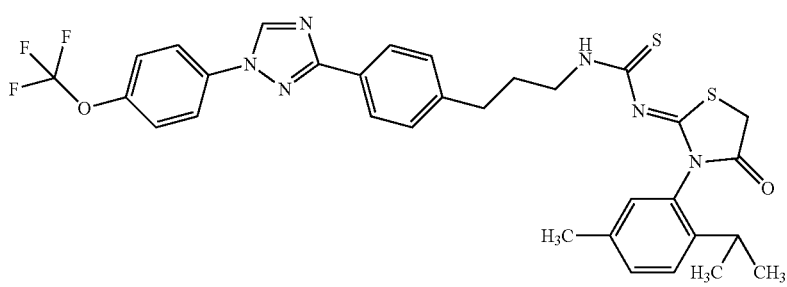
P103 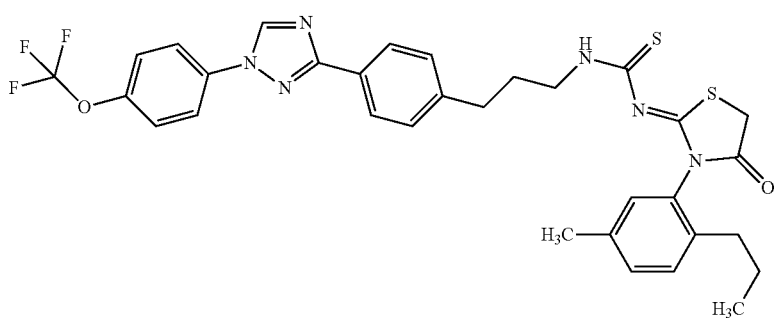 [SMILES: CCCc1ccc(C)cc1N1C(=O)CS/C1=N\C(=S)NCCCc1ccc(-c2ncn(-c3ccc(OC(F)(F)F)cc3)n2)cc1]
P104 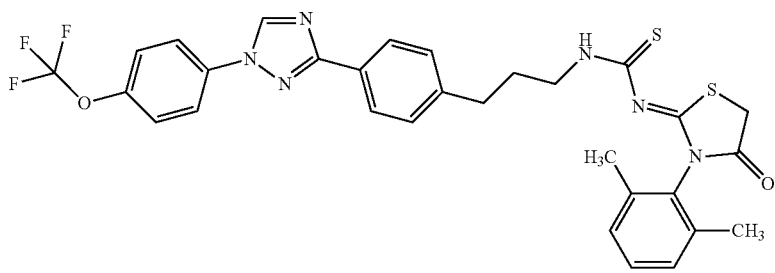 [SMILES: Cc1cccc(C)c1N1C(=O)CS/C1=N\C(=S)NCCCc1ccc(-c2ncn(-c3ccc(OC(F)(F)F)cc3)n2)cc1]

TABLE 1-continued
P105 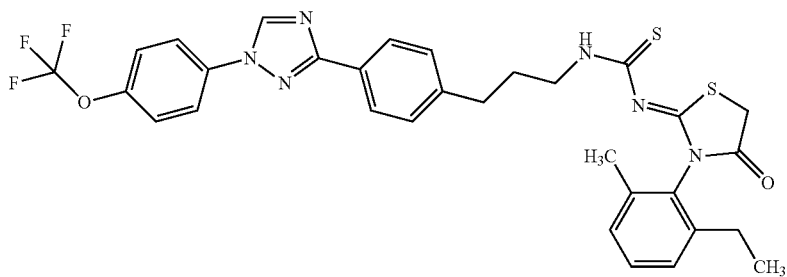 [SMILES: CCc1cccc(C)c1N1C(=O)CS/C1=N\C(=S)NCCCc1ccc(-c2ncn(-c3ccc(OC(F)(F)F)cc3)n2)cc1]
P106 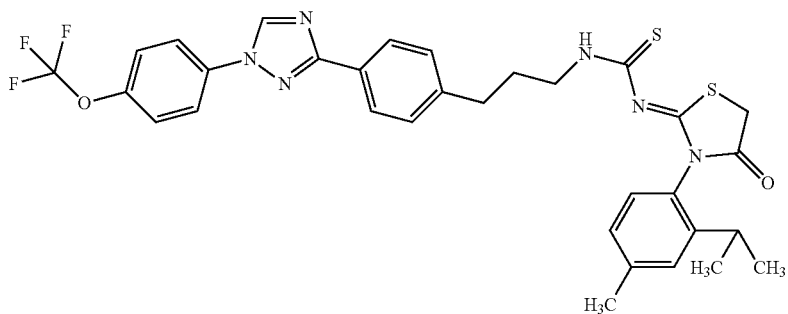 [SMILES: Cc1ccc(N2C(=O)CS/C2=N\C(=S)NCCCc2ccc(-c3ncn(-c4ccc(OC(F)(F)F)cc4)n3)cc2)c(C(C)C)c1]
P107 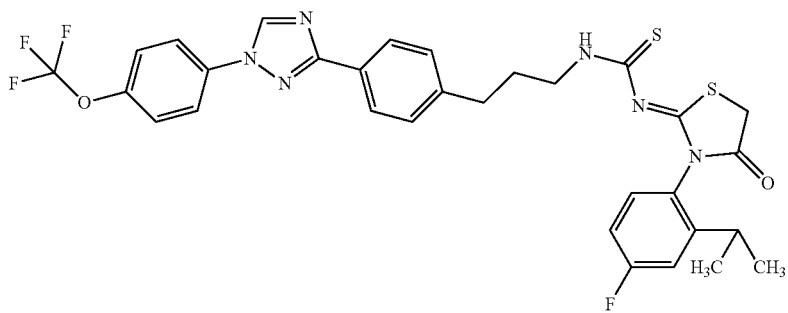 [SMILES: CC(C)c1cc(F)ccc1N1C(=O)CS/C1=N\C(=S)NCCCc1ccc(-c2ncn(-c3ccc(OC(F)(F)F)cc3)n2)cc1]
P108 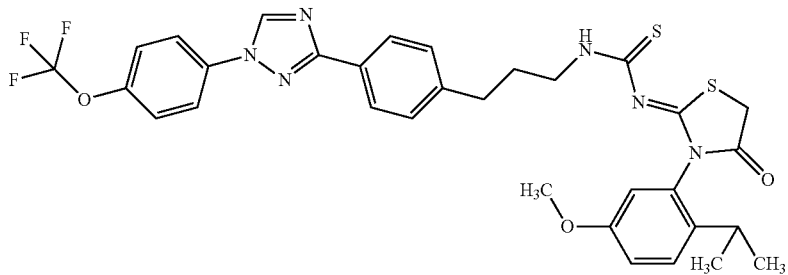 [SMILES: COc1ccc(C(C)C)c(N2C(=O)CS/C2=N\C(=S)NCCCc2ccc(-c3ncn(-c4ccc(OC(F)(F)F)cc4)n3)cc2)c1]
P109 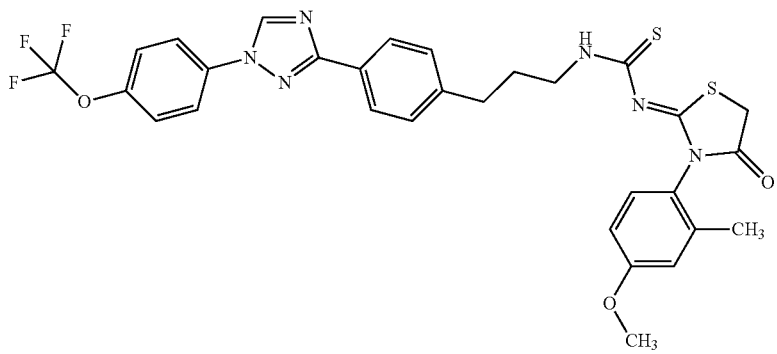 [SMILES: COc1ccc(N2C(=O)CS/C2=N\C(=S)NCCCc2ccc(-c3ncn(-c4ccc(OC(F)(F)F)cc4)n3)cc2)c(C)c1]

TABLE 1-continued
P110 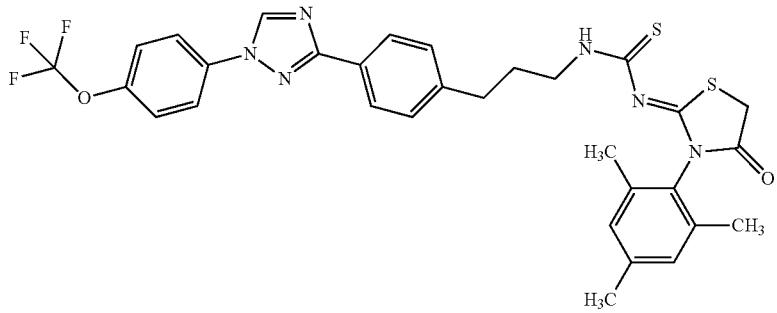 [SMILES: Cc1cc(C)c(N2C(=O)CS/C2=N\C(=S)NCCCc2ccc(-c3ncn(-c4ccc(OC(F)(F)F)cc4)n3)cc2)c(C)c1]
P111 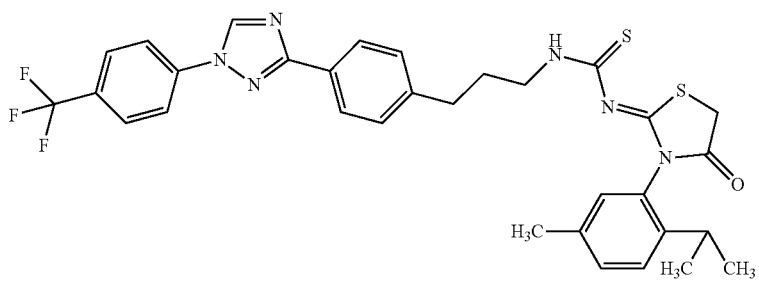 [SMILES: Cc1ccc(C(C)C)c(N2C(=O)CS/C2=N\C(=S)NCCCc2ccc(-c3ncn(-c4ccc(C(F)(F)F)cc4)n3)cc2)c1]
P112 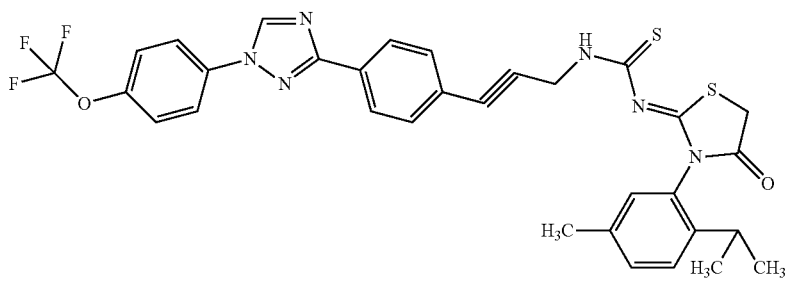 [SMILES: Cc1ccc(C(C)C)c(N2C(=O)CS/C2=N\C(=S)NCC#Cc2ccc(-c3ncn(-c4ccc(OC(F)(F)F)cc4)n3)cc2)c1]
P113 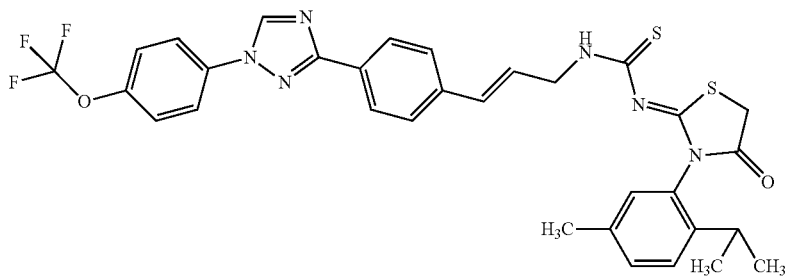
P114 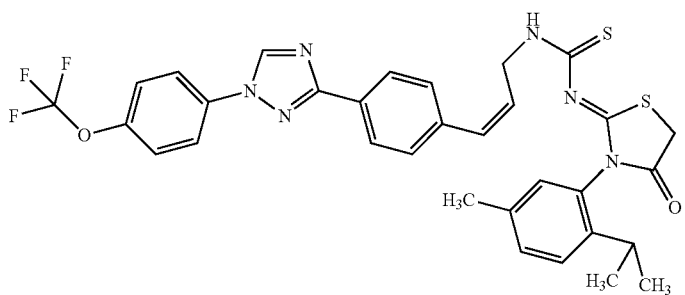 [SMILES: Cc1ccc(C(C)C)c(N2C(=O)CS/C2=N\C(=S)NC/C=C\c2ccc(-c3ncn(-c4ccc(OC(F)(F)F)cc4)n3)cc2)c1]

TABLE 1-continued
P115 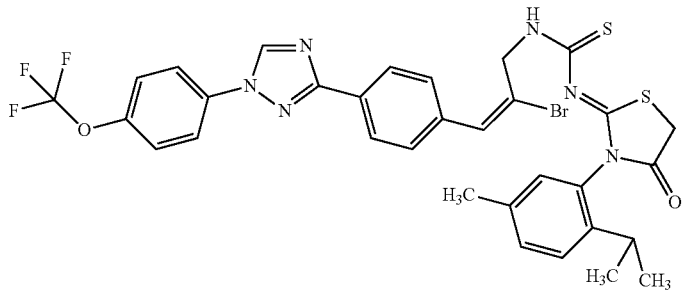 [SMILES: Cc1ccc(C(C)C)c(N2C(=O)CS/C2=N\C(=S)NC/C(Br)=C\c2ccc(-c3ncn(-c4ccc(OC(F)(F)F)cc4)n3)cc2)c1]
P116 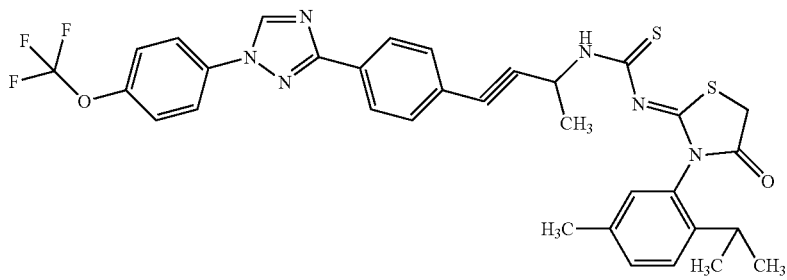 [SMILES: Cc1ccc(C(C)C)c(N2C(=O)CS/C2=N\C(=S)NC(C)C#Cc2ccc(-c3ncn(-c4ccc(OC(F)(F)F)cc4)n3)cc2)c1]
P117 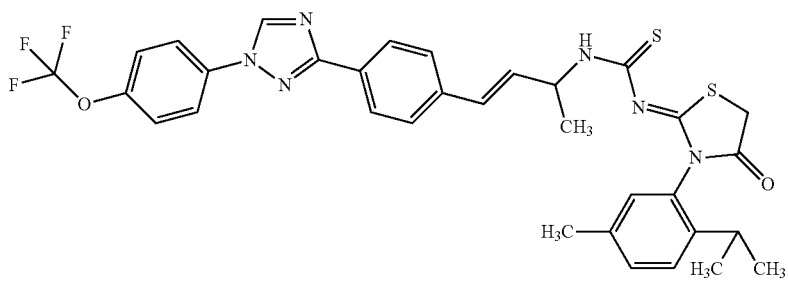
P118 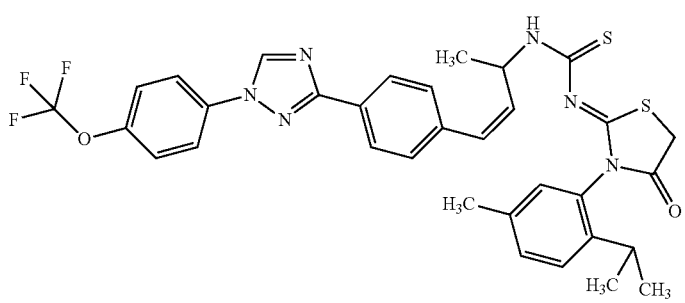 [SMILES: Cc1ccc(C(C)C)c(N2C(=O)CS/C2=N\C(=S)NC(C)/C=C\c2ccc(-c3ncn(-c4ccc(OC(F)(F)F)cc4)n3)cc2)c1]
P119 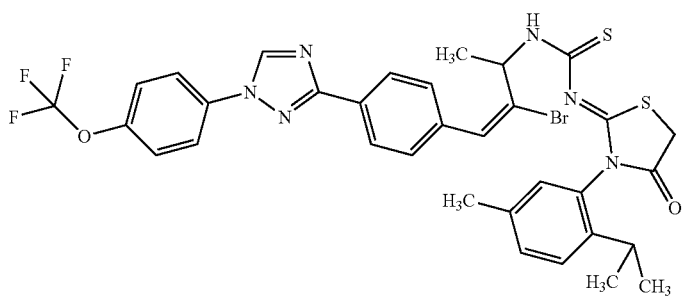 [SMILES: Cc1ccc(C(C)C)c(N2C(=O)CS/C2=N\C(=S)NC(C)/C(Br)=C\c2ccc(-c3ncn(-c4ccc(OC(F)(F)F)cc4)n3)cc2)c1]

TABLE 1-continued
P120 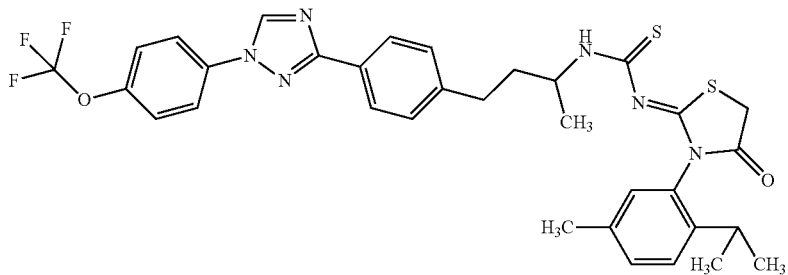 [SMILES: Cc1ccc(C(C)C)c(N2C(=O)CS/C2=N\C(=S)NC(C)CCc2ccc(-c3ncn(-c4ccc(OC(F)(F)F)cc4)n3)cc2)c1]
P121 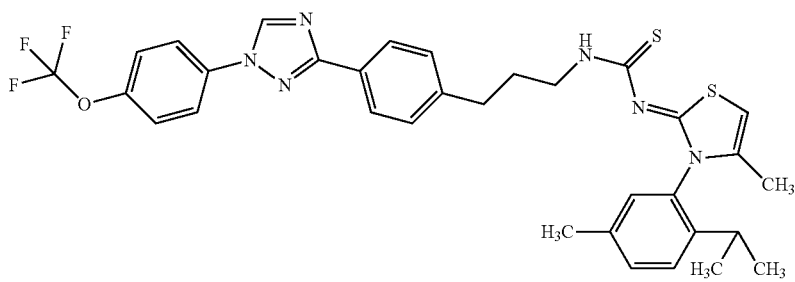 [SMILES: Cc1ccc(C(C)C)c(-n2c(C)cs/c2=N\C(=S)NCCCc2ccc(-c3ncn(-c4ccc(OC(F)(F)F)cc4)n3)cc2)c1]
P122 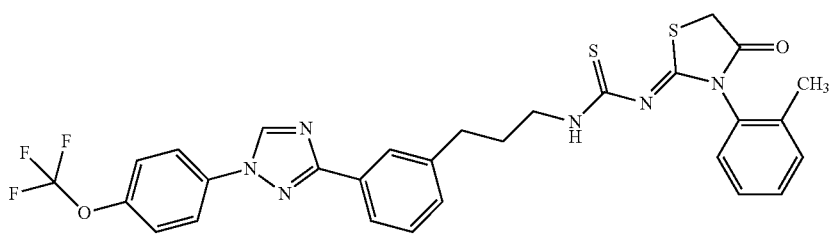 [SMILES: Cc1ccccc1N1C(=O)CS/C1=N\C(=S)NCCCc1cccc(-c2ncn(-c3ccc(OC(F)(F)F)cc3)n2)c1]
P123 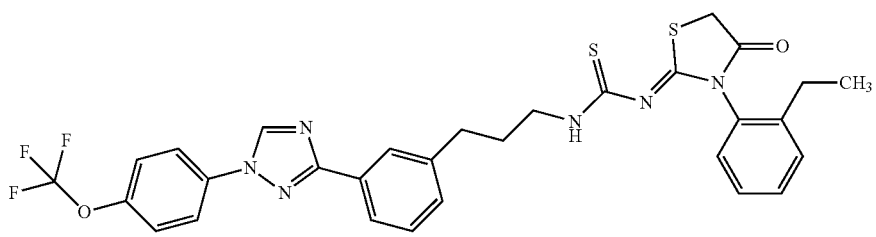 [SMILES: CCc1ccccc1N1C(=O)CS/C1=N\C(=S)NCCCc1cccc(-c2ncn(-c3ccc(OC(F)(F)F)cc3)n2)c1]
P124 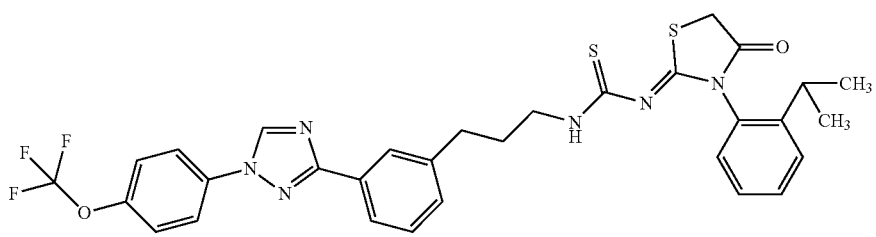 [SMILES: CC(C)c1ccccc1N1C(=O)CS/C1=N\C(=S)NCCCc1cccc(-c2ncn(-c3ccc(OC(F)(F)F)cc3)n2)c1]
P125 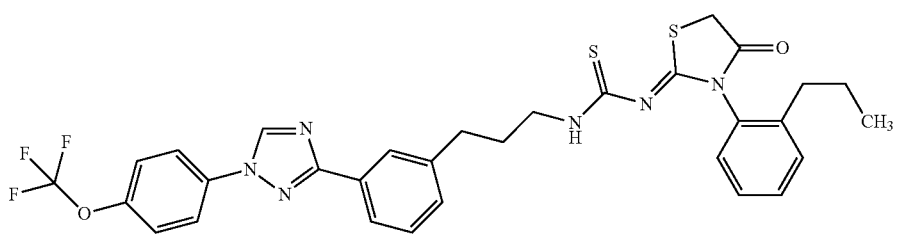 [SMILES: CCCc1ccccc1N1C(=O)CS/C1=N\C(=S)NCCCc1cccc(-c2ncn(-c3ccc(OC(F)(F)F)cc3)n2)c1]

TABLE 1-continued
P126 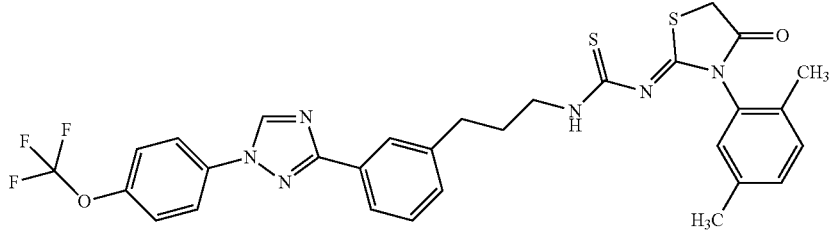 [SMILES: Cc1ccc(C)c(N2C(=O)CS/C2=N\C(=S)NCCCc2cccc(-c3ncn(-c4ccc(OC(F)(F)F)cc4)n3)c2)c1]
P127 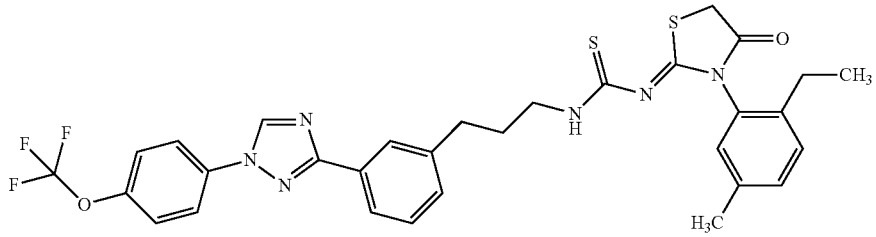 [SMILES: CCc1ccc(C)cc1N1C(=O)CS/C1=N\C(=S)NCCCc1cccc(-c2ncn(-c3ccc(OC(F)(F)F)cc3)n2)c1]
P128 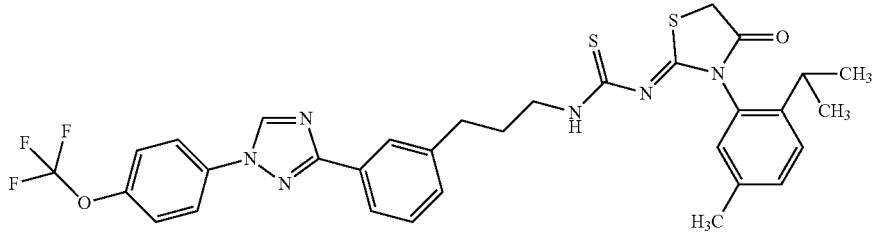
P129 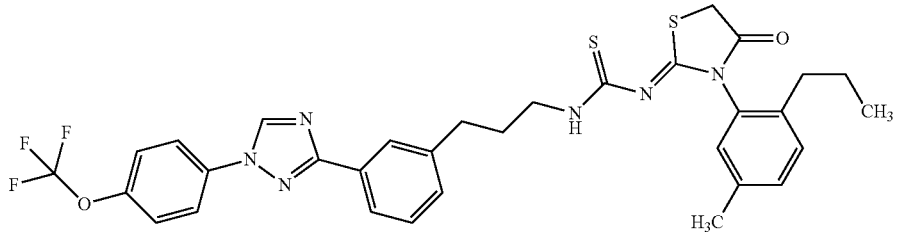 [SMILES: CCCc1ccc(C)cc1N1C(=O)CS/C1=N\C(=S)NCCCc1cccc(-c2ncn(-c3ccc(OC(F)(F)F)cc3)n2)c1]
P130 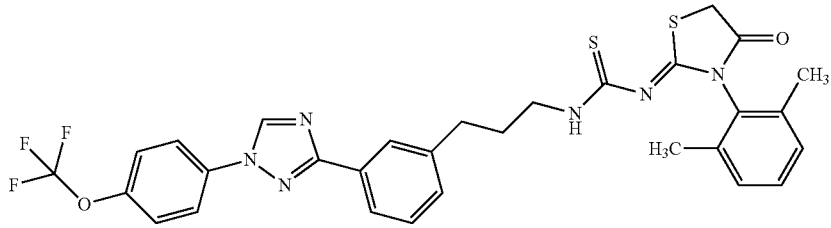 [SMILES: Cc1cccc(C)c1N1C(=O)CS/C1=N\C(=S)NCCCc1cccc(-c2ncn(-c3ccc(OC(F)(F)F)cc3)n2)c1]
P131 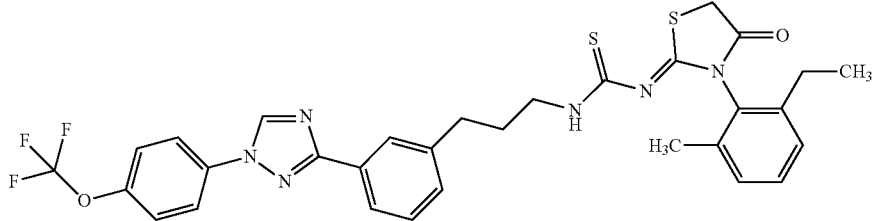 [SMILES: CCc1cccc(C)c1N1C(=O)CS/C1=N\C(=S)NCCCc1cccc(-c2ncn(-c3ccc(OC(F)(F)F)cc3)n2)c1]

TABLE 1-continued
P132 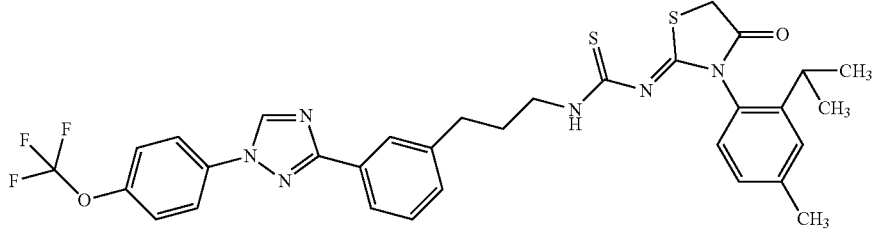 [SMILES: Cc1ccc(N2C(=O)CS/C2=N\C(=S)NCCCc2cccc(-c3ncn(-c4ccc(OC(F)(F)F)cc4)n3)c2)c(C(C)C)c1]
P133 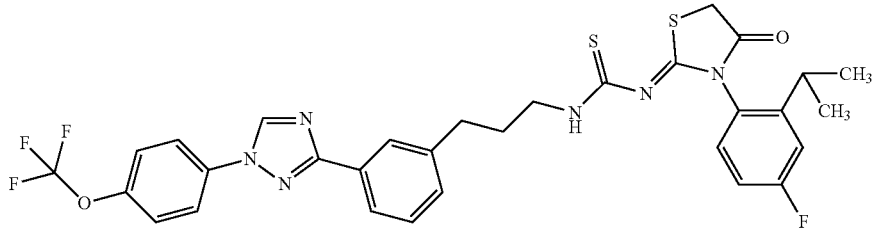 [SMILES: CC(C)c1cc(F)ccc1N1C(=O)CS/C1=N\C(=S)NCCCc1cccc(-c2ncn(-c3ccc(OC(F)(F)F)cc3)n2)c1]
P134 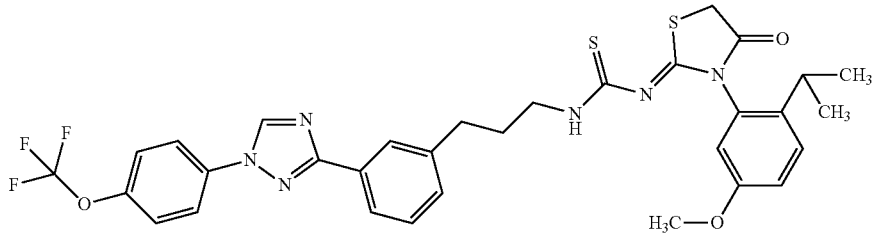 [SMILES: COc1ccc(C(C)C)c(N2C(=O)CS/C2=N\C(=S)NCCCc2cccc(-c3ncn(-c4ccc(OC(F)(F)F)cc4)n3)c2)c1]
P135 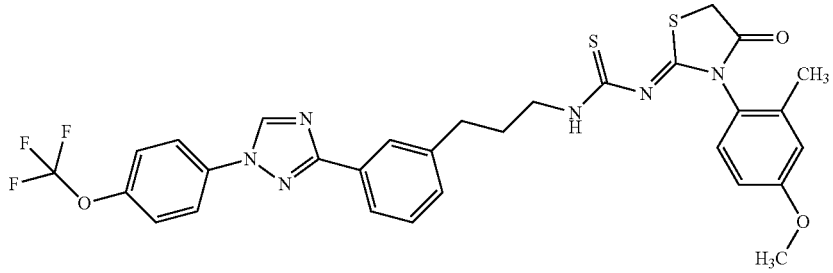 [SMILES: COc1ccc(N2C(=O)CS/C2=N\C(=S)NCCCc2cccc(-c3ncn(-c4ccc(OC(F)(F)F)cc4)n3)c2)c(C)c1]
P136 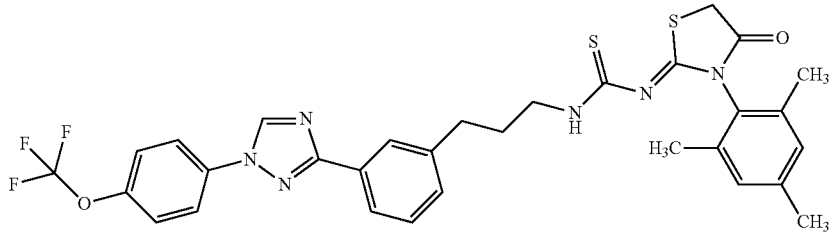 [SMILES: Cc1cc(C)c(N2C(=O)CS/C2=N\C(=S)NCCCc2cccc(-c3ncn(-c4ccc(OC(F)(F)F)cc4)n3)c2)c(C)c1]
P137 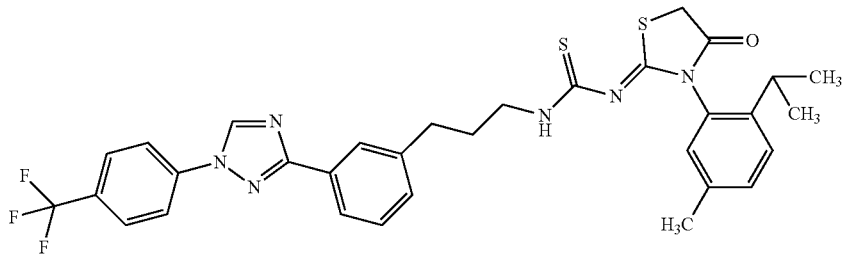 [SMILES: Cc1ccc(C(C)C)c(N2C(=O)CS/C2=N\C(=S)NCCCc2cccc(-c3ncn(-c4ccc(C(F)(F)F)cc4)n3)c2)c1]

TABLE 1-continued
P138 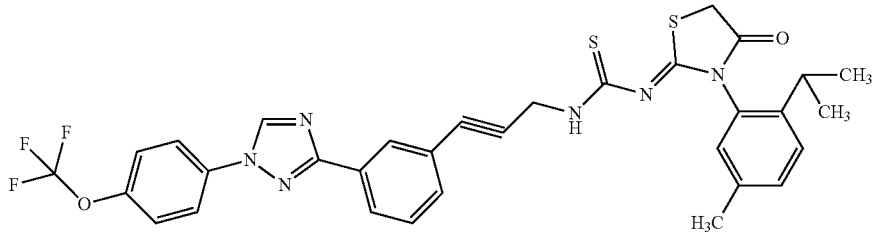 [SMILES: Cc1ccc(C(C)C)c(N2C(=O)CS/C2=N\C(=S)NCC#Cc2cccc(-c3ncn(-c4ccc(OC(F)(F)F)cc4)n3)c2)c1]
P139 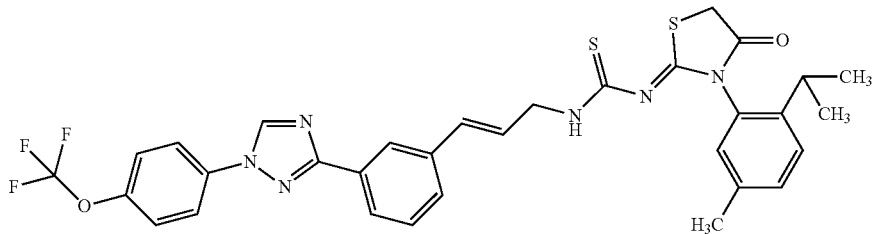
P140 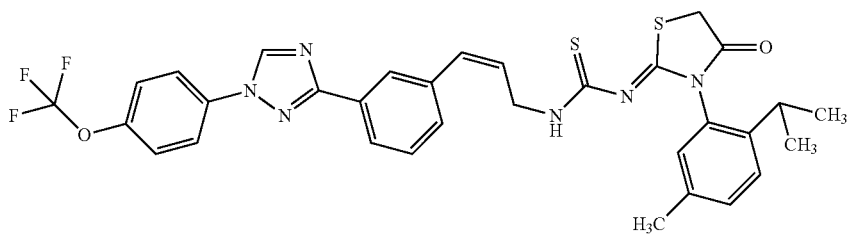
P141 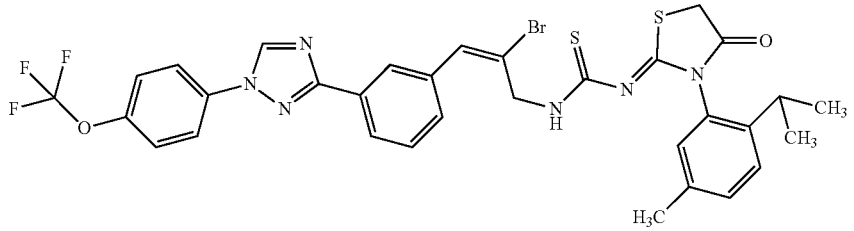
P142 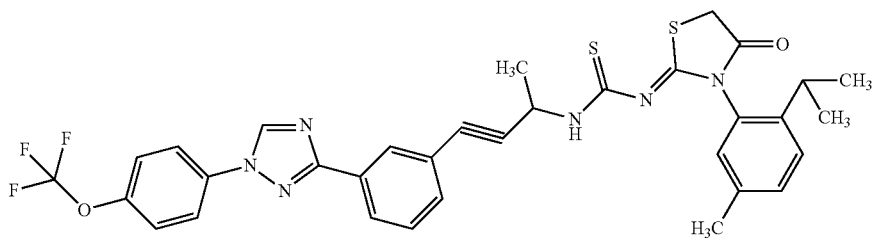
P143 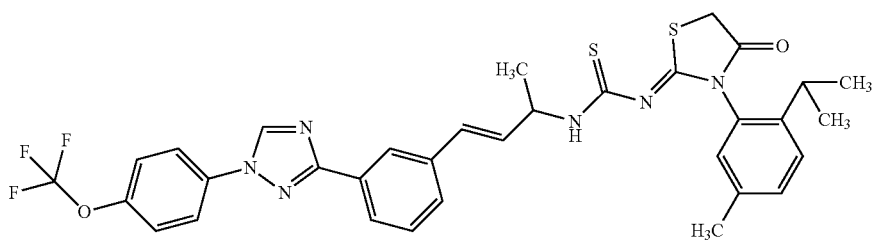 [SMILES: Cc1ccc(C(C)C)c(N2C(=O)CS/C2=N\C(=S)NC(C)/C=C/c2cccc(-c3ncn(-c4ccc(OC(F)(F)F)cc4)n3)c2)c1]

TABLE 1-continued
P144 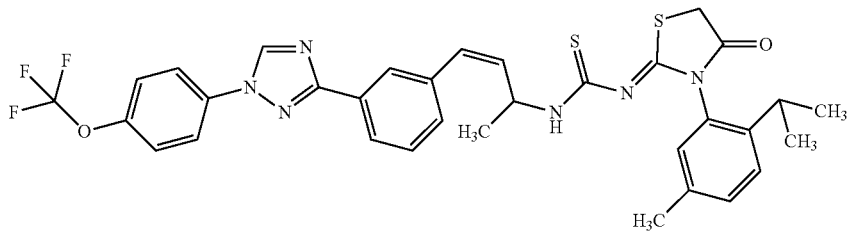 [SMILES: Cc1ccc(C(C)C)c(N2C(=O)CS/C2=N\C(=S)NC(C)/C=C\c2cccc(-c3ncn(-c4ccc(OC(F)(F)F)cc4)n3)c2)c1]
P145 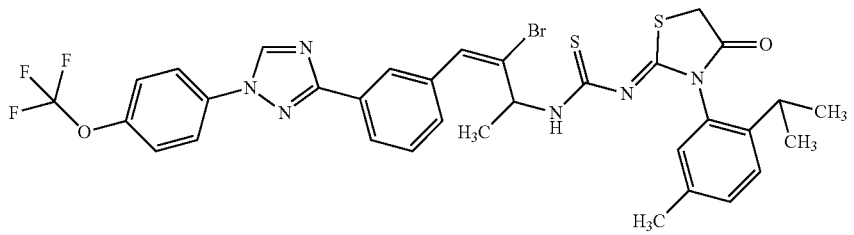 [SMILES: Cc1ccc(C(C)C)c(N2C(=O)CS/C2=N\C(=S)NC(C)/C(Br)=C\c2cccc(-c3ncn(-c4ccc(OC(F)(F)F)cc4)n3)c2)c1]
P146 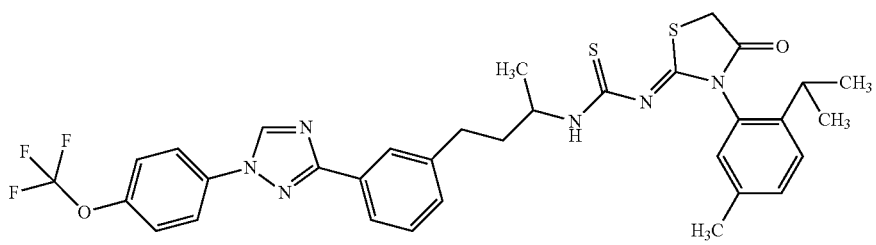 [SMILES: Cc1ccc(C(C)C)c(N2C(=O)CS/C2=N\C(=S)NC(C)CCc2cccc(-c3ncn(-c4ccc(OC(F)(F)F)cc4)n3)c2)c1]
P147 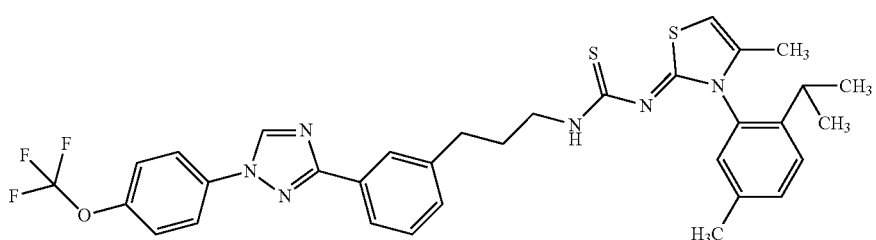
P148 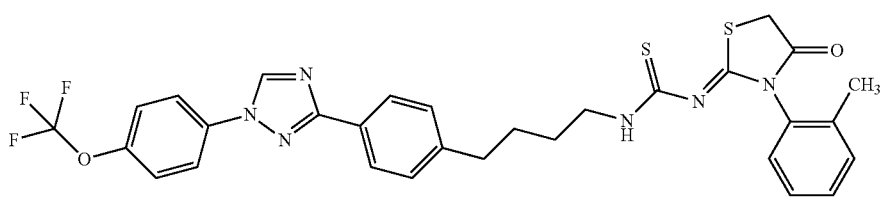 [SMILES: Cc1ccccc1N1C(=O)CS/C1=N\C(=S)NCCCCc1ccc(-c2ncn(-c3ccc(OC(F)(F)F)cc3)n2)cc1]
P149 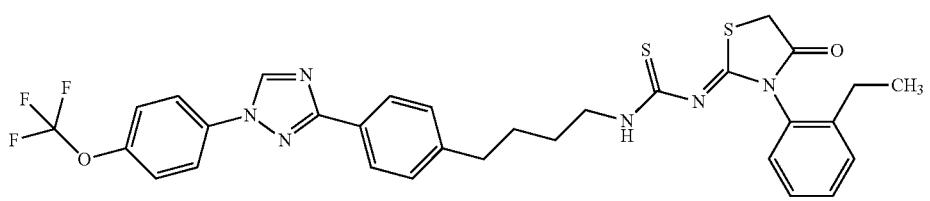 [SMILES: CCc1ccccc1N1C(=O)CS/C1=N\C(=S)NCCCCc1ccc(-c2ncn(-c3ccc(OC(F)(F)F)cc3)n2)cc1]
P150 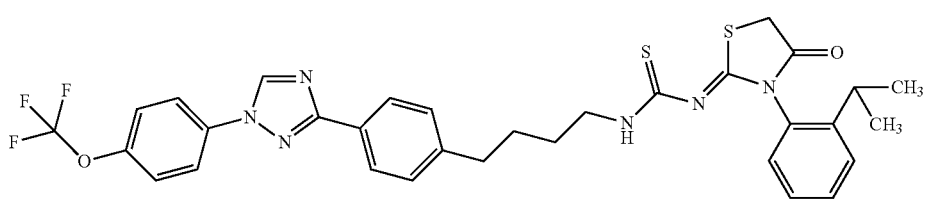 [SMILES: CC(C)c1ccccc1N1C(=O)CS/C1=N\C(=S)NCCCCc1ccc(-c2ncn(-c3ccc(OC(F)(F)F)cc3)n2)cc1]

TABLE 1-continued
P151 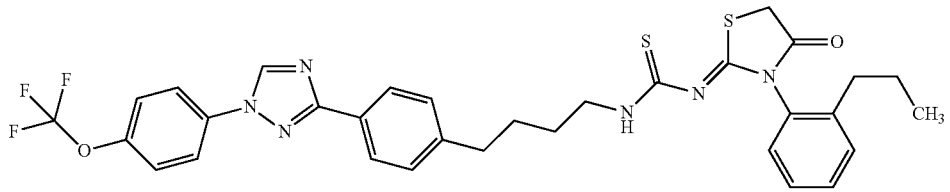 [SMILES: CCCc1ccccc1N1C(=O)CS/C1=N\C(=S)NCCCCc1ccc(-c2ncn(-c3ccc(OC(F)(F)F)cc3)n2)cc1]
P152 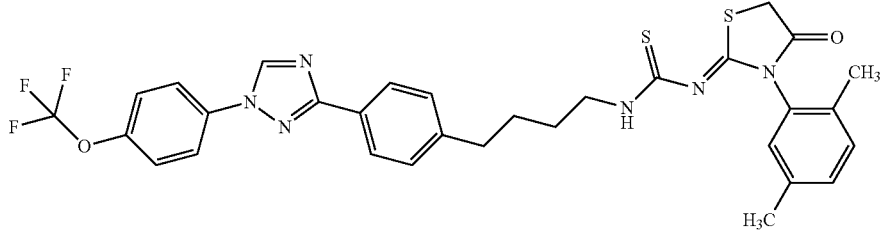 [SMILES: Cc1ccc(C)c(N2C(=O)CS/C2=N\C(=S)NCCCCc2ccc(-c3ncn(-c4ccc(OC(F)(F)F)cc4)n3)cc2)c1]
P153 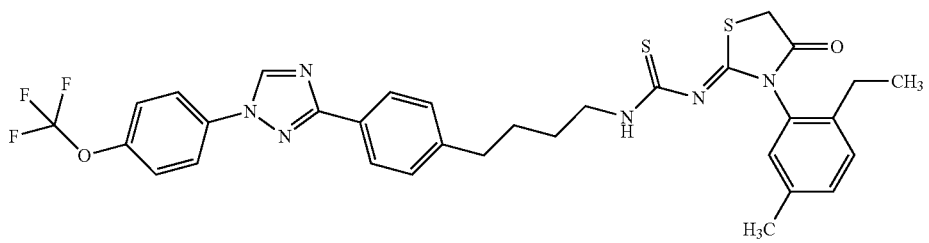 [SMILES: CCc1ccc(C)cc1N1C(=O)CS/C1=N\C(=S)NCCCCc1ccc(-c2ncn(-c3ccc(OC(F)(F)F)cc3)n2)cc1]
P154 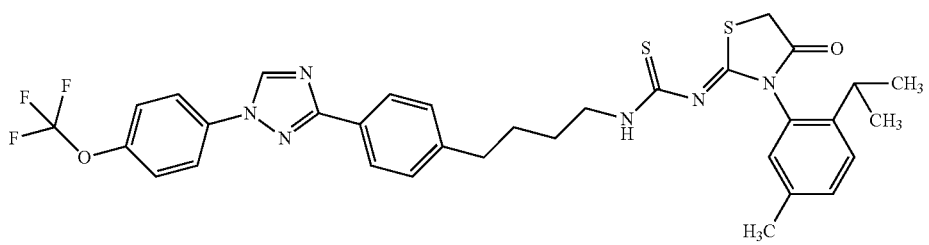
P155 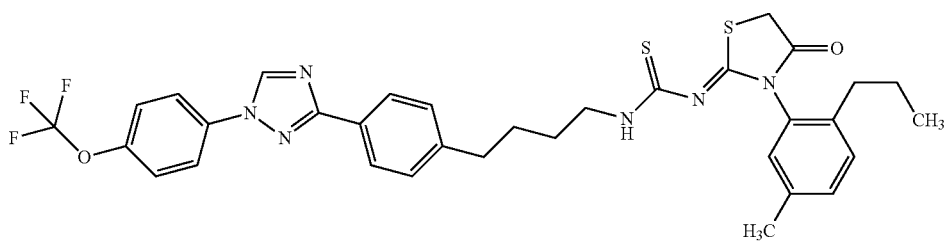 [SMILES: CCCc1ccc(C)cc1N1C(=O)CS/C1=N\C(=S)NCCCCc1ccc(-c2ncn(-c3ccc(OC(F)(F)F)cc3)n2)cc1]
P156 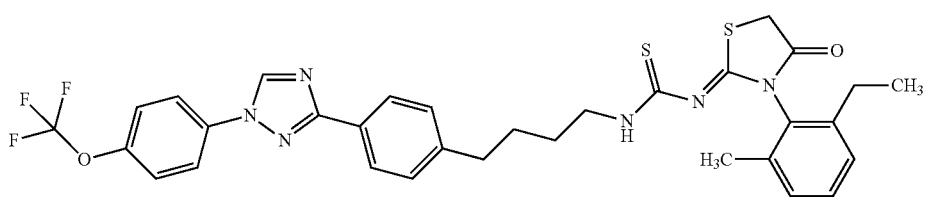 [SMILES: CCc1cccc(C)c1N1C(=O)CS/C1=N\C(=S)NCCCCc1ccc(-c2ncn(-c3ccc(OC(F)(F)F)cc3)n2)cc1]
P157 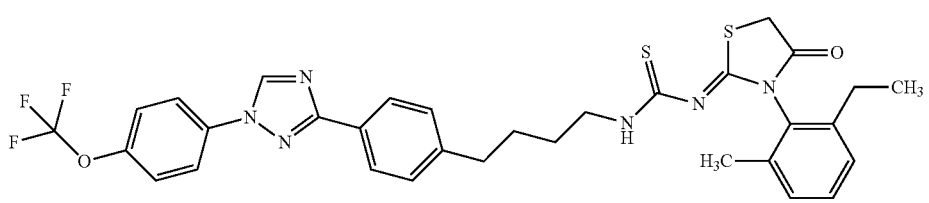 [SMILES: CCc1cccc(C)c1N1C(=O)CS/C1=N\C(=S)NCCCCc1ccc(-c2ncn(-c3ccc(OC(F)(F)F)cc3)n2)cc1]

TABLE 1-continued
P158 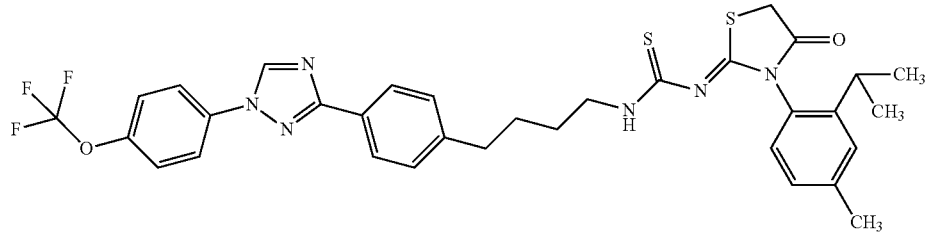 [SMILES: Cc1ccc(N2C(=O)CS/C2=N\C(=S)NCCCCc2ccc(-c3ncn(-c4ccc(OC(F)(F)F)cc4)n3)cc2)c(C(C)C)c1]
P159 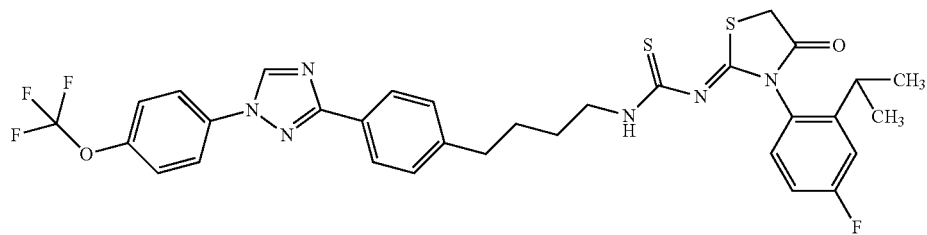 [SMILES: CC(C)c1cc(F)ccc1N1C(=O)CS/C1=N\C(=S)NCCCCc1ccc(-c2ncn(-c3ccc(OC(F)(F)F)cc3)n2)cc1]
P160 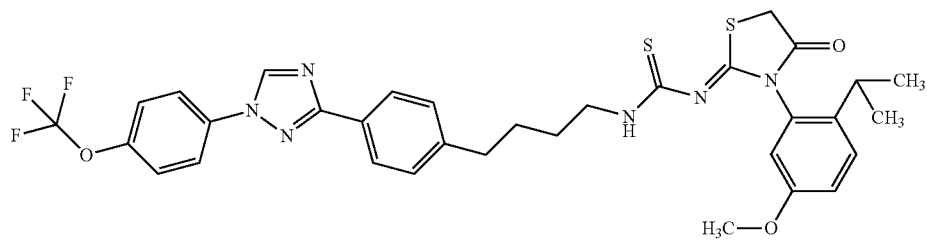 [SMILES: COc1ccc(C(C)C)c(N2C(=O)CS/C2=N\C(=S)NCCCCc2ccc(-c3ncn(-c4ccc(OC(F)(F)F)cc4)n3)cc2)c1]
P161 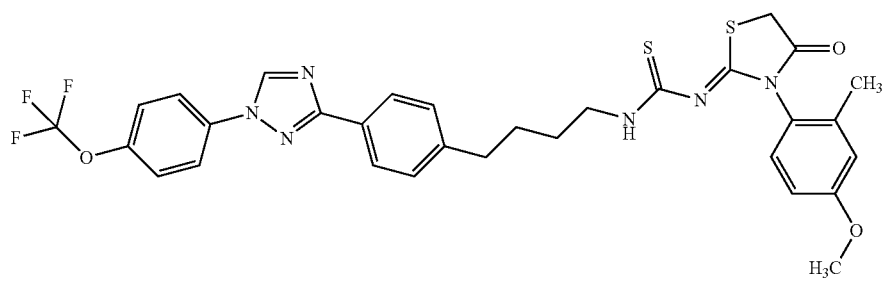 [SMILES: COc1ccc(N2C(=O)CS/C2=N\C(=S)NCCCCc2ccc(-c3ncn(-c4ccc(OC(F)(F)F)cc4)n3)cc2)c(C)c1]
P162 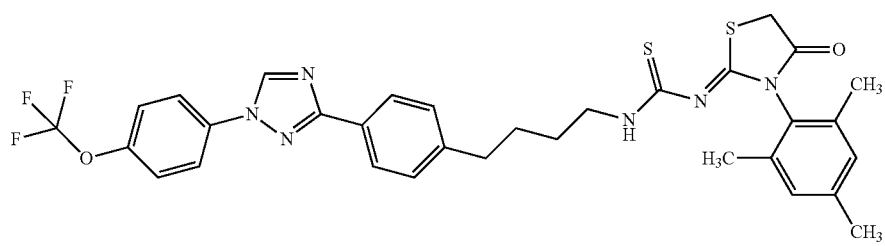 [SMILES: Cc1cc(C)c(N2C(=O)CS/C2=N\C(=S)NCCCCc2ccc(-c3ncn(-c4ccc(OC(F)(F)F)cc4)n3)cc2)c(C)c1]
P163 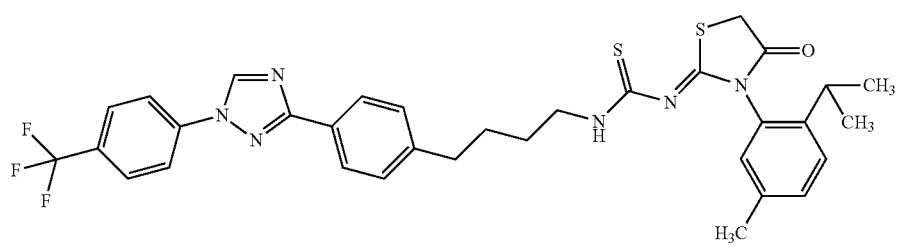 [SMILES: Cc1ccc(C(C)C)c(N2C(=O)CS/C2=N\C(=S)NCCCCc2ccc(-c3ncn(-c4ccc(C(F)(F)F)cc4)n3)cc2)c1]

TABLE 1-continued
P164 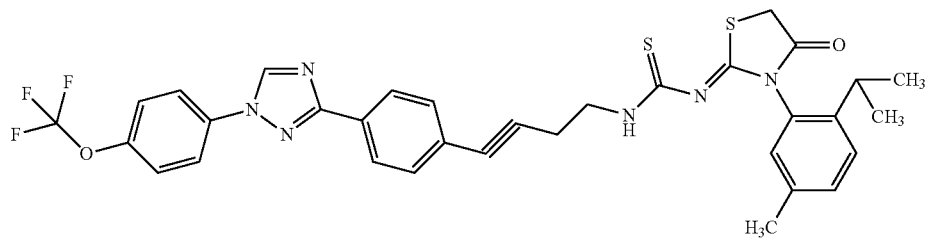 [SMILES: Cc1ccc(C(C)C)c(N2C(=O)CS/C2=N\C(=S)NCCC#Cc2ccc(-c3ncn(-c4ccc(OC(F)(F)F)cc4)n3)cc2)c1]
P165 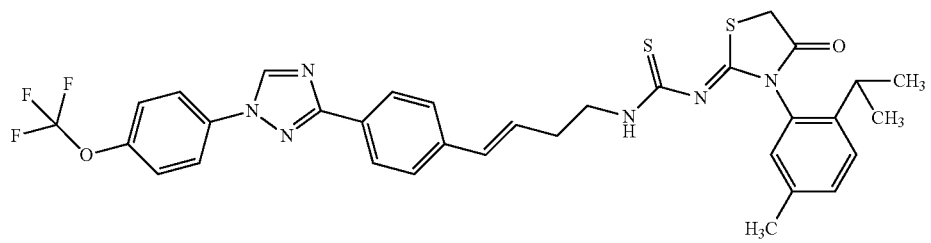 [SMILES: Cc1ccc(C(C)C)c(N2C(=O)CS/C2=N\C(=S)NCC/C=C/c2ccc(-c3ncn(-c4ccc(OC(F)(F)F)cc4)n3)cc2)c1]
P166 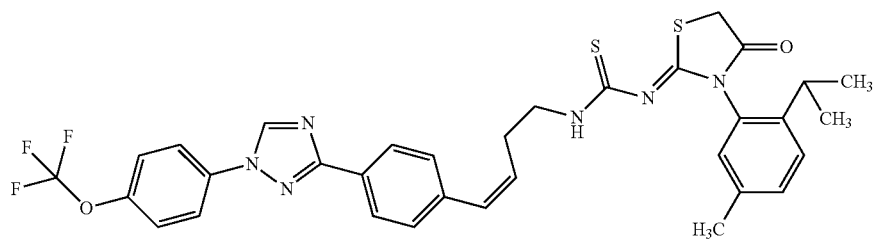 [SMILES: Cc1ccc(C(C)C)c(N2C(=O)CS/C2=N\C(=S)NCC/C=C\c2ccc(-c3ncn(-c4ccc(OC(F)(F)F)cc4)n3)cc2)c1]
P167 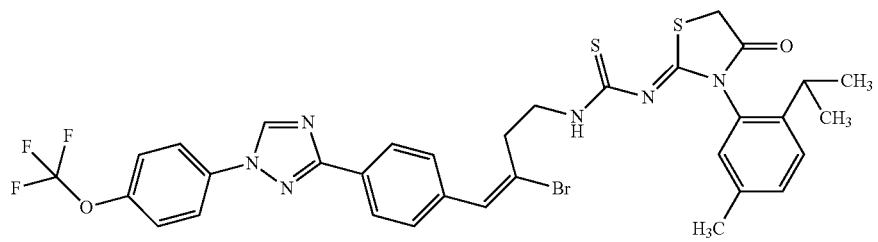
P168 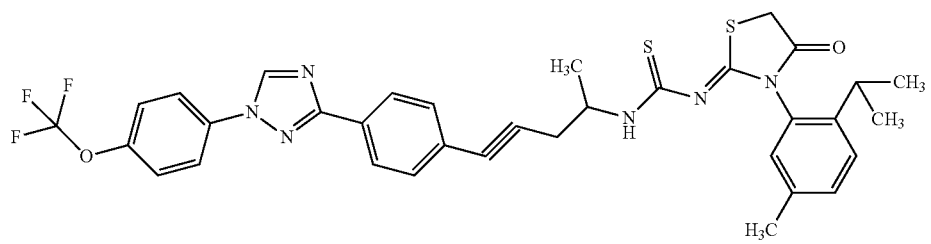 [SMILES: Cc1ccc(C(C)C)c(N2C(=O)CS/C2=N\C(=S)NC(C)CC#Cc2ccc(-c3ncn(-c4ccc(OC(F)(F)F)cc4)n3)cc2)c1]
P169 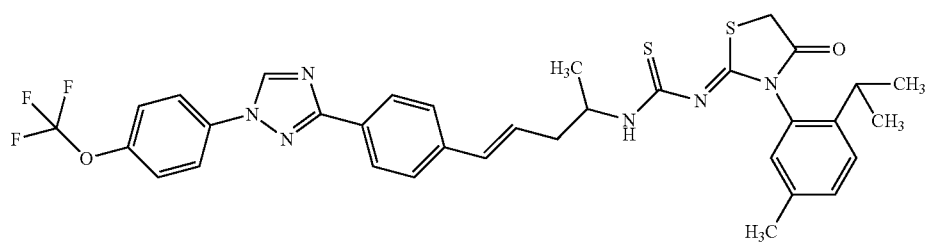

TABLE 1-continued
P170 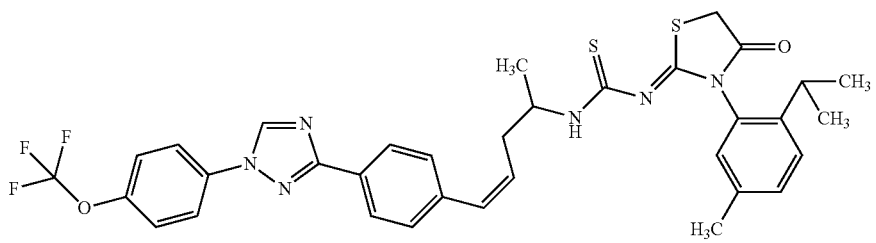
P171 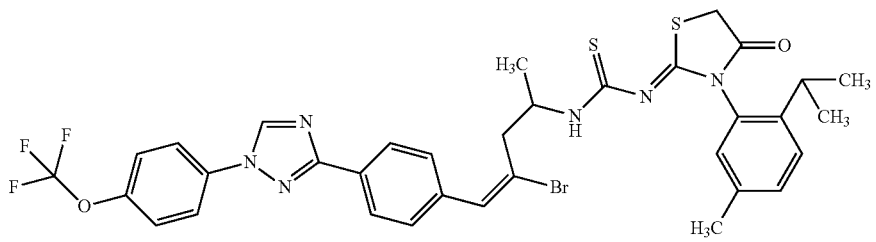
P172 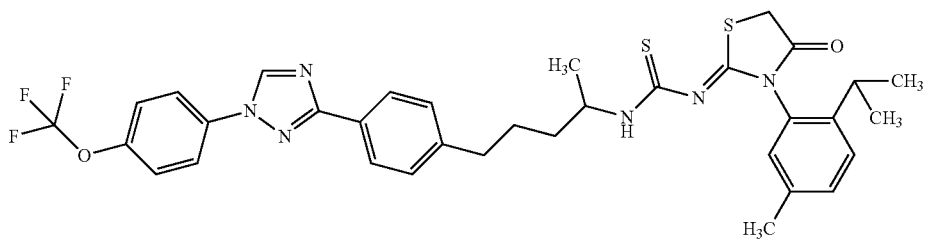
P173 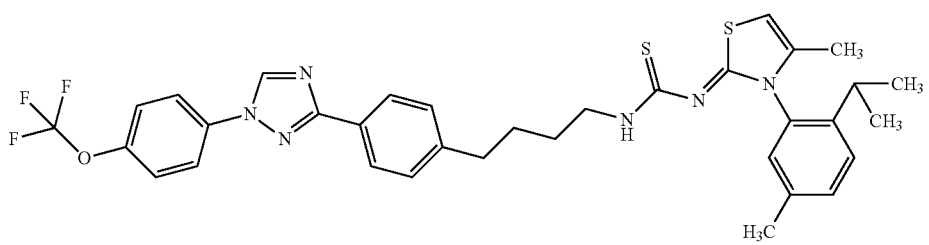
P174 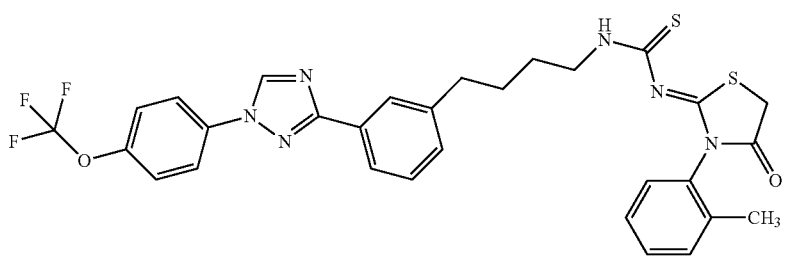 [SMILES: Cc1ccccc1N1C(=O)CS/C1=N\C(=S)NCCCCc1cccc(-c2ncn(-c3ccc(OC(F)(F)F)cc3)n2)c1]
P175 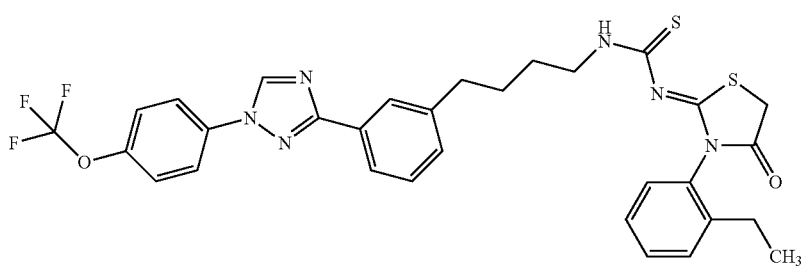 [SMILES: CCc1ccccc1N1C(=O)CS/C1=N\C(=S)NCCCCc1cccc(-c2ncn(-c3ccc(OC(F)(F)F)cc3)n2)c1]

TABLE 1-continued
P176 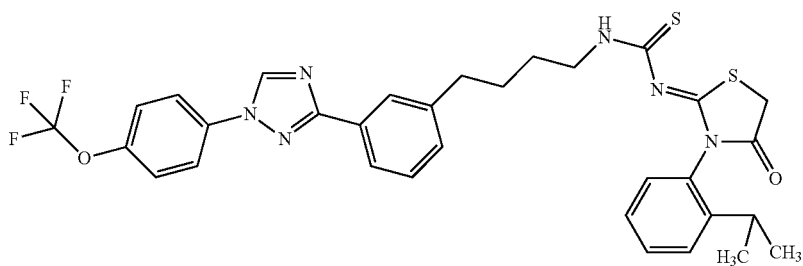 [SMILES: CC(C)c1ccccc1N1C(=O)CS/C1=N\C(=S)NCCCCc1cccc(-c2ncn(-c3ccc(OC(F)(F)F)cc3)n2)c1]
P177 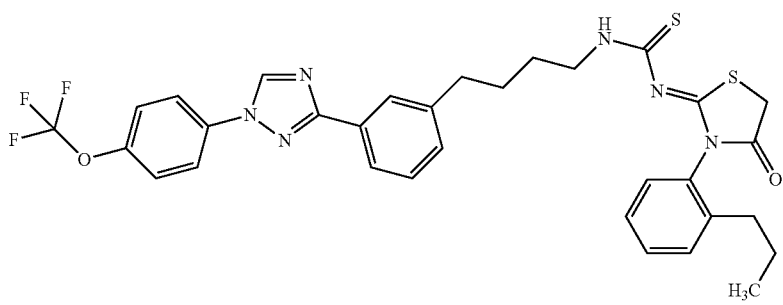 [SMILES: CCCc1ccccc1N1C(=O)CS/C1=N\C(=S)NCCCCc1cccc(-c2ncn(-c3ccc(OC(F)(F)F)cc3)n2)c1]
P178 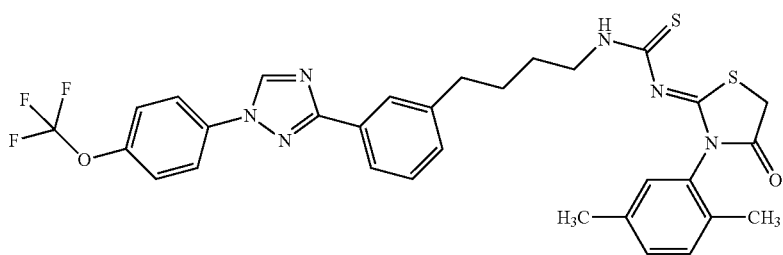 [SMILES: Cc1ccc(C)c(N2C(=O)CS/C2=N\C(=S)NCCCCc2cccc(-c3ncn(-c4ccc(OC(F)(F)F)cc4)n3)c2)c1]
P179 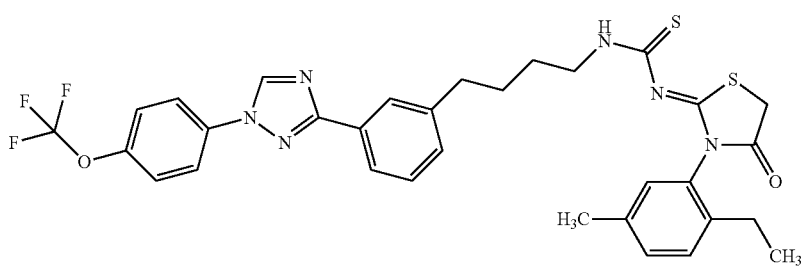 [SMILES: CCc1ccc(C)cc1N1C(=O)CS/C1=N\C(=S)NCCCCc1cccc(-c2ncn(-c3ccc(OC(F)(F)F)cc3)n2)c1]
P180 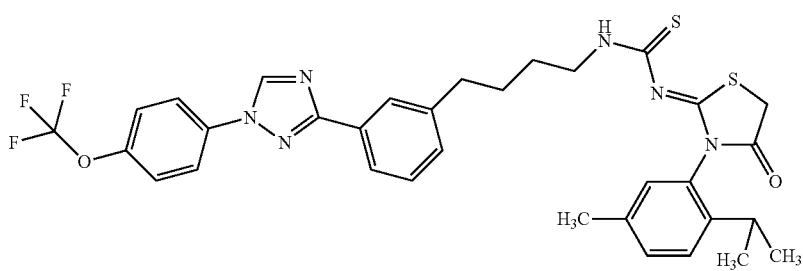 [SMILES: Cc1ccc(C(C)C)c(N2C(=O)CS/C2=N\C(=S)NCCCCc2cccc(-c3ncn(-c4ccc(OC(F)(F)F)cc4)n3)c2)c1]

TABLE 1-continued
P181 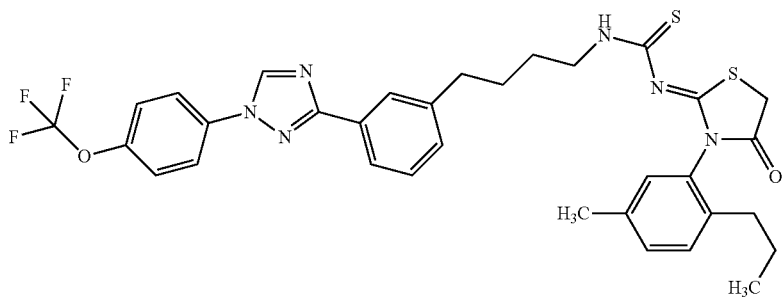 [SMILES: CCCc1ccc(C)cc1N1C(=O)CS/C1=N\C(=S)NCCCCc1cccc(-c2ncn(-c3ccc(OC(F)(F)F)cc3)n2)c1]
P182 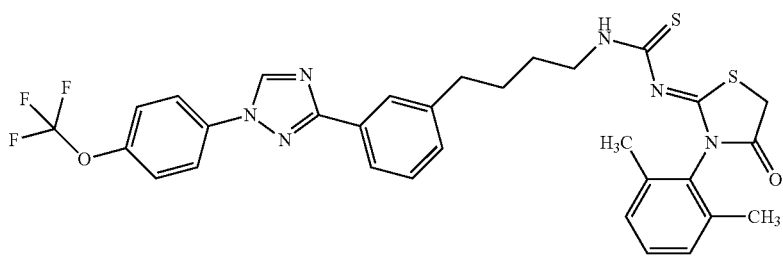 [SMILES: Cc1cccc(C)c1N1C(=O)CS/C1=N\C(=S)NCCCCc1cccc(-c2ncn(-c3ccc(OC(F)(F)F)cc3)n2)c1]
P183 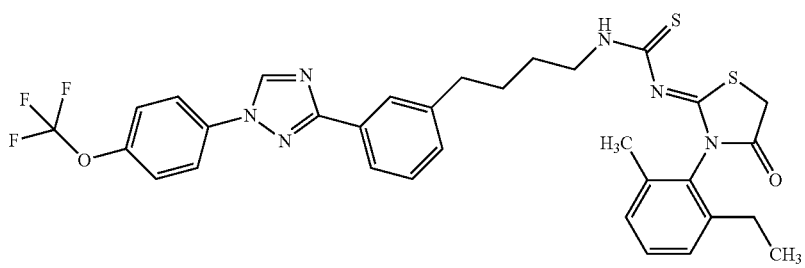 [SMILES: CCc1cccc(C)c1N1C(=O)CS/C1=N\C(=S)NCCCCc1cccc(-c2ncn(-c3ccc(OC(F)(F)F)cc3)n2)c1]
P184 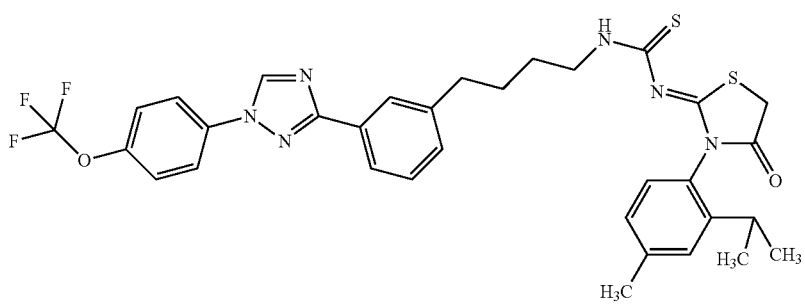 [SMILES: Cc1ccc(N2C(=O)CS/C2=N\C(=S)NCCCCc2cccc(-c3ncn(-c4ccc(OC(F)(F)F)cc4)n3)c2)c(C(C)C)c1]
P185 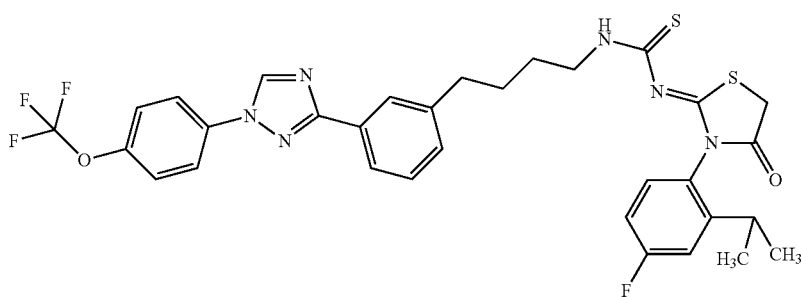 [SMILES: CC(C)c1cc(F)ccc1N1C(=O)CS/C1=N\C(=S)NCCCCc1cccc(-c2ncn(-c3ccc(OC(F)(F)F)cc3)n2)c1]

TABLE 1-continued
P186 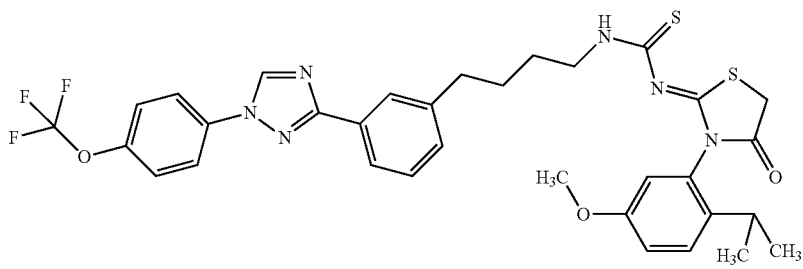 [SMILES: COc1ccc(C(C)C)c(N2C(=O)CS/C2=N\C(=S)NCCCCc2cccc(-c3ncn(-c4ccc(OC(F)(F)F)cc4)n3)c2)c1]
P187 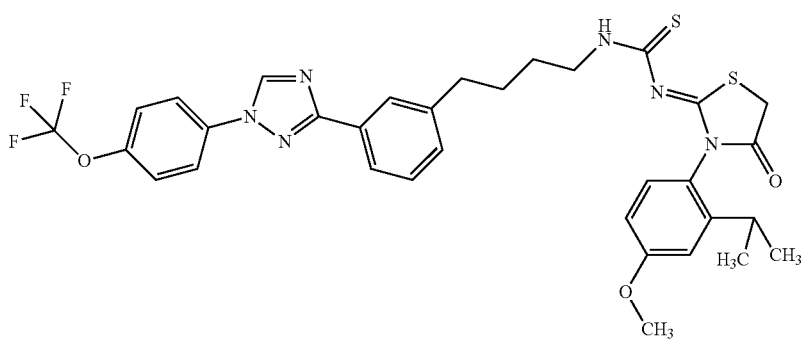 [SMILES: COc1ccc(N2C(=O)CS/C2=N\C(=S)NCCCCc2cccc(-c3ncn(-c4ccc(OC(F)(F)F)cc4)n3)c2)c(C(C)C)c1]
P188 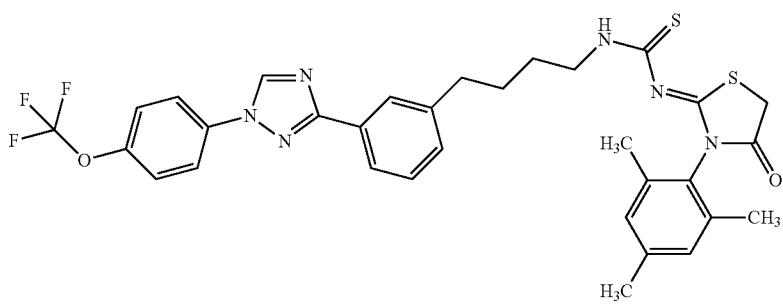 [SMILES: Cc1cc(C)c(N2C(=O)CS/C2=N\C(=S)NCCCCc2cccc(-c3ncn(-c4ccc(OC(F)(F)F)cc4)n3)c2)c(C)c1]
P189 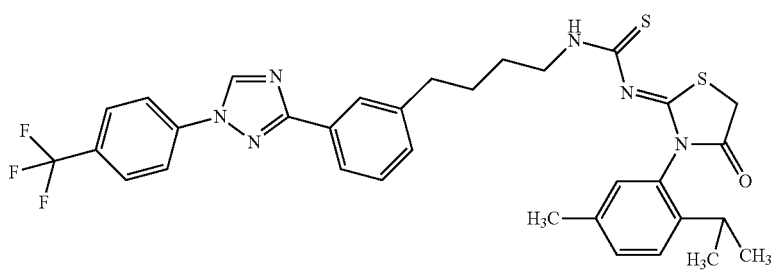 [SMILES: Cc1ccc(C(C)C)c(N2C(=O)CS/C2=N\C(=S)NCCCCc2cccc(-c3ncn(-c4ccc(C(F)(F)F)cc4)n3)c2)c1]
P190 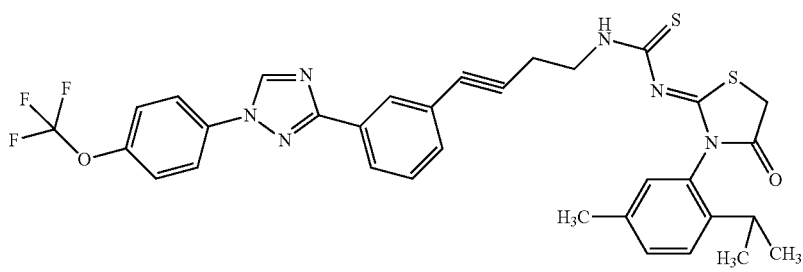

TABLE 1-continued
P191 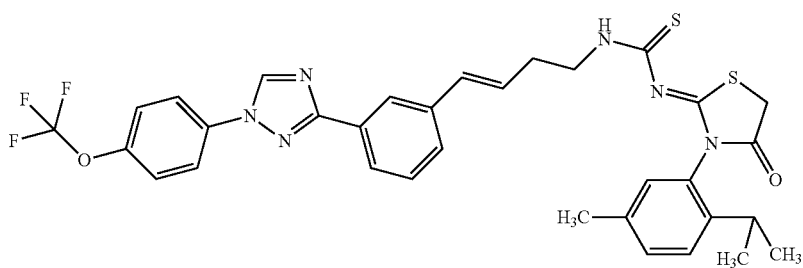
P192 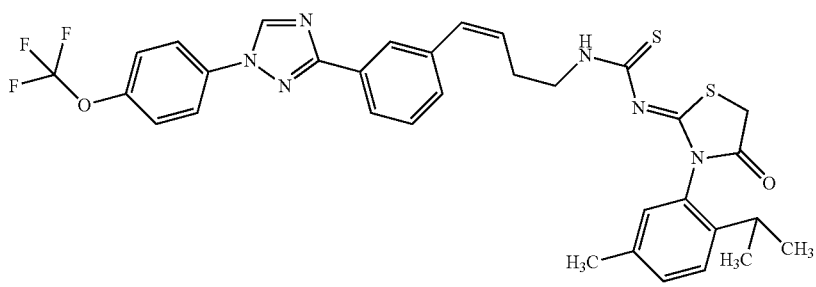 [SMILES: Cc1ccc(C(C)C)c(N2C(=O)CS/C2=N\C(=S)NCC/C=C\c2cccc(-c3ncn(-c4ccc(OC(F)(F)F)cc4)n3)c2)c1]
P193 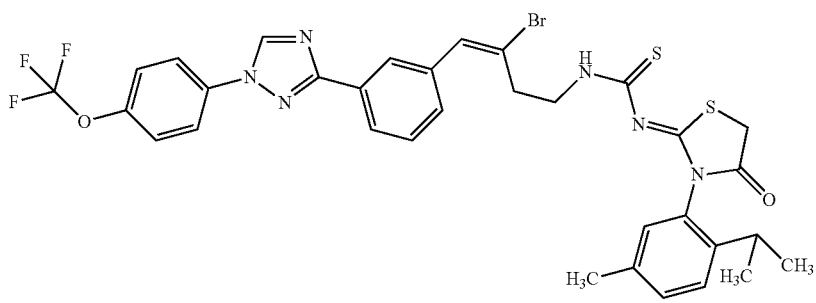 [SMILES: Cc1ccc(C(C)C)c(N2C(=O)CS/C2=N\C(=S)NCC/C(Br)=C\c2cccc(-c3ncn(-c4ccc(OC(F)(F)F)cc4)n3)c2)c1]
P194 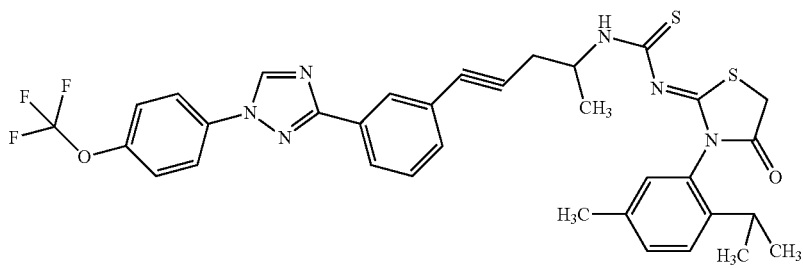 [SMILES: Cc1ccc(C(C)C)c(N2C(=O)CS/C2=N\C(=S)NC(C)CC#Cc2cccc(-c3ncn(-c4ccc(OC(F)(F)F)cc4)n3)c2)c1]
P195 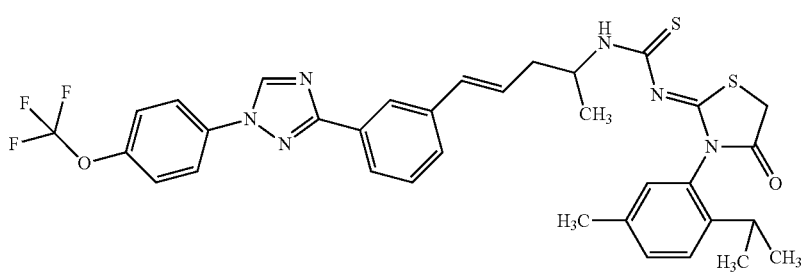

TABLE 1-continued
P196 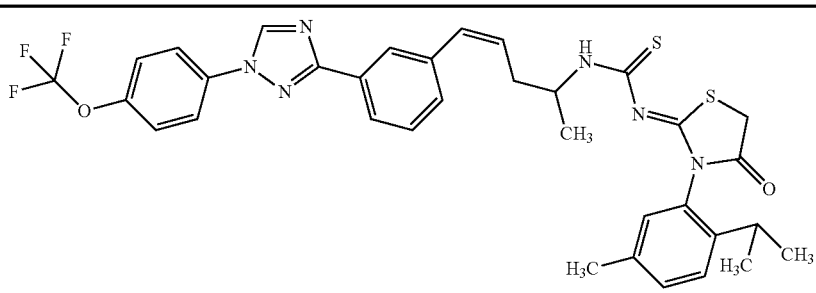
P197 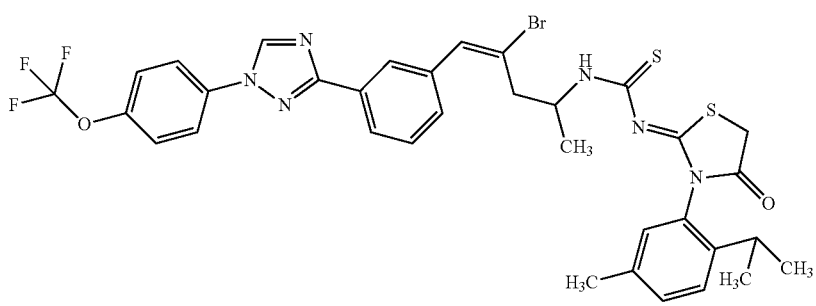 [SMILES: Cc1ccc(C(C)C)c(N2C(=O)CS/C2=N\C(=S)NC(C)C/C(Br)=C\c2cccc(-c3ncn(-c4ccc(OC(F)(F)F)cc4)n3)c2)c1]
P198 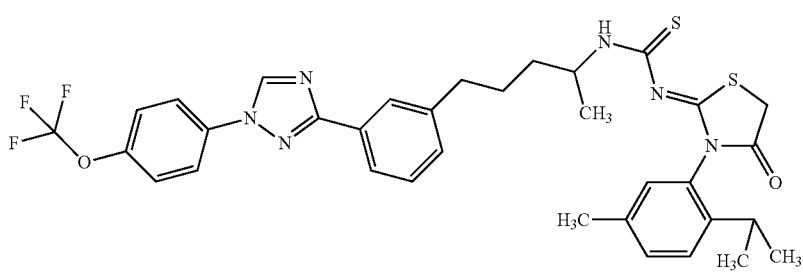
P199 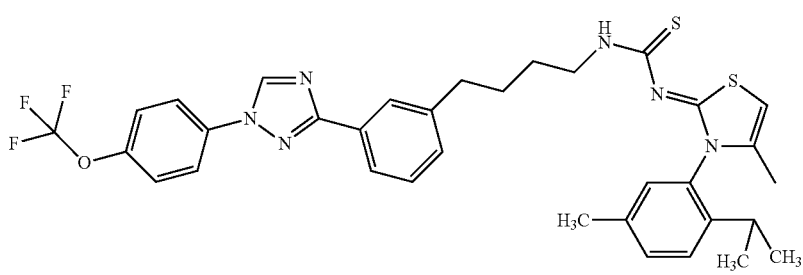
P200 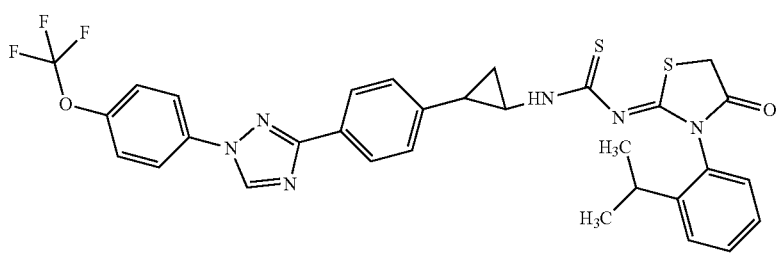 [SMILES: CC(C)c1ccccc1N1C(=O)CS/C1=N\C(=S)NC1CC1c1ccc(-c2ncn(-c3ccc(OC(F)(F)F)cc3)n2)cc1]
P201 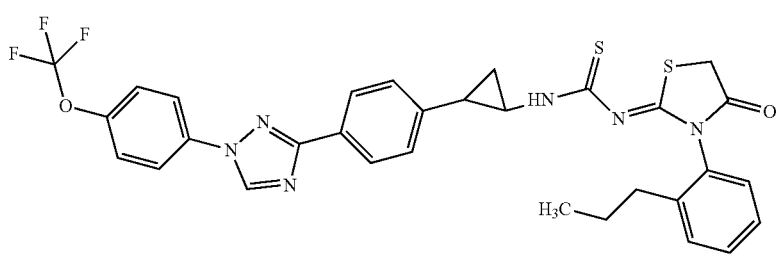 [SMILES: CCCc1ccccc1N1C(=O)CS/C1=N\C(=S)NC1CC1c1ccc(-c2ncn(-c3ccc(OC(F)(F)F)cc3)n2)cc1]

TABLE 1-continued
P202 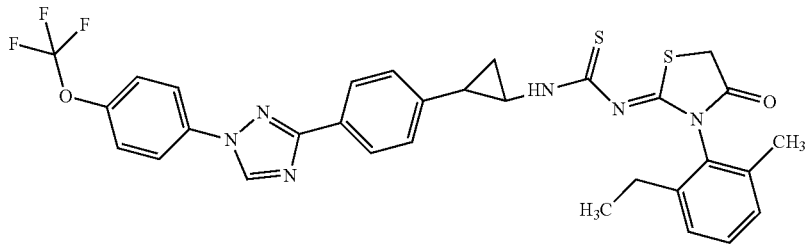 [SMILES: CCc1cccc(C)c1N1C(=O)CS/C1=N\C(=S)NC1CC1c1ccc(-c2ncn(-c3ccc(OC(F)(F)F)cc3)n2)cc1]
P203 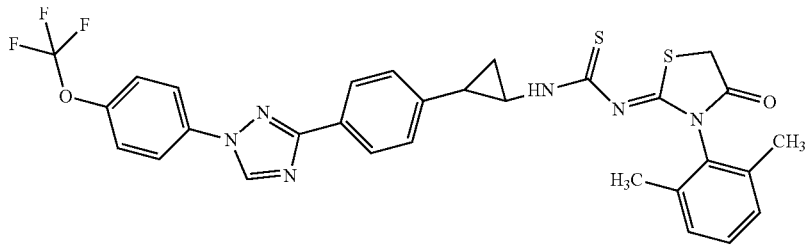 [SMILES: Cc1cccc(C)c1N1C(=O)CS/C1=N\C(=S)NC1CC1c1ccc(-c2ncn(-c3ccc(OC(F)(F)F)cc3)n2)cc1]
P204 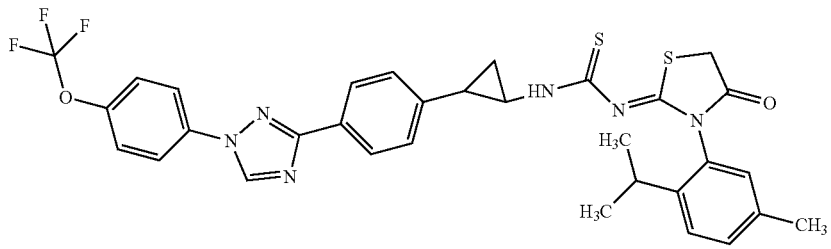 [SMILES: Cc1ccc(C(C)C)c(N2C(=O)CS/C2=N\C(=S)NC2CC2c2ccc(-c3ncn(-c4ccc(OC(F)(F)F)cc4)n3)cc2)c1]
P205 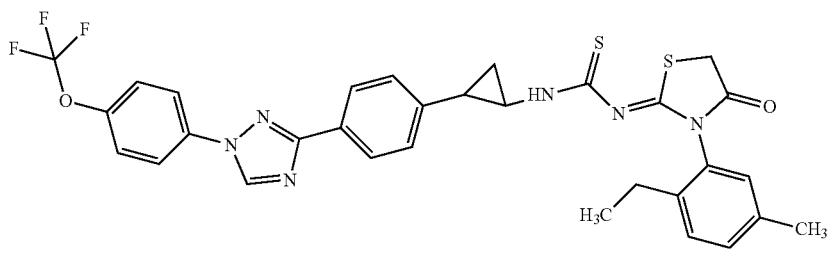 [SMILES: CCc1ccc(C)cc1N1C(=O)CS/C1=N\C(=S)NC1CC1c1ccc(-c2ncn(-c3ccc(OC(F)(F)F)cc3)n2)cc1]
P206 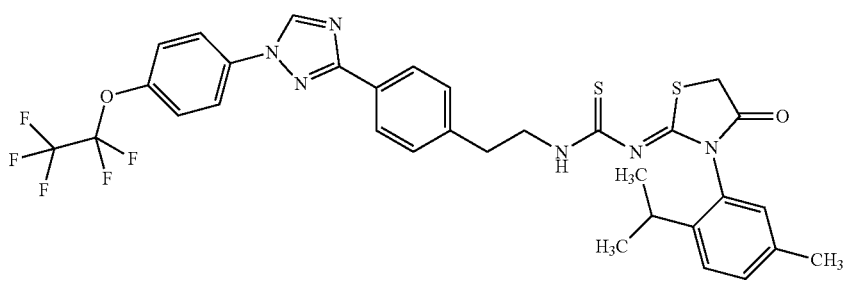 [SMILES: Cc1ccc(C(C)C)c(N2C(=O)CS/C2=N\C(=S)NCCc2ccc(-c3ncn(-c4ccc(OC(F)(F)C(F)(F)F)cc4)n3)cc2)c1]
P207 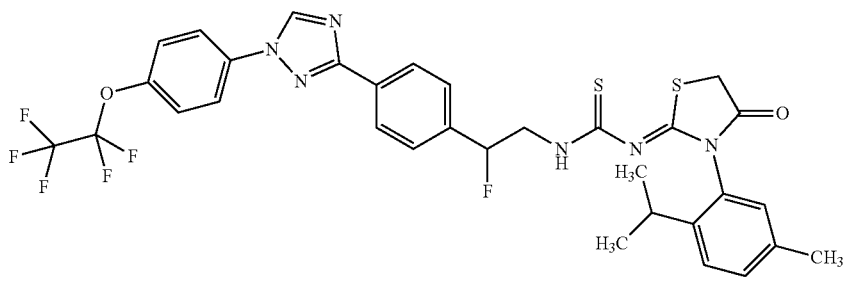 [SMILES: Cc1ccc(C(C)C)c(N2C(=O)CS/C2=N\C(=S)NCC(F)c2ccc(-c3ncn(-c4ccc(OC(F)(F)C(F)(F)F)cc4)n3)cc2)c1]

TABLE 1-continued
P208 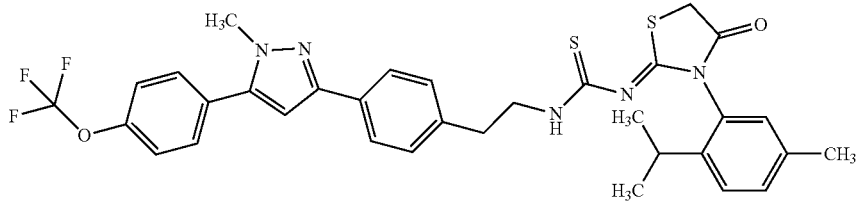 [SMILES: Cc1ccc(C(C)C)c(N2C(=O)CS/C2=N\C(=S)NCCc2ccc(-c3cc(-c4ccc(OC(F)(F)F)cc4)n(C)n3)cc2)c1]
P209 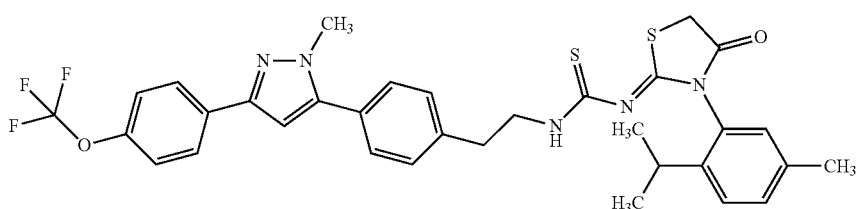
P210 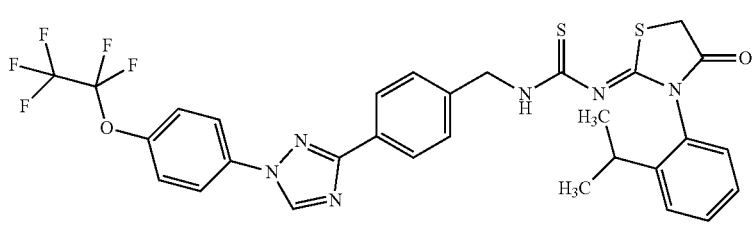 [SMILES: CC(C)c1ccccc1N1C(=O)CS/C1=N\C(=S)NCc1ccc(-c2ncn(-c3ccc(OC(F)(F)C(F)(F)F)cc3)n2)cc1]
P211 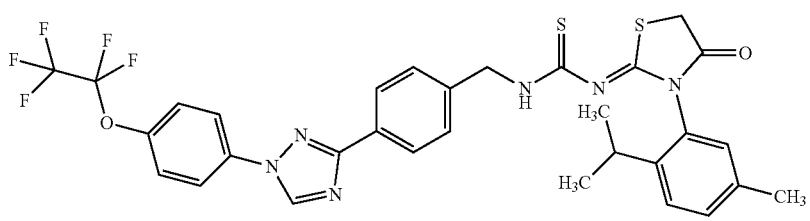 [SMILES: Cc1ccc(C(C)C)c(N2C(=O)CS/C2=N\C(=S)NCc2ccc(-c3ncn(-c4ccc(OC(F)(F)C(F)(F)F)cc4)n3)cc2)c1]
P212 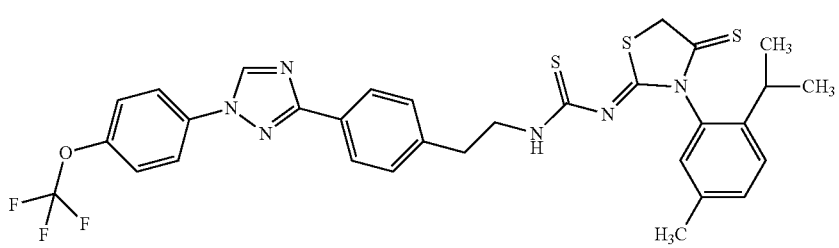 [SMILES: Cc1ccc(C(C)C)c(N2C(=S)CS/C2=N\C(=S)NCCc2ccc(-c3ncn(-c4ccc(OC(F)(F)F)cc4)n3)cc2)c1]
P213 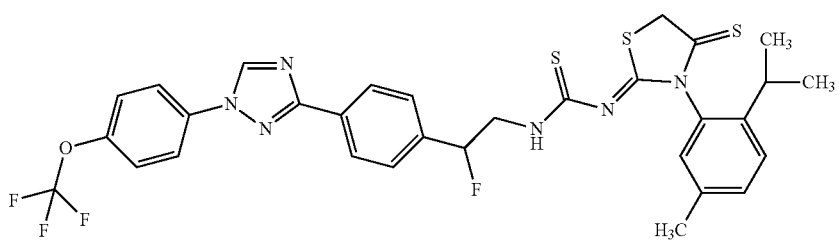 [SMILES: Cc1ccc(C(C)C)c(N2C(=S)CS/C2=N\C(=S)NCC(F)c2ccc(-c3ncn(-c4ccc(OC(F)(F)F)cc4)n3)cc2)c1]
Using the procedures disclosed herein the following list of molecules are also provided as examples (Table 2).

TABLE 2
F1
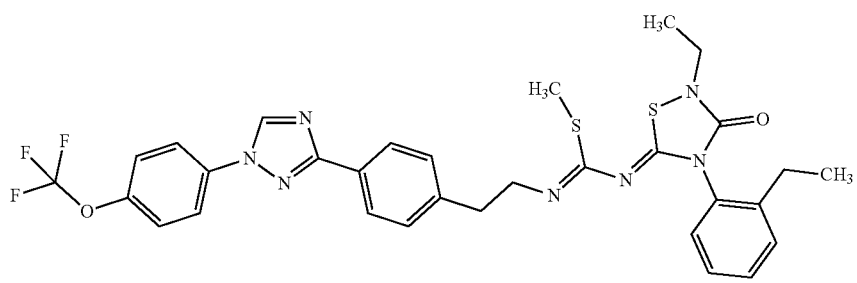 [SMILES: CCc1ccccc1-n1c(=O)n(CC)s/c1=N\C(=N\CCc1ccc(-c2ncn(-c3ccc(OC(F)(F)F)cc3)n2)cc1)SC]
F2
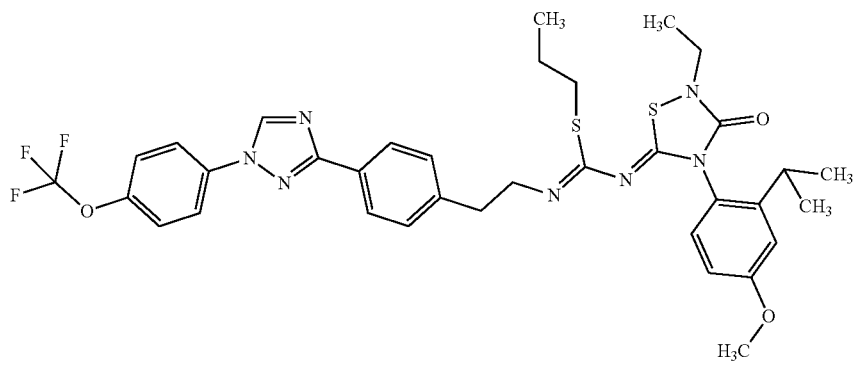 [SMILES: CCCSC(=N\CCc1ccc(-c2ncn(-c3ccc(OC(F)(F)F)cc3)n2)cc1)/N=c1\sn(CC)c(=O)n1-c1ccc(OC)cc1C(C)C]
F3
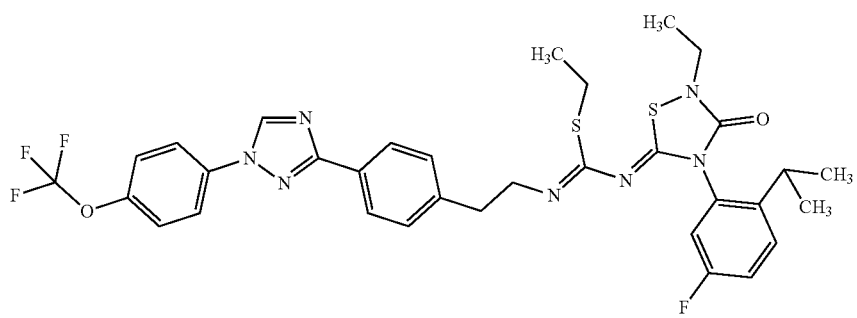 [SMILES: CCSC(=N\CCc1ccc(-c2ncn(-c3ccc(OC(F)(F)F)cc3)n2)cc1)/N=c1\sn(CC)c(=O)n1-c1cc(F)ccc1C(C)C]
F4
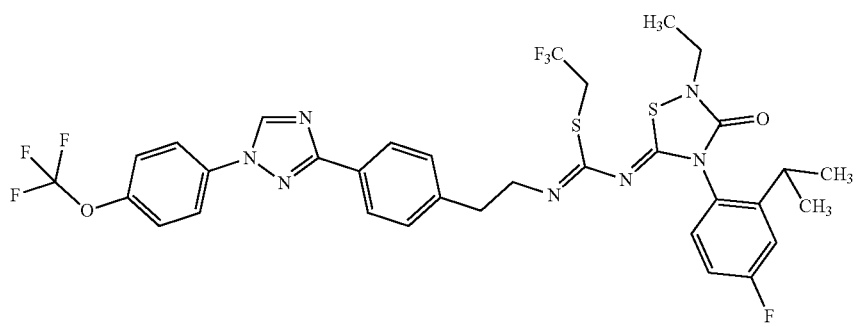 [SMILES: CCn1s/c(=N\C(=N\CCc2ccc(-c3ncn(-c4ccc(OC(F)(F)F)cc4)n3)cc2)SCC(F)(F)F)n(-c2ccc(F)cc2C(C)C)c1=O]
F5
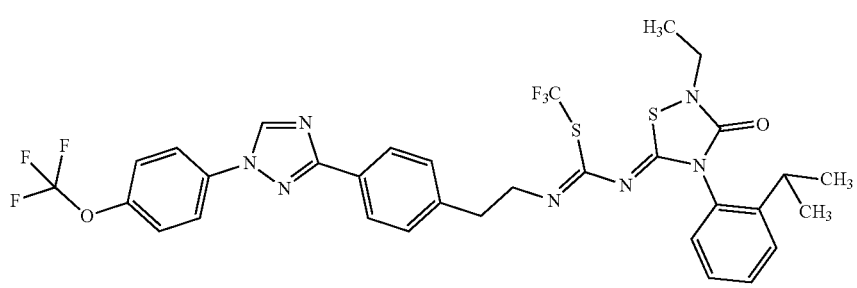 [SMILES: CCn1s/c(=N\C(=N\CCc2ccc(-c3ncn(-c4ccc(OC(F)(F)F)cc4)n3)cc2)SC(F)(F)F)n(-c2ccccc2C(C)C)c1=O]

TABLE 2-continued
F6
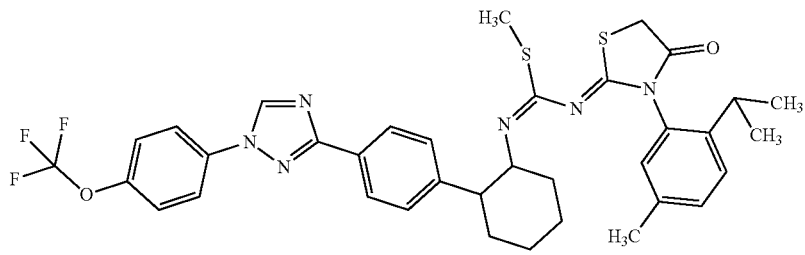 [SMILES: CSC(/N=C1\SCC(=O)N1c1cc(C)ccc1C(C)C)=N/C1CCCCC1c1ccc(-c2ncn(-c3ccc(OC(F)(F)F)cc3)n2)cc1]
F7
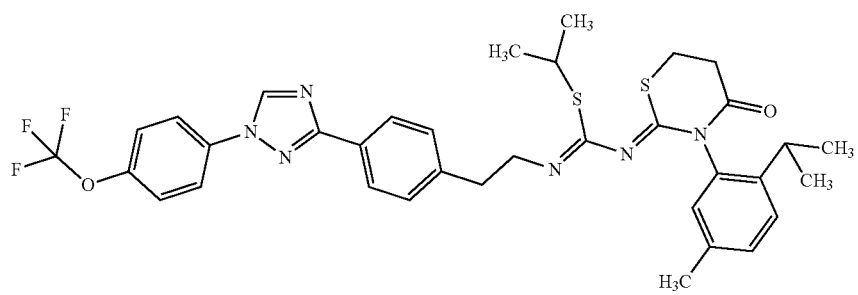 [SMILES: Cc1ccc(C(C)C)c(N2C(=O)CCS/C2=N\C(=N\CCc2ccc(-c3ncn(-c4ccc(OC(F)(F)F)cc4)n3)cc2)SC(C)C)c1]
F8
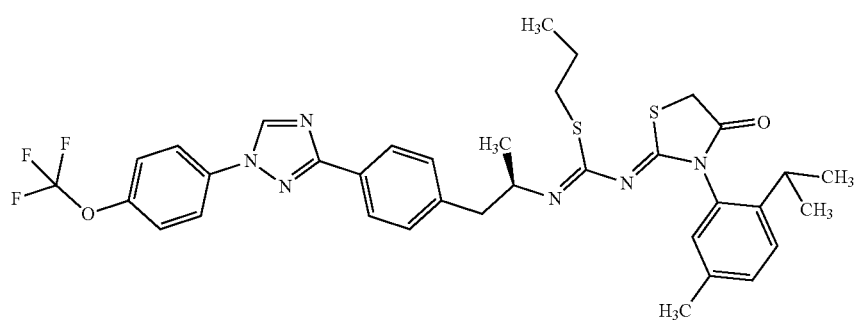 [SMILES: CCCSC(=N\[C@H](C)Cc1ccc(-c2ncn(-c3ccc(OC(F)(F)F)cc3)n2)cc1)/N=C1\SCC(=O)N1c1cc(C)ccc1C(C)C]
F9
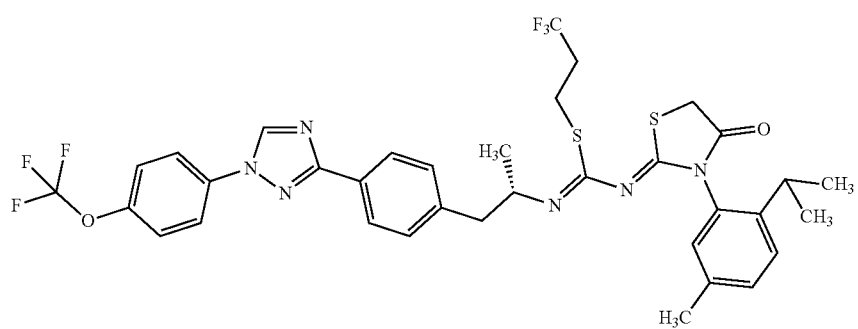 [SMILES: Cc1ccc(C(C)C)c(N2C(=O)CS/C2=N\C(=N\[C@@H](C)Cc2ccc(-c3ncn(-c4ccc(OC(F)(F)F)cc4)n3)cc2)SCCC(F)(F)F)c1]
F10
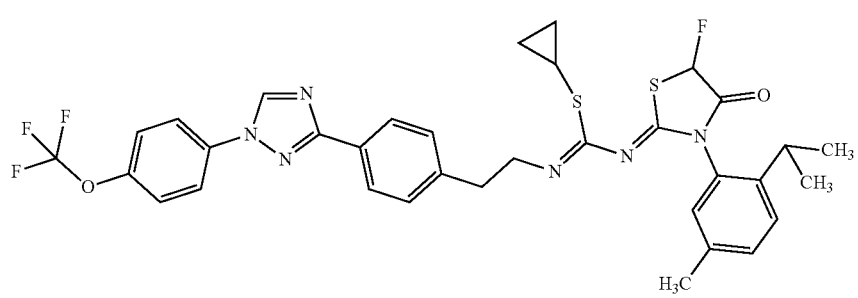 [SMILES: Cc1ccc(C(C)C)c(N2C(=O)C(F)S/C2=N\C(=N\CCc2ccc(-c3ncn(-c4ccc(OC(F)(F)F)cc4)n3)cc2)SC2CC2)c1]

TABLE 2-continued
F11
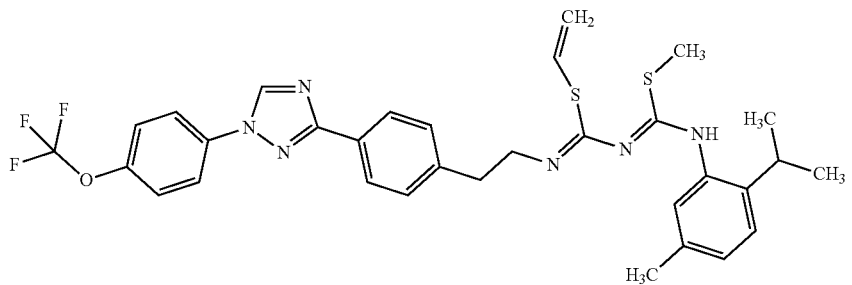 [SMILES: C=CSC(=N\CCc1ccc(-c2ncn(-c3ccc(OC(F)(F)F)cc3)n2)cc1)/N=C(/Nc1cc(C)ccc1C(C)C)SC]
F12
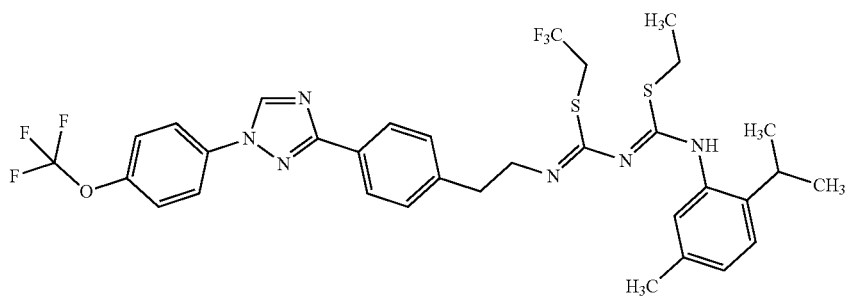 [SMILES: CCS/C(=N\C(=N\CCc1ccc(-c2ncn(-c3ccc(OC(F)(F)F)cc3)n2)cc1)SCC(F)(F)F)Nc1cc(C)ccc1C(C)C]
F13
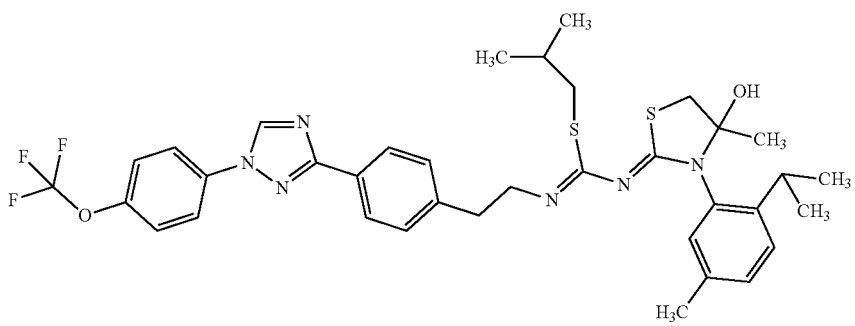 [SMILES: Cc1ccc(C(C)C)c(N2/C(=N/C(=N/CCc3ccc(-c4ncn(-c5ccc(OC(F)(F)F)cc5)n4)cc3)SCC(C)C)SCC2(C)O)c1]
F14
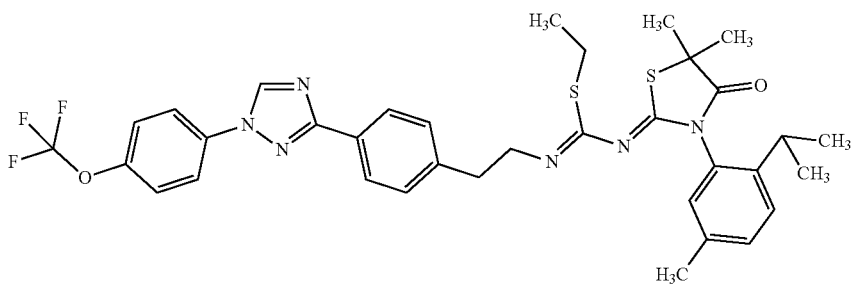 [SMILES: CCSC(=N\CCc1ccc(-c2ncn(-c3ccc(OC(F)(F)F)cc3)n2)cc1)/N=C1\SC(C)(C)C(=O)N1c1cc(C)ccc1C(C)C]
F15
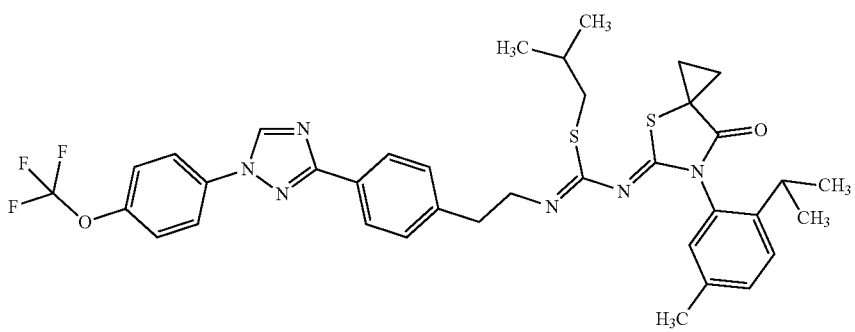 [SMILES: Cc1ccc(C(C)C)c(N2C(=O)C3(CC3)S/C2=N\C(=N\CCc2ccc(-c3ncn(-c4ccc(OC(F)(F)F)cc4)n3)cc2)SCC(C)C)c1]

TABLE 2-continued

F16

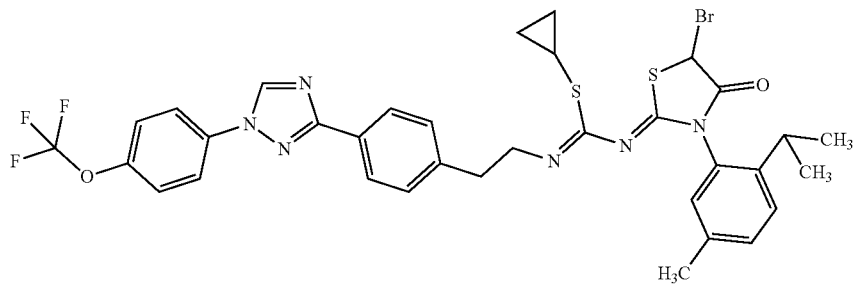

Example A: Bioassays on Beet Armyworm (*Spodoptera exigua*) ("BAW") AND Cabbage Looper (*Trichoplusia ni*) ("CL")

Beet Armyworm has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. The Cabbage Looper is a member of the moth family Noctuidae. It is found throughout the world. It attacks cabbage, cauliflower, broccoli, Brussel sprouts, tomatoes, cucumbers, potatoes, kale, turnips, mustard, peppers, eggplant, watermelons, melons, squash, cantaloupe, peas, beans, collards, lettuce, spinach, celery, parsley, beets, peas, alfalfa, soybeans, and cotton. This species is very destructive to plants due to its voracious consumption of leaves. In the case of cabbage, however, they feed not only on the wrapper leaves, but also may bore into the developing head. The larvae consume three times their weight in plant material daily. The feeding sites are marked by large accumulations of sticky, wet fecal material.

Consequently, because of the above factors control of these pests is important. Furthermore, molecules that control these pests (BAW and CL), which are known as chewing pests, are useful in controlling other pests that chew on plants.

Certain molecules disclosed in this document were tested against BAW and CL using procedures described in the following examples. In the reporting of the results, the "BAW & CL Rating Table" was used (See Table Section).
Bioassays on BAW.

Bioassays on BAW were conducted using a 128-well diet tray assay. One to five second instar BAW larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).
Bioassays on Cabbage Looper in CL Bioassays on CL were conducted using a 128-well diet tray assay. one to five second instar CL larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B: Bioassays on Green Peach Aphid ("GPA") (*Myzus Persicae*)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides. Consequently, because of the above factors control of this pest is important. Furthermore, molecules that control this pest (GPA), which is known as a sucking pest, are useful in controlling other pests that suck on plants.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

Corrected % Control=100*(X−Y)/X where
X=No. of live aphids on solvent check plants and
Y=No. of live aphids on treated plants The results are indicated in the table entitled "Table ABC: Biological Results" (See Table Section).

Example C: Bioassays on Yellow Fever Mosquito "YFM" (*Aedes Aegypti*)

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "YFM Rating Table" was used (See Table Section).

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water:acetone mixture is added to each well. A robot (Biomek® NXP Laboratory Automation Workstation) is programmed to dispense 15 µL aspirations from the master plate into an empty 96-well shallow plate ("daughter" plate). There are 6 reps ("daughter" plates) created per master. The created daughter plates are then immediately infested with YFM larvae.

The day before plates are to be treated, mosquito eggs are placed in Millipore water containing liver powder to begin hatching (4 g. into 400 mL). After the daughter plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality.

Agriculturally Acceptable Acid Addition Salts, Salt Derivatives, Solvates, Ester Derivatives, Polymorphs, Isotopes, and Radionuclides Molecules of Formula One and/or Formula Two may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One and/or Formula Two may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One and/or Formula Two may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One and/or Formula Two may be made into ester derivatives. These ester derivatives can then be applied in the same manner as the molecules disclosed in this document is applied.

Molecules of Formula One and/or Formula Two may be made as various crystal polymorphs. Polymorphism is important in the development of agrochemicals since different crystal polymorphs or structures of the same molecule can have vastly different physical properties and biological performances.

Molecules of Formula One and/or Formula Two may be made with different isotopes. Of particular importance are molecules having $^2H$ (also known as deuterium) in place of $^1H$.

Molecules of Formula One and/or Formula Two may be made with different radionuclides. Of particular importance are molecules having $^{14}C$.

Stereoisomers

Molecules of Formula One and/or Formula Two may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

In another embodiment, molecules of Formula One and/or Formula Two may be used in combination (such as, in a compositional mixture, or a simultaneous or sequential application) with one or more compounds each having a mode of action that is the same as, similar to, or different from, the mode of action ("MoA") of the molecules of Formula One and/or Formula Two. Modes of action include, for example the following: Acetylcholinesterase (AChE) inhibitors; GABA-gated chloride channel antagonists; Sodium channel modulators; Nicotinic acetylcholine (nAChR) agonists; Nicotinic acetylcholine receptor (nAChR) allosteric activators; Chloride channel activators; Juvenile hormone mimics; Miscellaneous non-specific (multi-site) inhibitors; Selective homopteran feeding blockers; Mite growth inhibitors; Microbial disruptors of insect midgut membranes; Inhibitors of mitochondrial ATP synthase; Uncouplers of oxidative phosphorylation via disruption of the proton gradient; Nicotinic acetylcholine receptor (nAChR) channel blockers; Inhibitors of chitin biosynthesis, type 0; Inhibitors of chitin biosynthesis, type 1; Moulting disruptor, Dipteran; Ecdysone receptor agonists; Octopamine receptor agonists; Mitochondrial complex III electron transport inhibitors; Mitochondrial complex I electron transport inhibitors; Voltage-dependent sodium channel blockers; Inhibitors of acetyl CoA carboxylase; Mitochondrial complex IV electron transport inhibitors; Mitochondrial complex II electron transport inhibitors; and Ryanodine receptor modulators.

In another embodiment, molecules of Formula One and/or Formula Two may be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

In another embodiment, the molecules of Formula One and/or Formula Two may be used in combination (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

In another embodiment, the molecules of Formula One and/or Formula Two may be used in combination (such as, in a compositional mixture, or a simultaneous or sequential application) with one or more of the following compounds—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-diolamine, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acynonapyr, acypetacs, acypetacs-copper, acypetacs-zinc, afidopyropen, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris (2-hydroxypropyl)ammonium, aminopyrifen, amiprofos-methyl, amiprophos, amisulbrom, amiton, amiton oxalate, amitraz, amitrole, ammonium sulfamate, ammonium α-naphthaleneacetate, amobam, ampropylfos, anabasine, anabasine sulfate, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzovindiflupyr, benzoximate, benzoylprop, benzoylprop-ethyl, benzpyrimoxan, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, broflanilide, brofluthrinate, bromacil, bromacil-lithium, bromacil-sodium, alpha-bromadiolone, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloroprallethrin, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clacyfos, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclaniliprole, cyclethrin, cycloate, cycloheximide, cyclorate, cycloprothrin, cyclopyrimorate, cyclosulfamuron, cycloxydim, cycluron, cyenopyrafen, cyflufenamid, cyflumetofen, cyfluthrin, cyhalodiamide, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlobentiazox, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-P-potassium, dichlorprop-P-sodium, dichlorprop-sodium, dichlorvos, dichlozoline, diclobutrazol, diclocymet, diclofop, diclofop-methyl, diclomezine, diclomezine-sodium, dicloran, dicloromezotiaz, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipymetitrone, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, enoxastrobin, EPN, epocholeone, epofenonane, epoxiconazole, eprinomectin, epronaz, epsilon-metofluthrin, epsilon-momfluorothrin, EPTC, erbon, ergocalciferol, erlujixiancaoan, esdepallethrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpicoxamid, fenpirithrin, fenpropathrin, fenpropidin, fenpropimorph, fenpyrazamine, fenpyroximate, fenquinotrione, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, florpyrauxifen, fluacrypyrim, fluazaindolizine, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenoxystrobin, flufenprox, flufenpyr, flufenpyr-ethyl, flufiprole, fluhexafon, fluindapyr, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrimin, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxametamide, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halauxifen, halauxifen-methyl, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptafluthrin, heptenophos, heptopargil, herbimycin, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, inpyrfluxam, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, ipfentrifluconazole, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isofetamid, isoflucypram, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, kappa-bifenthrin, kappa-tefluthrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, lancotrione, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandestrobin, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefentrifluconazole, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metcamifen, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, momfluorothrin, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, napropamide-M, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxathiapiprolin, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentachlorophenyl laurate, pentanochlor, penthiopyrad, pentmethrin, pentoxazone, perfluidone, permethrin, pethoxamid, phenamacril, phenazine oxide, phenisopham, phenkapton, phenmedipham, phenmediphamethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picarbutrazox, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pydiflumetofen, pyflubumide, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrapropoyne, pyrasulfotole, pyraziflumid, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyriminostrobin, pyrimisulfan, pyrimitate, pyrinuron, pyriofenone, pyriprole, pyripropanol, pyriproxyfen, pyrisoxazole, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinofumelin, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, rescalure, resmethrin, rhodethanil, rhodojaponin-lll, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spiropidion, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetraniliprole, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiafenacil, tiaojiean, tiocarbazil, tioclorim, tioxazafen, tioxymid, tirpate, tolclofos-methyl, tolfenpyrad, tolprocarb, tolpyralate, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyrethyl, triclopyricarb, triclopyr-triethylammonium, tricyclazole, tridemorph, tridiphane, trietazine, trifenmorph, trifenofos, trifloxystrobin, trifloxysulfuron, trifloxysulfuron-sodium, trifludimoxazin, triflumezopyrim, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, tyclopyrazoflor, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood.net/pesticides/index.html. Also consult "THE PESTICIDE MANUAL" 15th Edition, edited by C D S Tomlin, copyright 2009 by British Crop Production Council, or its prior, or more recent editions.

In another embodiment, molecules of Formula One and/or Formula Two may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on: entomopathogenic fungi (e.g. *Metarhizium anisopliae*); entomopathogenic nematodes (e.g. *Steinernema feltiae*); and entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One and/or Formula Two may be used with one or more biopesticides in the area of seed treatments and soil amendments. The Manual of Biocontrol Agents gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

In another embodiment, the above possible combinations may be used in a wide variety of weight ratios. For example, a two component mixture, the weight ratio of a molecule of Formula One and/or Formula Two to another compound, can be from about 100:1 to about 1:100; in another example the weight ratio can be about 50:1 to about 1:50; in another example the weight ratio can be about 20:1 to about 1:20; in another example the weight ratio can be about 10:1 to about 1:10; in another example the weight ratio can be about 5:1 to 1:5; in another example the weight ratio can be about 3:1 to about 1:3; and in a final example the weight ratio can be about 1:1. However, preferably, weight ratios less than about 10:1 to about 1:10 are preferred. It is also preferred sometimes to use a three or four component mixture comprising one or more molecules of Formula One and/or Formula Two and one or more other compounds from the above possible combinations.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions. For further information on formulation types see "Catalogue of Pesticide Formulation Types and International Coding System" Technical Monograph no 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One and/or Formula Two may be used to control pests e.g. ants, aphids, beetles, bristletails, cockroaches, crickets, earwigs, fleas, flies, grasshoppers, leafhoppers, lice, locusts, mites, moths, nematodes, scales, symphylans, termites, thrips, ticks, wasps, and whiteflies.

In another embodiment, the molecules of Formula One and/or Formula Two may be used to control pests in the Phyla Nematoda and/or Arthropoda.

In another embodiment, the molecules of Formula One and/or Formula Two may be used to control pests in the Subphyla Chelicerata, Myriapoda, and/or Hexapoda.

In another embodiment, the molecules of Formula One and/or Formula Two may be used to control pests in the Classes of Arachnida, Symphyla, and/or Insecta.

In another embodiment, the molecules of Formula One and/or Formula Two may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the molecules of Formula One and/or Formula Two may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the molecules of Formula One and/or Formula Two may be used to control pests of the Order Dermaptera.

In another embodiment, the molecules of Formula One and/or Formula Two may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In another embodiment, the molecules of Formula One and/or Formula Two may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In another embodiment, the molecules of Formula One and/or Formula Two may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax*

*striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana*.

In another embodiment, the molecules of Formula One and/or Formula Two may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile*.

In another embodiment, the molecules of Formula One and/or Formula Two may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus*.

In another embodiment, the molecules of Formula One and/or Formula Two may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina*.

In another embodiment, the molecules of Formula One and/or Formula Two may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis*.

In another embodiment, the molecules of Formula One and/or Formula Two may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata*.

In another embodiment, the molecules of Formula One and/or Formula Two may be used to control pests of the Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans*.

In another embodiment, the molecules of Formula One and/or Formula Two may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis,* and *Taeniothrips rhopalantennalis, Thrips hawaiiensis, Thrips nigropilosus, Thrips orientalis, Thrips tabaci*.

In another embodiment, the molecules of Formula One and/or Formula Two may be used to control pests of the Order Thysanura. A non-exhaustive list of particular genera includes, but is not limited to, *Lepisma* spp. and *Thermobia* spp.

In another embodiment, the molecules of Formula One and/or Formula Two may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In another embodiment, the molecules of Formula One and/or Formula Two may be used to control pest of the Order Symphyla. A non-exhaustive list of particular sp. includes, but is not limited to, *Scutigerella immaculata*.

In another embodiment, the molecules of Formula One and/or Formula Two may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Controlling pests of Phyla Nematoda, Arthropoda, and/or Mollusca generally means that pest populations, pest activity, or both, are reduced in an locus. This can come about when:

(a) pest populations are repulsed from a locus;
(b) pests are incapacitated in, or around, a locus; or
(c) pests are exterminated in, or around, a locus.

Of course, a combination of these results can occur. Generally, pest populations, activity, or both are desirably reduced more than fifty percent, preferably more than 90 percent, and most preferably more than 98 percent. Generally, the locus is not in, or on, a human; consequently, the locus is generally a non-human locus.

In another embodiment, the locus to which a molecule of Formula One and/or Formula Two is applied can be any locus that is inhabited, or that may become inhabited, or that may be traversed, by a pest of Phyla Nematoda, Arthropoda, and/or Mollusca. For example, the locus can be:

(a) where crops, trees, fruits, cereals, fodder species, vines, turf, and/or ornamental plants, are growing;
(b) where domesticated animals are residing;
(c) the interior or exterior surfaces of buildings (such as places where grains are stored);
(d) the materials of construction used in buildings (such as impregnated wood); and
(e) the soil around buildings.

Particular crop areas to use a molecule of Formula One and/or Formula Two include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One and/or Formula Two when growing various plants.

In another embodiment, molecules of Formula One and/or Formula Two are generally used in amounts from about 0.0001 grams per hectare to about 5000 grams per hectare to provide control. In another embodiment, it is preferred that molecules of Formula One and/or Formula Two are used in amounts from about 0.001 grams per hectare to about 500 grams per hectare. In another embodiment, it is more preferred that molecules of Formula One and/or Formula Two are used in amounts from about 0.01 gram per hectare to about 50 grams per hectare.

The molecules of Formula One and/or Formula Two may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One and/or Formula Two can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One and/or Formula Two can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One and/or Formula Two.

The molecules of Formula One and/or Formula Two can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One and/or Formula Two may be desirable to control newly emerged larvae.

Systemic movement of pesticides in plants may be utilized to control pests on one portion of the plant by applying (for example by spraying an area) the molecules of Formula One and/or Formula Two to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One and/or Formula Two may further enhance the ability of a plant to better withstand stressful growing conditions. This results in a healthier, more vigorous plant, which can lead to higher yields at harvest time. Generally, about 1 gram of the molecules of Formula One and/or Formula Two to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One and/or Formula Two may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One and/or Formula Two may be used for controlling endoparasites and ectoparasites in the veterinary medicine sector or in the field of non-human animal keeping. The molecules of Formula One and/or Formula Two are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One and/or Formula Two may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One and/or Formula Two may also be used for controlling parasitic worms, especially of the intestine, in the animals listed above.

The molecules of Formula One and/or Formula Two may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One and/or Formula Two may also be used on such new invasive species to control them in such new environment.

The molecules of Formula One and/or Formula Two may be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One and/or Formula Two can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Combinations

In another embodiment of this invention, molecules of Formula One/Formula Two may be used in combination (such as, in a compositional mixture, or a simultaneous or sequential application) with one or more active ingredients.

In another embodiment of this invention, molecules of Formula One/Formula Two may be used in combination (such as, in a compositional mixture, or a simultaneous or sequential application) with one or more active ingredients each having a MoA that is the same as, similar to, but more likely—different from, the MoA of the molecules of Formula One/Formula Two.

In another embodiment, molecules of Formula One/Formula Two may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula One/Formula Two may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula One/Formula Two may also be used in combination (such as in a compositional mixture, or a simultaneous or sequential application) with one or more biopesticides.

In another embodiment, in a pesticidal composition combinations of a molecule of Formula One/Formula Two and an active ingredient may be used in a wide variety of weight ratios. For example, in a two-component mixture, the weight ratio of a molecule of Formula One/Formula Two to an active ingredient, the weight ratios in Table A may be used.

However, in general, weight ratios less than about 10:1 to about 1:10 are preferred. It is also preferred sometimes to use a three, four, five, six, seven, or more, component mixture comprising a molecule of Formula One/Formula Two and an additional two or more active ingredients.

TABLE A

Weight Ratios
Molecule of the Formula One/Formula Two: active ingredient

100:1 to 1:100
50:1 to 1:50
20:1 to 1:20
10:1 to 1:10
5:1 to 1:5
3:1 to 1:3
2:1 to 1:2
1:1

Weight ratios of a molecule of Formula One/Formula Two to an active ingredient may also be depicted as X:Y; wherein X is the parts by weight of a molecule of Formula One/Formula Two and Y is the parts by weight of active ingredient. The numerical range of the parts by weight for X is $0<X\leq100$ and the parts by weight for Y is $0<Y\leq100$ and is shown graphically in Table B. By way of non-limiting example, the weight ratio of a molecule of Formula One/Formula Two to an active ingredient may be 20:1.

Ranges of weight ratios of a molecule of Formula One/Formula Two to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1>Y_1$ and $X_2<Y_2$. By way of non-limiting example, the range of a weight ratio of a molecule of Formula One/Formula Two to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of a molecule of Formula One/Formula Two to an active ingredient may be between 15:1 and 3:1, inclusive of the endpoints.

In another embodiment, the range of weight ratios may be $X_1:Y_1$ to $X_2:Y_2$, wherein $X_1<Y_1$ and $X_2<Y_2$. By way of non-limiting example, the range of weight ratios of a molecule of Formula One/Formula Two to an active ingredient may be between about 1:3 and about 1:20, inclusive of the endpoints.

It is envisioned that certain weight ratios of a molecule of Formula One/Formula Two to an active ingredient, as presented in Table A and B, may be synergistic.

contacting the crop plant (e.g., foliage, flowers, fruit or roots) or the seed from which the crop plant is grown with a compound of Formula One/Formula Two in amount sufficient to achieve the desired plant vigor effect (i.e. biologically effective amount). Typically the compound of Formula One/Formula Two is applied in a formulated composition. Although the compound of Formula One/Formula Two is often applied directly to the crop plant or its seed, it can also be applied to the locus of the crop plant, i.e. the environment of the crop plant, particularly the portion of the environment in close enough proximity to allow the compound of Formula One/Formula Two to migrate to the crop plant. The locus relevant to this method most commonly comprises the growth medium (i.e. medium providing nutrients to the plant), typically soil in which the plant is grown. Treatment of a crop plant to increase vigor of the crop plant thus comprises contacting the crop plant, the seed from which the crop plant is grown or the locus of the crop plant with a biologically effective amount of a compound of Formula One/Formula Two.

Increased crop vigor can result in one or more of the following observed effects: (a) optimal crop establishment as demonstrated by excellent seed germination, crop emergence and crop stand; (b) enhanced crop growth as demonstrated by rapid and robust leaf growth (e.g., measured by leaf area index), plant height, number of tillers (e.g., for rice), root mass and overall dry weight of vegetative mass of the crop; (c) improved crop yields, as demonstrated by time to flowering, duration of flowering, number of flowers, total biomass accumulation (i.e. yield quantity) and/or fruit or grain grade marketability of produce (i.e. yield quality); (d) enhanced ability of the crop to withstand or prevent plant disease infections and arthropod, nematode or mollusk pest infestations; and (e) increased ability of the crop to withstand environmental stresses such as exposure to thermal extremes, suboptimal moisture or phytotoxic chemicals.

The compounds of the present invention can increase the vigor of treated plants compared to untreated plants by killing or otherwise preventing feeding of phytophagous invertebrate pests in the environment of the plants. In the absence of such control of phytophagous invertebrate pests, the pests reduce plant vigor by consuming plant tissues or sap, or transmitting plant pathogens such as viruses. Even in the absence of phytophagous invertebrate pests, the compounds of the invention may increase plant vigor by modifying metabolism of plants. Generally, the vigor of a crop plant will be most significantly increased by treating the plant with a compound of the invention if the plant is grown in a nonideal environment, i.e. an environment comprising

TABLE B

| active ingredient (Y) Parts by weight | | | | | | | | | |
|---|---|---|---|---|---|---|---|---|---|
| 100 | X, Y | | X, Y | | | X, Y | | | |
| 50 | X, Y | X, Y | X, Y | | | X, Y | X, Y | | |
| 20 | X, Y | | X, Y | X, Y | | X, Y | | X, Y | |
| 15 | X, Y | X, Y | | | | | X, Y | X, Y | X, Y |
| 10 | X, Y | | X, Y | | | | | | |
| 5 | X, Y | X, Y | X, Y | | | X, Y | | | |
| 3 | X, Y | X, Y | | X, Y | X, Y | | X, Y | X, Y | X, Y |
| 2 | X, Y | | X, Y | X, Y | | X, Y | | X, Y | |
| 1 | X, Y | X, Y | X, Y | X, Y | X, Y | X, Y | X, Y | X, Y | X, Y |
| | 1 | 2 | 3 | 5 | 10 | 15 | 20 | 50 | 100 |
| | molecule of Formula One/Formula Two (X) Parts by weight | | | | | | | | |

Compounds of the present invention may also be useful for increasing vigor of a crop plant. This method comprises one or more aspects adverse to the plant achieving the full genetic potential it would exhibit in an ideal environment.

Of note is the present method for increasing vigor of a crop plant wherein the crop plant is grown in an environment comprising phytophagous invertebrate pests. Also of note is the present method for increasing vigor of a crop plant wherein the crop plant is grown in an environment not comprising phytophagous invertebrate pests. Also of note is the present method for increasing vigor of a crop plant wherein the crop plant is grown in an environment comprising an amount of moisture less than ideal for supporting growth of the crop plant. Of note is the present method for increasing vigor of a crop plant wherein the crop is rice. Also of note is the present method for increasing vigor of a crop plant wherein the crop is maize (corn). Also of note is the present method for increasing vigor of a crop plant wherein the crop is soybean.

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula One/Formula Two, at least one additional component selected from the group consisting of surfactants, solid diluents and liquid diluents, and at least one additional biologically active compound or agent. For mixtures of the present invention, the other biologically active compounds or agents can be formulated together with the present compounds, including the compounds of Formula One/Formula Two, to form a premix, or the other biologically active compounds or agents can be formulated separately from the present compounds, including the compounds of Formula One/Formula Two, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, acynonapyr, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl]methyl cyclopropanecarboxylate), amidoflumet, amitraz, avermectin, azadirachtin, azinphos-methyl, benfuracarb, bensultap, benzpyrimoxan, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1H-pyrazole-5-carboxamide), cycloprothrin, cycloxaprid ((5S,8R)-1-[(6-chloro-3-pyridinyl)methyl]-2,3,5,6,7,8-hexahydro-9-nitro-5,8-epoxy-1H-imidazo[1,2-a]azepine), cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin (2-ethyl-3,7-dimethyl-6-[4-(trifluoromethoxy)phenoxy]-4-quinolinyl methyl carbonate), flonicamid, fluazaindolizine, flubendiamide, flucythrinate, flufenerim, flufenoxuron, flufenoxystrobin (methyl (αE)-2-[[2-chloro-4-(trifluoromethyl)phenoxy]methyl]-α-(methoxymethylene)benzeneacetate), fluensulfone (5-chloro-2-[(3,4,4-trifluoro-3-buten-1-yl)sulfonyl]thiazole), fluhexafon, fluopyram, flufiprole (1-[2,6-dichloro-4-(trifluoromethyl)phenyl]-5-[(2-methyl-2-propen-1-yl)amino]-4-[(trifluoromethyl)sulfinyl]-1H-pyrazole-3-carbonitrile), flupyradifurone (4-[[(6-chloro-3-pyridinyl)methyl](2,2-difluoroethyl)amino]-2(5H)-furanone), flypyrimin, fluvalinate, tau-fluvalinate, fonophos, formetanate, fosthiazate, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl] cyclopropanecarboxylate), hexaflumuron, hexythiazox, hydramethylnon, imidacloprid, indoxacarb, insecticidal soaps, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methiocarb, methomyl, methoprene, methoxychlor, methoxyfenozide, metofluthrin, monocrotophos, monofluorothrin ([2,3,5,6-tetrafluoro-4-(methoxymethyl)phenyl]methyl 3-(2-cyano-1-propen-1-yl)-2,2-dimethylcyclopropanecarboxylate), nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]pheny]-1H-pyrazole-4-carboxamide), pymetrozine, pyrafluprole, pyrethrin, pyridaben, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxymethylene)benzeneacetate), pyriprole, pyriproxyfen, rotenone, ryanodine, silafluofen, spinetoram, spinosad, spirodiclofen, spirodion, spiromesifen, spirotetramat, sulprofos, sulfoxaflor (N-[methyloxido[1-[6-(trifluoromethyl)-3-pyridinyl]ethyl]-A4-sulfanylidene]cyanamide), tebufenozide, tebufenpyrad, teflubenzuron, tefluthrin, terbufos, tetrachlorvinphos, tetramethrin, tetramethylfluthrin ([2,3,5,6-tetrafluoro-4-(methoxymethyl)phenyl]methyl 2,2,3,3-tetramethylcyclopropanecarboxylate), tetraniliprole, thiacloprid, thiamethoxam, thiodicarb, thiosultap-sodium, tioxazafen (3-phenyl-5-(2-thienyl)-1,2,4-oxadiazole), tolfenpyrad, tralomethrin, triazamate, trichlorfon, triflumezopyrim (2,4-dioxo-1-(5-pyrimidinylmethyl)-3-[3-(trifluoromethyl)phenyl]-2H-pyrido[1,2-a]pyrimidinium inner salt), triflumuron, tyclopyrazoflor, *Bacillus thuringiensis* delta-endotoxins, entomopathogenic bacteria, entomopathogenic viruses and entomopathogenic fungi.

Of note are insecticides such as abamectin, acetamiprid, acrinathrin, acynonapyr, afidopyropen, amitraz, avermectin, azadirachtin, benfuracarb, bensultap, benzpyrimoxan, bifenthrin, buprofezin, cadusafos, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, flufensulfone, flupiprole, flupyradifurone, flupyrimin, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spiropidion, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, tyclopyrazoflor, *Bacillus thuringiensis* delta-endotoxins, all strains of *Bacillus thuringiensis* and all strains of nucleo polyhedrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedrovirus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula One/Formula Two. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, acetylcholinesterase (AChE) inhibitors such as the carbamates methomyl, oxamyl, thiodicarb, triazamate, and the organophosphates chlorpyrifos; GABA-gated chloride channel antagonists such as the cyclodienes dieldrin and endosulfan, and the phenylpyrazoles ethiprole and fipronil; sodium channel modulators such as the pyrethroids bifenthrin, cyfluthrin, beta-cyfluthrin, cyhalothrin, lambda-cyhalothrin, cypermethrin, deltamethrin, dimefluthrin, esfenvalerate, metofluthrin and profluthrin; nicotinic acetylcholinereceptor (nAChR) agonists such as the neonicotinoids acetamiprid, clothianidin, dinotefuran, imidacloprid, nitenpyram, nithiazine, thiacloprid, and thiamethoxam, and sulfoxaflor; nicotinic acetylcholine receptor (nAChR) allosteric activators such as the spinosyns spinetoram and spinosad; chloride channel activators such as the avermectins abamectin and emamectin; juvenile hormone mimics such as diofenolan, methoprene, fenoxycarb and pyriproxyfen; selective homopteran feeding blockers such as pymetrozine and flonicamid; mite growth inhibitors such as etoxazole; inhibitors of mitochondrial ATP synthase such as propargite; ucouplers of oxidative phosphorylation via disruption of the proton gradient such as chlorfenapyr; nicotinic acetylcholine receptor (nAChR) channel blockers such as the nereistoxin analogs cartap; inhibitors of chitin biosynthesis such as the benzoylureas flufenoxuron, hexaflumuron, lufenuron, novaluron, noviflumuron and triflumuron, and buprofezin; dipteran moulting disrupters such as cyromazine; ecdysone receptor agonists such as the diacylhydrazines methoxyfenozide and tebufenozide; octopamine receptor agonists such as amitraz; mitochondrial complex III electron transport inhibitors such as hydramethylnon; mitochondrial complex I electron transport inhibitors such as pyridaben; voltage-dependent sodium channel blockers such as indoxacarb; inhibitors of acetyl CoA carboxylase such as the tetronic and tetramic acids spirodiclofen, spiromesifen and spirotetramat; mitochondrial complex II electron transport inhibitors such as the β-ketonitriles cyenopyrafen and cyflumetofen; ryanidine receptor modulators such as the anthranilic diamides chlorantraniliprole, cyantraniliprole and cyantraniliprole, diamides such as flubendiamide, and ryanodine receptor ligands such as ryanodine; compounds wherein the target site responsible for biological activity is unknown or uncharacterized such as azadirachtin, bifenazate, pyridalyl, pyrifluquinazon and triflumezopyrim; microbial disrupters of insect midgut membranes such as *Bacillus thuringensis* and the delta-endotoxins they produce and *Bacillus sphaericus*; and biological agents including nucleo polyhedro viruses (NPV) and other naturally occurring or genetically modified insecticidal viruses.

Further examples of biologically active compounds or agents with which compounds of this invention can be formulated are: fungicides such as acibenzolar-S-methyl, aldimorph, ametoctradin, aminopyrifen, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, etaconazole, edifenphos, enoxastrobin (also known as enestroburin), epoxiconazole, ethaboxam, ethirimol, etridiazole, famoxadone, fenamidone, fenaminstrobin, fenarimol, fenbuconazole, fenfuram, fenhexamide, fenoxanil, fenpiclonil, fenpropidin, fenpropimorph, fenpyrazamine, fentin acetate, fentin hydroxide, ferbam, ferimzone, flometoquin, fluazinam, fludioxonil, flufenoxystrobin, fluindapyr, flumorph, fluopicolide, fluopyram, fluoxastrobin, fluquinconazole, flusilazole, flusulfamide, flutianil, flutolanil, flutriafol, fluxapyroxad, folpet, fthalide (also known as phthalide), fuberidazole, furalaxyl, furametpyr, hexaconazole, hymexazole, guazatine, imazalil, imibenconazole, iminoctadine albesilate, iminoctadine triacetate, inpyrfluxam, iodicarb, ipconazole, isofetamid, isoflucypram, iprobenfos, iprodione, iprovalicarb, isoprothiolane, isopyrazam, isotianil, kasugamycin, kresoxim-methyl, mancozeb, mandipropamid, mandestrobin, maneb, mapanipyrin, mepronil, meptyldinocap, metalaxyl (including metalaxyl-M/mefenoxam), metconazole, methasulfocarb, metiram, metominostrobin, metrafenone, myclobutanil, naftitine, neo-asozin (ferric methanearsonate), nuarimol, octhilinone, ofurace, orysastrobin, oxadixyl, oxathiapiprolin, oxolinic acid, oxpoconazole, oxycarboxin, oxytetracycline, penconazole, pencycuron, penflufen, penthiopyrad, perfurazoate, phosphorous acid (including salts thereof, e.g., fosetyl-aluminum), picarbutratox, picoxystrobin, piperalin, polyoxin, probenazole, prochloraz, procymidone, propamocarb, propiconazole, propineb, proquinazid, prothiocarb, prothioconazole, pydiflumetofen, pyraclostrobin, pyrametostrobin, pyraoxystrobin, pyrapropoyne, pyrazophos, pyribencarb, pyributacarb, pyrifenox, pyriofenone, perisoxazole, pyrimethanil, pyrifenox, pyrrolnitrin, pyroquilon, quinconazole, quinmethionate, quinoxyfen, quintozene, silthiofam, sedaxane, simeconazole, spiroxamine, streptomycin, sulfur, tebuconazole, tebufloquin, teclofthalam, tecloftalam, tecnazene, terbinafine, tetraconazole, thiabendazole, thifluzamide, thiophanate, thiophanate-methyl, thiram, tiadinil, tolclofos-methyl, tolprocarb, tolyfluanid, triadimefon, triadimenol, triarimol, triazoxide, tribasic copper sulfate, triclopyricarb, tridemorph, trifloxystrobin, triflumizole, trimoprhamide tricyclazole, triforine, triticonazole, uniconazole, validamycin, valifenalate (also known as valifenal), vinclozolin, zineb, ziram and zoxamide; nematocides such as fluopyram, spirotetramat, thiodicarb, fosthiazate, abamectin, iprodione, fluensulfone, dimethyl disulfide, tioxazafen, 1,3-dichloropropene (1,3-D), metam (sodium and potassium), dazomet, chloropicrin, fenamiphos, ethoprophos, cadusaphos, terbufos, imicyafos, oxamyl, carbofuran, tioxazafen, *Bacillus firmus* and *Pasteuria nishizawae*; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include The Pesticide Manual, 13th Edition, C. D. S. Tomlin, Ed., British Crop Protection Council, Farnham, Surrey, U. K., 2003 and The BioPesticide Manual, $2^{nd}$ Edition, L. G. Copping, Ed., British Crop Protection Council, Farnham, Surrey, U. K., 2001.

Compounds of this invention can be combined or formulated with polynucleotides including, but not limited to, DNA, RNA, and/or chemically modified nucleotides influencing the amount of a particular target through down regulation, interference, suppression or silencing of the genetically derived transcript that render an insecticidal effect.

For embodiments where one or more of these various mixing partners are used, the weight ratio of these various mixing partners (in total) to the compound of Formula One/Formula Two is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula One/Formula Two alone.

Table C lists specific combinations of a compound of Formula One/Formula Two with other invertebrate pest control agents illustrative of the mixtures, compositions and methods of the present invention. The first column of Table C lists the specific invertebrate pest control agents (e.g., "Abamectin" in the first line). The second column of Table C lists the mode of action (if known) or chemical class of the invertebrate pest control agents. The third column of Table C lists embodiment(s) of ranges of weight ratios for rates at which the invertebrate pest control agent can be applied relative to a compound of Formula One/Formula Two (e.g., "50:1 to 1:50" of abamectin relative to a compound of Formula One/Formula Two by weight). Thus, for example, the first line of Table C specifically discloses the combination of a compound of Formula One/Formula Two with abamectin can be applied in a weight ratio between 50:1 to 1:50. The remaining lines of Table C are to be construed similarly. Of further note Table C lists specific combinations of a compound of Formula One/Formula Two with other invertebrate pest control agents illustrative of the mixtures, compositions and methods of the present invention and includes additional embodiments of weight ratio ranges for application rates.

TABLE C

| Invertebrate Pest Control Agent | Mode of Action or Chemical Class | Typical Weight Ratio |
|---|---|---|
| Abamectin | Chloride channel activator | 50:1 to 1:50 |
| Acetamiprid | Nicotinic acetylcholine receptor (nAChR) agonist | 150:1 to 1:200 |
| Amitraz | Octopamine receptor agonist | 200:1 to 1:100 |
| Avermectin | Macrocyclic lactones | 50:1 to 1:50 |
| Azadirachtin | Unknown site of action | 100:1 to 1:120 |
| Beta-cyfluthrin | Sodium channel modulators | 150:1 to 1:200 |
| Bifenthrin | Sodium channel modulators | 100:1 to 1:10 |
| Buprofezin | Chitin biosynthesis inhibitors | 500:1 to 1:50 |
| Cartap | Nicotinic acetylcholine receptor (nAChR) channel blocker | 100:1 to 1:200 |
| Chlorantraniliprole | Ryanodine receptor modulator | 100:1 to 1:120 |
| Chlorfenapyr | Uncouplers of oxidative phosphorylation | 300:1 to 1:200 |
| Chlorpyrifos | Acetylcholine esterase inhibitor | 500:1 to 1:200 |
| Clothianidin | Nicotinic acetylcholine receptor (nAChR) agonist | 100:1 to 1:400 |
| Cyantraniliprole | Ryanodine receptor modulator | 100:1 to 1:120 |
| Cyfluthrin | Sodium channel modulator | 150:1 to 1:200 |
| Cyhalothrin | Sodium channel modulator | 150:1 to 1:200 |
| Cypermethrin | Sodium channel modulator | 150:1 to 1:200 |
| Cyromazine | Dipteran moulting disrupter | 400:1 to 1:50 |
| Deltamethrin | Sodium channel modulators | 50:1 to 1:400 |
| Dieldrin | GABA-gated chloride channel antagonist | 200:1 to 1:100 |

TABLE C-continued

| Invertebrate Pest Control Agent | Mode of Action or Chemical Class | Typical Weight Ratio |
|---|---|---|
| Dinotefuran | Nicotinic acetylcholine receptor (nAChR) agonist | 150:1 to 1:200 |
| Diofenolan | Juvenile hormone mimic | 150:1 to 1:200 |
| Emamectin | Chloride channel activator | 50:1 to 1:10 |
| Endosulfan | GABA-gated chloride channel antagonist | 200:1 to 1:100 |
| Esfenvalerate | Sodium channel modulator | 100:1 to 1:400 |
| Ethiprole | GABA-regulated chloride channel antagonist | 200:1 to 1:100 |
| Fenothiocarb | | 150:1 to 1:200 |
| Fenoxycarb | Juvenile hormone mimic | 500:1 to 1:100 |
| Fenvalerate | Sodium channel modulator | 150:1 to 1:200 |
| Fipronil | GABA-regulated chloride channel antagonist | 150:1 to 1:100 |
| Flonicamid | Selective homopteran feeding blocker | 200:1 to 1:100 |
| Flubendiamide | Ryanodine receptor modulator | 100:1 to 1:120 |
| Flufenoxuron | Chitin biosynthesis inhibitor | 200:1 to 1:100 |
| Hexaflumuron | Chitin biosynthesis inhibitor | 300:1 to 1:50 |
| Hydramethylnon | Mitochondrial complex III electron transport inhibitor | 150:1 to 1:250 |
| Imidacloprid | Nicotinic acetylcholone receptor (nAChR) agonist | 1000:1 to 1:1000 |
| Indoxacarb | Voltage-dependent sodium channel blocker | 200:1 to 1:50 |
| Lambda-cyhalothrin | Sodium channel modulator | 50:1 to 1:250 |
| Lufenuron | Chitin biosynthesis inhibitor | 500:1 to 1:250 |
| Metaflumizone | Voltage-depedent sodium channel blocker | 200:1 to 1:200 |
| Methomyl | Acetylcholine esterase inhibitor | 500:1 to 1:100 |
| Methoprene | Juvenile hormone mimic | 500:1 to 1:100 |
| Methoxyfenozide | Ecdysone receptor agonist | 50:1 to 1:50 |
| Nitenpyram | Nicotinic acetylcholine receptor (nAChR) agonist | 150:1 to 1:200 |
| Nithiazine | Nicotinic acetylcholine receptor (nAChR) agonist | 150:1 to 1:200 |
| Novaluron | Chitin biosynthesis inhibitor | 500:1 to 1:150 |
| Oxamyl | Acetylcholine esterase inhibitor | 200:1 to 1:200 |
| Pymetrozine | Selective homopteran feeding blocker | 200:1 to 1:100 |
| Pyrethrin | Sodium channel modulator | 100:1 to 1:10 |
| Pyridaben | Mitochondrial complex I electron transport inhibitor | 200:1 to 1:100 |
| Pyridalyl | Unknown site of action | 200:1 to 1:100 |
| Pyriproxyfen | Juventile hormone mimic | 500:1 to 1:100 |
| Ryanodine | Ryanodine receptor ligand | 100:1 to 1:120 |
| Spinetoram | Nicotinic acetylcholine receptor (nAChR) allosteric activator | 150:1 to 1:100 |
| Spinosad | Nicotinic acetylcholine receptor (nAChR) allosteric activator | 500:1 to 1:10 |
| Spirodiclofen | Acetyl CoA carboxylase inhibitor | 200:1 to 1:200 |
| Spiromesifen | Acetyl CoA carboxylase inhibitor | 200:1 to 1:200 |
| Tebufenozide | Ecdsone receptor agonist | 500:1 to 1:250 |
| Thiacloprid | Nicotinic acetylcholine receptor (nAChR) agonist | 100:1 to 1:200 |
| Thiamethoxam | Nicotinic acetylcholine receptor (nAChR) agonist | 1250:1 to 1:1000 |
| Thiodicarb | Acetylcholine esterase inhibitor | 500:1 to 1:400 |
| Thiosultap-sodium | Nicotinic acetylcholine receptor (nAChR) channel blocker | 150:1 to 1:100 |
| Tralomethrin | Sodium channel modulator | 150:1 to 1:200 |
| Triazamate | Acetylcholine esterase inhibitor | 250:1 to 1:100 |
| Triflumezopyrim | | 100:1 to 1:100 |
| Triflumuron | Chitin synthesis inhibitor | 200:1 to 1:100 |
| Bacillus thuringiensis | Biological agents | 50:1 to 1:10 |
| Bacillus thuringiensis Delta-endotoxin | Biological agents | 50:1 to 1:10 |
| NPV (e.g., Gemstar) | Biological agents | 50:1 to 1:10 |

TABLE SECTION

| % Control (or Mortality) | Rating |
|---|---|
| BAW and CL Rating Table | |
| 50-100 | A |
| More than 0-Less than 50 | B |
| Not Tested | C |
| No activity noticed in this bioassay | D |
| GPA & YFM Rating Table | |
| 80-100 | A |
| More than 0-Less than 80 | B |
| Not Tested | C |
| No activity noticed in this bioassay | D |

Molecules (compounds) according to Formula One and/or Formula Two as disclosed in Table 1 and Table 2 herein are tested to determine their efficacy against pests, and generally show activities in the A and/or B categories.

We claim:

1. A molecule having the following formula

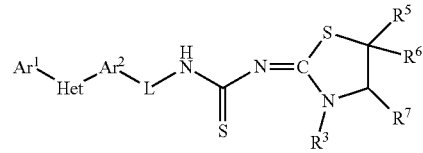

wherein:
(A) $Ar^1$ is selected from
  (1) furanyl, phenyl, pyridazinyl, pyridyl, pyrimidinyl, or thienyl, or
  (2) substituted furanyl, substituted phenyl, substituted pyridazinyl, substituted pyridyl, substituted pyrimidinyl, or substituted thienyl,
    wherein said substituted furanyl, substituted phenyl, substituted pyridazinyl, substituted pyridyl, substituted pyrimidinyl, or substituted thienyl, has one or more substituents independently selected from H, F, Cl, Br, I, CN, $NO_2$, $(C_1$-$C_8)$alkyl, $(C_1$-$C_8)$haloalkyl, $(C_3$-$C_8)$cycloalkyl, $(C_1$-$C_8)$alkoxy, $(C_1$-$C_8)$haloalkoxy, $(C_2$-$C_8)$alkenyl, $(C_2$-$C_8)$alkynyl, $S(O)_n$—$(C_1$-$C_8)$alkyl, $OSO_2$—$(C_1$-$C_8)$alkyl, $C(O)$-$NR^xR^y$, $(C_1$-$C_8)$alkyl-$NR^xR^y$, $C(O)$—$(C_1$-$C_8)$alkyl, $C(O)O$—$(C_1$-$C_8)$alkyl, $C(O)$—$(C_3$-$C_8)$cycloalkyl, $C(O)O$—$(C_3$-$C_8)$cycloalkyl, $C(O)$—$(C_2$-$C_8)$alkenyl, $C(O)O$—$(C_2$-$C_8)$alkenyl, $(C_1$-$C_8)$alkyl-$O$—$(C_1$-$C_8)$alkyl, $(C_1$-$C_8)$alkyl-$S(O)_n$—$(C_1$-$C_8)$alkyl, $C(O)$—$(C_1$-$C_8)$alkyl-$C(O)O$—$(C_1$-$C_8)$alkyl, phenyl, and phenoxy,
    wherein each alkyl, cycloalkyl, alkoxy, alkenyl, alkynyl, phenyl, and phenoxy substituent may be optionally substituted with one or more substituents independently selected from the group consisting of H, F, Cl, Br, I, CN, $NO_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_1-C_8)$haloalkyl, $C(O)O$—$(C_1-C_8)$haloalkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-O—$(C_1-C_8)$alkyl, $(C_1-C_8)$alkyl-$S(O)$—$(C_1-C_8)$alkyl, $C(O)$—$(C_1-C_8)$alkyl-$C(O)O$—$(C_1-C_8)$alkyl, phenyl, and phenoxy;

(B) Het is a 5- or 6-membered, saturated or unsaturated, heterocyclic ring, containing one or more heteroatoms independently selected from nitrogen, sulfur, or oxygen, and where $Ar^1$ and $Ar^2$ are not ortho to each other (but may be mew or para, such as, for a five-membered ring they are 1,3 and for a 6-membered ring they are either 1,3 or 1,4) and where said heterocyclic ring may also be substituted with one or more substituents independently selected from the group consisting of H, F, Cl, Br, I, CN, $NO_2$, oxo, $(C_1-C_8)$alkyl, $(C_3-C_8)$cycloalkyl, $(C_1-C_8)$alkoxy, $(C_2-C_8)$alkenyl, $(C_2-C_8)$alkynyl, $S(O)_n$—$(C_1-C_8)$alkyl, $OSO_2$—$(C_1-C_8)$alkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl-$C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-O—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy, wherein each alkyl, cycloalkyl, alkoxy, alkenyl, alkynyl, phenyl, and phenoxy substituent may be optionally substituted with one or more substituents independently selected from the group consisting of H, F, Cl, Br, I, CN, $NO_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_1-C_8)$haloalkyl, $C(O)O$—$(C_1-C_8)$haloalkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-O—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy;

(C) $Ar^2$ is selected from
(1) furanyl, phenyl, pyridazinyl, pyridyl, pyrimidinyl, or thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, or substituted thienyl, has one or more substituents independently selected from H, F, Cl, Br, I, CN, $NO_2$, $NR^xR^y$, $(C_1-C_8)$alkyl, $(C_1-C_8)$haloalkyl, $(C_3-C_8)$cycloalkyk $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $OSO_2$—$(C_1-C_8)$alkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-O—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy, wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, $NO_2$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_1-C_8)$haloalkyl, $C(O)O$—$(C_1-C_8)$haloalkyl, $C(O)$—$(C_3-C_8)$cycloalkyl, $C(O)O$—$(C_3-C_8)$cycloalkyl, $C(O)$—$(C_2-C_8)$alkenyl, $C(O)O$—$(C_2-C_8)$alkenyl, $(C_1-C_8)$alkyl-O—$(C_1-C_8)$alkyl, $(C_1-C_8)$alkyl-$S(O)_n$—$(C_1-C_8)$alkyl, $C(O)$—$(C_1-C_8)$alkyl-$C(O)O$—$(C_1-C_8)$alkyl, phenyl, and phenoxy;

(D) L is linker selected from
(1) a saturated or unsaturated, substituted or unsubstituted, linear $(C_1-C_4)$hydrocarbyl linker, and
(2) a saturated or unsaturated, substituted or unsubstituted, cyclic $(C_3-C_8)$hydrocarbyl group linker,
wherein each of said linkers connects $Ar^2$ to —NH— and
wherein said substituted linear $(C_1-C_4)$hydrocarbyl linker and substituted cyclic $(C_3-C_8)$hydrocarbyl linker has one or more substituents independently selected from $R^8$, $R^9$, $R^{10}$, $R^{11}$, and $R^{12}$, wherein each $R^8$, $R^9$, $R^{10}$, $R^{11}$, and $R^{12}$, is selected from F, Cl, Br, I, CN, oxo, $(C_1-C_6)$alkyl, $(C_2-C_6)$alkenyl, $(C_2-C_6)$haloalkenyl, $(C_2-C_6)$alkynyl, $(C_1-C_6)$haloalkyl, $(C_3-C_6)$cycloalkyl, $(C_3-C_6)$cycloalkenyl, $(C_3-C_6)$halocycloalkyl, $(C_1-C_6)$alkoxy, $(C_1-C_6)$haloalkoxy, or phenyl;

(H) $R^3$ is selected from the group consisting of $(C_3-C_8)$cycloalkyl, phenyl, $(C_1-C_8)$alkylphenyl, $(C_1-C_8)$alkyl-O-phenyl, $(C_2-C_8)$alkenyl-O-phenyl, (Het-1), $(C_1-C_8)$alkyl-(Het-1), and $(C_1-C_8)$alkyl-O-(Het-1),
wherein each alkyl, cycloalkyl, alkenyl, phenyl, and (Het-1) may be optionally substituted with one or more substituents independently selected from the group consisting of H, F, Cl, Br, I, CN, $NO_2$, $NR^xR^y$, $(C_1-C_8)$alkyl, $(C_1-C_8)$haloalkyl, $(C_3-C_8)$cycloalkyl, $(C_1-C_8)$alkoxy, $(C_1-C_8)$haloalkoxy, $(C_2-C_8)$alkenyl, $(C_2-C_8)$alkynyl, $S(O)_n$—$(C_1-C_8)$alkyl, $S(O)_n$—$(C_1-C_8)$haloalkyl, $OSO_2$—$(C_1-C_8)$alkyl, $OSO_2$—$(C_1-C_8)$haloalkyl, $C(O)H$, $C(O)$—$NR^xR^y$, $(C_1-C_8)$alkyl-$NR^xR^y$, $C(O)$—$(C_1-C_8)$alkyl, $C(O)O$—$(C_1-C_8)$alkyl, $C(O)$—$(C_1-C_8)$haloalkyl, $C(O)O$—$(C_1-C_8)$haloalkyl, C(O)—(C$_3$-C$_5$)cycloalkyl, C(O)O—(C$_1$-C$_8$)cycloalkyl, C(O)—(C$_2$-C$_8$)alkenyl, C(O)O—(C$_2$-C$_8$)alkenyl, O—(C$_1$-C$_8$)alkyl, S—(C$_1$-C$_8$)alkyl, (C$_1$-C$_8$)alkyl-O—(C$_1$-C$_8$)alkyl, C(O)—(C$_1$-C$_8$)alkyl-C(O)O—(C$_1$-C$_8$)alkyl, phenyl, phenoxy, and (Het-1), (J) R$^5$, R$^6$, and R$^7$ are each independently selected from the group consisting of H, F, Cl, Br, I, CN, OH, SH, NO$_2$, NR$^x$R$^y$, oxo, thioxo, (C$_1$-C$_8$)alkyl, (C$_1$-C$_8$)haloalkyl, (C$_3$-C$_8$)cycloalkyl, (C$_1$-C$_8$)alkoxy, (C$_1$-C$_8$)haloalkoxy, (C$_2$-C$_8$)alkenyl, (C$_2$-C$_8$)alkynyl, S(C$_1$-C$_8$ alkyl), S(C$_1$-C$_8$ haloalkyl), S(O)$_n$—(C$_1$-C$_8$)alkyl, S(O)$_n$—(C$_1$-C$_8$)haloalkyl, OSO$_2$—(C$_1$-C$_8$)alkyl, OSO$_2$—(C$_1$-C$_8$)haloalkyl, C(O)H, C(O)—(C$_1$-C$_8$)alkyl, C(O)O—(C$_1$-C$_8$)alkyl, C(O)—(C$_1$-C$_8$)haloalkyl, C(O)O—(C$_1$-C$_8$)haloalkyl, C(O)—(C$_3$-C$_8$)cycloalkyl, C(O)O—(C$_3$-C$_8$)cycloalkyl, C(O)—(C$_2$-C$_8$)alkenyl, C(O)O—(C$_2$-C$_8$)alkenyl, (C$_1$-C$_8$)alkyl-O—(C$_1$-C$_8$)alkyl, (C$_1$-C$_8$)alkyl-S(O)$_n$—(C$_1$-C$_8$)alkyl, C(O)—(C$_1$-C$_8$)alkyl-C(O)O—(C$_1$-C$_8$)alkyl, phenyl, and (Het-1);

(K) R$^x$ and R$^y$ are each independently selected from the group consisting of H, (C$_1$-C$_8$)alkyl, (C$_3$-C$_8$)cycloalkyl, (C$_1$-C$_8$)alkoxy, (C$_2$-C$_8$)alkenyl, (C$_2$-C$_8$)alkynyl, S(O)$_n$—(C$_1$-C$_8$)alkyl, OSO$_2$—(C$_1$-C$_8$)alkyl, C(O)H, C(O)—(C$_1$-C$_8$)alkyl, C(O)O—(C$_1$-C$_8$)alkyl-C(O)—(C$_3$-C$_8$)cycloalkyl, C(O)O—(C$_3$-C$_8$)cycloalkyl, C(O)—(C$_2$-C$_8$)alkenyl, C(O)O—(C$_2$-C$_8$)alkenyl, (C$_1$-C$_8$)alkyl-O—(C$_1$-C$_8$)alkyl, (C$_1$-C$_8$)alkyl-S(O)$_n$—(C$_1$-C$_8$)alkyl, C(O)—(C$_1$-C$_8$)alkyl-C(O)O—(C$_1$-C$_8$)alkyl, phenyl, and (C$_1$-C$_8$)alkylphenyl, wherein each alkyl, cycloalkyl, alkoxy, alkenyl, alkynyl, phenyl, and alkylphenyl may be optionally substituted with one or more substituents independently selected from the group consisting of H, F, Cl, Br, I, CN, NO$_2$, (C$_1$-C$_8$)alkyl, (C$_1$-C$_8$)haloalkyl, (C$_3$-C$_8$)cycloalkyl, (C$_1$-C$_8$)alkoxy, (C$_1$-C$_8$)haloalkoxy, (C$_2$-C$_8$)alkenyl, (C$_2$-C$_8$)alkynyl, S(O)$_n$—(C$_1$-C$_8$)alkyl, S(O)$_n$—(C$_1$-C$_8$)haloalkyl, OSO$_2$—(C$_1$-C$_8$)alkyl, OSO$_2$—(C$_1$-C$_8$)haloalkyl, C(O)H, C(O)—(C$_1$-C$_8$)alkyl, C(O)O—(C$_1$-C$_8$)alkyl, C(O)—(C$_1$-C$_8$)haloalkyl, C(O)O—(C$_1$-C$_8$)haloalkyl, C(O)—(C$_3$-C$_8$)cycloalkyl, C(O)O—(C$_3$-C$_8$)cycloalkyl, C(O)—(C$_2$-C$_8$)alkenyl, C(O)O—(C$_2$-C$_8$)alkenyl, (C$_1$-C$_8$)alkyl-O—(C$_1$-C$_8$)alkyl, (C$_1$-C$_8$)alkyl-S(O)$_n$—(C$_1$-C$_8$)alkyl, C(O)—(C$_1$-C$_8$)alkyl-C(O)O—(C$_1$-C$_8$)alkyl, phenyl, and (Het-1);

(L) (Het-1) is a 5- or 6-membered, saturated or unsaturated, heterocyclic ring, containing one or more heteroatoms independently selected from nitrogen, sulfur or oxygen, wherein said heterocyclic ring may be optionally substituted with one or more substituents independently selected from the group consisting of H, F, Cl, Br, I, CN, NO$_2$, oxo, (C$_1$-C$_8$)alkyl, (C$_3$-C$_8$)cycloalkyl, (C$_1$-C$_8$)alkoxy, (C$_2$-C$_8$)alkenyl, (C$_2$-C$_8$)alkynyl, S(O)$_n$—(C$_1$-C$_8$)alkyl, OSO$_2$—(C$_1$-C$_8$)alkyl, C(O)—NR$^x$R$^y$, (C$_1$-C$_8$)alkyl-NR$^x$R$^y$, C(O)—(C$_1$-C$_8$)alkyl, C(O)O—(C$_1$-C$_8$)alkyl, C(O)—(C$_3$-C$_8$)cycloalkyl, C(O)O—(C$_3$-C$_8$)cycloalkyl, C(O)—(C$_2$-C$_8$)alkenyl, C(O)O—(C$_2$-C$_8$)alkenyl, (C$_1$-C$_8$)alkyl-O—(C$_1$-C$_8$)alkyl, (C$_1$-C$_8$)alkyl-S(O)$_n$—(C$_1$-C$_8$)alkyl, C(O)—(C$_1$-C$_8$)alkyl-C(O)O—(C$_1$-C$_8$)alkyl, phenyl, and phenoxy, wherein each alkyl, cycloalkyl, alkoxy, alkenyl, alkynyl, phenyl, and phenoxy substituent may be optionally substituted with one or more substituents independently selected from the group consisting of H, F, Cl, Br, I, CN, NO$_2$, (C$_1$-C$_8$)alkyl, (C$_1$-C$_8$)haloalkyl, (C$_3$-C$_8$)cycloalkyl, (C$_1$-C$_8$)alkoxy, (C$_1$-C$_8$)haloalkoxy, (C$_2$-C$_8$)alkenyl, (C$_2$-C$_8$)alkynyl, S(O)$_n$—(C$_1$-C$_8$)alkyl, S(O)$_n$—(C$_1$-C$_8$)haloalkyl, OSO$_2$—(C$_1$-C$_8$)alkyl, OSO$_2$—(C$_1$-C$_8$)haloalkyl, C(O)—NR$^x$R$^y$, (C$_1$-C$_8$)alkyl-NR$^x$R$^y$, C(O)—(C$_1$-C$_8$)alkyl, C(O)O—(C$_1$-C$_8$)alkyl, C(O)—(C$_1$-C$_8$)haloalkyl, C(O)O—(C$_1$-C$_8$)haloalkyl, C(O)—(C$_3$-C$_8$)cycloalkyl, C(O)O—(C$_3$-C$_8$)cycloalkyl, C(O)—(C$_2$-C$_8$)alkenyl, C(O)O—(C$_2$-C$_8$)alkenyl, (C$_1$-C$_8$)alkyl-O—(C$_1$-C$_8$)alkyl, (C$_1$-C$_8$)alkyl-S(O)$_n$—(C$_1$-C$_8$)alkyl, C(O)—(C$_1$-C$_8$)alkyl-C(O)O—(C$_1$-C$_8$)alkyl, phenyl, and phenoxy;

(M) n is each individually 0, 1, or 2; and

N-oxides, agriculturally acceptable acid addition salts, salts, solvates, esters, crystal polymorphs, isotopes, and resolved stereoisomers thereof.

2. A molecule according to claim 1, wherein:

(A) Ar$^1$ is substituted phenyl wherein said substituted phenyl has one or more substituents independently selected from (C$_1$-C$_6$)alkyl, (C$_1$-C$_6$)haloalkyl, (C$_1$-C$_6$)alkoxy and (C$_1$-C$_6$)haloalkoxy;

(B) Het is triazolyl;

(C) Ar$^2$ is phenyl, or substituted phenyl wherein said substituted phenyl has one or more substituents independently selected from F, Cl, Br, I, CN, NO$_2$, NR$^x$R$^y$, (C$_1$-C$_6$)alkyl, and (C$_1$-C$_6$)haloalkyl;

(G) R$^3$ is phenyl, wherein said phenyl is optionally substituted with one or more substituents independently selected from F, Cl, Br, I, CN, NO$_2$, NR$^x$R$^y$, (C$_1$-C$_6$)alkyl, (C$_1$-C$_6$)haloalkyl, phenyl, (C$_1$-C$_6$)alkoxy, and (C$_1$-C$_6$)haloalkoxy;

(J) each R$^5$, R$^6$, and R$^7$ is selected from H, F, Cl, Br, I, CN, OH, SH, NO$_2$, NR$^x$R$^y$, (C$_1$-C$_6$)alkyl, (C$_1$-C$_6$)haloalkyl, (C$_1$-C$_6$)alkoxy, (C$_1$-C$_6$)haloalkoxy, S(C$_1$-C$_6$ alkyl), S(C$_1$-C$_6$ haloalkyl), phenyl, and oxo;

(K) R$^x$ and R$^y$ are independently selected from H, C$_1$-C$_6$ alkyl, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ alkynyl, and phenyl; and (L) L is linker selected from (1) a saturated or unsaturated, substituted or unsubstituted, linear (C$_1$-C$_4$)hydrocarbyl linker, and (2) a saturated or unsaturated, substituted or unsubstituted, cyclic (C$_3$-C$_8$)hydrocarbyl group linker, wherein each of said linkers connects Ar$^2$ to —NH— and wherein said substituted linear (C$_1$-C$_4$)hydrocarbyl linker and substituted cyclic (C$_3$-C$_8$)hydrocarbyl linker has one or more substituents independently selected from R$^8$, R$^9$, R$^{10}$, R$^{11}$, and R$^{12}$, wherein each R$^8$, R$^9$, R$^{10}$, R$^{11}$, and R$^{12}$, is selected from F, Cl, Br, I, CN, oxo, (C$_1$-C$_6$)alkyl, (C$_2$-C$_6$)alkenyl, (C$_2$-C$_6$)haloalkenyl, (C$_2$-C$_6$)alkynyl, (C$_1$-C$_6$)haloalkyl, (C$_3$-C$_6$)cycloalkyl, (C$_3$-C$_6$)cycloalkenyl, (C$_3$-C$_6$)halocycloalkyl, and phenyl.

3. A molecule according to claim 1 having a structure from compounds listed below:

P1 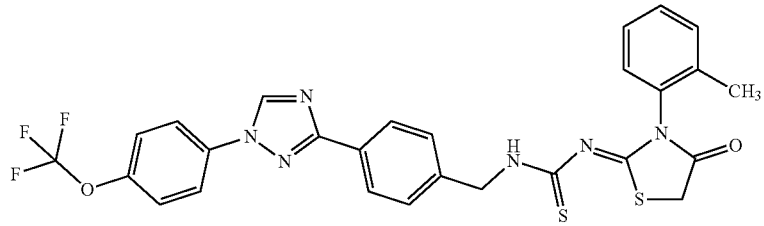 [SMILES: Cc1ccccc1N1C(=O)CS/C1=N\C(=S)NCc1ccc(-c2ncn(-c3ccc(OC(F)(F)F)cc3)n2)cc1]
P2 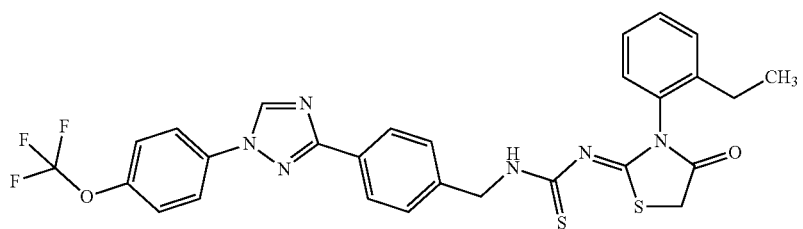 [SMILES: CCc1ccccc1N1C(=O)CS/C1=N\C(=S)NCc1ccc(-c2ncn(-c3ccc(OC(F)(F)F)cc3)n2)cc1]
P3 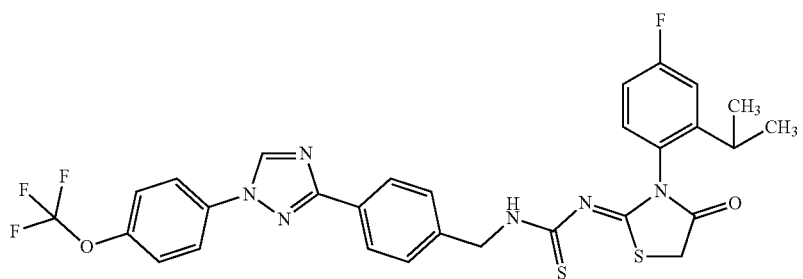 [SMILES: CC(C)c1cc(F)ccc1N1C(=O)CS/C1=N\C(=S)NCc1ccc(-c2ncn(-c3ccc(OC(F)(F)F)cc3)n2)cc1]
P4 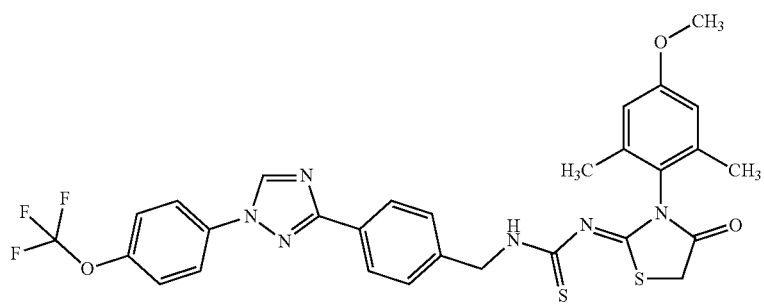 [SMILES: COc1cc(C)c(N2C(=O)CS/C2=N\C(=S)NCc2ccc(-c3ncn(-c4ccc(OC(F)(F)F)cc4)n3)cc2)c(C)c1]
P5 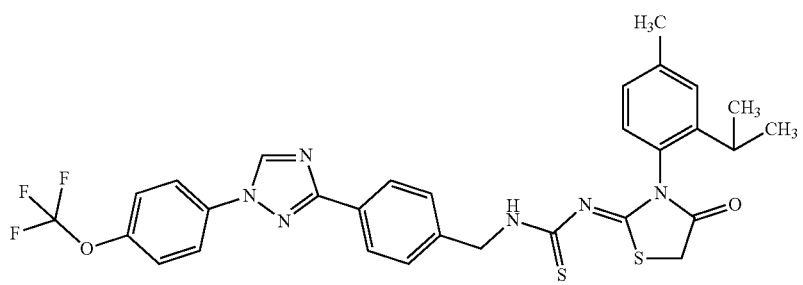 [SMILES: Cc1ccc(N2C(=O)CS/C2=N\C(=S)NCc2ccc(-c3ncn(-c4ccc(OC(F)(F)F)cc4)n3)cc2)c(C(C)C)c1]
P6 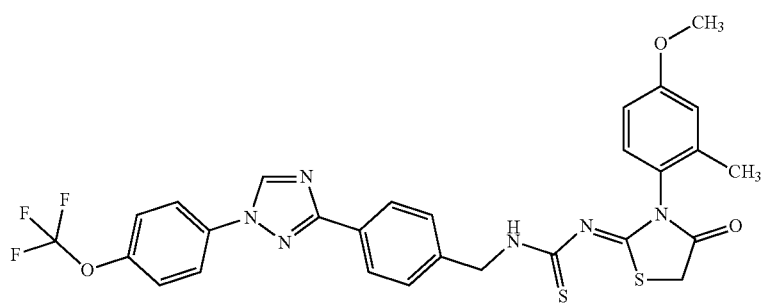 [SMILES: COc1ccc(N2C(=O)CS/C2=N\C(=S)NCc2ccc(-c3ncn(-c4ccc(OC(F)(F)F)cc4)n3)cc2)c(C)c1]

-continued
P7
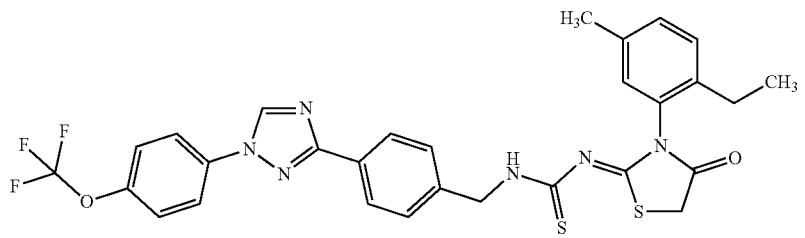 [SMILES: CCc1ccc(C)cc1N1C(=O)CS/C1=N\C(=S)NCc1ccc(-c2ncn(-c3ccc(OC(F)(F)F)cc3)n2)cc1]
P8
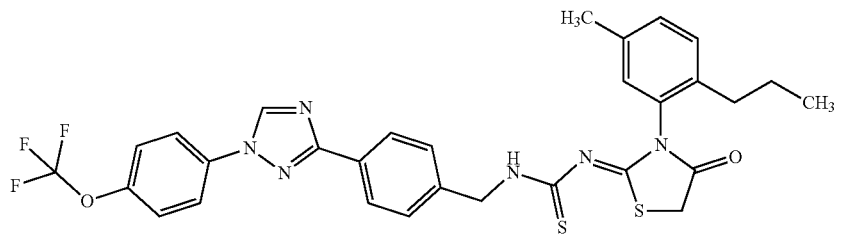 [SMILES: CCCc1ccc(C)cc1N1C(=O)CS/C1=N\C(=S)NCc1ccc(-c2ncn(-c3ccc(OC(F)(F)F)cc3)n2)cc1]
P9
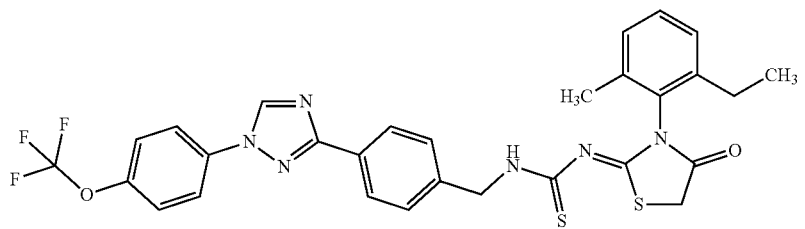 [SMILES: CCc1cccc(C)c1N1C(=O)CS/C1=N\C(=S)NCc1ccc(-c2ncn(-c3ccc(OC(F)(F)F)cc3)n2)cc1]
P10
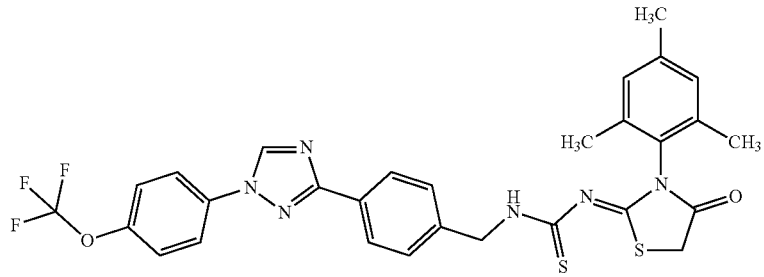 [SMILES: Cc1cc(C)c(N2C(=O)CS/C2=N\C(=S)NCc2ccc(-c3ncn(-c4ccc(OC(F)(F)F)cc4)n3)cc2)c(C)c1]
P11
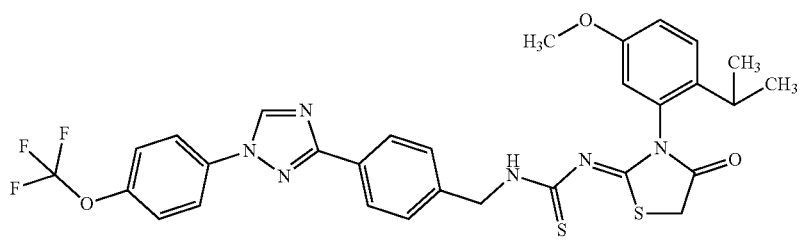 [SMILES: COc1ccc(C(C)C)c(N2C(=O)CS/C2=N\C(=S)NCc2ccc(-c3ncn(-c4ccc(OC(F)(F)F)cc4)n3)cc2)c1]
P12
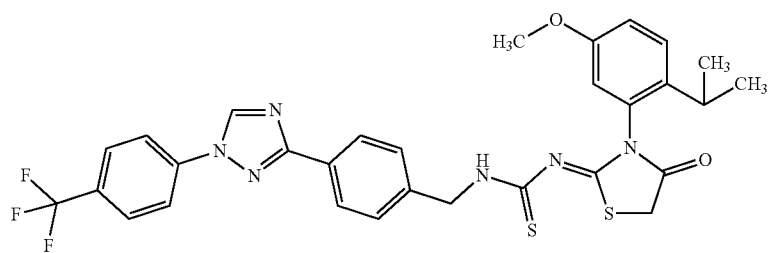 [SMILES: COc1ccc(C(C)C)c(N2C(=O)CS/C2=N\C(=S)NCc2ccc(-c3ncn(-c4ccc(C(F)(F)F)cc4)n3)cc2)c1]

-continued
P13
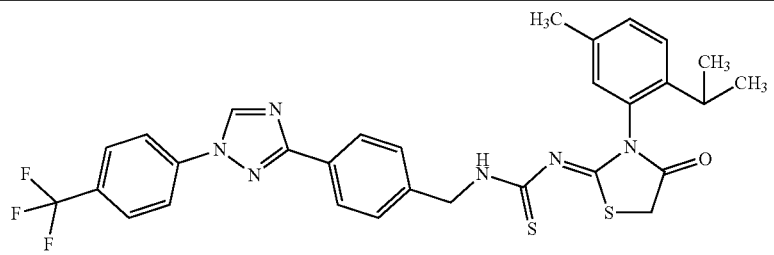
P14
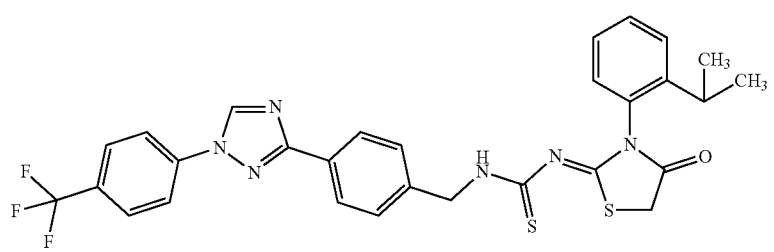 [SMILES: CC(C)c1ccccc1N1C(=O)CS/C1=N\C(=S)NCc1ccc(-c2ncn(-c3ccc(C(F)(F)F)cc3)n2)cc1]
P15
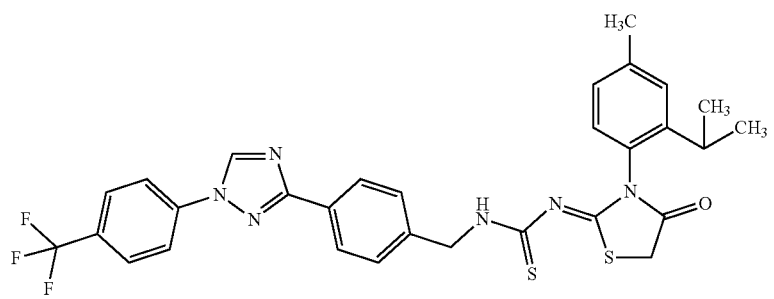 [SMILES: Cc1ccc(N2C(=O)CS/C2=N\C(=S)NCc2ccc(-c3ncn(-c4ccc(C(F)(F)F)cc4)n3)cc2)c(C(C)C)c1]
P16
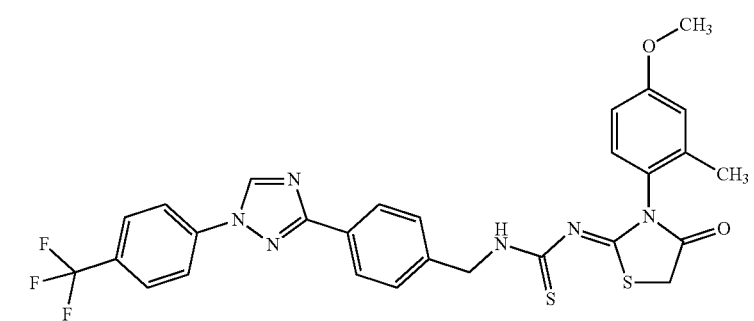 [SMILES: COc1ccc(N2C(=O)CS/C2=N\C(=S)NCc2ccc(-c3ncn(-c4ccc(C(F)(F)F)cc4)n3)cc2)c(C)c1]
P17
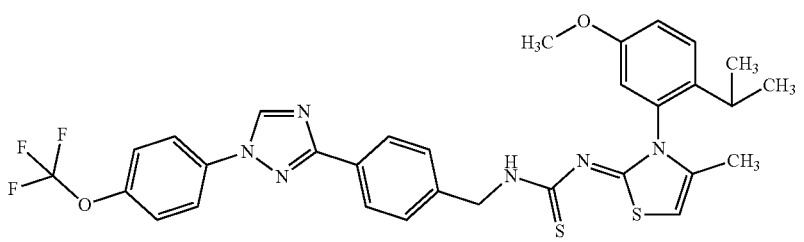 [SMILES: COc1ccc(C(C)C)c(-n2c(C)cs/c2=N\C(=S)NCc2ccc(-c3ncn(-c4ccc(OC(F)(F)F)cc4)n3)cc2)c1]
P18
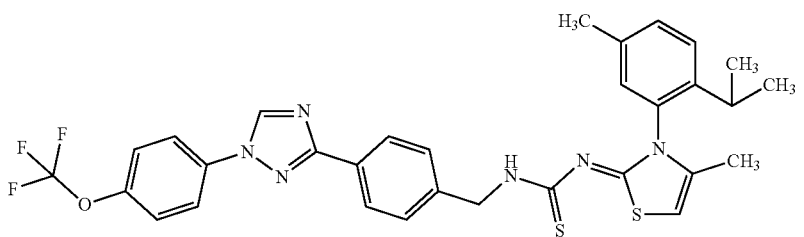 [SMILES: Cc1ccc(C(C)C)c(-n2c(C)cs/c2=N\C(=S)NCc2ccc(-c3ncn(-c4ccc(OC(F)(F)F)cc4)n3)cc2)c1]

-continued
P19
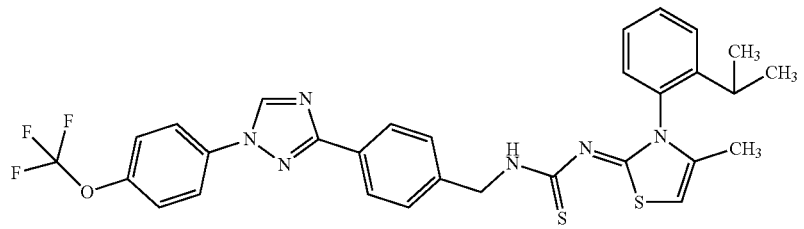 [SMILES: Cc1cs/c(=N\C(=S)NCc2ccc(-c3ncn(-c4ccc(OC(F)(F)F)cc4)n3)cc2)n1-c1ccccc1C(C)C]
P20
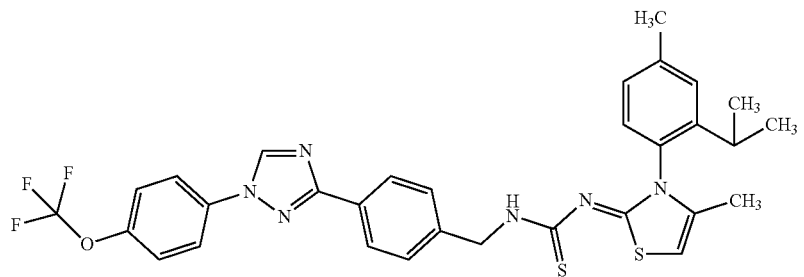 [SMILES: Cc1ccc(-n2c(C)cs/c2=N\C(=S)NCc2ccc(-c3ncn(-c4ccc(OC(F)(F)F)cc4)n3)cc2)c(C(C)C)c1]
P21
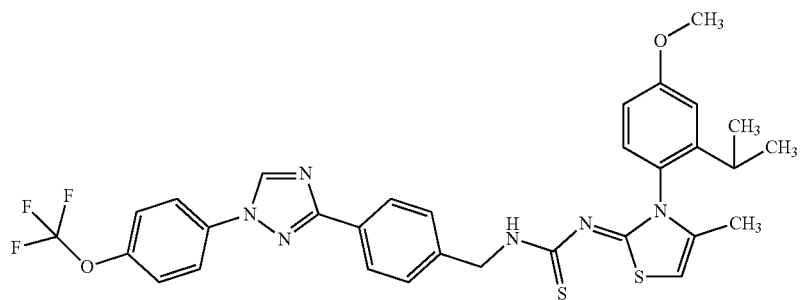 [SMILES: COc1ccc(-n2c(C)cs/c2=N\C(=S)NCc2ccc(-c3ncn(-c4ccc(OC(F)(F)F)cc4)n3)cc2)c(C(C)C)c1]
P22
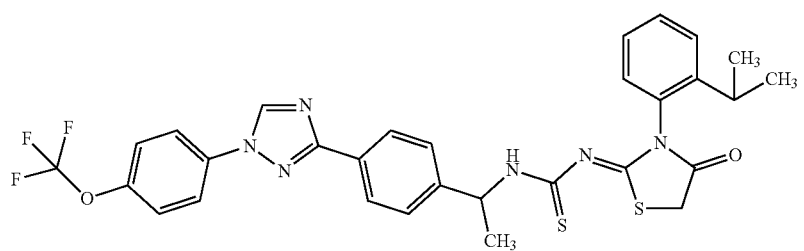 [SMILES: CC(C)c1ccccc1N1C(=O)CS/C1=N\C(=S)NC(C)c1ccc(-c2ncn(-c3ccc(OC(F)(F)F)cc3)n2)cc1]
P23
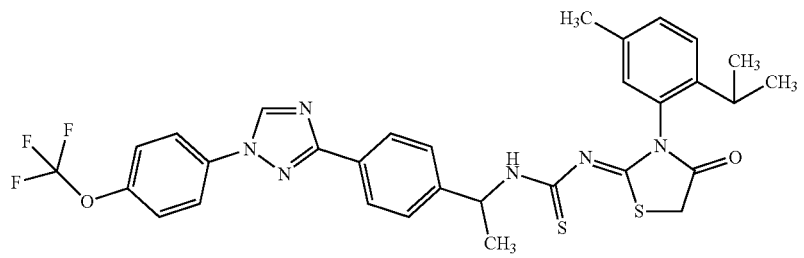 [SMILES: Cc1ccc(C(C)C)c(N2C(=O)CS/C2=N\C(=S)NC(C)c2ccc(-c3ncn(-c4ccc(OC(F)(F)F)cc4)n3)cc2)c1]
P24
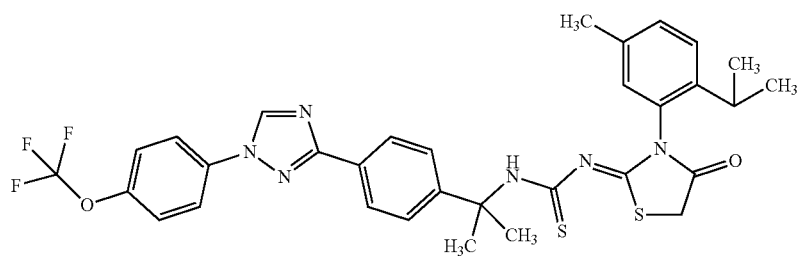 [SMILES: Cc1ccc(C(C)C)c(N2C(=O)CS/C2=N\C(=S)NC(C)(C)c2ccc(-c3ncn(-c4ccc(OC(F)(F)F)cc4)n3)cc2)c1]

-continued
P25
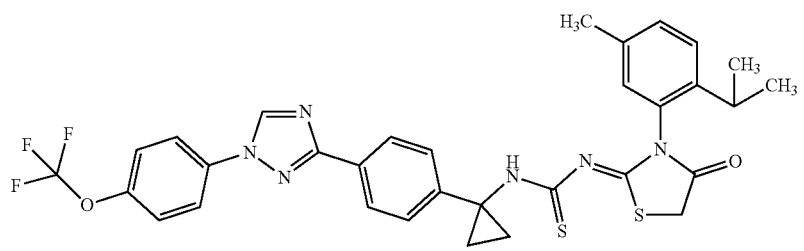 [SMILES: Cc1ccc(C(C)C)c(N2C(=O)CS/C2=N\C(=S)NC2(c3ccc(-c4ncn(-c5ccc(OC(F)(F)F)cc5)n4)cc3)CC2)c1]
P26
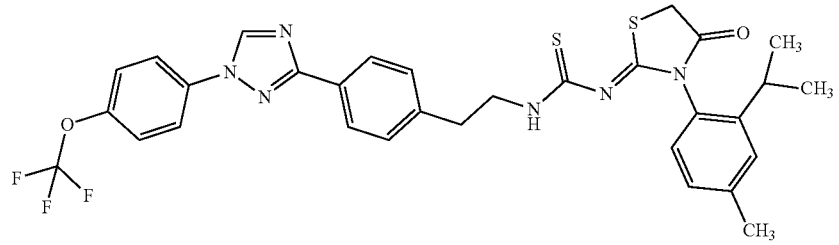 [SMILES: Cc1ccc(N2C(=O)CS/C2=N\C(=S)NCCc2ccc(-c3ncn(-c4ccc(OC(F)(F)F)cc4)n3)cc2)c(C(C)C)c1]
P27
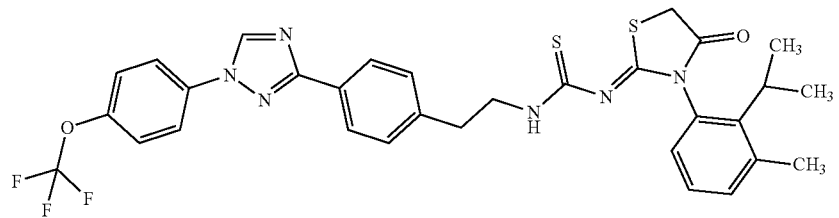 [SMILES: Cc1cccc(N2C(=O)CS/C2=N\C(=S)NCCc2ccc(-c3ncn(-c4ccc(OC(F)(F)F)cc4)n3)cc2)c1C(C)C]
P28
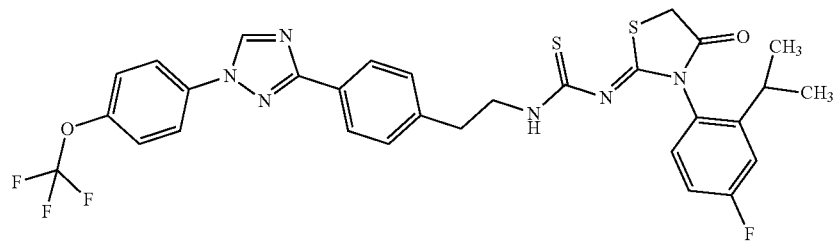 [SMILES: CC(C)c1cc(F)ccc1N1C(=O)CS/C1=N\C(=S)NCCc1ccc(-c2ncn(-c3ccc(OC(F)(F)F)cc3)n2)cc1]
P29
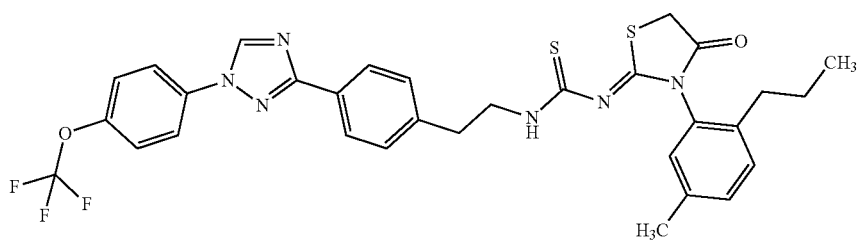 [SMILES: CCCc1ccc(C)cc1N1C(=O)CS/C1=N\C(=S)NCCc1ccc(-c2ncn(-c3ccc(OC(F)(F)F)cc3)n2)cc1]
P30
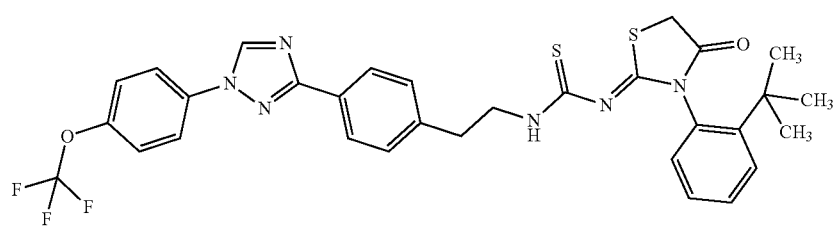 [SMILES: CC(C)(C)c1ccccc1N1C(=O)CS/C1=N\C(=S)NCCc1ccc(-c2ncn(-c3ccc(OC(F)(F)F)cc3)n2)cc1]

-continued
P31 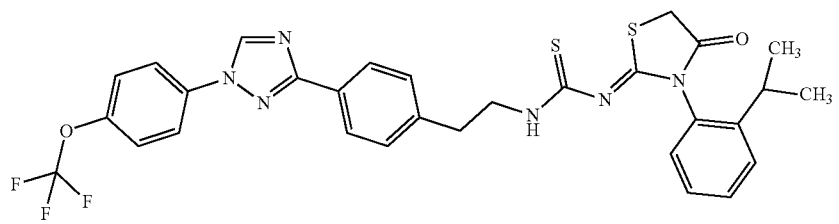 [SMILES: CC(C)c1ccccc1N1C(=O)CS/C1=N\C(=S)NCCc1ccc(-c2ncn(-c3ccc(OC(F)(F)F)cc3)n2)cc1]
P32 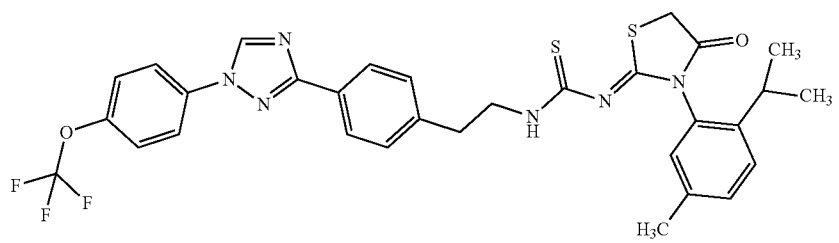 [SMILES: Cc1ccc(C(C)C)c(N2C(=O)CS/C2=N\C(=S)NCCc2ccc(-c3ncn(-c4ccc(OC(F)(F)F)cc4)n3)cc2)c1]
P33 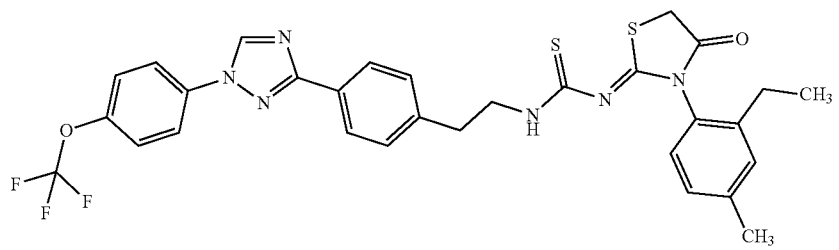 [SMILES: CCc1cc(C)ccc1N1C(=O)CS/C1=N\C(=S)NCCc1ccc(-c2ncn(-c3ccc(OC(F)(F)F)cc3)n2)cc1]
P34 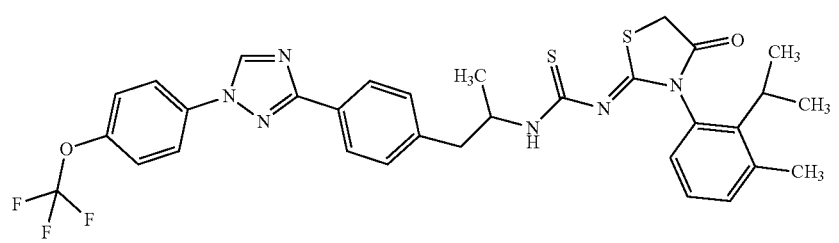 [SMILES: Cc1cccc(N2C(=O)CS/C2=N\C(=S)NC(C)Cc2ccc(-c3ncn(-c4ccc(OC(F)(F)F)cc4)n3)cc2)c1C(C)C]
P35 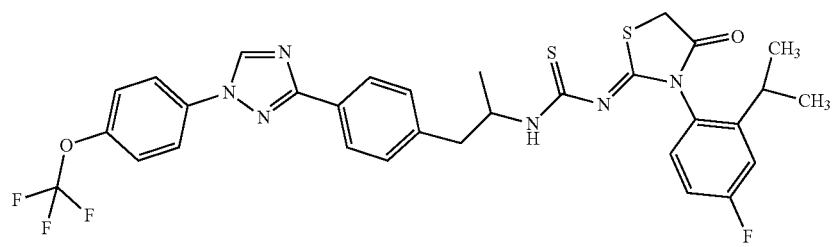 [SMILES: CC(Cc1ccc(-c2ncn(-c3ccc(OC(F)(F)F)cc3)n2)cc1)NC(=S)/N=C1\SCC(=O)N1c1ccc(F)cc1C(C)C]
P36 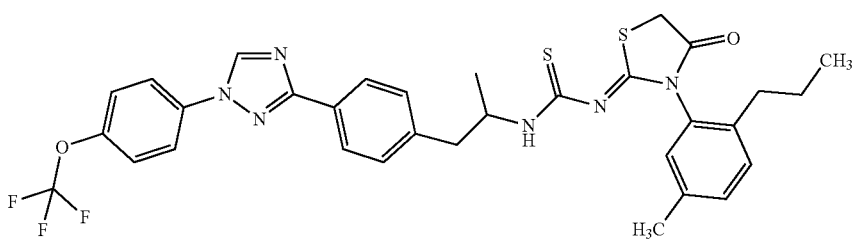

-continued
P37
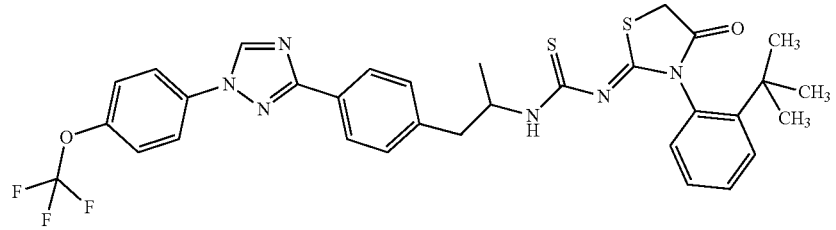 [SMILES: CC(Cc1ccc(-c2ncn(-c3ccc(OC(F)(F)F)cc3)n2)cc1)NC(=S)/N=C1\SCC(=O)N1c1ccccc1C(C)(C)C]
P38
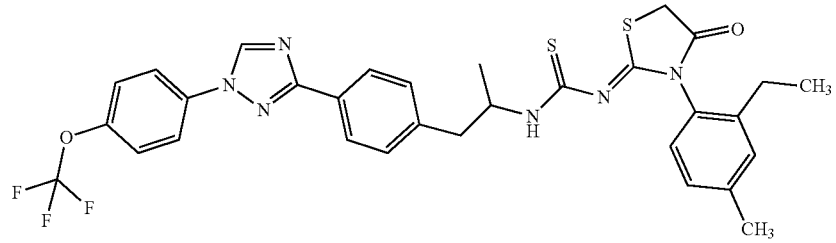 [SMILES: CCc1cc(C)ccc1N1C(=O)CS/C1=N\C(=S)NC(C)Cc1ccc(-c2ncn(-c3ccc(OC(F)(F)F)cc3)n2)cc1]
P39
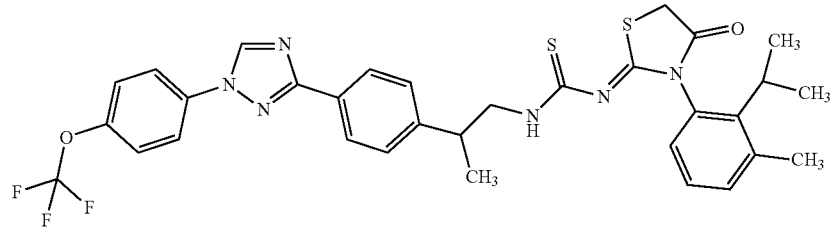 [SMILES: Cc1cccc(N2C(=O)CS/C2=N\C(=S)NCC(C)c2ccc(-c3ncn(-c4ccc(OC(F)(F)F)cc4)n3)cc2)c1C(C)C]
P40
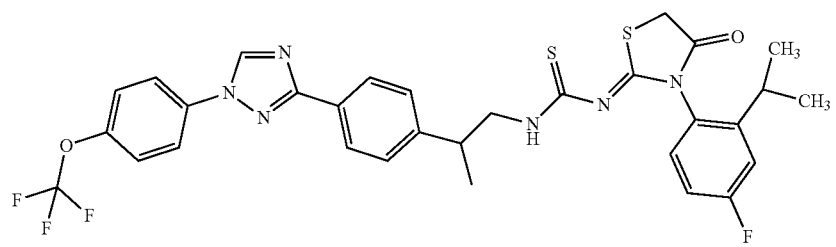 [SMILES: CC(C)c1cc(F)ccc1N1C(=O)CS/C1=N\C(=S)NCC(C)c1ccc(-c2ncn(-c3ccc(OC(F)(F)F)cc3)n2)cc1]
P41
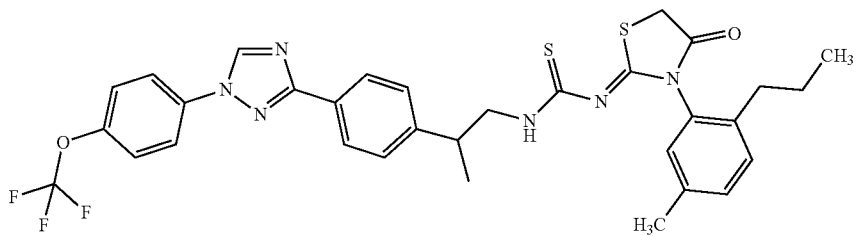 [SMILES: CCCc1ccc(C)cc1N1C(=O)CS/C1=N\C(=S)NCC(C)c1ccc(-c2ncn(-c3ccc(OC(F)(F)F)cc3)n2)cc1]
P42
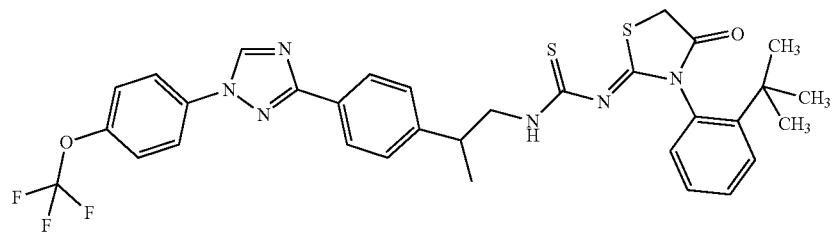 [SMILES: CC(CNC(=S)/N=C1\SCC(=O)N1c1ccccc1C(C)(C)C)c1ccc(-c2ncn(-c3ccc(OC(F)(F)F)cc3)n2)cc1]

P43 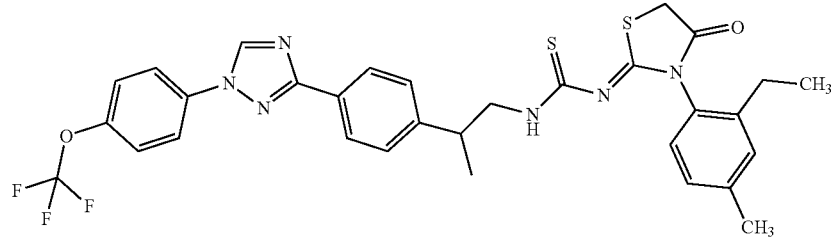 [SMILES: CCc1cc(C)ccc1N1C(=O)CS/C1=N\C(=S)NCC(C)c1ccc(-c2ncn(-c3ccc(OC(F)(F)F)cc3)n2)cc1]
P44 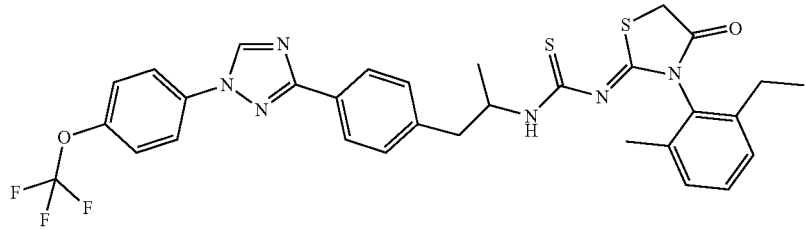 [SMILES: CCc1cccc(C)c1N1C(=O)CS/C1=N\C(=S)NC(C)Cc1ccc(-c2ncn(-c3ccc(OC(F)(F)F)cc3)n2)cc1]
P45 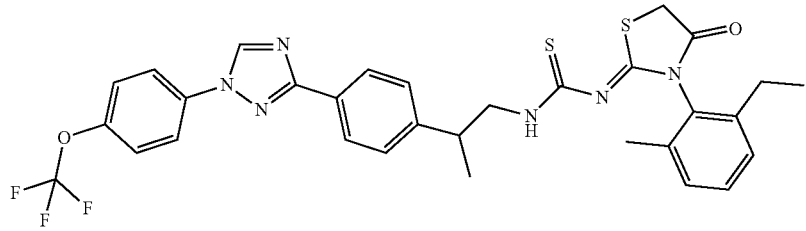 [SMILES: CCc1cccc(C)c1N1C(=O)CS/C1=N\C(=S)NCC(C)c1ccc(-c2ncn(-c3ccc(OC(F)(F)F)cc3)n2)cc1]
P46 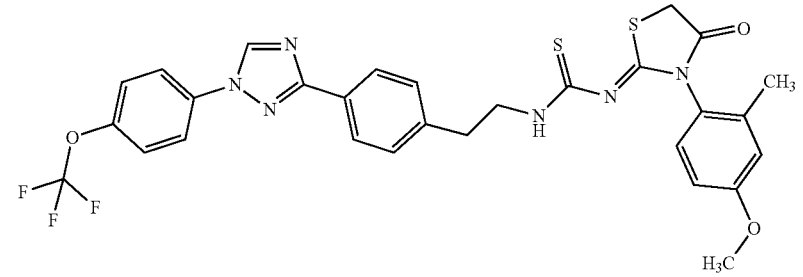 [SMILES: COc1ccc(N2C(=O)CS/C2=N\C(=S)NCCc2ccc(-c3ncn(-c4ccc(OC(F)(F)F)cc4)n3)cc2)c(C)c1]
P47 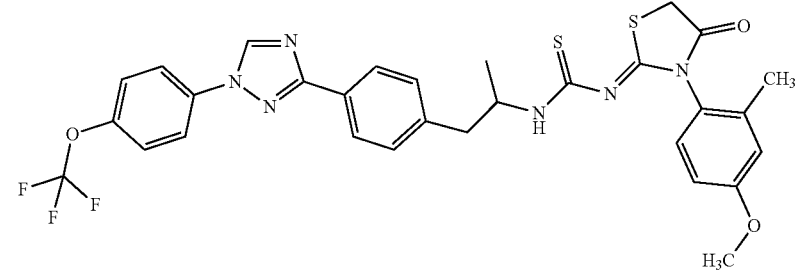
P48 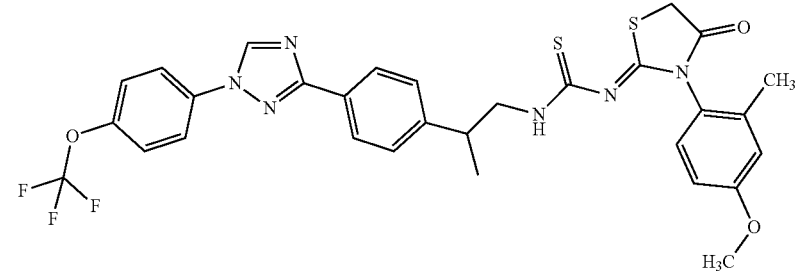

-continued
P49 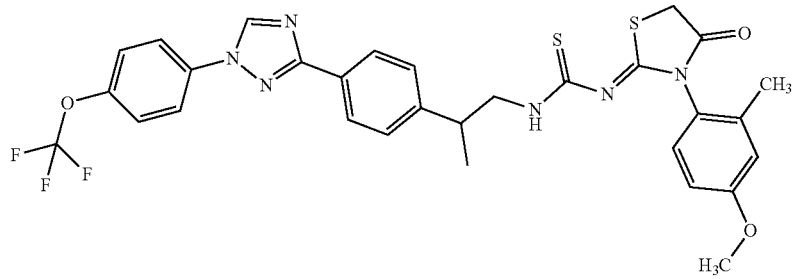 [SMILES: COc1ccc(N2C(=O)CS/C2=N\C(=S)NCC(C)c2ccc(-c3ncn(-c4ccc(OC(F)(F)F)cc4)n3)cc2)c(C)c1]
P50 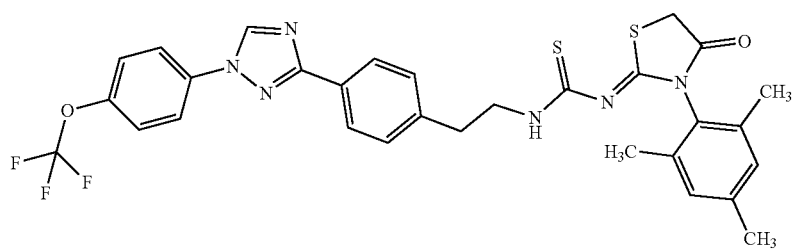 [SMILES: Cc1cc(C)c(N2C(=O)CS/C2=N\C(=S)NCCc2ccc(-c3ncn(-c4ccc(OC(F)(F)F)cc4)n3)cc2)c(C)c1]
P51 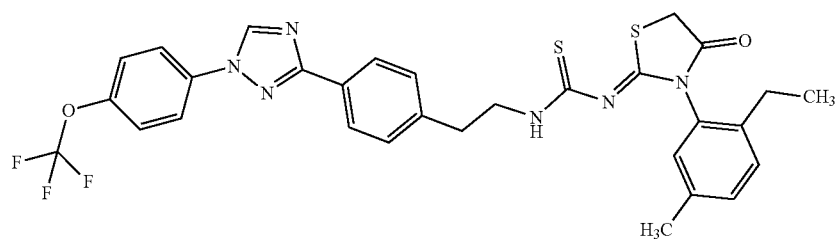 [SMILES: CCc1ccc(C)cc1N1C(=O)CS/C1=N\C(=S)NCCc1ccc(-c2ncn(-c3ccc(OC(F)(F)F)cc3)n2)cc1]
P52 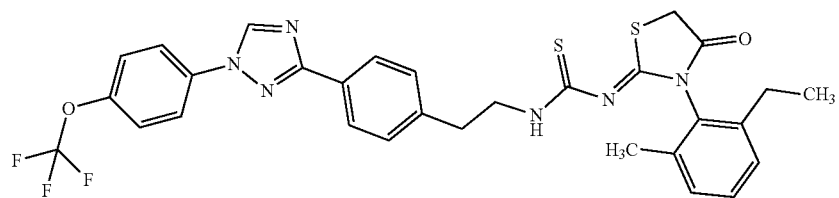 [SMILES: CCc1cccc(C)c1N1C(=O)CS/C1=N\C(=S)NCCc1ccc(-c2ncn(-c3ccc(OC(F)(F)F)cc3)n2)cc1]
P53 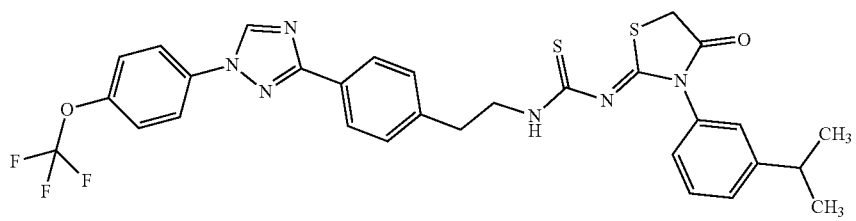 [SMILES: CC(C)c1cccc(N2C(=O)CS/C2=N\C(=S)NCCc2ccc(-c3ncn(-c4ccc(OC(F)(F)F)cc4)n3)cc2)c1]
P54 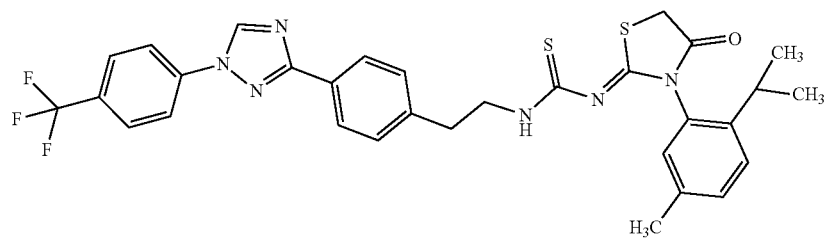 [SMILES: Cc1ccc(C(C)C)c(N2C(=O)CS/C2=N\C(=S)NCCc2ccc(-c3ncn(-c4ccc(C(F)(F)F)cc4)n3)cc2)c1]

-continued
P55 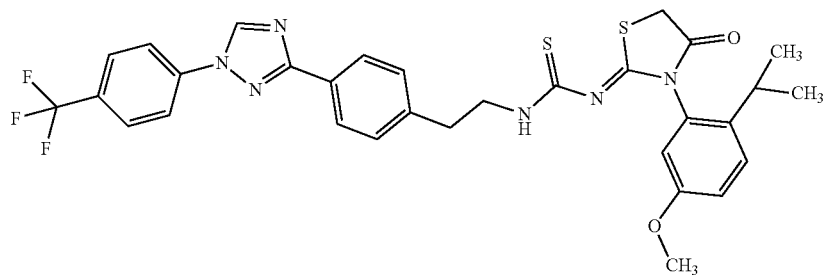 [SMILES: COc1ccc(C(C)C)c(N2C(=O)CS/C2=N\C(=S)NCCc2ccc(-c3ncn(-c4ccc(C(F)(F)F)cc4)n3)cc2)c1]
P56 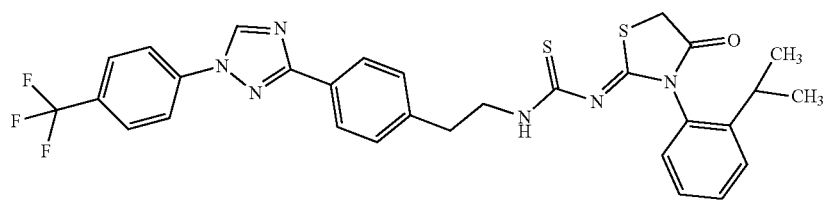 [SMILES: CC(C)c1ccccc1N1C(=O)CS/C1=N\C(=S)NCCc1ccc(-c2ncn(-c3ccc(C(F)(F)F)cc3)n2)cc1]
P57 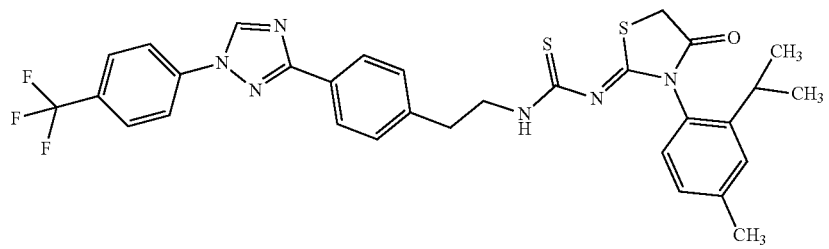 [SMILES: Cc1ccc(N2C(=O)CS/C2=N\C(=S)NCCc2ccc(-c3ncn(-c4ccc(C(F)(F)F)cc4)n3)cc2)c(C(C)C)c1]
P58 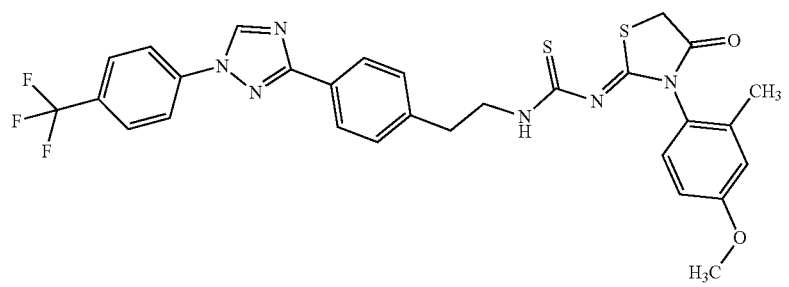 [SMILES: COc1ccc(N2C(=O)CS/C2=N\C(=S)NCCc2ccc(-c3ncn(-c4ccc(C(F)(F)F)cc4)n3)cc2)c(C)c1]
P59 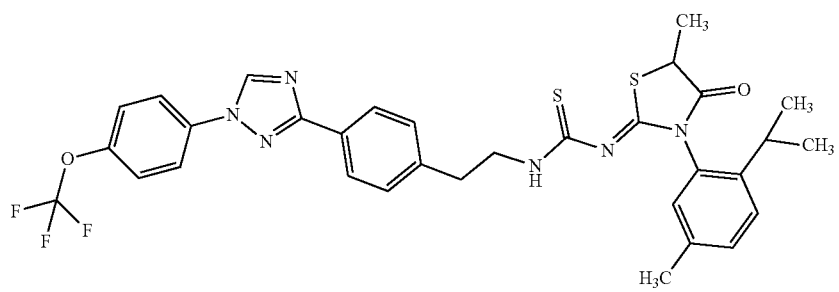 [SMILES: Cc1ccc(C(C)C)c(N2C(=O)C(C)S/C2=N\C(=S)NCCc2ccc(-c3ncn(-c4ccc(OC(F)(F)F)cc4)n3)cc2)c1]
P60 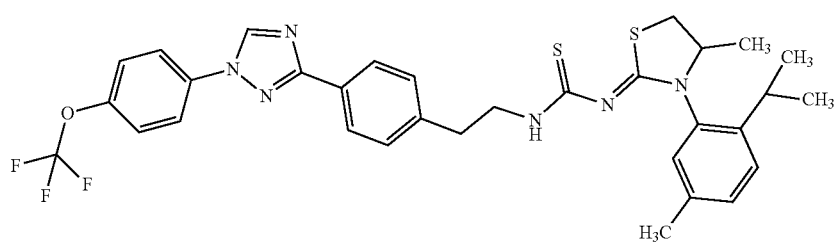 [SMILES: Cc1ccc(C(C)C)c(N2/C(=N/C(=S)NCCc3ccc(-c4ncn(-c5ccc(OC(F)(F)F)cc5)n4)cc3)SCC2C)c1]

-continued
P61 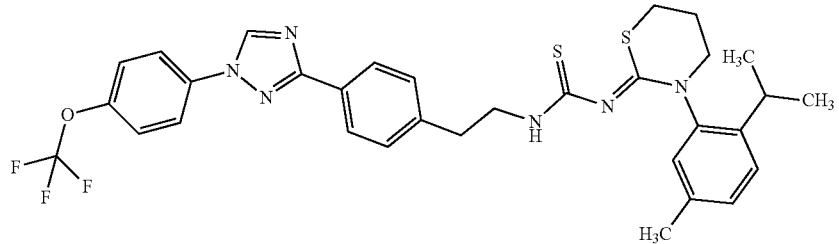
P62 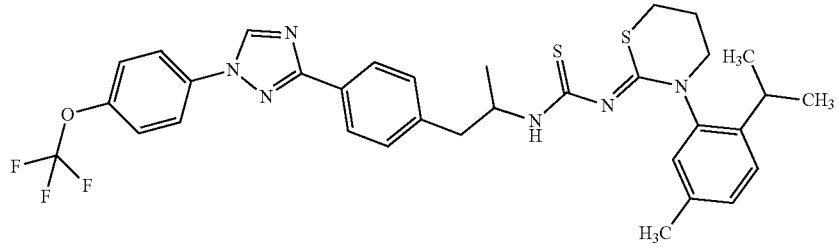 [SMILES: Cc1ccc(C(C)C)c(N2CCCS/C2=N\C(=S)NC(C)Cc2ccc(-c3ncn(-c4ccc(OC(F)(F)F)cc4)n3)cc2)c1]
P63 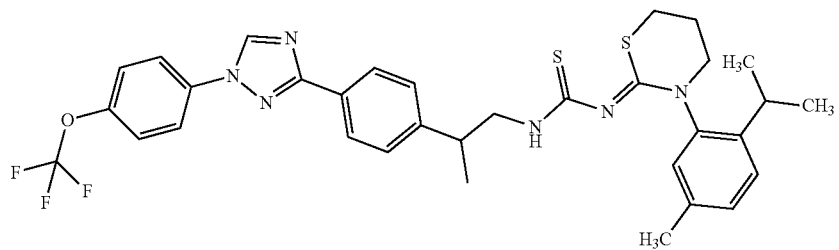 [SMILES: Cc1ccc(C(C)C)c(N2CCCS/C2=N\C(=S)NCC(C)c2ccc(-c3ncn(-c4ccc(OC(F)(F)F)cc4)n3)cc2)c1]
P64 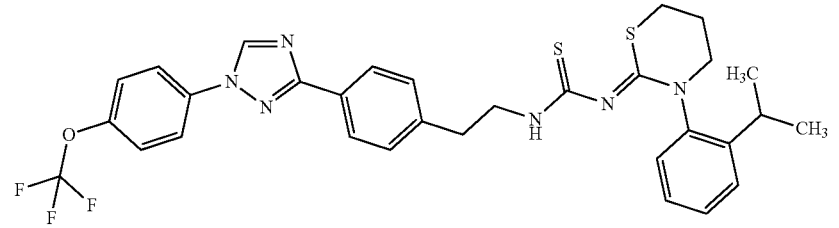 [SMILES: CC(C)c1ccccc1N1CCCS/C1=N\C(=S)NCCc1ccc(-c2ncn(-c3ccc(OC(F)(F)F)cc3)n2)cc1]
P65 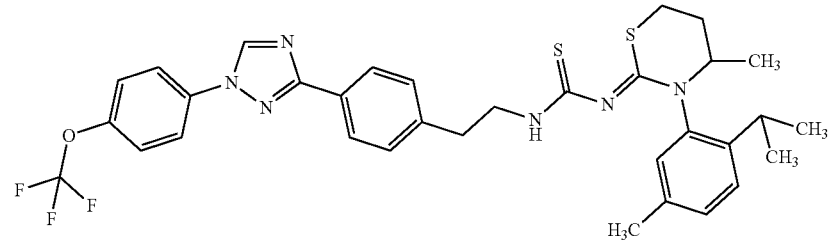 [SMILES: Cc1ccc(C(C)C)c(N2/C(=N/C(=S)NCCc3ccc(-c4ncn(-c5ccc(OC(F)(F)F)cc5)n4)cc3)SCCC2C)c1]
P66 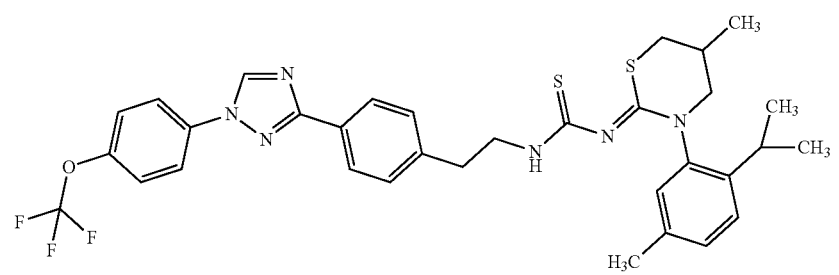 [SMILES: Cc1ccc(C(C)C)c(N2CC(C)CS/C2=N\C(=S)NCCc2ccc(-c3ncn(-c4ccc(OC(F)(F)F)cc4)n3)cc2)c1]

P67 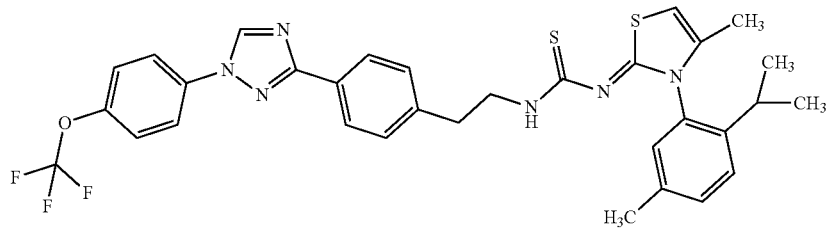 [SMILES: Cc1ccc(C(C)C)c(-n2c(C)cs/c2=N\C(=S)NCCc2ccc(-c3ncn(-c4ccc(OC(F)(F)F)cc4)n3)cc2)c1]
P68 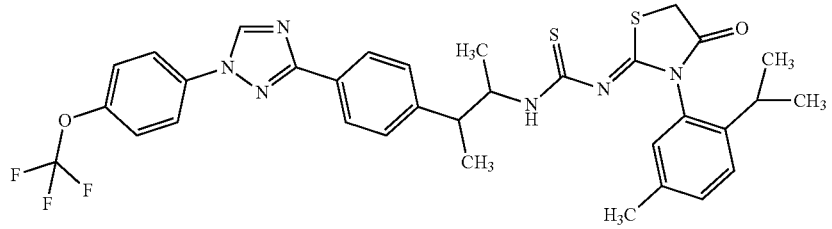 [SMILES: Cc1ccc(C(C)C)c(N2C(=O)CS/C2=N\C(=S)NC(C)C(C)c2ccc(-c3ncn(-c4ccc(OC(F)(F)F)cc4)n3)cc2)c1]
P69 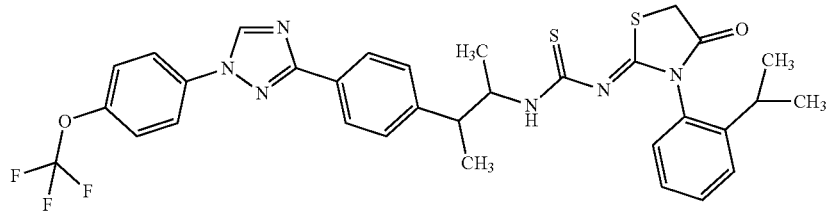 [SMILES: CC(C)c1ccccc1N1C(=O)CS/C1=N\C(=S)NC(C)C(C)c1ccc(-c2ncn(-c3ccc(OC(F)(F)F)cc3)n2)cc1]
P70 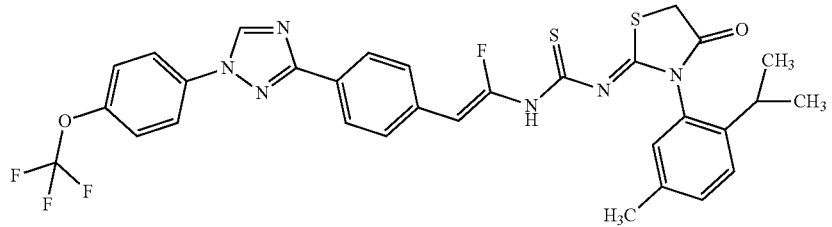 [SMILES: Cc1ccc(C(C)C)c(N2C(=O)CS/C2=N\C(=S)N/C(F)=C/c2ccc(-c3ncn(-c4ccc(OC(F)(F)F)cc4)n3)cc2)c1]
P71 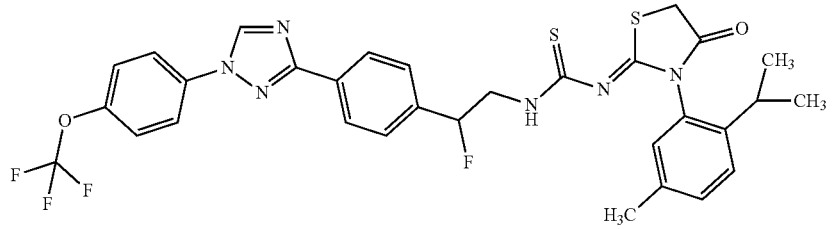 [SMILES: Cc1ccc(C(C)C)c(N2C(=O)CS/C2=N\C(=S)NCC(F)c2ccc(-c3ncn(-c4ccc(OC(F)(F)F)cc4)n3)cc2)c1]
P72 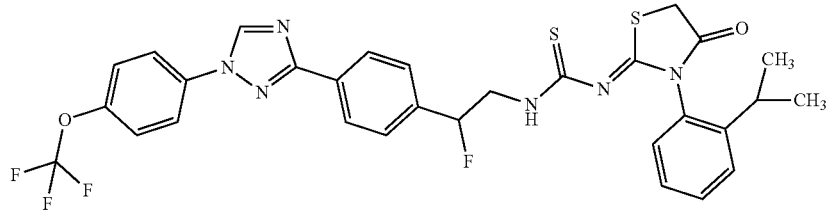 [SMILES: CC(C)c1ccccc1N1C(=O)CS/C1=N\C(=S)NCC(F)c1ccc(-c2ncn(-c3ccc(OC(F)(F)F)cc3)n2)cc1]
P73 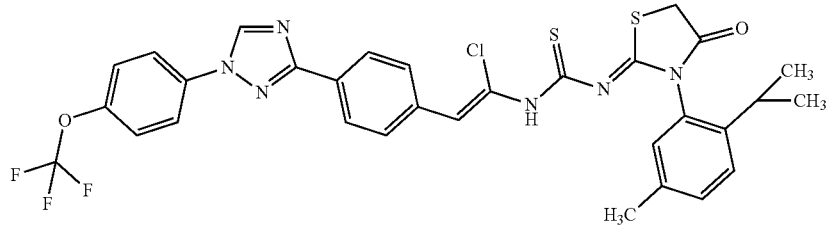 [SMILES: Cc1ccc(C(C)C)c(N2C(=O)CS/C2=N\C(=S)N/C(Cl)=C/c2ccc(-c3ncn(-c4ccc(OC(F)(F)F)cc4)n3)cc2)c1]

P74 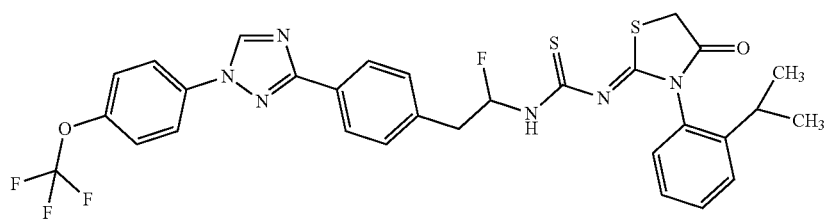 [SMILES: CC(C)c1ccccc1N1C(=O)CS/C1=N\C(=S)NC(F)Cc1ccc(-c2ncn(-c3ccc(OC(F)(F)F)cc3)n2)cc1]
P75 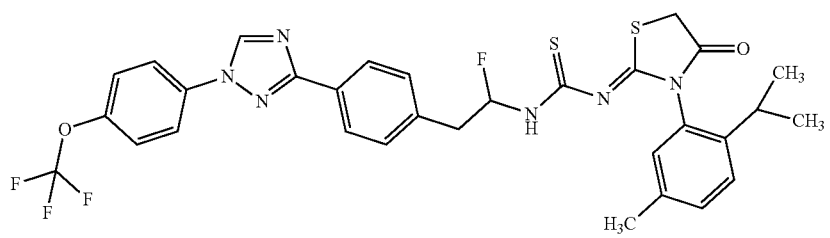 [SMILES: Cc1ccc(C(C)C)c(N2C(=O)CS/C2=N\C(=S)NC(F)Cc2ccc(-c3ncn(-c4ccc(OC(F)(F)F)cc4)n3)cc2)c1]
P76 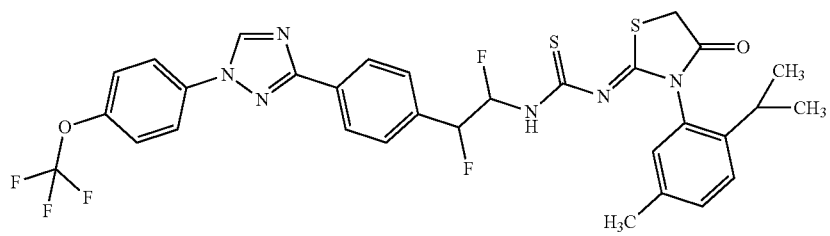 [SMILES: Cc1ccc(C(C)C)c(N2C(=O)CS/C2=N\C(=S)NC(F)C(F)c2ccc(-c3ncn(-c4ccc(OC(F)(F)F)cc4)n3)cc2)c1]
P77 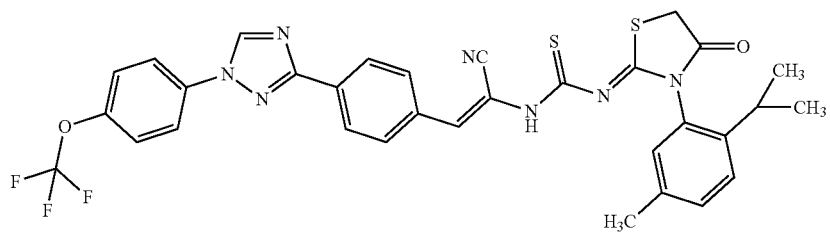 [SMILES: Cc1ccc(C(C)C)c(N2C(=O)CS/C2=N\C(=S)N/C(C#N)=C/c2ccc(-c3ncn(-c4ccc(OC(F)(F)F)cc4)n3)cc2)c1]
P78 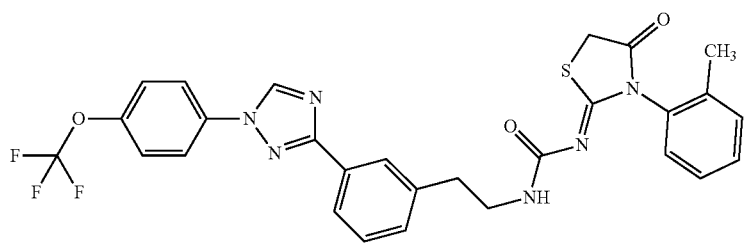 [SMILES: Cc1ccccc1N1C(=O)CS/C1=N\C(=O)NCCc1cccc(-c2ncn(-c3ccc(OC(F)(F)F)cc3)n2)c1]
P79 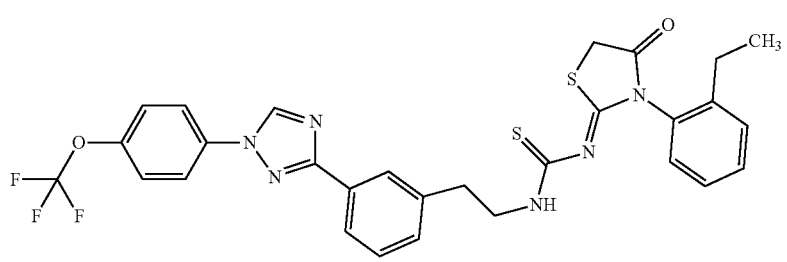 [SMILES: CCc1ccccc1N1C(=O)CS/C1=N\C(=S)NCCc1cccc(-c2ncn(-c3ccc(OC(F)(F)F)cc3)n2)c1]

-continued
P80
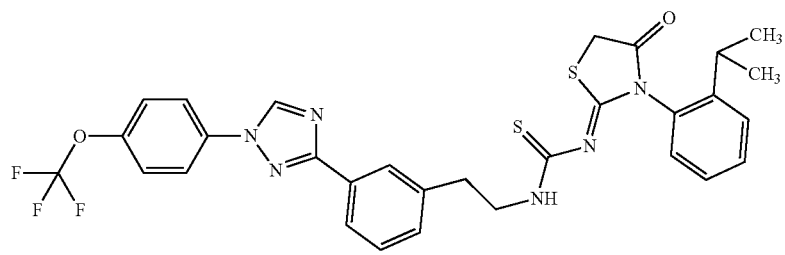 [SMILES: CC(C)c1ccccc1N1C(=O)CS/C1=N\C(=S)NCCc1cccc(-c2ncn(-c3ccc(OC(F)(F)F)cc3)n2)c1]
P81
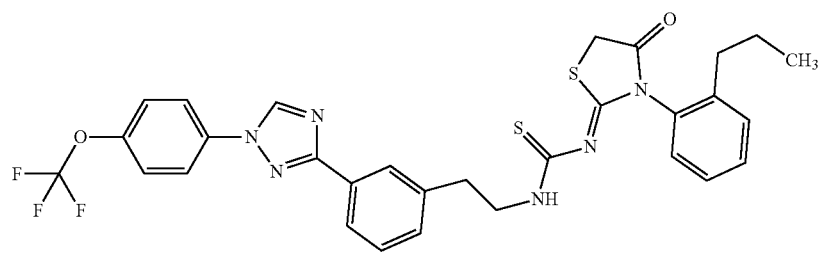 [SMILES: CCCc1ccccc1N1C(=O)CS/C1=N\C(=S)NCCc1cccc(-c2ncn(-c3ccc(OC(F)(F)F)cc3)n2)c1]
P82
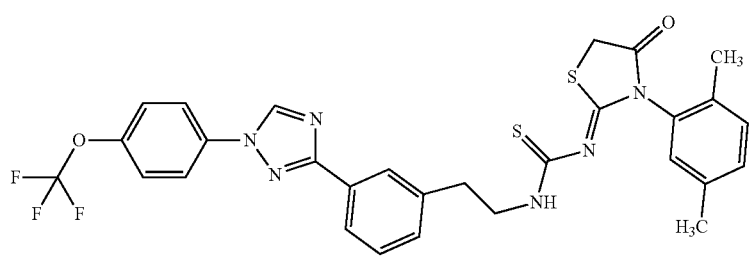 [SMILES: Cc1ccc(C)c(N2C(=O)CS/C2=N\C(=S)NCCc2cccc(-c3ncn(-c4ccc(OC(F)(F)F)cc4)n3)c2)c1]
P83
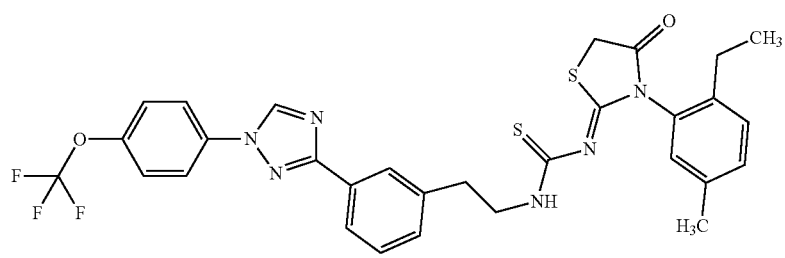 [SMILES: CCc1ccc(C)cc1N1C(=O)CS/C1=N\C(=S)NCCc1cccc(-c2ncn(-c3ccc(OC(F)(F)F)cc3)n2)c1]
P84
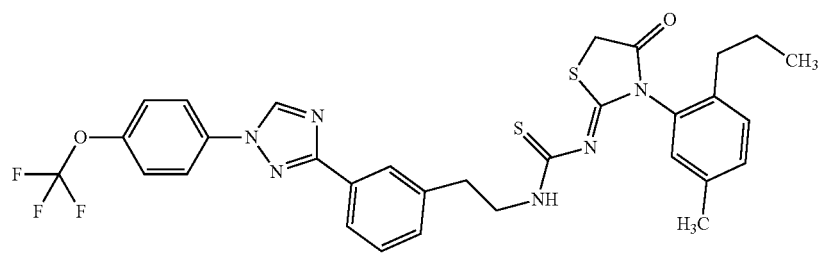 [SMILES: CCCc1ccc(C)cc1N1C(=O)CS/C1=N\C(=S)NCCc1cccc(-c2ncn(-c3ccc(OC(F)(F)F)cc3)n2)c1]
P85
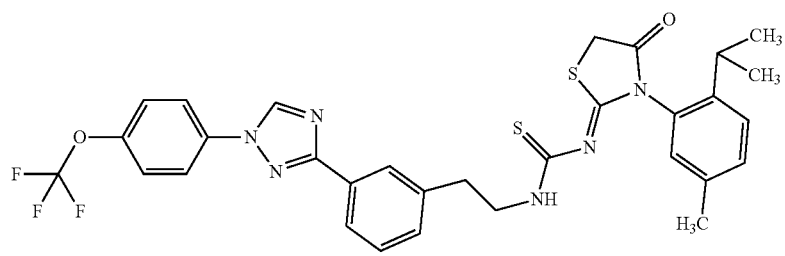 [SMILES: Cc1ccc(C(C)C)c(N2C(=O)CS/C2=N\C(=S)NCCc2cccc(-c3ncn(-c4ccc(OC(F)(F)F)cc4)n3)c2)c1]

-continued
P86
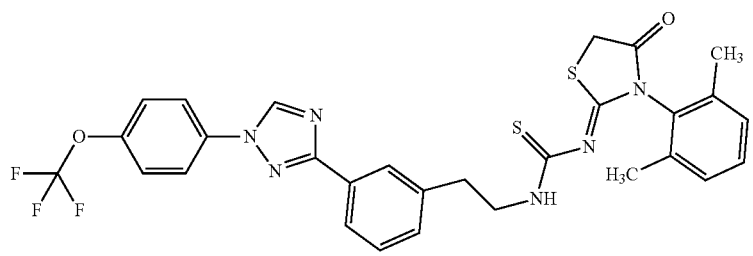 [SMILES: Cc1cccc(C)c1N1C(=O)CS/C1=N\C(=S)NCCc1cccc(-c2ncn(-c3ccc(OC(F)(F)F)cc3)n2)c1]
P87
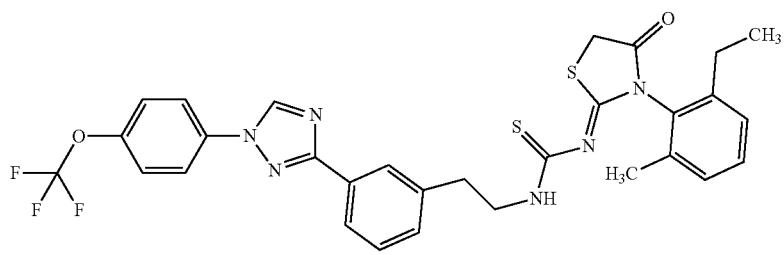 [SMILES: CCc1cccc(C)c1N1C(=O)CS/C1=N\C(=S)NCCc1cccc(-c2ncn(-c3ccc(OC(F)(F)F)cc3)n2)c1]
P88
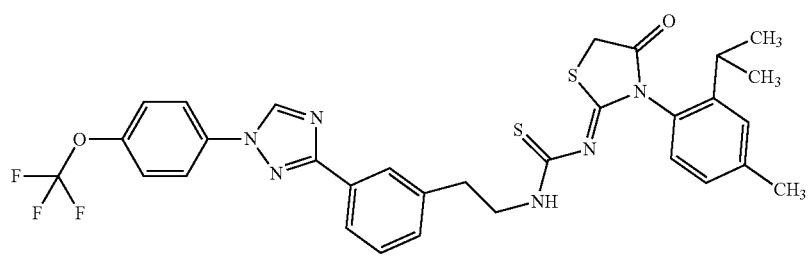 [SMILES: Cc1ccc(N2C(=O)CS/C2=N\C(=S)NCCc2cccc(-c3ncn(-c4ccc(OC(F)(F)F)cc4)n3)c2)c(C(C)C)c1]
P89
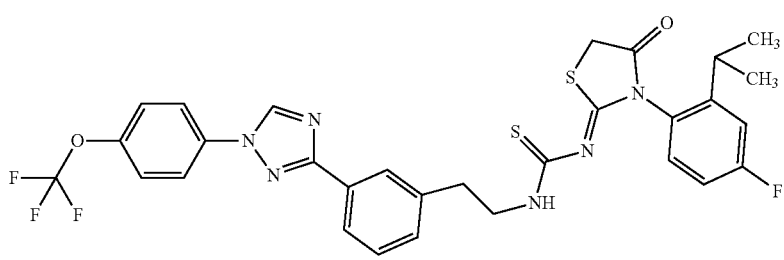 [SMILES: CC(C)c1cc(F)ccc1N1C(=O)CS/C1=N\C(=S)NCCc1cccc(-c2ncn(-c3ccc(OC(F)(F)F)cc3)n2)c1]
P90
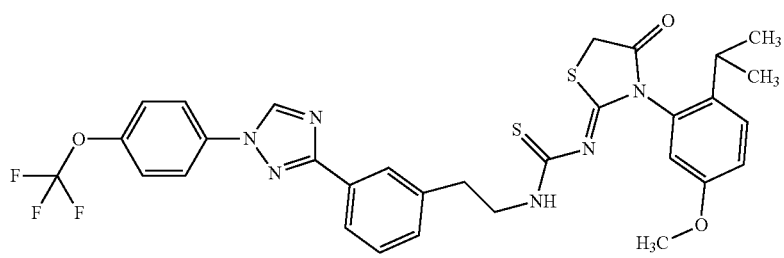 [SMILES: COc1ccc(C(C)C)c(N2C(=O)CS/C2=N\C(=S)NCCc2cccc(-c3ncn(-c4ccc(OC(F)(F)F)cc4)n3)c2)c1]
P91
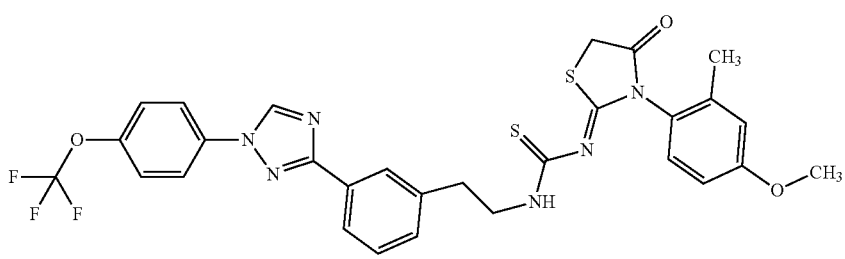 [SMILES: COc1ccc(N2C(=O)CS/C2=N\C(=S)NCCc2cccc(-c3ncn(-c4ccc(OC(F)(F)F)cc4)n3)c2)c(C)c1]

-continued
P92 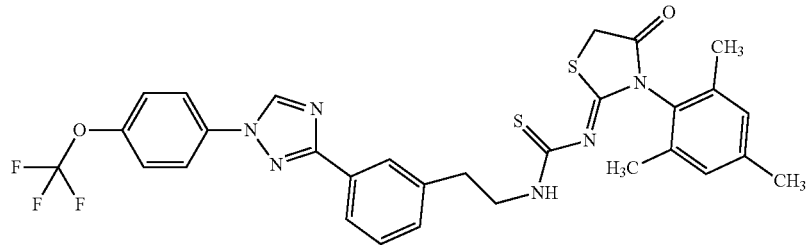 [SMILES: Cc1cc(C)c(N2C(=O)CS/C2=N\C(=S)NCCc2cccc(-c3ncn(-c4ccc(OC(F)(F)F)cc4)n3)c2)c(C)c1]
P93 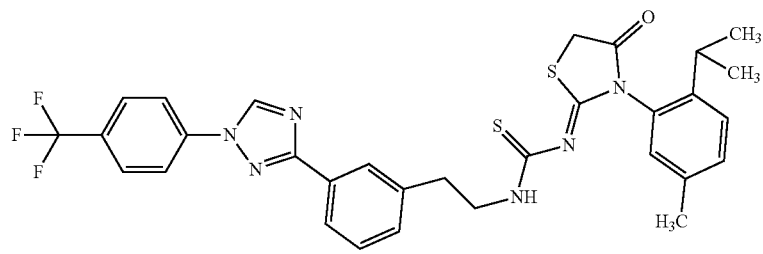 [SMILES: Cc1ccc(C(C)C)c(N2C(=O)CS/C2=N\C(=S)NCCc2cccc(-c3ncn(-c4ccc(C(F)(F)F)cc4)n3)c2)c1]
P94 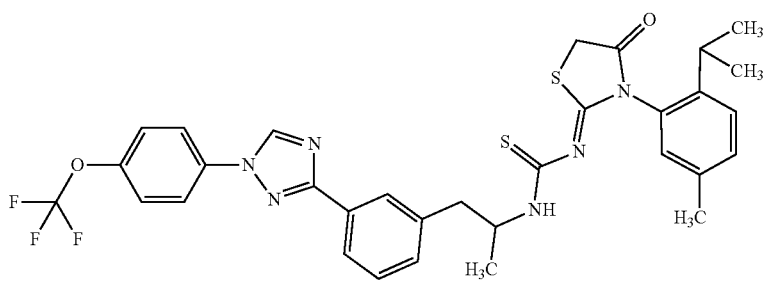 [SMILES: Cc1ccc(C(C)C)c(N2C(=O)CS/C2=N\C(=S)NC(C)Cc2cccc(-c3ncn(-c4ccc(OC(F)(F)F)cc4)n3)c2)c1]
P95 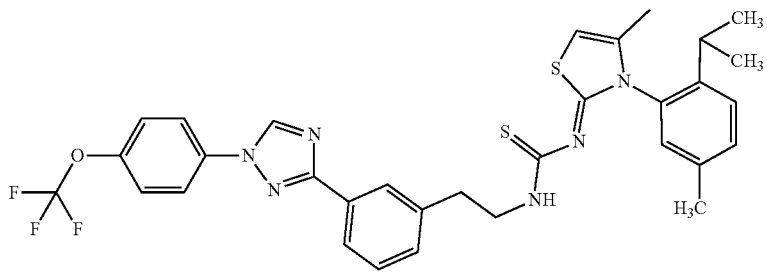 [SMILES: Cc1ccc(C(C)C)c(-n2c(C)cs/c2=N\C(=S)NCCc2cccc(-c3ncn(-c4ccc(OC(F)(F)F)cc4)n3)c2)c1]
P96 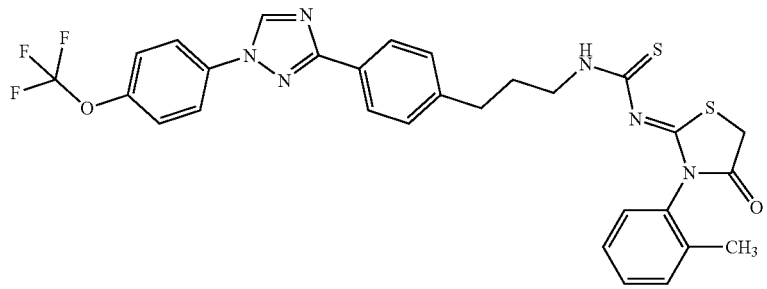 [SMILES: Cc1ccccc1N1C(=O)CS/C1=N\C(=S)NCCCc1ccc(-c2ncn(-c3ccc(OC(F)(F)F)cc3)n2)cc1]

P97 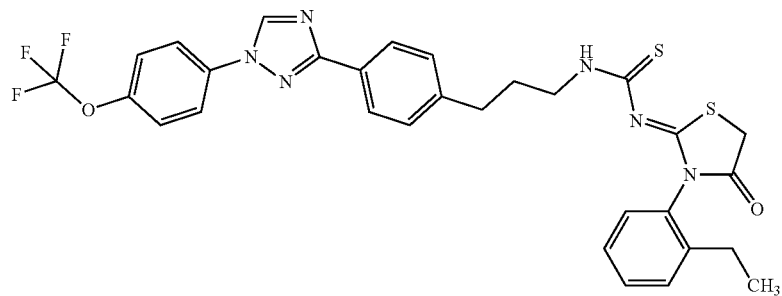 [SMILES: CCc1ccccc1N1C(=O)CS/C1=N\C(=S)NCCCc1ccc(-c2ncn(-c3ccc(OC(F)(F)F)cc3)n2)cc1]
P98 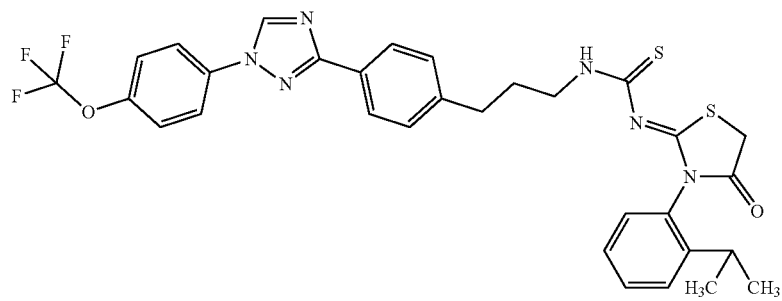 [SMILES: CC(C)c1ccccc1N1C(=O)CS/C1=N\C(=S)NCCCc1ccc(-c2ncn(-c3ccc(OC(F)(F)F)cc3)n2)cc1]
P99 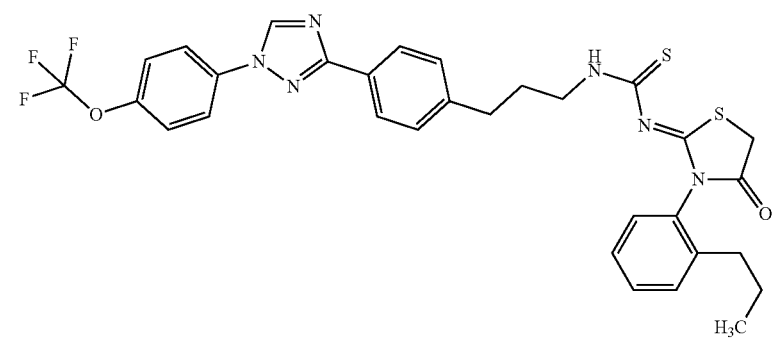 [SMILES: CCCc1ccccc1N1C(=O)CS/C1=N\C(=S)NCCCc1ccc(-c2ncn(-c3ccc(OC(F)(F)F)cc3)n2)cc1]
P100 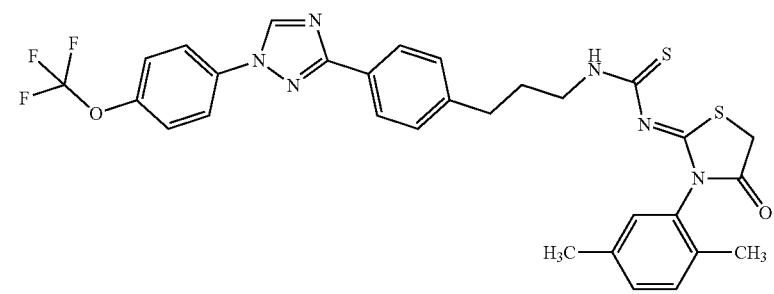 [SMILES: Cc1ccc(C)c(N2C(=O)CS/C2=N\C(=S)NCCCc2ccc(-c3ncn(-c4ccc(OC(F)(F)F)cc4)n3)cc2)c1]
P101 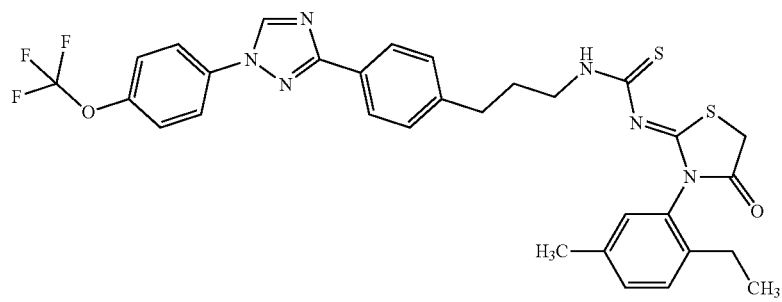 [SMILES: CCc1ccc(C)cc1N1C(=O)CS/C1=N\C(=S)NCCCc1ccc(-c2ncn(-c3ccc(OC(F)(F)F)cc3)n2)cc1]

P102 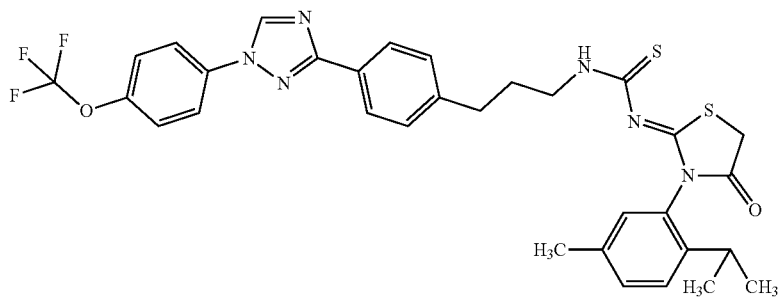 [SMILES: Cc1ccc(C(C)C)c(N2C(=O)CS/C2=N\C(=S)NCCCc2ccc(-c3ncn(-c4ccc(OC(F)(F)F)cc4)n3)cc2)c1]
P103 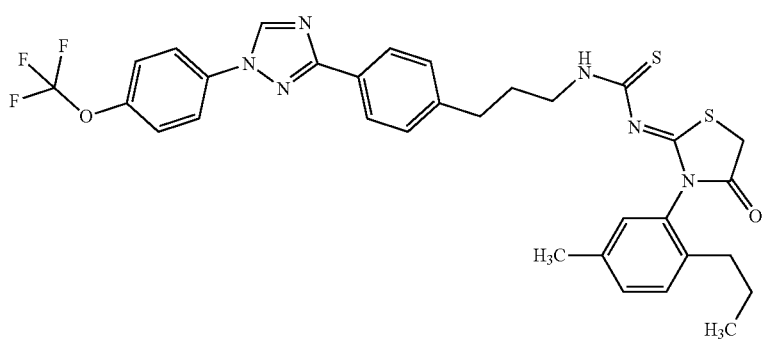 [SMILES: CCCc1ccc(C)cc1N1C(=O)CS/C1=N\C(=S)NCCCc1ccc(-c2ncn(-c3ccc(OC(F)(F)F)cc3)n2)cc1]
P104 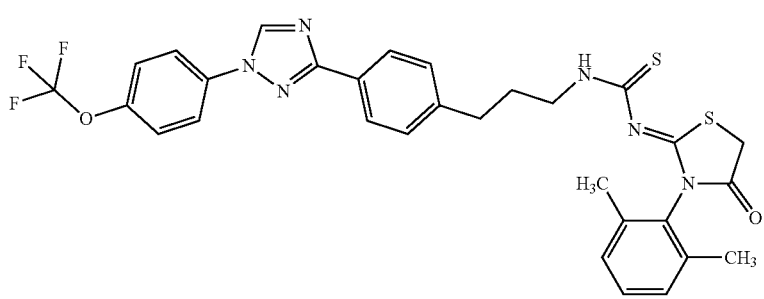 [SMILES: Cc1cccc(C)c1N1C(=O)CS/C1=N\C(=S)NCCCc1ccc(-c2ncn(-c3ccc(OC(F)(F)F)cc3)n2)cc1]
P105 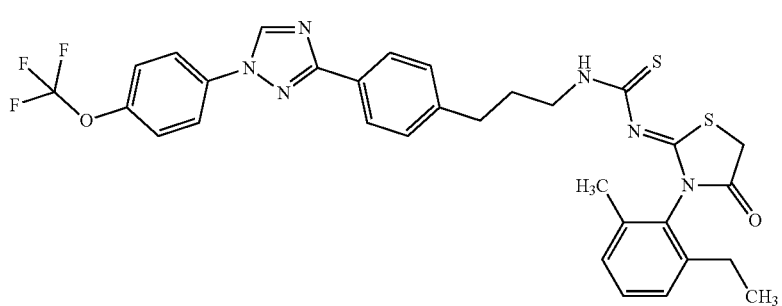 [SMILES: CCc1cccc(C)c1N1C(=O)CS/C1=N\C(=S)NCCCc1ccc(-c2ncn(-c3ccc(OC(F)(F)F)cc3)n2)cc1]
P106 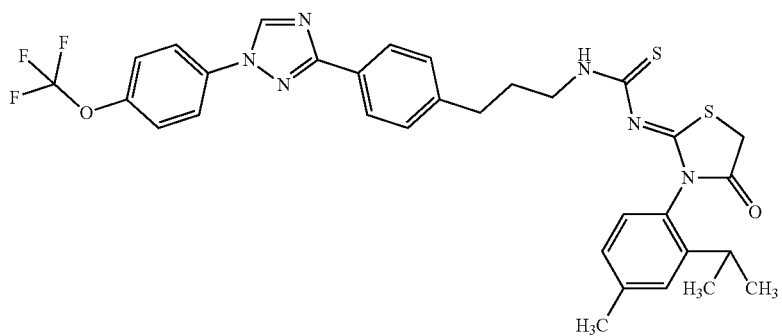 [SMILES: Cc1ccc(N2C(=O)CS/C2=N\C(=S)NCCCc2ccc(-c3ncn(-c4ccc(OC(F)(F)F)cc4)n3)cc2)c(C(C)C)c1]

P107 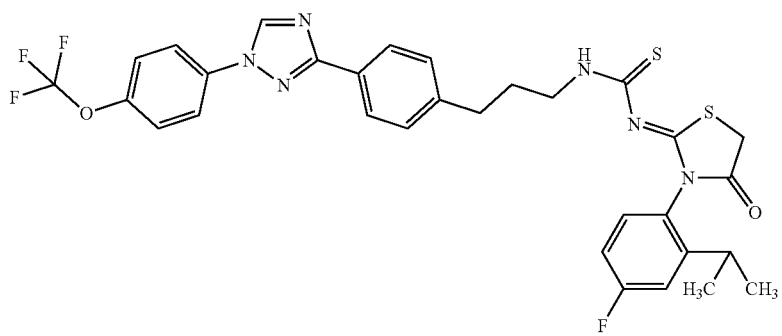 [SMILES: CC(C)c1cc(F)ccc1N1C(=O)CS/C1=N\C(=S)NCCCc1ccc(-c2ncn(-c3ccc(OC(F)(F)F)cc3)n2)cc1]
P108 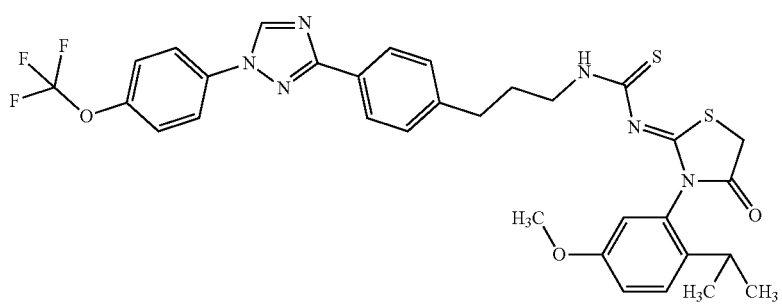 [SMILES: COc1ccc(C(C)C)c(N2C(=O)CS/C2=N\C(=S)NCCCc2ccc(-c3ncn(-c4ccc(OC(F)(F)F)cc4)n3)cc2)c1]
P109 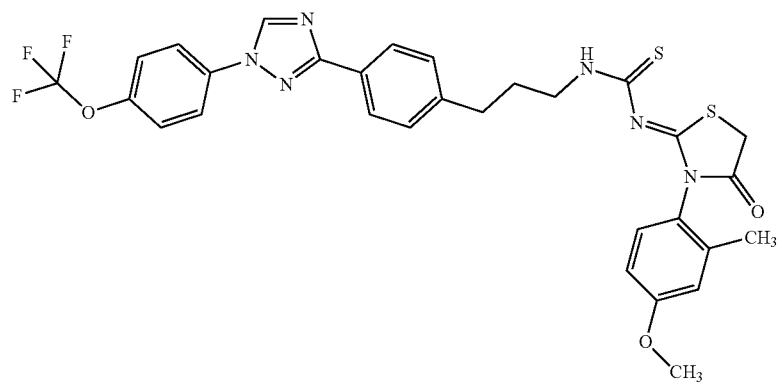 [SMILES: COc1ccc(N2C(=O)CS/C2=N\C(=S)NCCCc2ccc(-c3ncn(-c4ccc(OC(F)(F)F)cc4)n3)cc2)c(C)c1]
P110 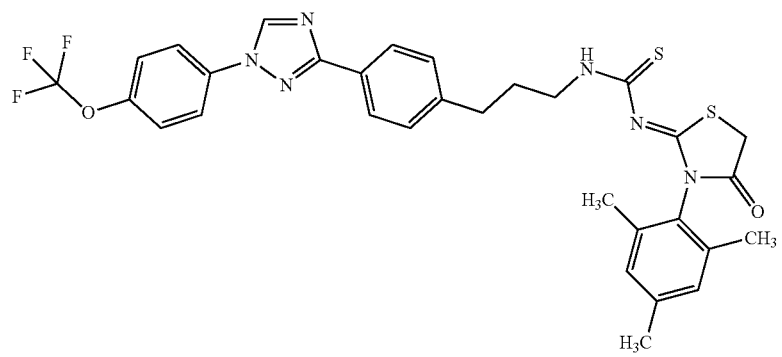 [SMILES: Cc1cc(C)c(N2C(=O)CS/C2=N\C(=S)NCCCc2ccc(-c3ncn(-c4ccc(OC(F)(F)F)cc4)n3)cc2)c(C)c1]

P111 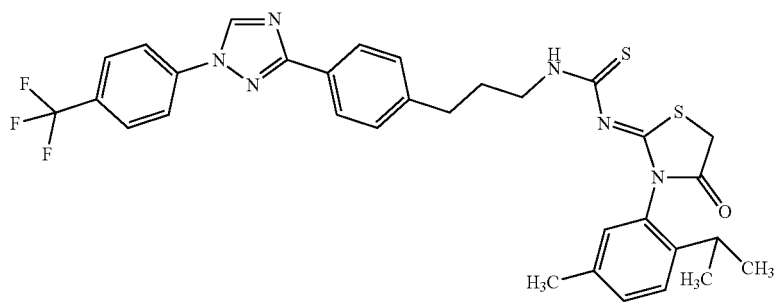 [SMILES: Cc1ccc(C(C)C)c(N2C(=O)CS/C2=N\C(=S)NCCCc2ccc(-c3ncn(-c4ccc(C(F)(F)F)cc4)n3)cc2)c1]
P112 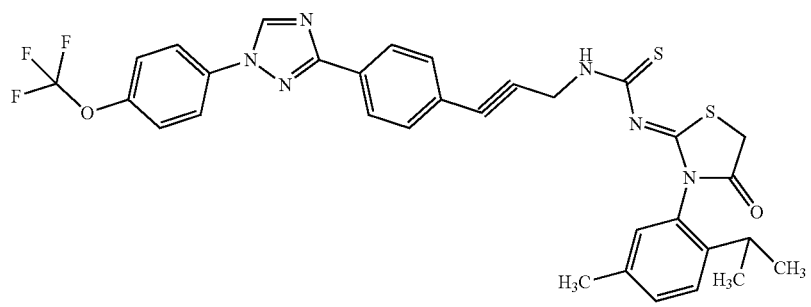 [SMILES: Cc1ccc(C(C)C)c(N2C(=O)CS/C2=N\C(=S)NCC#Cc2ccc(-c3ncn(-c4ccc(OC(F)(F)F)cc4)n3)cc2)c1]
P113 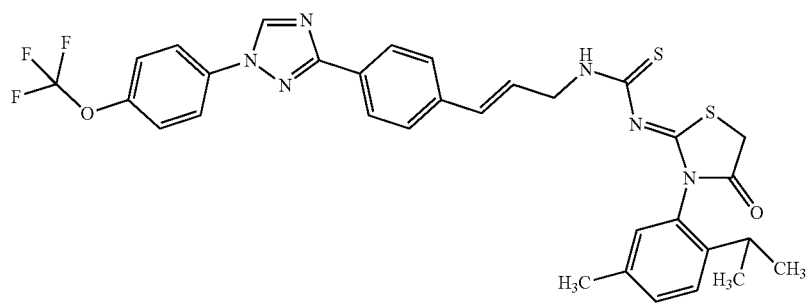 [SMILES: Cc1ccc(C(C)C)c(N2C(=O)CS/C2=N\C(=S)NC/C=C/c2ccc(-c3ncn(-c4ccc(OC(F)(F)F)cc4)n3)cc2)c1]
P114 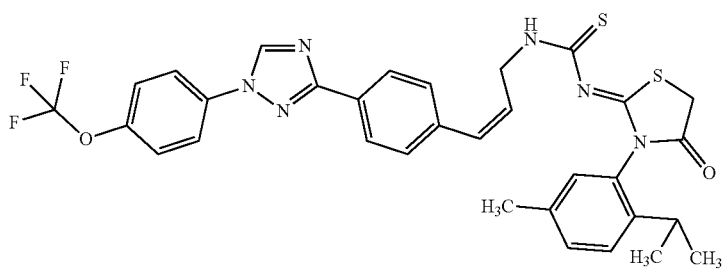 [SMILES: Cc1ccc(C(C)C)c(N2C(=O)CS/C2=N\C(=S)NC/C=C\c2ccc(-c3ncn(-c4ccc(OC(F)(F)F)cc4)n3)cc2)c1]
P115 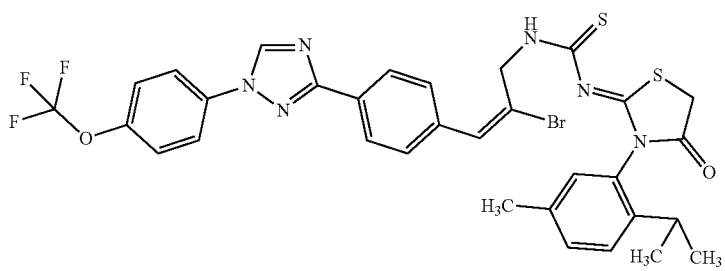 [SMILES: Cc1ccc(C(C)C)c(N2C(=O)CS/C2=N\C(=S)NC/C(Br)=C\c2ccc(-c3ncn(-c4ccc(OC(F)(F)F)cc4)n3)cc2)c1]

P116 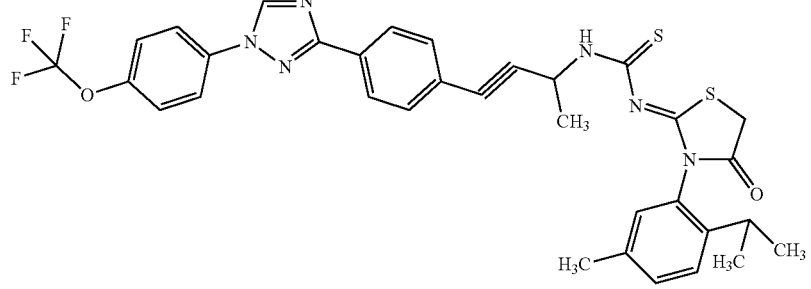
P117 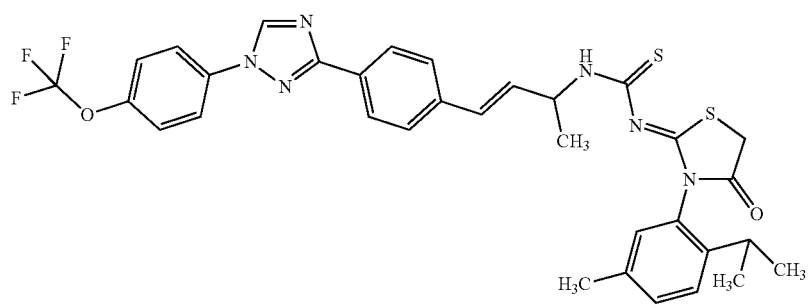 [SMILES: Cc1ccc(C(C)C)c(N2C(=O)CS/C2=N\C(=S)NC(C)/C=C/c2ccc(-c3ncn(-c4ccc(OC(F)(F)F)cc4)n3)cc2)c1]
P118 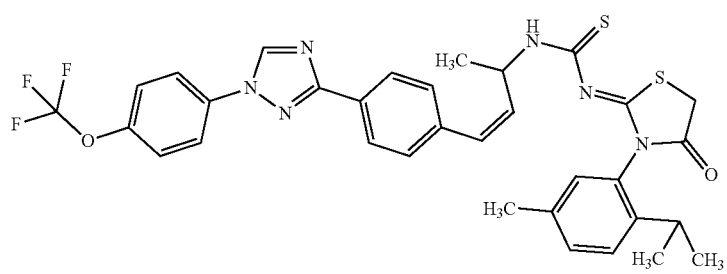 [SMILES: Cc1ccc(C(C)C)c(N2C(=O)CS/C2=N\C(=S)NC(C)/C=C\c2ccc(-c3ncn(-c4ccc(OC(F)(F)F)cc4)n3)cc2)c1]
P119 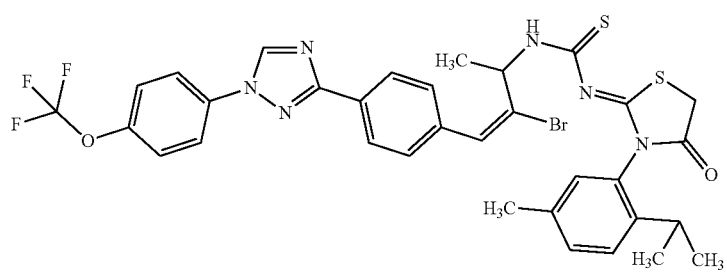
P120 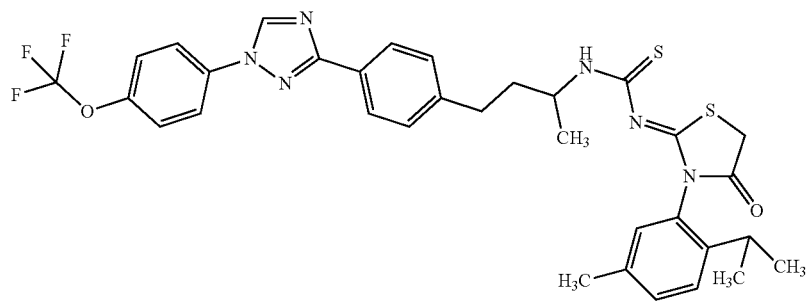

P121 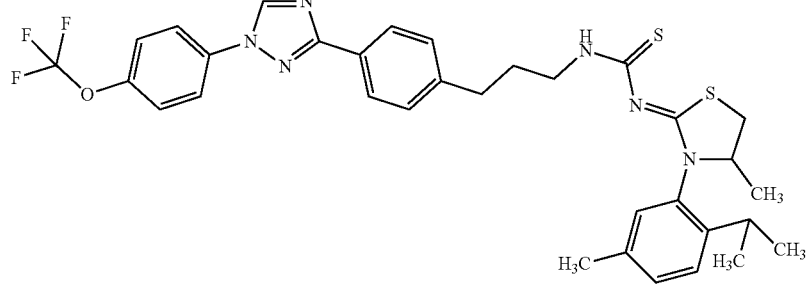
P122 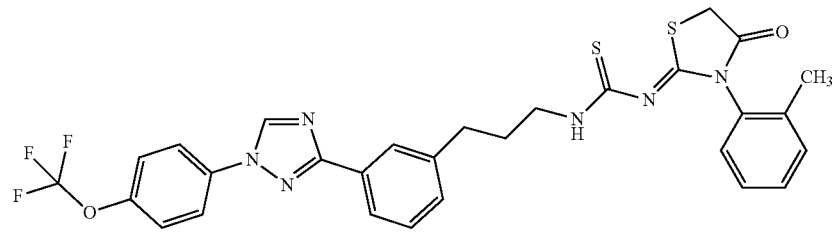 [SMILES: Cc1ccccc1N1C(=O)CS/C1=N\C(=S)NCCCc1cccc(-c2ncn(-c3ccc(OC(F)(F)F)cc3)n2)c1]
P123 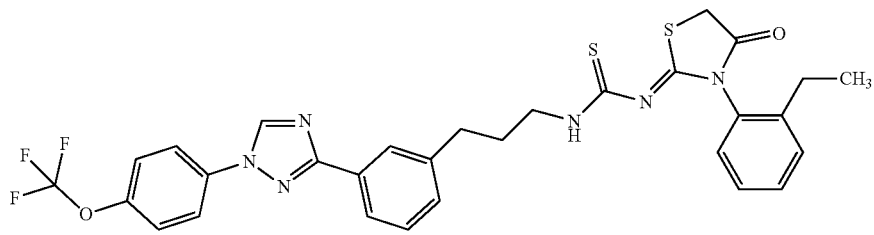 [SMILES: CCc1ccccc1N1C(=O)CS/C1=N\C(=S)NCCCc1cccc(-c2ncn(-c3ccc(OC(F)(F)F)cc3)n2)c1]
P124 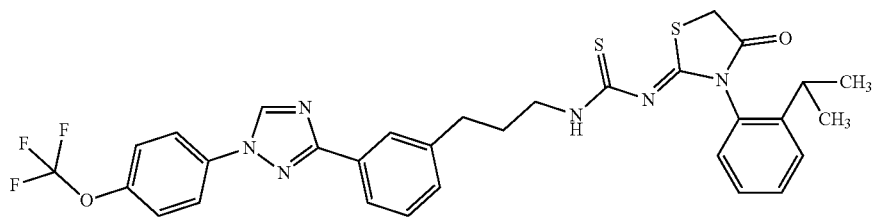 [SMILES: CC(C)c1ccccc1N1C(=O)CS/C1=N\C(=S)NCCCc1cccc(-c2ncn(-c3ccc(OC(F)(F)F)cc3)n2)c1]
P125 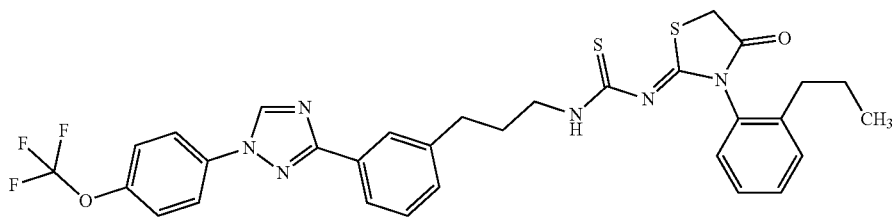 [SMILES: CCCc1ccccc1N1C(=O)CS/C1=N\C(=S)NCCCc1cccc(-c2ncn(-c3ccc(OC(F)(F)F)cc3)n2)c1]
P126 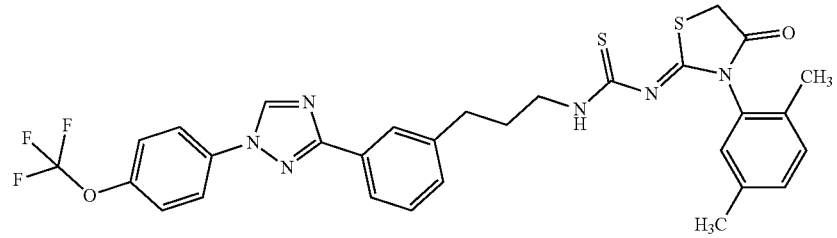 [SMILES: Cc1ccc(C)c(N2C(=O)CS/C2=N\C(=S)NCCCc2cccc(-c3ncn(-c4ccc(OC(F)(F)F)cc4)n3)c2)c1]

-continued
P127
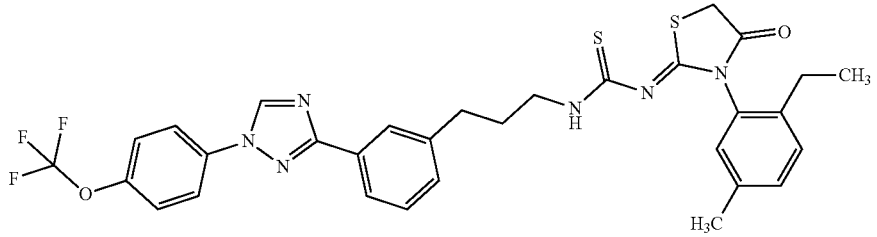 [SMILES: CCc1ccc(C)cc1N1C(=O)CS/C1=N\C(=S)NCCCc1cccc(-c2ncn(-c3ccc(OC(F)(F)F)cc3)n2)c1]
P128
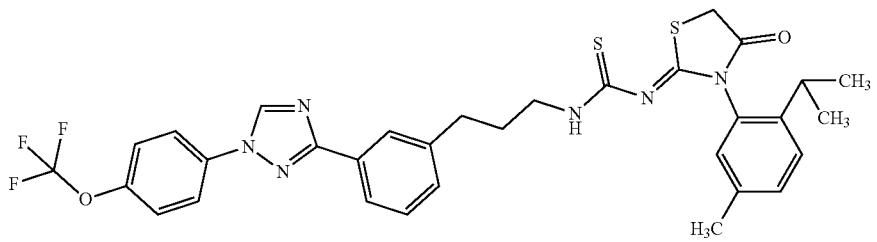 [SMILES: Cc1ccc(C(C)C)c(N2C(=O)CS/C2=N\C(=S)NCCCc2cccc(-c3ncn(-c4ccc(OC(F)(F)F)cc4)n3)c2)c1]
P129
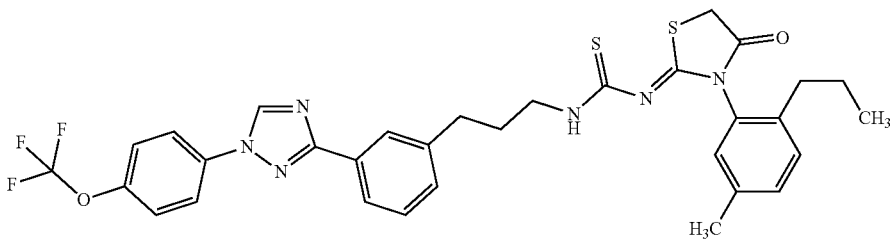 [SMILES: CCCc1ccc(C)cc1N1C(=O)CS/C1=N\C(=S)NCCCc1cccc(-c2ncn(-c3ccc(OC(F)(F)F)cc3)n2)c1]
P130
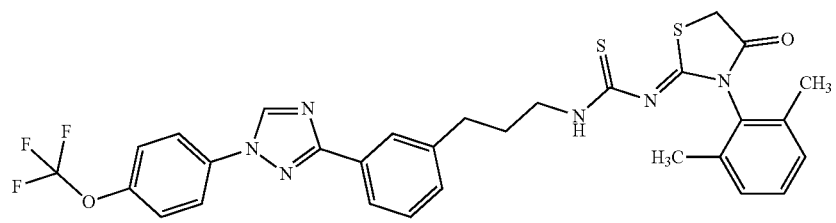 [SMILES: Cc1cccc(C)c1N1C(=O)CS/C1=N\C(=S)NCCCc1cccc(-c2ncn(-c3ccc(OC(F)(F)F)cc3)n2)c1]
P131
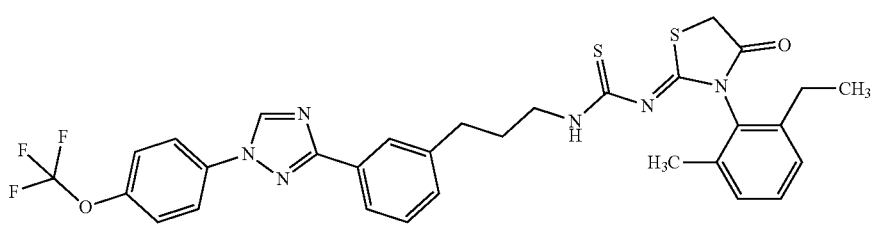 [SMILES: CCc1cccc(C)c1N1C(=O)CS/C1=N\C(=S)NCCCc1cccc(-c2ncn(-c3ccc(OC(F)(F)F)cc3)n2)c1]
P132
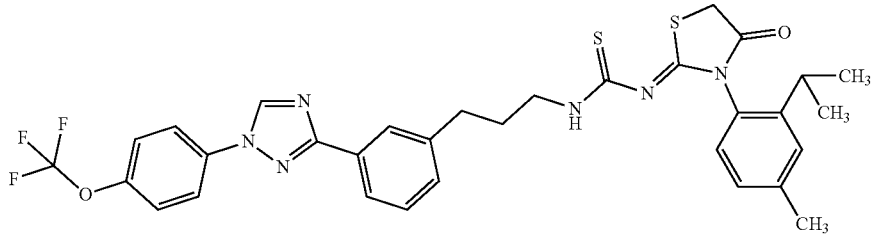 [SMILES: Cc1ccc(N2C(=O)CS/C2=N\C(=S)NCCCc2cccc(-c3ncn(-c4ccc(OC(F)(F)F)cc4)n3)c2)c(C(C)C)c1]

-continued
P133
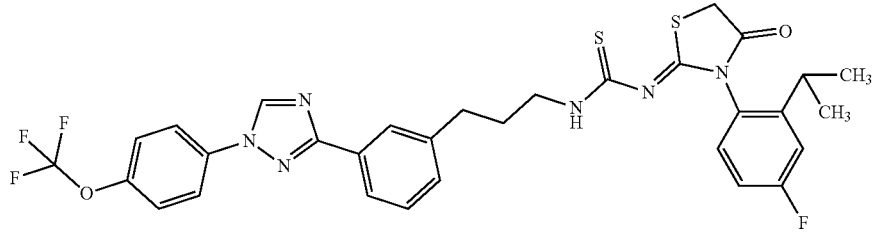 [SMILES: CC(C)c1cc(F)ccc1N1C(=O)CS/C1=N\C(=S)NCCCc1cccc(-c2ncn(-c3ccc(OC(F)(F)F)cc3)n2)c1]
P134
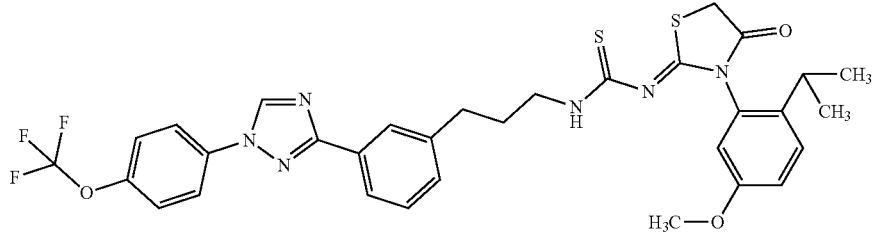 [SMILES: COc1ccc(C(C)C)c(N2C(=O)CS/C2=N\C(=S)NCCCc2cccc(-c3ncn(-c4ccc(OC(F)(F)F)cc4)n3)c2)c1]
P135
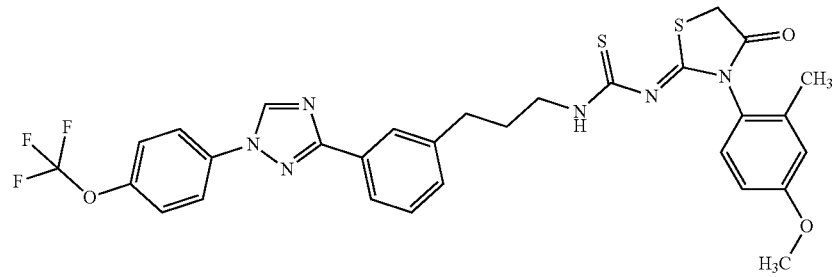 [SMILES: COc1ccc(N2C(=O)CS/C2=N\C(=S)NCCCc2cccc(-c3ncn(-c4ccc(OC(F)(F)F)cc4)n3)c2)c(C)c1]
P136
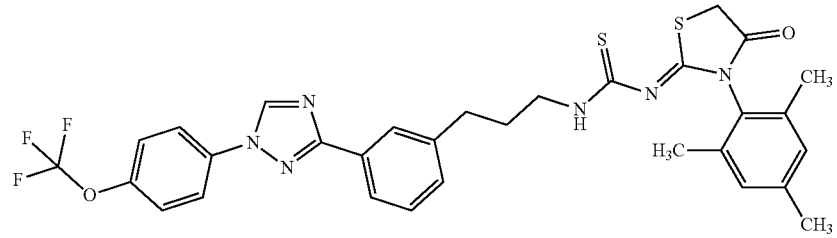 [SMILES: Cc1cc(C)c(N2C(=O)CS/C2=N\C(=S)NCCCc2cccc(-c3ncn(-c4ccc(OC(F)(F)F)cc4)n3)c2)c(C)c1]
P137
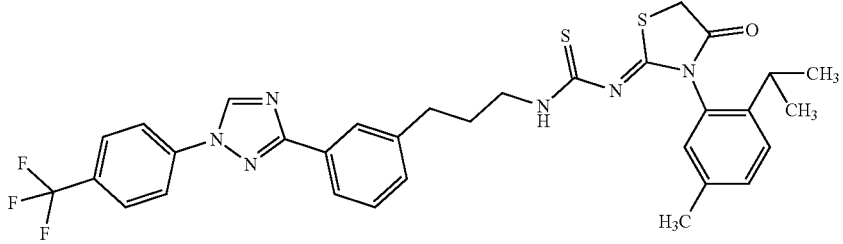 [SMILES: Cc1ccc(C(C)C)c(N2C(=O)CS/C2=N\C(=S)NCCCc2cccc(-c3ncn(-c4ccc(C(F)(F)F)cc4)n3)c2)c1]
P138
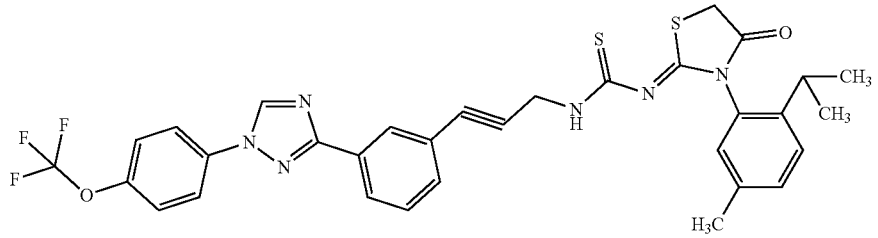 [SMILES: Cc1ccc(C(C)C)c(N2C(=O)CS/C2=N\C(=S)NCC#Cc2cccc(-c3ncn(-c4ccc(OC(F)(F)F)cc4)n3)c2)c1]

P139 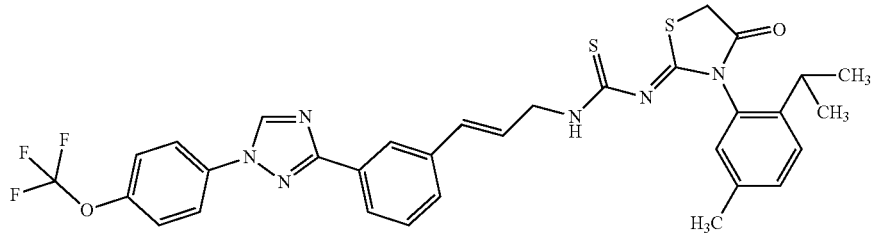 [SMILES: Cc1ccc(C(C)C)c(N2C(=O)CS/C2=N\C(=S)NC/C=C/c2cccc(-c3ncn(-c4ccc(OC(F)(F)F)cc4)n3)c2)c1]
P140 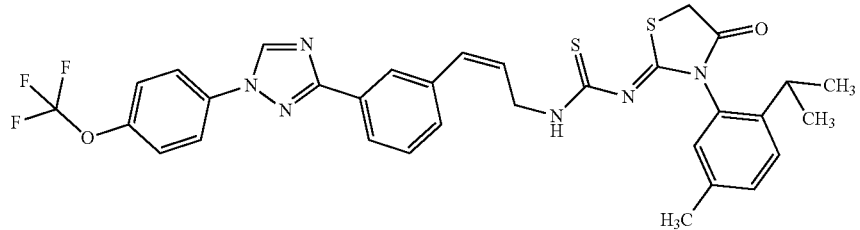 [SMILES: Cc1ccc(C(C)C)c(N2C(=O)CS/C2=N\C(=S)NC/C=C\c2cccc(-c3ncn(-c4ccc(OC(F)(F)F)cc4)n3)c2)c1]
P141 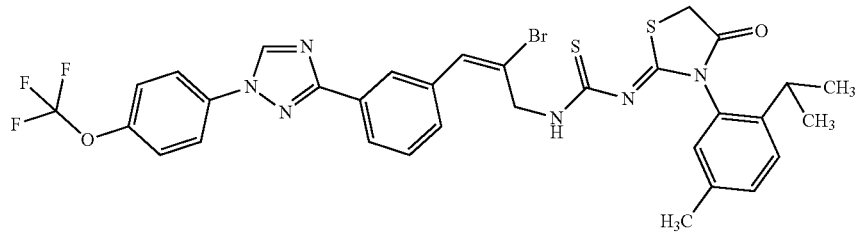
P142 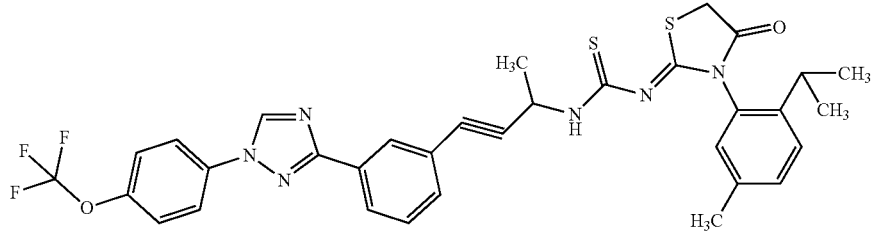 [SMILES: Cc1ccc(C(C)C)c(N2C(=O)CS/C2=N\C(=S)NC(C)C#Cc2cccc(-c3ncn(-c4ccc(OC(F)(F)F)cc4)n3)c2)c1]
P143 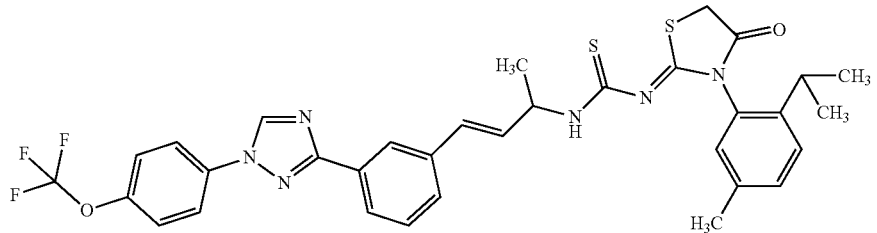
P144 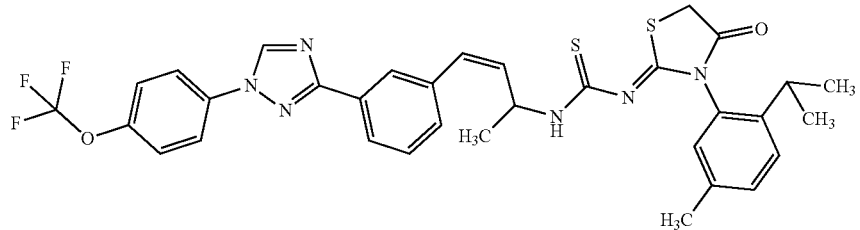

-continued
P145
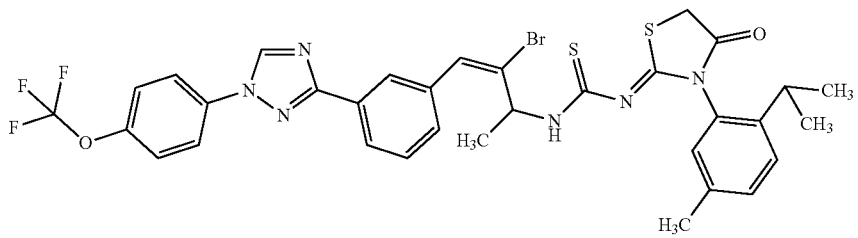 [SMILES: Cc1ccc(C(C)C)c(N2C(=O)CS/C2=N\C(=S)NC(C)/C(Br)=C\c2cccc(-c3ncn(-c4ccc(OC(F)(F)F)cc4)n3)c2)c1]
P146
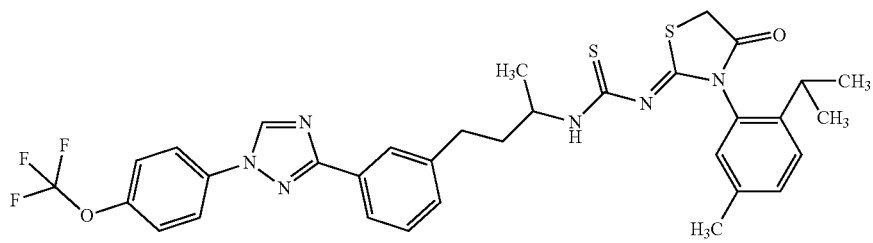 [SMILES: Cc1ccc(C(C)C)c(N2C(=O)CS/C2=N\C(=S)NC(C)CCc2cccc(-c3ncn(-c4ccc(OC(F)(F)F)cc4)n3)c2)c1]
P147
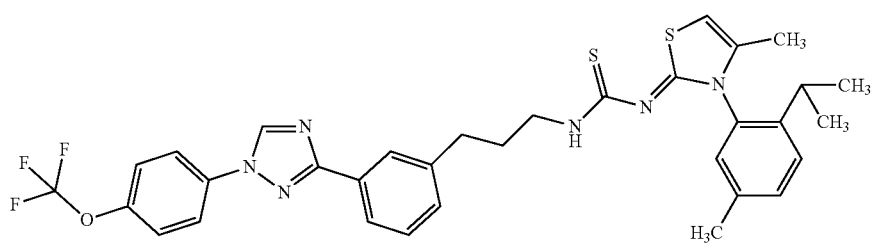 [SMILES: Cc1ccc(C(C)C)c(-n2c(C)cs/c2=N\C(=S)NCCCc2cccc(-c3ncn(-c4ccc(OC(F)(F)F)cc4)n3)c2)c1]
P148
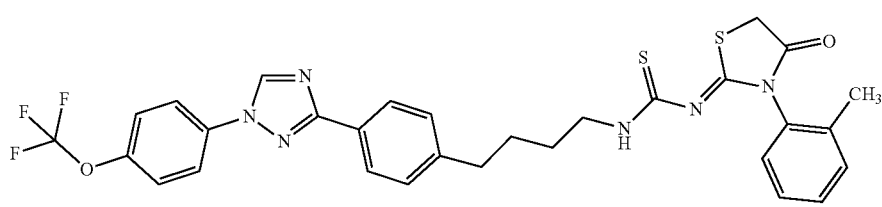 [SMILES: Cc1ccccc1N1C(=O)CS/C1=N\C(=S)NCCCCc1ccc(-c2ncn(-c3ccc(OC(F)(F)F)cc3)n2)cc1]
P149
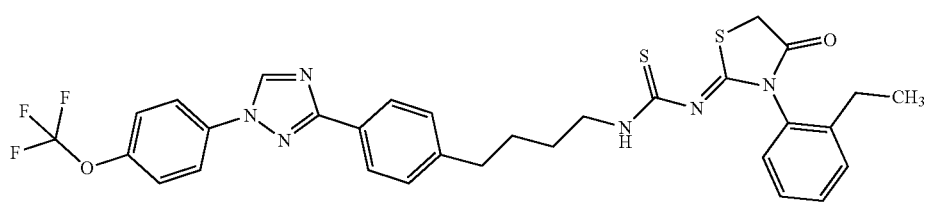 [SMILES: CCc1ccccc1N1C(=O)CS/C1=N\C(=S)NCCCCc1ccc(-c2ncn(-c3ccc(OC(F)(F)F)cc3)n2)cc1]
P150
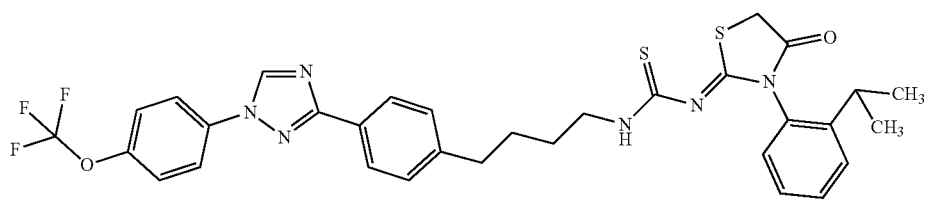 [SMILES: CC(C)c1ccccc1N1C(=O)CS/C1=N\C(=S)NCCCCc1ccc(-c2ncn(-c3ccc(OC(F)(F)F)cc3)n2)cc1]
P151
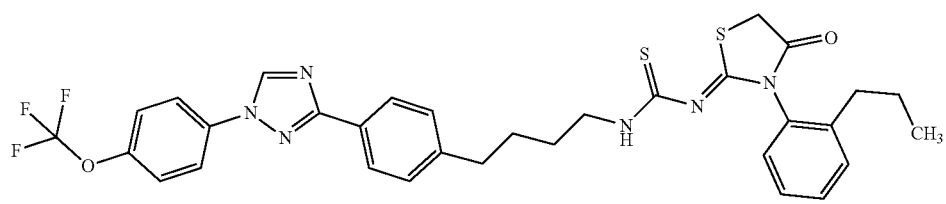 [SMILES: CCCc1ccccc1N1C(=O)CS/C1=N\C(=S)NCCCCc1ccc(-c2ncn(-c3ccc(OC(F)(F)F)cc3)n2)cc1]

P152 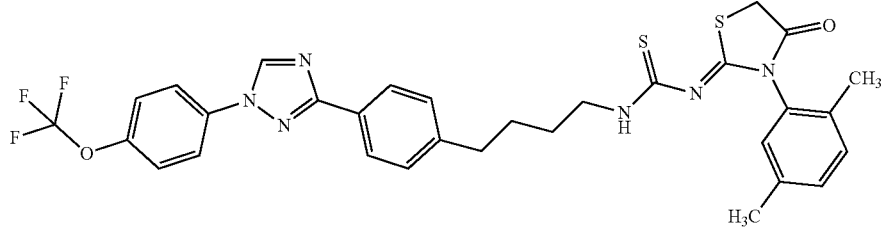 [SMILES: Cc1ccc(C)c(N2C(=O)CS/C2=N\C(=S)NCCCCc2ccc(-c3ncn(-c4ccc(OC(F)(F)F)cc4)n3)cc2)c1]
P153 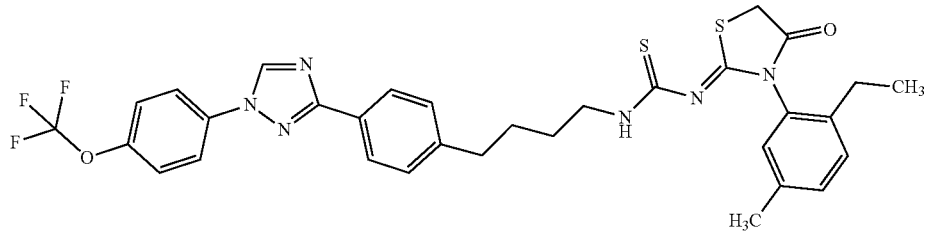 [SMILES: CCc1ccc(C)cc1N1C(=O)CS/C1=N\C(=S)NCCCCc1ccc(-c2ncn(-c3ccc(OC(F)(F)F)cc3)n2)cc1]
P154 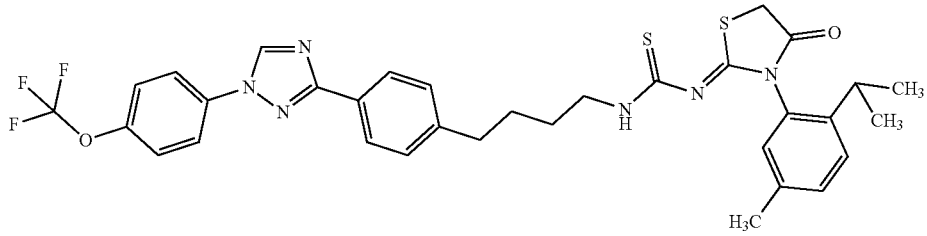 [SMILES: Cc1ccc(C(C)C)c(N2C(=O)CS/C2=N\C(=S)NCCCCc2ccc(-c3ncn(-c4ccc(OC(F)(F)F)cc4)n3)cc2)c1]
P155 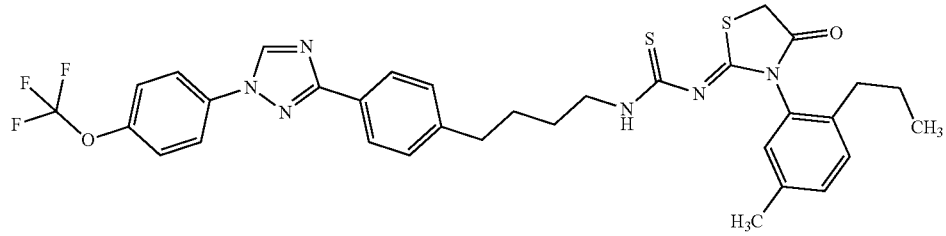 [SMILES: CCCc1ccc(C)cc1N1C(=O)CS/C1=N\C(=S)NCCCCc1ccc(-c2ncn(-c3ccc(OC(F)(F)F)cc3)n2)cc1]
P156 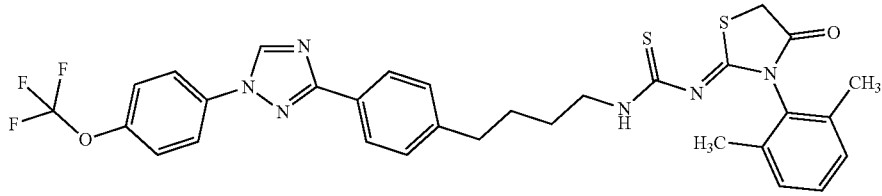 [SMILES: Cc1cccc(C)c1N1C(=O)CS/C1=N\C(=S)NCCCCc1ccc(-c2ncn(-c3ccc(OC(F)(F)F)cc3)n2)cc1]
P157 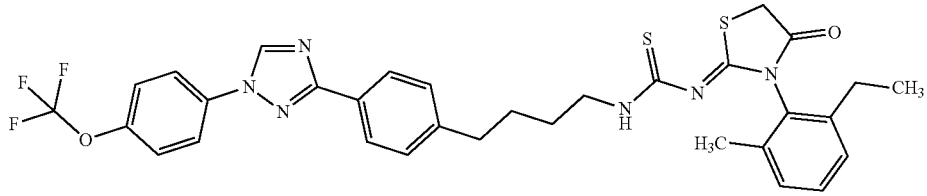 [SMILES: CCc1cccc(C)c1N1C(=O)CS/C1=N\C(=S)NCCCCc1ccc(-c2ncn(-c3ccc(OC(F)(F)F)cc3)n2)cc1]
P158 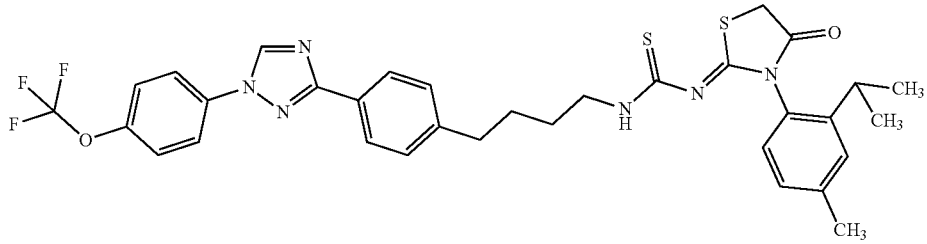 [SMILES: Cc1ccc(N2C(=O)CS/C2=N\C(=S)NCCCCc2ccc(-c3ncn(-c4ccc(OC(F)(F)F)cc4)n3)cc2)c(C(C)C)c1]

P159 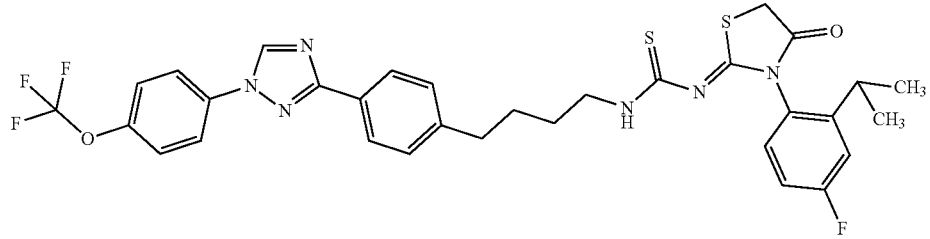 [SMILES: CC(C)c1cc(F)ccc1N1C(=O)CS/C1=N\C(=S)NCCCCc1ccc(-c2ncn(-c3ccc(OC(F)(F)F)cc3)n2)cc1]
P160 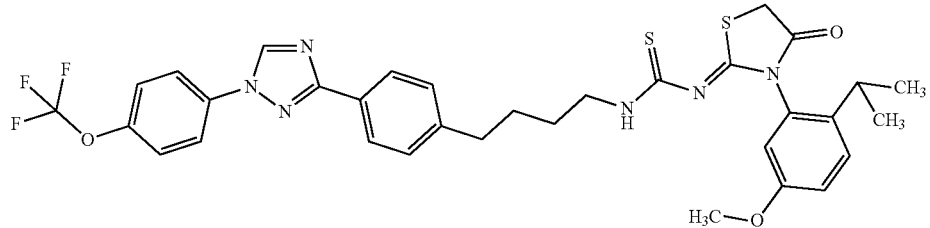 [SMILES: COc1ccc(C(C)C)c(N2C(=O)CS/C2=N\C(=S)NCCCCc2ccc(-c3ncn(-c4ccc(OC(F)(F)F)cc4)n3)cc2)c1]
P161 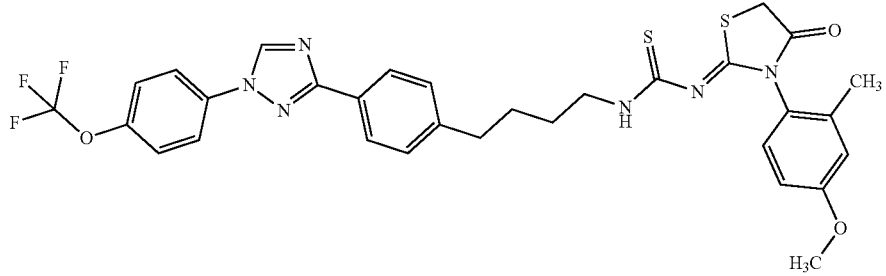 [SMILES: COc1ccc(N2C(=O)CS/C2=N\C(=S)NCCCCc2ccc(-c3ncn(-c4ccc(OC(F)(F)F)cc4)n3)cc2)c(C)c1]
P162 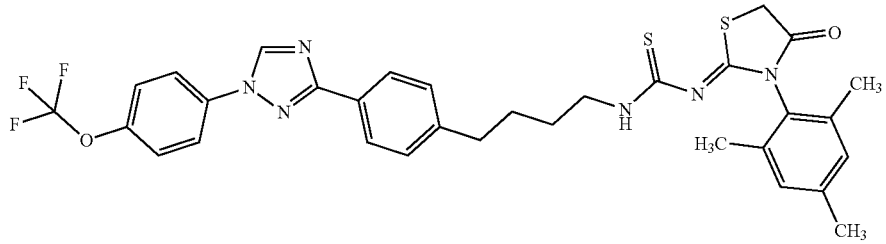 [SMILES: Cc1cc(C)c(N2C(=O)CS/C2=N\C(=S)NCCCCc2ccc(-c3ncn(-c4ccc(OC(F)(F)F)cc4)n3)cc2)c(C)c1]
P163 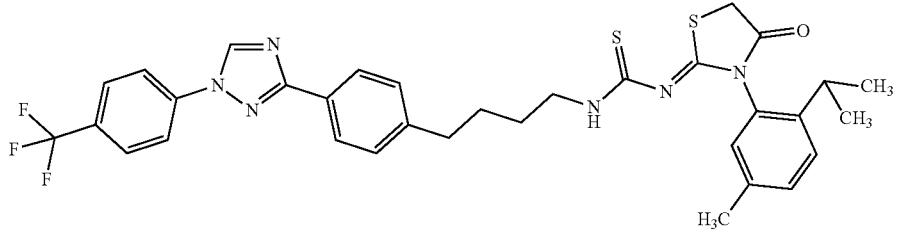 [SMILES: Cc1ccc(C(C)C)c(N2C(=O)CS/C2=N\C(=S)NCCCCc2ccc(-c3ncn(-c4ccc(C(F)(F)F)cc4)n3)cc2)c1]
P164 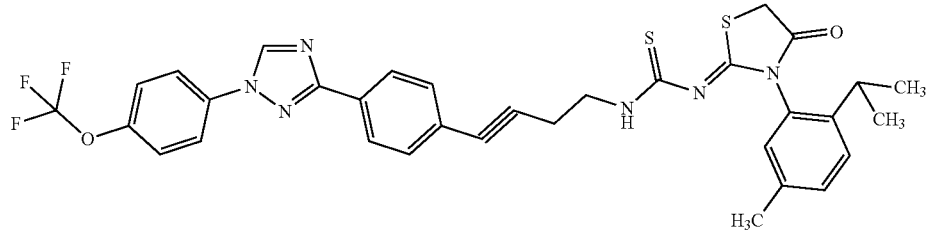 [SMILES: Cc1ccc(C(C)C)c(N2C(=O)CS/C2=N\C(=S)NCCC#Cc2ccc(-c3ncn(-c4ccc(OC(F)(F)F)cc4)n3)cc2)c1]

-continued
P165
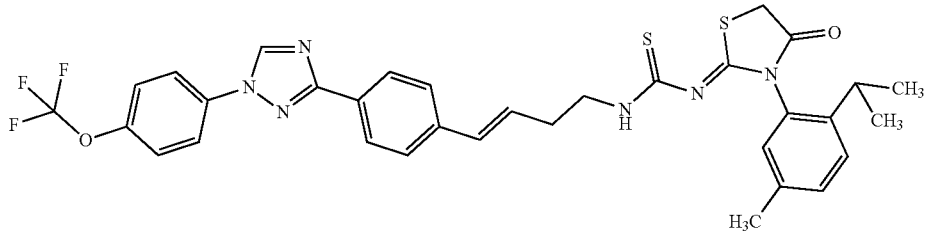
P166
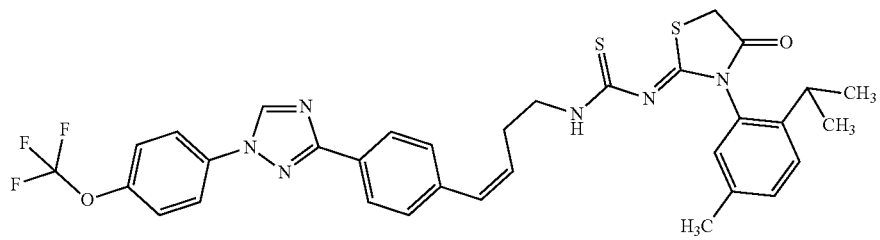
P167
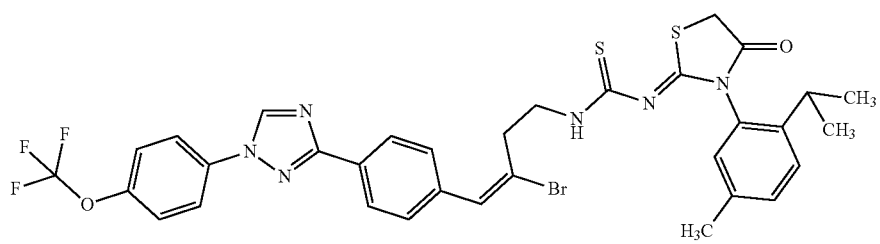 [SMILES: Cc1ccc(C(C)C)c(N2C(=O)CS/C2=N\C(=S)NCC/C(Br)=C\c2ccc(-c3ncn(-c4ccc(OC(F)(F)F)cc4)n3)cc2)c1]
P168
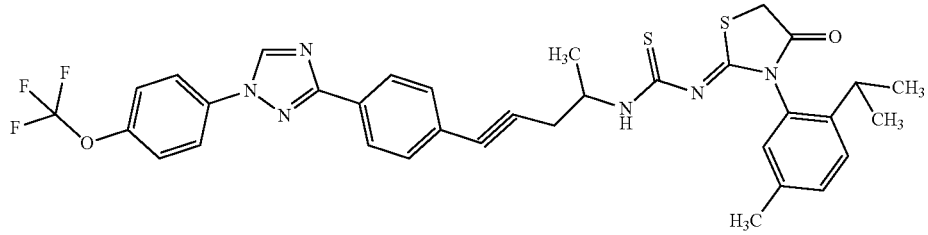 [SMILES: Cc1ccc(C(C)C)c(N2C(=O)CS/C2=N\C(=S)NC(C)CC#Cc2ccc(-c3ncn(-c4ccc(OC(F)(F)F)cc4)n3)cc2)c1]
P169
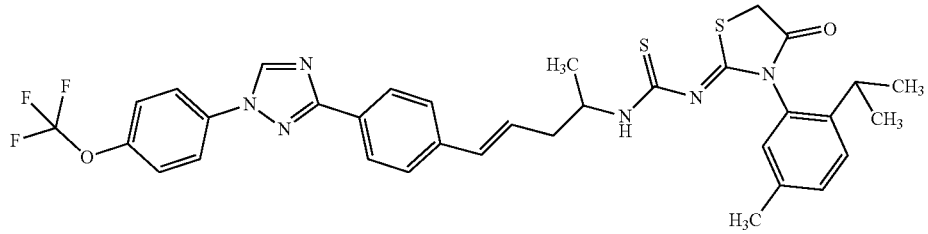 [SMILES: Cc1ccc(C(C)C)c(N2C(=O)CS/C2=N\C(=S)NC(C)C/C=C/c2ccc(-c3ncn(-c4ccc(OC(F)(F)F)cc4)n3)cc2)c1]
P170
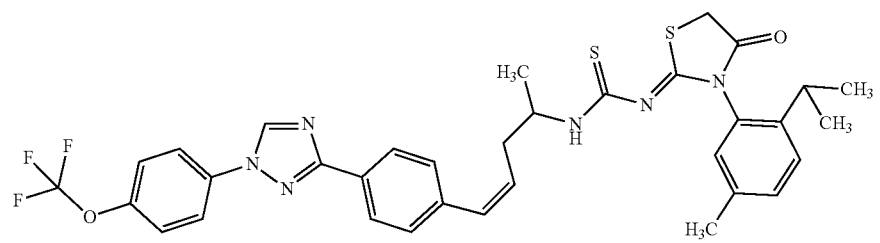 [SMILES: Cc1ccc(C(C)C)c(N2C(=O)CS/C2=N\C(=S)NC(C)C/C=C\c2ccc(-c3ncn(-c4ccc(OC(F)(F)F)cc4)n3)cc2)c1]

-continued
P171
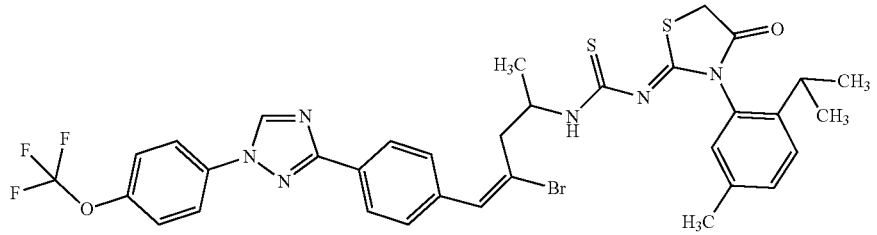 [SMILES: Cc1ccc(C(C)C)c(N2C(=O)CS/C2=N\C(=S)NC(C)C/C(Br)=C\c2ccc(-c3ncn(-c4ccc(OC(F)(F)F)cc4)n3)cc2)c1]
P172
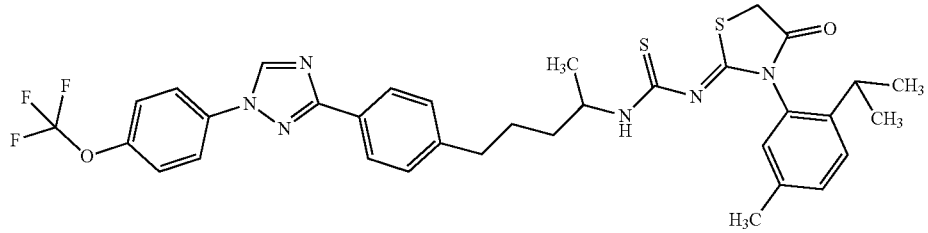
P173
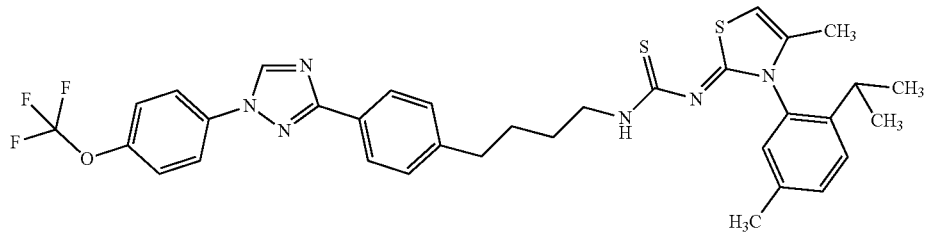 [SMILES: Cc1ccc(C(C)C)c(-n2c(C)cs/c2=N\C(=S)NCCCCc2ccc(-c3ncn(-c4ccc(OC(F)(F)F)cc4)n3)cc2)c1]
P174
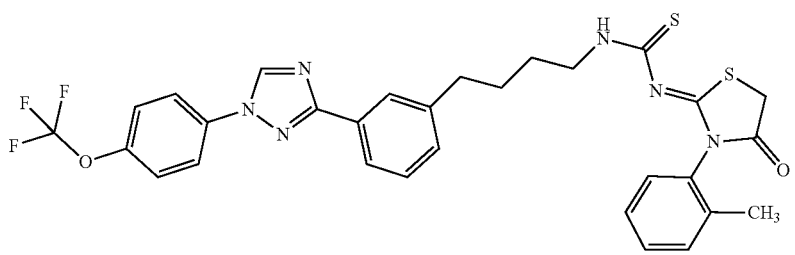 [SMILES: Cc1ccccc1N1C(=O)CS/C1=N\C(=S)NCCCCc1cccc(-c2ncn(-c3ccc(OC(F)(F)F)cc3)n2)c1]
P175
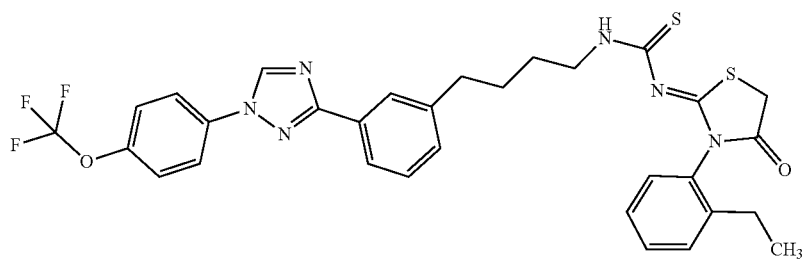 [SMILES: CCc1ccccc1N1C(=O)CS/C1=N\C(=S)NCCCCc1cccc(-c2ncn(-c3ccc(OC(F)(F)F)cc3)n2)c1]
P176
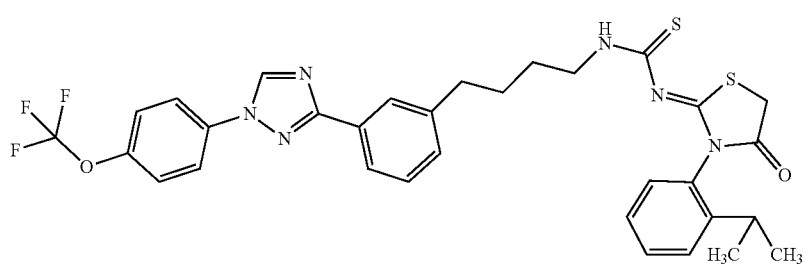 [SMILES: CC(C)c1ccccc1N1C(=O)CS/C1=N\C(=S)NCCCCc1cccc(-c2ncn(-c3ccc(OC(F)(F)F)cc3)n2)c1]

P177 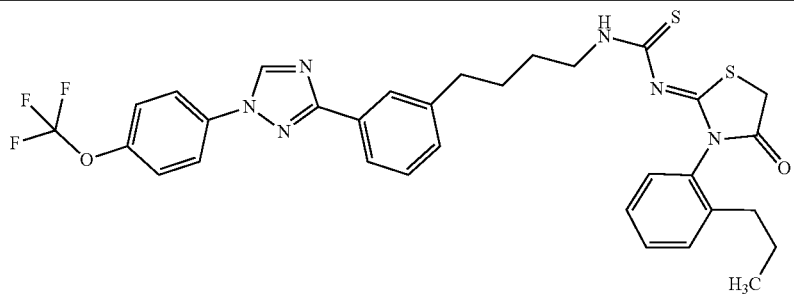
P178 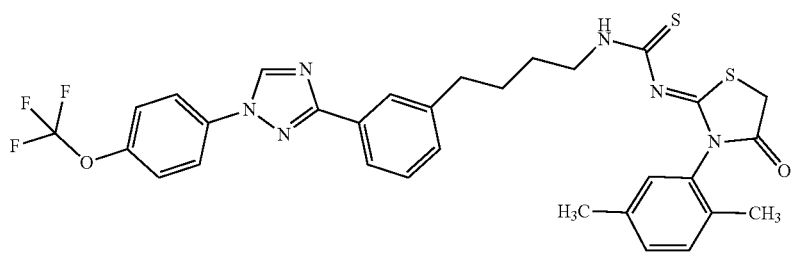 [SMILES: Cc1ccc(C)c(N2C(=O)CS/C2=N\C(=S)NCCCCc2cccc(-c3ncn(-c4ccc(OC(F)(F)F)cc4)n3)c2)c1]
P179 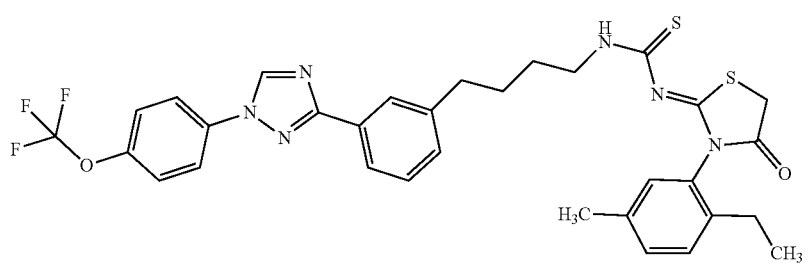 [SMILES: CCc1ccc(C)cc1N1C(=O)CS/C1=N\C(=S)NCCCCc1cccc(-c2ncn(-c3ccc(OC(F)(F)F)cc3)n2)c1]
P180 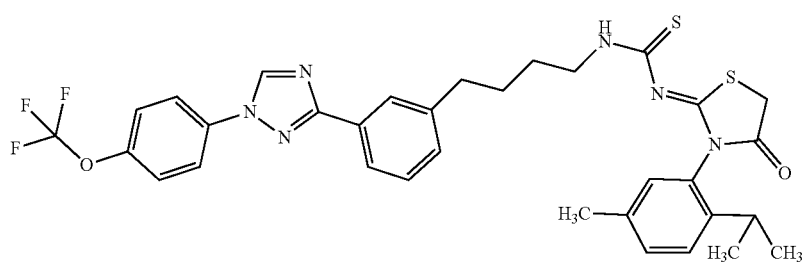
P181 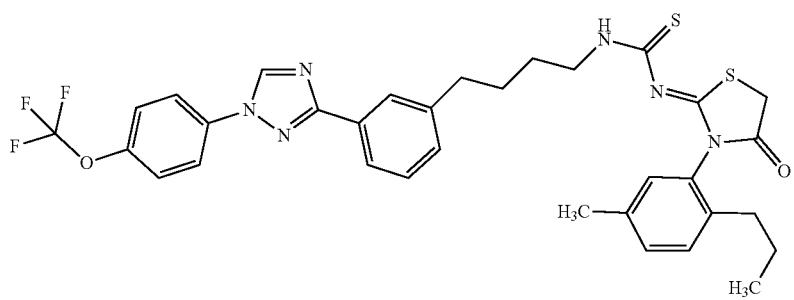 [SMILES: CCCc1ccc(C)cc1N1C(=O)CS/C1=N\C(=S)NCCCCc1cccc(-c2ncn(-c3ccc(OC(F)(F)F)cc3)n2)c1]
P182 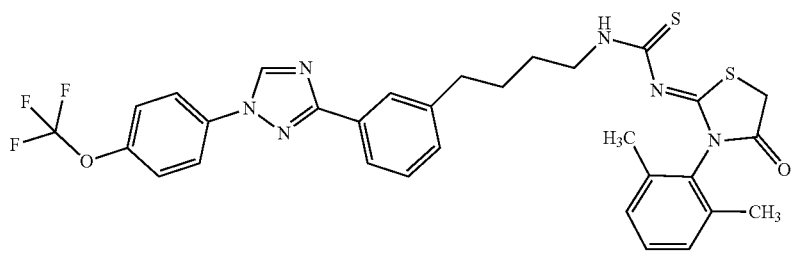 [SMILES: Cc1cccc(C)c1N1C(=O)CS/C1=N\C(=S)NCCCCc1cccc(-c2ncn(-c3ccc(OC(F)(F)F)cc3)n2)c1]

P183 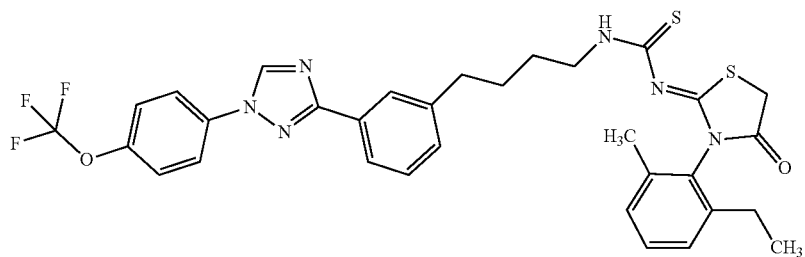 [SMILES: CCc1cccc(C)c1N1C(=O)CS/C1=N\C(=S)NCCCCc1cccc(-c2ncn(-c3ccc(OC(F)(F)F)cc3)n2)c1]
P184 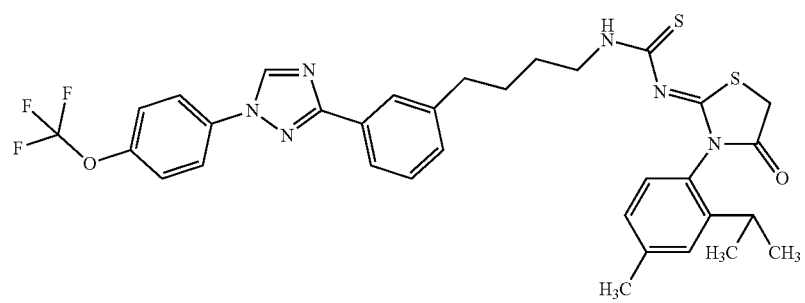 [SMILES: Cc1ccc(N2C(=O)CS/C2=N\C(=S)NCCCCc2cccc(-c3ncn(-c4ccc(OC(F)(F)F)cc4)n3)c2)c(C(C)C)c1]
P185 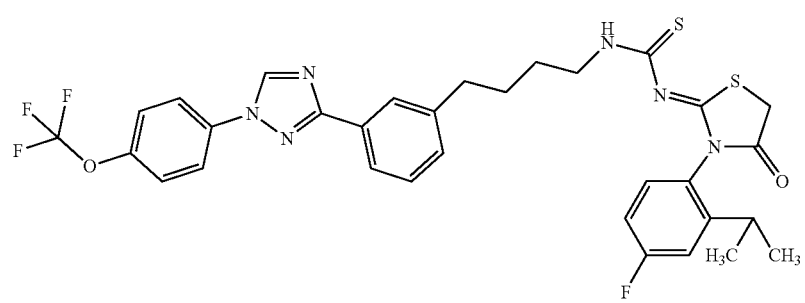 [SMILES: CC(C)c1cc(F)ccc1N1C(=O)CS/C1=N\C(=S)NCCCCc1cccc(-c2ncn(-c3ccc(OC(F)(F)F)cc3)n2)c1]
P186 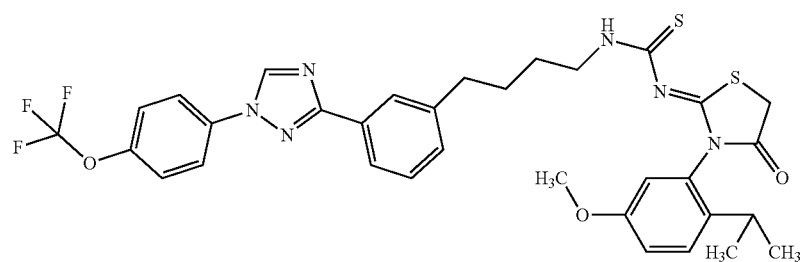 [SMILES: COc1ccc(C(C)C)c(N2C(=O)CS/C2=N\C(=S)NCCCCc2cccc(-c3ncn(-c4ccc(OC(F)(F)F)cc4)n3)c2)c1]
P187 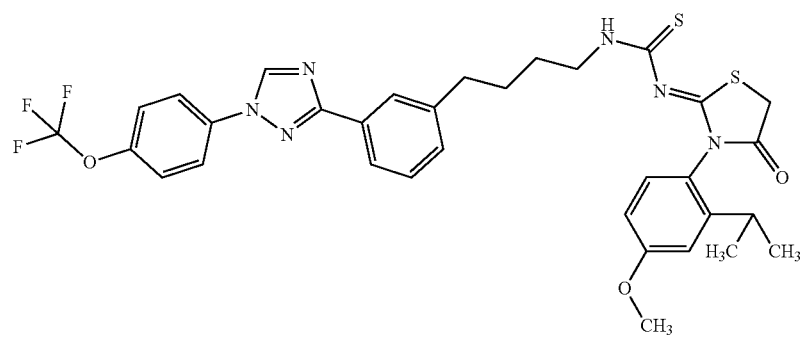 [SMILES: COc1ccc(N2C(=O)CS/C2=N\C(=S)NCCCCc2cccc(-c3ncn(-c4ccc(OC(F)(F)F)cc4)n3)c2)c(C(C)C)c1]

-continued
P188
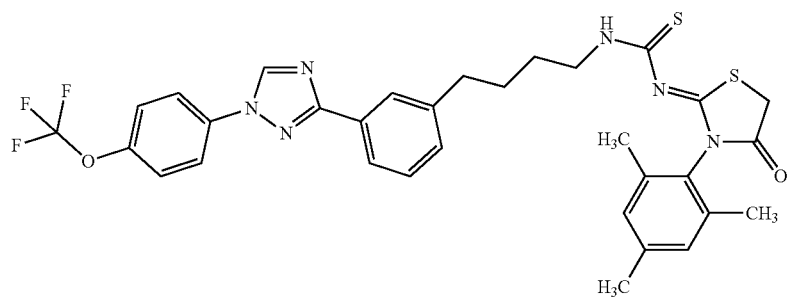 [SMILES: Cc1cc(C)c(N2C(=O)CS/C2=N\C(=S)NCCCCc2cccc(-c3ncn(-c4ccc(OC(F)(F)F)cc4)n3)c2)c(C)c1]
P189
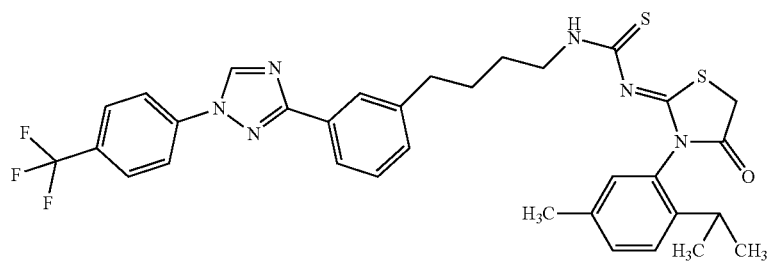 [SMILES: Cc1ccc(C(C)C)c(N2C(=O)CS/C2=N\C(=S)NCCCCc2cccc(-c3ncn(-c4ccc(C(F)(F)F)cc4)n3)c2)c1]
P190
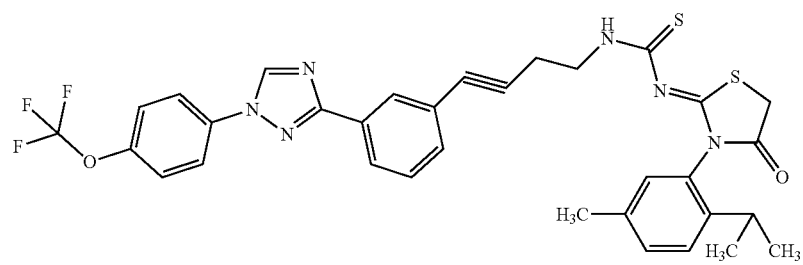 [SMILES: Cc1ccc(C(C)C)c(N2C(=O)CS/C2=N\C(=S)NCCC#Cc2cccc(-c3ncn(-c4ccc(OC(F)(F)F)cc4)n3)c2)c1]
P191
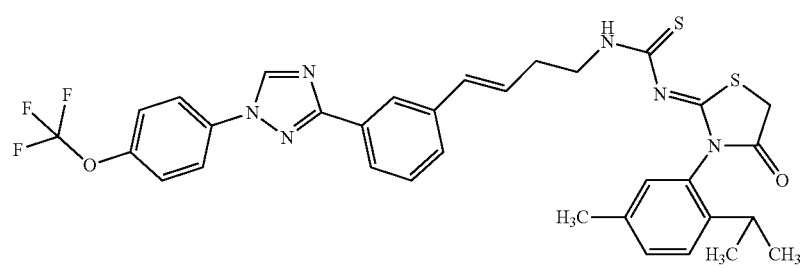 [SMILES: Cc1ccc(C(C)C)c(N2C(=O)CS/C2=N\C(=S)NCC/C=C/c2cccc(-c3ncn(-c4ccc(OC(F)(F)F)cc4)n3)c2)c1]
P192
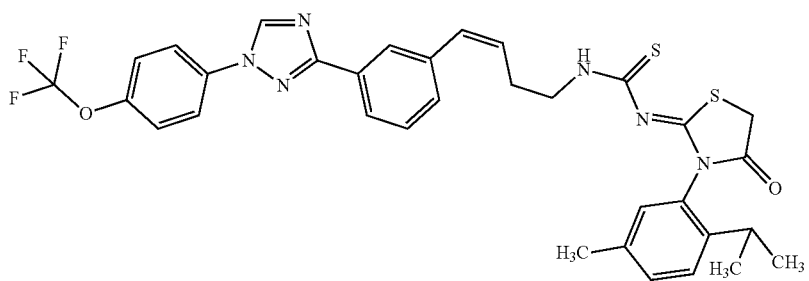 [SMILES: Cc1ccc(C(C)C)c(N2C(=O)CS/C2=N\C(=S)NCC/C=C\c2cccc(-c3ncn(-c4ccc(OC(F)(F)F)cc4)n3)c2)c1]

P193 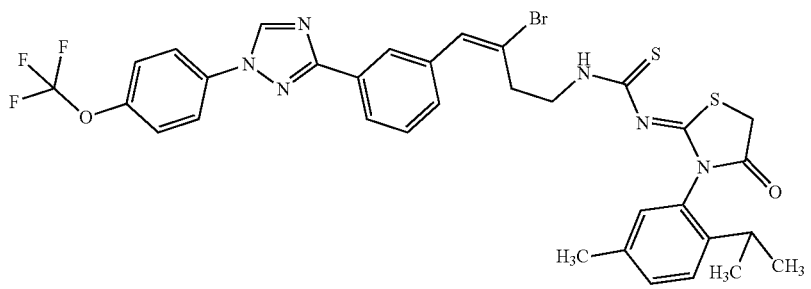 [SMILES: Cc1ccc(C(C)C)c(N2C(=O)CS/C2=N\C(=S)NCC/C(Br)=C\c2cccc(-c3ncn(-c4ccc(OC(F)(F)F)cc4)n3)c2)c1]
P194 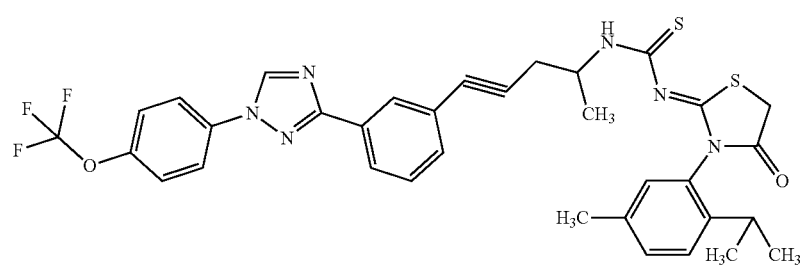 [SMILES: Cc1ccc(C(C)C)c(N2C(=O)CS/C2=N\C(=S)NC(C)CC#Cc2cccc(-c3ncn(-c4ccc(OC(F)(F)F)cc4)n3)c2)c1]
P195 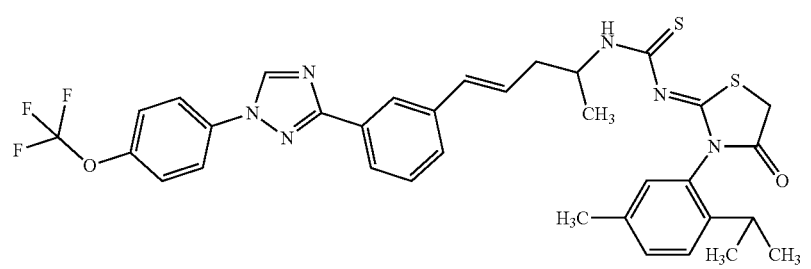 [SMILES: Cc1ccc(C(C)C)c(N2C(=O)CS/C2=N\C(=S)NC(C)C/C=C/c2cccc(-c3ncn(-c4ccc(OC(F)(F)F)cc4)n3)c2)c1]
P196 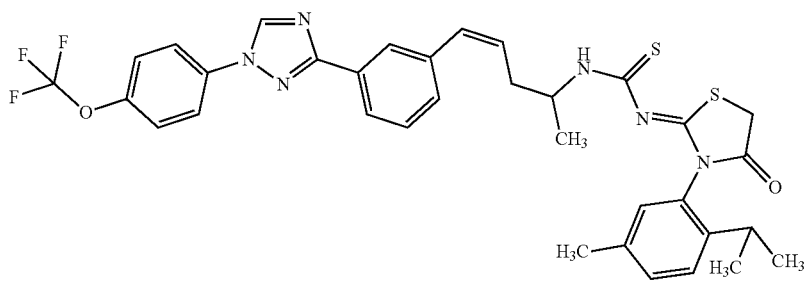 [SMILES: Cc1ccc(C(C)C)c(N2C(=O)CS/C2=N\C(=S)NC(C)C/C=C\c2cccc(-c3ncn(-c4ccc(OC(F)(F)F)cc4)n3)c2)c1]
P197 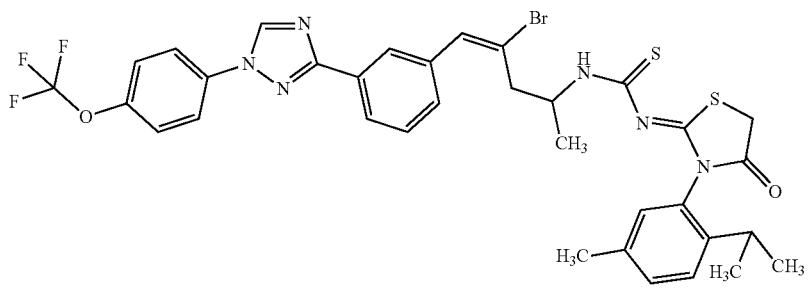 [SMILES: Cc1ccc(C(C)C)c(N2C(=O)CS/C2=N\C(=S)NC(C)C/C(Br)=C\c2cccc(-c3ncn(-c4ccc(OC(F)(F)F)cc4)n3)c2)c1]

P198 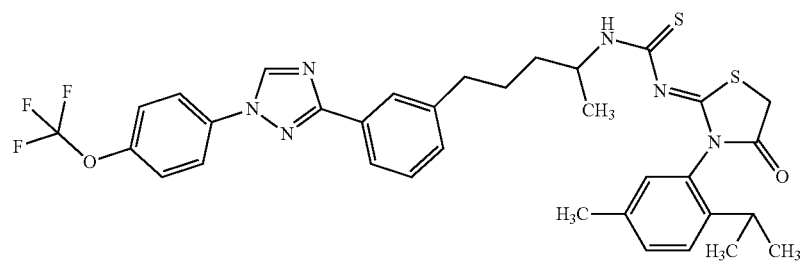 [SMILES: Cc1ccc(C(C)C)c(N2C(=O)CS/C2=N\C(=S)NC(C)CCCc2cccc(-c3ncn(-c4ccc(OC(F)(F)F)cc4)n3)c2)c1]
P199 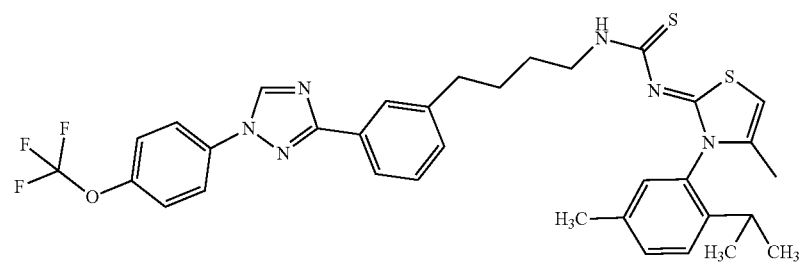 [SMILES: Cc1ccc(C(C)C)c(-n2c(C)cs/c2=N\C(=S)NCCCCc2cccc(-c3ncn(-c4ccc(OC(F)(F)F)cc4)n3)c2)c1]
P200 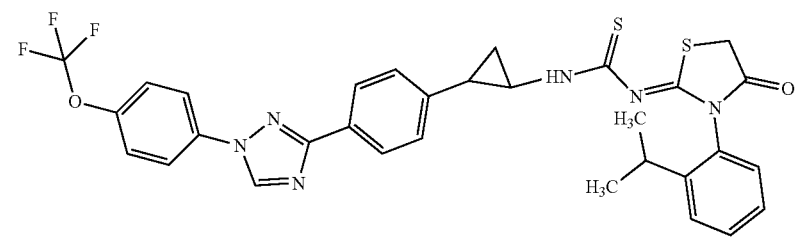 [SMILES: CC(C)c1ccccc1N1C(=O)CS/C1=N\C(=S)NC1CC1c1ccc(-c2ncn(-c3ccc(OC(F)(F)F)cc3)n2)cc1]
P201 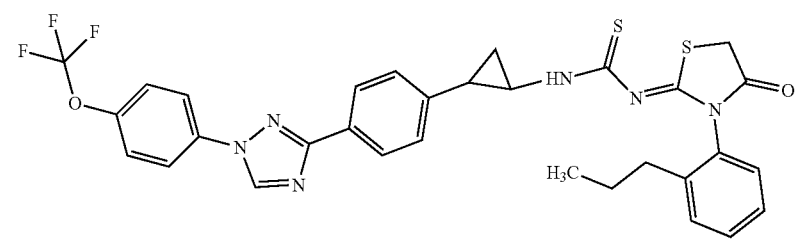 [SMILES: CCCc1ccccc1N1C(=O)CS/C1=N\C(=S)NC1CC1c1ccc(-c2ncn(-c3ccc(OC(F)(F)F)cc3)n2)cc1]
P202 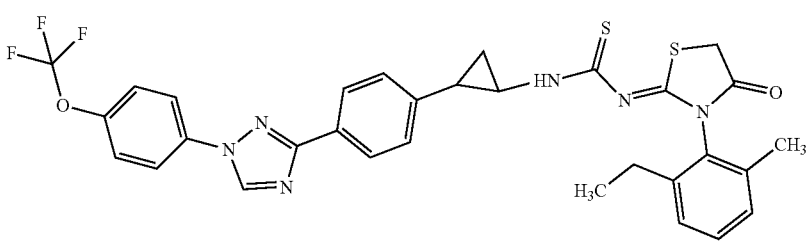 [SMILES: CCc1cccc(C)c1N1C(=O)CS/C1=N\C(=S)NC1CC1c1ccc(-c2ncn(-c3ccc(OC(F)(F)F)cc3)n2)cc1]
P203 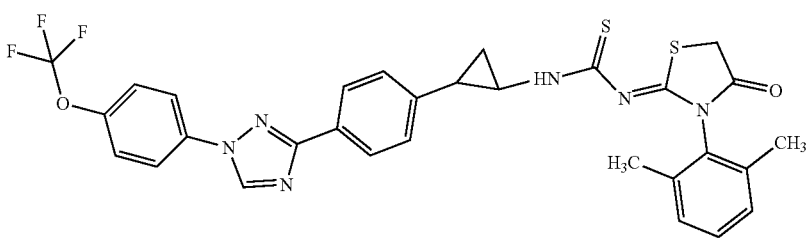 [SMILES: Cc1cccc(C)c1N1C(=O)CS/C1=N\C(=S)NC1CC1c1ccc(-c2ncn(-c3ccc(OC(F)(F)F)cc3)n2)cc1]

-continued
P204 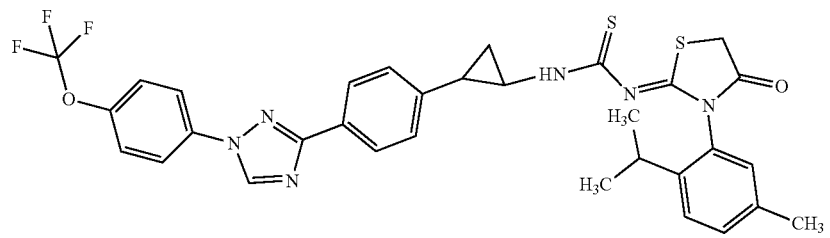 [SMILES: Cc1ccc(C(C)C)c(N2C(=O)CS/C2=N\C(=S)NC2CC2c2ccc(-c3ncn(-c4ccc(OC(F)(F)F)cc4)n3)cc2)c1]
P205 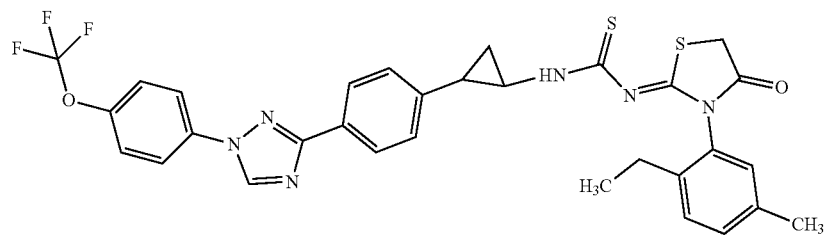 [SMILES: CCc1ccc(C)cc1N1C(=O)CS/C1=N\C(=S)NC1CC1c1ccc(-c2ncn(-c3ccc(OC(F)(F)F)cc3)n2)cc1]
P206 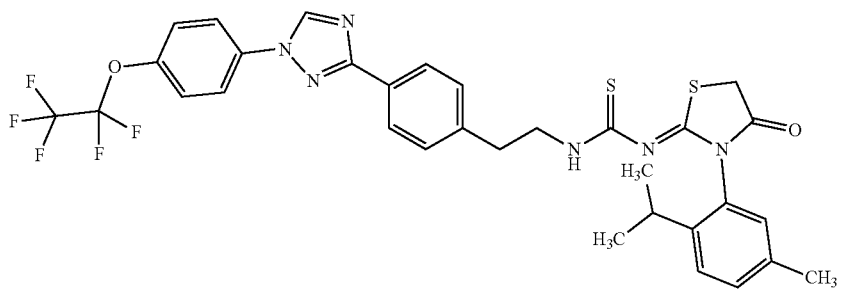 [SMILES: Cc1ccc(C(C)C)c(N2C(=O)CS/C2=N\C(=S)NCCc2ccc(-c3ncn(-c4ccc(OC(F)(F)C(F)(F)F)cc4)n3)cc2)c1]
P207 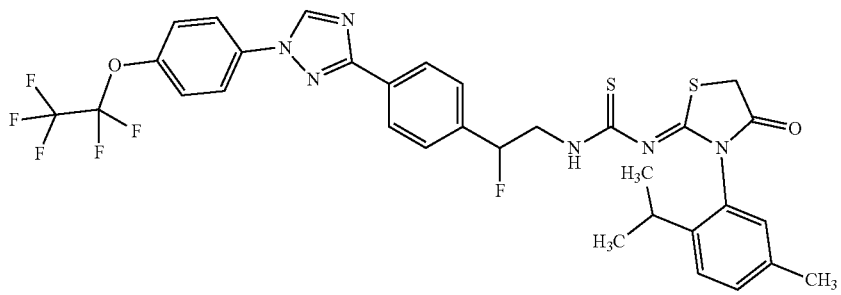 [SMILES: Cc1ccc(C(C)C)c(N2C(=O)CS/C2=N\C(=S)NCC(F)c2ccc(-c3ncn(-c4ccc(OC(F)(F)C(F)(F)F)cc4)n3)cc2)c1]
P208 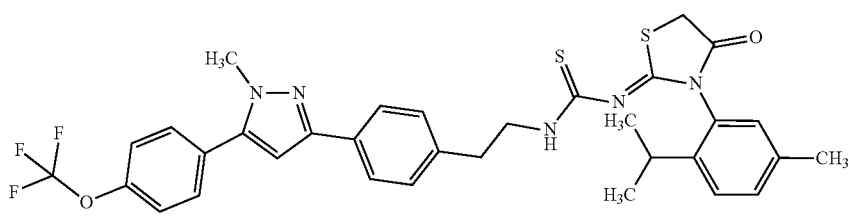 [SMILES: Cc1ccc(C(C)C)c(N2C(=O)CS/C2=N\C(=S)NCCc2ccc(-c3cc(-c4ccc(OC(F)(F)F)cc4)n(C)n3)cc2)c1]
P209 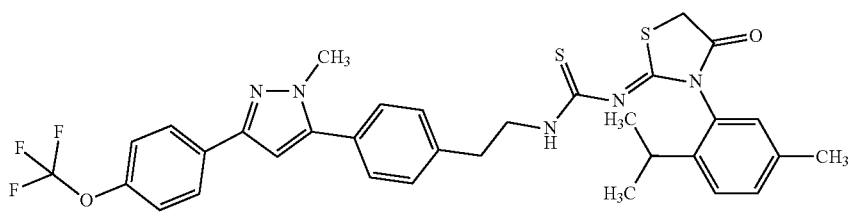 [SMILES: Cc1ccc(C(C)C)c(N2C(=O)CS/C2=N\C(=S)NCCc2ccc(-c3cc(-c4ccc(OC(F)(F)F)cc4)nn3C)cc2)c1]

-continued

P210 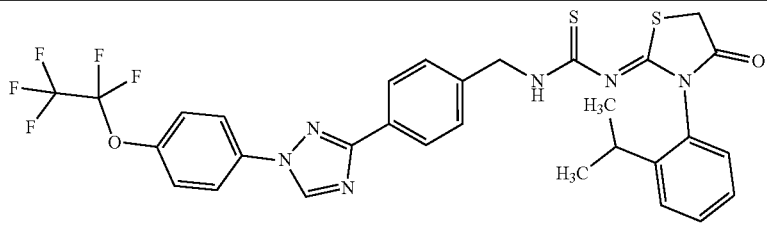

P211 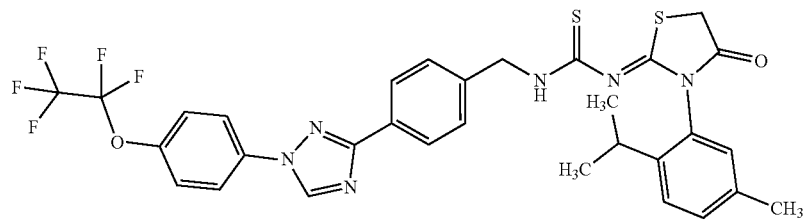 [SMILES: Cc1ccc(C(C)C)c(N2C(=O)CS/C2=N\C(=S)NCc2ccc(-c3ncn(-c4ccc(OC(F)(F)C(F)(F)F)cc4)n3)cc2)c1]

P212 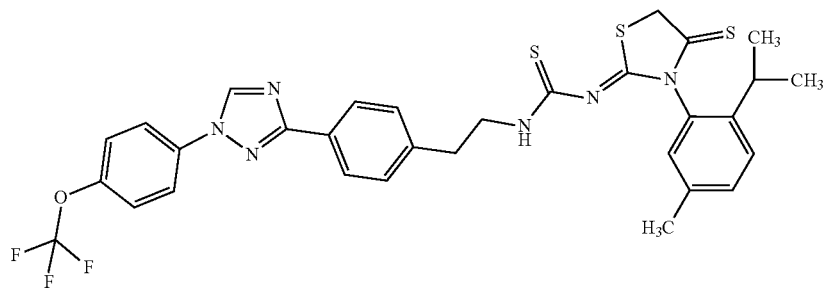 [SMILES: Cc1ccc(C(C)C)c(N2C(=S)CS/C2=N\C(=S)NCCc2ccc(-c3ncn(-c4ccc(OC(F)(F)F)cc4)n3)cc2)c1]

P213 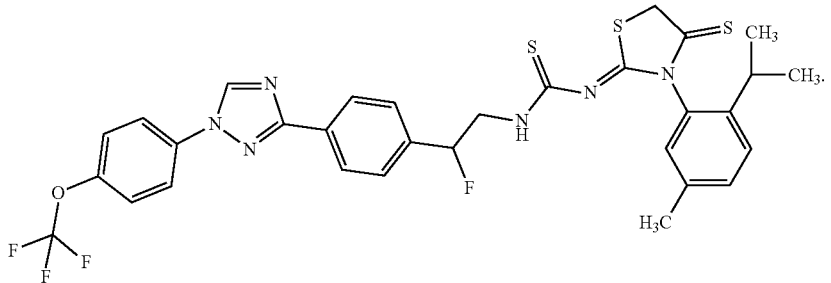 [SMILES: Cc1ccc(C(C)C)c(N2C(=S)CS/C2=N\C(=S)NCC(F)c2ccc(-c3ncn(-c4ccc(OC(F)(F)F)cc4)n3)cc2)c1]

4. A molecule according to claim 1 wherein at least one H is $^2$H or at least one C is $^{14}$C.

5. A composition comprising a biologically effective amount of a molecule according to claim 1 and at least one other compound having insecticidal, herbicidal, acaricidal, nematicidal, or fungicidal activity.

6. A composition comprising a biologically effective amount of a molecule according to claim 1 and a seed.

7. A process of treating plants or seeds comprising applying a biologically effective amount of a molecule according to claim 1 to a genetically modified plant, or genetically-modified seed, which has been genetically modified to express one or more specialized traits.

8. A process of controlling endoparasites, ectoparasites, or both comprising: orally administering; or topically applying; a biologically effective amount of a molecule according to claim 1, to a non-human animal.

* * * * *